(12) United States Patent
Tawa et al.

(10) Patent No.: US 8,362,062 B2
(45) Date of Patent: Jan. 29, 2013

(54) PHARMACEUTICAL COMPOSITIONS WITH IMPROVED DISSOLUTION

(75) Inventors: Mark Tawa, West Roxbury, MA (US); Julius Remenar, Framingham, MA (US); Matthew L. Peterson, Hopkinton, MA (US); Örn Almarsson, Shrewsbury, MA (US); Hector Guzman, Jamaica Plain, MA (US); Hongming Chen, Acton, MA (US); Mark Oliveira, Framingham, MA (US)

(73) Assignee: McNeil-PPC, Inc., Skillman, NJ (US)

( * ) Notice: Subject to any disclaimer, the term of this patent is extended or adjusted under 35 U.S.C. 154(b) by 1581 days.

(21) Appl. No.: 10/541,216

(22) PCT Filed: Dec. 24, 2003

(86) PCT No.: PCT/US03/41273
§ 371 (c)(1),
(2), (4) Date: Jun. 29, 2005

(87) PCT Pub. No.: WO2004/061433
PCT Pub. Date: Jul. 22, 2004

(65) Prior Publication Data
US 2006/0134198 A1    Jun. 22, 2006

Related U.S. Application Data

(60) Continuation-in-part of application No. 10/601,092, filed on Jun. 20, 2003, now abandoned, and a continuation-in-part of application No. PCT/US03/19754, filed on Jun. 20, 2003, and a continuation-in-part of application No.
(Continued)

(51) Int. Cl.
*A01N 43/56* (2006.01)
*A61K 31/18* (2006.01)

(52) U.S. Cl. .......................... 514/403; 514/406; 514/602

(58) Field of Classification Search .................. 514/403, 514/406, 602
See application file for complete search history.

(56) References Cited

U.S. PATENT DOCUMENTS

| | | |
|---|---|---|
| 2,665,277 A | 1/1954 | Cochran et al. |
| 2,711,411 A | 6/1955 | Holbert et al. |
| 3,028,420 A | 4/1962 | Petrow et al. |
| 3,536,809 A | 10/1970 | Applezweig et al. |
| 3,598,123 A | 8/1971 | Zaffaroni |
| 3,845,770 A | 11/1974 | Theeuwes et al. |
| 3,916,899 A | 11/1975 | Theeuwes et al. |
| 3,970,651 A | 7/1976 | Kaplan et al. |
| 4,008,321 A | 2/1977 | Kamishita et al. |
| 4,008,719 A | 2/1977 | Theeuwes et al. |
| 4,198,507 A | 4/1980 | Barry et al. |
| 4,267,179 A | 5/1981 | Heeres et al. |
| 4,368,197 A | 1/1983 | Shefter et al. |
| 4,513,006 A | 4/1985 | Maryanoff et al. |
| 4,764,604 A | 8/1988 | Muller |
| 4,853,379 A | 8/1989 | Shroot et al. |
| 4,916,134 A | 4/1990 | Heeres et al. |
| 4,925,674 A | 5/1990 | Giannini et al. |
| 4,927,855 A | 5/1990 | Lafon |
| 4,994,604 A | 2/1991 | Tung et al. |
| 5,006,513 A | 4/1991 | Hector et al. |
| 5,023,092 A | 6/1991 | DuRoss |
| 5,059,595 A | 10/1991 | Le Grazie |
| 5,073,543 A | 12/1991 | Marshall et al. |
| 5,096,926 A | 3/1992 | Fiorini et al. |
| 5,120,548 A | 6/1992 | McClelland et al. |
| 5,177,262 A | 1/1993 | Taylor et al. |
| 5,242,942 A | 9/1993 | Costanzo et al. |
| 5,273,760 A | 12/1993 | Oshlack et al. |
| 5,286,493 A | 2/1994 | Oshlack et al. |
| 5,324,351 A | 6/1994 | Oshlack et al. |
| 5,332,834 A | 7/1994 | Bhattacharya et al. |
| 5,338,644 A | 8/1994 | Taylor et al. |
| 5,354,556 A | 10/1994 | Sparks et al. |
| 5,356,467 A | 10/1994 | Oshlack et al. |
| 5,360,615 A | 11/1994 | Yu et al. |
| 5,366,738 A | 11/1994 | Rork et al. |
| 5,380,867 A | 1/1995 | Bhattacharya et al. |
| 5,384,327 A | 1/1995 | Costanzo et al. |
| 5,412,094 A | 5/1995 | Amos et al. |
| 5,414,997 A | 5/1995 | Tailer |
| 5,466,823 A | 11/1995 | Talley et al. |
| 5,472,712 A | 12/1995 | Oshlack et al. |

(Continued)

FOREIGN PATENT DOCUMENTS

| | | |
|---|---|---|
| CA | 1101840 A1 | 5/1981 |
| EP | 0310122 B1 | 4/1989 |

(Continued)

OTHER PUBLICATIONS

Aakeröy, C. et al. "Crystal engineering of hydrogen-bonded assemblies—a progress report" *Aust. J. Chem.*, 2001, pp. 409-421, vol. 54.

Bingham, A. et al. "Over one hundred solvates of sulfathiazole" *Chem. Commun.*, 2001, pp. 603-604.

Byriel, K., et al. "Molecular cocrystals of carboxylic acids. IX. Carboxylic acid interactions with organic heterocyclic bases. The crystal structures of the adducts of (2,4-dichlorophenoxy) acetic acid with 3-hydroxypyridine, 2,4,6,-trinitrobenzoic acid with 2-aminopyrimidine, and 4-nitrobenzoic acid with 3-amino-1,2,4-triazole" *Aust. J. Chem.*, 1992, pp. 969-981, vol. 45, No. 6.

Salmon, J. et al. "Supramolecular chemistry of boronic acids (Abstract)" 38th Midwest Regional Meeting of the American Chemical Society in Columbia, MO., Nov. 5-7, 2003, published by the American Chemical Society, Washington, D.C.

(Continued)

*Primary Examiner* — Renee Claytor
(74) *Attorney, Agent, or Firm* — Laura A. Donnelly

(57) ABSTRACT

The invention relates to methods of screening mixtures containing a pharmaceutical compound and an excipient to identify properties of the pharmaceutical compound/excipient combination that retard solid-state nucleation. The invention further relates to increasing the solubility, dissolution and bioavailability of a drug with low solubility in gastric fluids conditions by combining the drug with a precipitation retardant and an optional enhancer.

15 Claims, 113 Drawing Sheets
(3 of 113 Drawing Sheet(s) Filed in Color)

Related U.S. Application Data

PCT/US03/27772, filed on Sep. 4, 2003, which is a continuation-in-part of application No. 10/378,956, filed on Mar. 3, 2003, application No. 10/541,216, which is a continuation-in-part of application No. 10/660,202, filed on Sep. 11, 2003, now Pat. No. 7,927,613, which is a continuation-in-part of application No. PCT/US03/27772, filed on Sep. 4, 2003, which is a continuation-in-part of application No. 10/378,956, said application No. 10/660,202 is a continuation-in-part of application No. 10/637,829, filed on Aug. 8, 2003, which is a division of application No. 10/295,995, filed on Nov. 18, 2002, which is a continuation of application No. 10/232,589, filed on Sep. 3, 2002, said application No. 10/660,202 is a continuation-in-part of application No. 10/449,307, filed on May 30, 2003, and a continuation-in-part of application No. 10/601,092, application No. 10/541,216, which is a continuation-in-part of application No. PCT/US03/28982, filed on Sep. 16, 2003.

(60) Provisional application No. 60/441,335, filed on Jan. 21, 2003, provisional application No. 60/456,608, filed on Mar. 21, 2003, provisional application No. 60/459,501, filed on Apr. 1, 2003, provisional application No. 60/486,713, filed on Jul. 11, 2003, provisional application No. 60/456,027, filed on Mar. 18, 2003, provisional application No. 60/437,516, filed on Dec. 30, 2002, provisional application No. 60/451,213, filed on Feb. 28, 2003, provisional application No. 60/487,064, filed on Jul. 11, 2003, provisional application No. 60/390,881, filed on Jun. 21, 2002, provisional application No. 60/426,275, filed on Nov. 14, 2002, provisional application No. 60/427,086, filed on Nov. 15, 2002, provisional application No. 60/429,515, filed on Nov. 26, 2002, provisional application No. 60/360,768, filed on Mar. 1, 2002, provisional application No. 60/463,962, filed on Apr. 18, 2003, provisional application No. 60/406,974, filed on Aug. 30, 2002, provisional application No. 60/380,288, filed on May 15, 2002, provisional application No. 60/356,764, filed on Feb. 15, 2002, provisional application No. 60/444,315, filed on Jan. 31, 2003, provisional application No. 60/439,282, filed on Jan. 10, 2003, provisional application No. 60/384,152, filed on May 31, 2002, provisional application No. 60/412,459, filed on Sep. 20, 2002.

(56) References Cited

U.S. PATENT DOCUMENTS

| | | |
|---|---|---|
| 5,474,997 A | 12/1995 | Gray et al. |
| 5,510,496 A | 4/1996 | Talley et al. |
| 5,521,207 A | 5/1996 | Graneto |
| 5,523,090 A | 6/1996 | Znaiden et al. |
| 5,563,165 A | 10/1996 | Talley et al. |
| 5,591,767 A | 1/1997 | Mohr et al. |
| 5,614,342 A | 3/1997 | Molaire et al. |
| 5,631,250 A | 5/1997 | Bunnell et al. |
| 5,633,015 A | 5/1997 | Gilis et al. |
| 5,633,272 A | 5/1997 | Talley et al. |
| 5,639,476 A | 6/1997 | Oshlack et al. |
| 5,641,512 A | 6/1997 | Cimiluca |
| 5,661,151 A | 8/1997 | Saksena et al. |
| 5,674,533 A | 10/1997 | Santus et al. |
| 5,703,232 A | 12/1997 | Bunnell et al. |
| 5,707,975 A | 1/1998 | Francois et al. |
| 5,733,566 A | 3/1998 | Lewis |
| 5,736,541 A | 4/1998 | Bunnell et al. |
| 5,753,688 A | 5/1998 | Talley et al. |
| 5,753,693 A | 5/1998 | Shank |
| 5,760,007 A | 6/1998 | Shank et al. |
| 5,760,068 A | 6/1998 | Talley et al. |
| 5,932,598 A | 8/1999 | Talley et al. |
| 5,935,933 A | 8/1999 | Shank et al. |
| 5,952,187 A | 9/1999 | Stenglein et al. |
| 5,972,986 A | 10/1999 | Seibert et al. |
| 5,985,902 A | 11/1999 | Talley et al. |
| 5,994,365 A | 11/1999 | Zaworotko et al. |
| 5,998,380 A | 12/1999 | Ehrenberg et al. |
| 5,998,413 A | 12/1999 | Heeres et al. |
| 6,001,996 A | 12/1999 | Amos et al. |
| 6,054,136 A | 4/2000 | Farah et al. |
| 6,071,537 A | 6/2000 | Shank |
| 6,132,420 A | 10/2000 | Dionne et al. |
| 6,156,781 A | 12/2000 | Talley et al. |
| 6,191,117 B1 | 2/2001 | Kozachuk |
| 6,201,010 B1 | 3/2001 | Cottrell |
| 6,245,357 B1 | 6/2001 | Edgren et al. |
| 6,268,385 B1 | 7/2001 | Whittle et al. |
| 6,270,787 B1 | 8/2001 | Ayer |
| 6,283,953 B1 | 9/2001 | Ayer et al. |
| 6,287,295 B1 | 9/2001 | Chen et al. |
| 6,294,192 B1 | 9/2001 | Patel et al. |
| 6,319,903 B1 | 11/2001 | Carrazana et al. |
| 6,323,266 B2 | 11/2001 | Phillips |
| 6,333,050 B2 | 12/2001 | Wong et al. |
| 6,342,249 B1 | 1/2002 | Wong et al. |
| 6,348,458 B1 | 2/2002 | Hamied et al. |
| 6,365,185 B1 | 4/2002 | Ritschel et al. |
| 6,368,626 B1 | 4/2002 | Bhatt et al. |
| 6,375,978 B1 | 4/2002 | Kleiner et al. |
| 6,384,034 B2 | 5/2002 | Simitchieva et al. |
| 6,403,640 B1 | 6/2002 | Stoner et al. |
| 6,413,965 B1 | 7/2002 | Mylari |
| 6,420,394 B1 | 7/2002 | Supersaxo |
| 6,488,962 B1 | 12/2002 | Berner et al. |
| 6,503,884 B1 | 1/2003 | Ehrenberg et al. |
| 6,559,293 B1 | 5/2003 | Almarsson et al. |
| 6,570,036 B1 | 5/2003 | Reuter |
| 6,579,895 B2 | 6/2003 | Karim et al. |
| 6,613,790 B2 * | 9/2003 | Carter ............ 514/406 |
| 6,699,840 B2 | 3/2004 | Almarsson et al. |
| 7,078,526 B2 | 7/2006 | Remenar et al. |
| 7,132,570 B2 | 11/2006 | Neckebrock et al. |
| 7,172,769 B2 * | 2/2007 | Kararli et al. ............ 424/501 |
| 7,205,413 B2 | 4/2007 | Morissette et al. |
| 7,446,107 B2 | 11/2008 | Remenar et al. |
| 7,452,555 B2 | 11/2008 | Childs |
| 7,459,449 B2 | 12/2008 | Keltjens |
| 2002/0006951 A1 | 1/2002 | Hageman et al. |
| 2002/0013357 A1 | 1/2002 | Nadkarni et al. |
| 2002/0015735 A1 | 2/2002 | Hedden et al. |
| 2002/0034542 A1 | 3/2002 | Thombre et al. |
| 2002/0037925 A1 | 3/2002 | Dewey et al. |
| 2002/0042446 A1 | 4/2002 | Dewey et al. |
| 2002/0071857 A1 | 6/2002 | Kararli et al. |
| 2002/0107250 A1 | 8/2002 | Hariharan et al. |
| 2002/0119193 A1 | 8/2002 | Le et al. |
| 2003/0069190 A1 | 4/2003 | Abdel-Magid et al. |
| 2003/0072802 A1 | 4/2003 | Cutler |
| 2003/0096014 A1 | 5/2003 | Sherman |
| 2003/0162226 A1 | 8/2003 | Cima et al. |
| 2003/0166581 A1 | 9/2003 | Almarsson et al. |
| 2003/0224006 A1 | 12/2003 | Zaworotko et al. |
| 2004/0019211 A1 | 1/2004 | Remenar et al. |
| 2004/0029946 A1 * | 2/2004 | Arora et al. ............ 514/406 |
| 2004/0053853 A1 | 3/2004 | Almarsson et al. |
| 2004/0106052 A1 | 6/2004 | Molaire |
| 2004/0106053 A1 | 6/2004 | Molaire et al. |
| 2004/0106055 A1 | 6/2004 | Molaire et al. |
| 2004/0154890 A1 | 8/2004 | Liu |
| 2004/0171062 A1 | 9/2004 | Hirth et al. |
| 2004/0176335 A1 | 9/2004 | Childs |
| 2004/0242640 A1 | 12/2004 | Desai et al. |
| 2005/0070551 A1 | 3/2005 | Remenar et al. |
| 2005/0169982 A1 | 8/2005 | Almarsson et al. |

| | | | |
|---|---|---|---|
| 2005/0181041 | A1 | 8/2005 | Goldman |
| 2005/0252649 | A1 | 11/2005 | Chiu et al. |
| 2005/0256127 | A1 | 11/2005 | Ku et al. |
| 2006/0052432 | A1* | 3/2006 | Remenar et al. ............ 514/406 |
| 2006/0134198 | A1 | 6/2006 | Tawa et al. |
| 2006/0223794 | A1 | 10/2006 | Hickey et al. |
| 2007/0015841 | A1* | 1/2007 | Tawa et al. ................... 514/738 |
| 2007/0021510 | A1 | 1/2007 | Hickey et al. |
| 2007/0026078 | A1 | 2/2007 | Almarsson et al. |
| 2007/0059356 | A1 | 3/2007 | Almarsson et al. |
| 2007/0293674 | A1 | 12/2007 | Scoppettuolo et al. |
| 2009/0088443 | A1 | 4/2009 | Remenar et al. |
| 2010/0331285 | A1 | 12/2010 | Almarsson et al. |

FOREIGN PATENT DOCUMENTS

| | | |
|---|---|---|
| EP | 0283992 B1 | 9/1992 |
| EP | 413528 B1 | 11/1995 |
| EP | 731795 B1 | 12/1999 |
| EP | 1167355 | 10/2003 |
| EP | 1364649 A1 | 11/2003 |
| FR | 769586 | 6/1934 |
| FR | 2849029 A1 | 6/2004 |
| GB | 1 297 261 A | 11/1972 |
| GB | 2169601 A | 7/1986 |
| IN | 182620 | 12/1994 |
| IT | 01303251 | 11/2000 |
| JP | 46-33588 | 10/1971 |
| JP | 54-16494 | 2/1979 |
| JP | 54-095589 | 7/1979 |
| WO | WO 94/16733 A1 | 8/1994 |
| WO | WO 95/17407 A1 | 6/1995 |
| WO | 95/23596 | 9/1995 |
| WO | WO 96/07331 A1 | 3/1996 |
| WO | WO 96/33193 A1 | 10/1996 |
| WO | WO 98/57967 A1 | 12/1998 |
| WO | WO 00/07583 A2 | 2/2000 |
| WO | 00/32189 | 6/2000 |
| WO | WO 00/50020 A2 | 8/2000 |
| WO | WO 00/53283 A1 | 9/2000 |
| WO | WO 00/72841 A1 | 12/2000 |
| WO | WO 01/13904 A2 | 3/2001 |
| WO | 01/41536 | 6/2001 |
| WO | 01/41760 | 6/2001 |
| WO | 01/42221 | 6/2001 |
| WO | 01/42222 | 6/2001 |
| WO | 01/45706 | 6/2001 |
| WO | 01/51919 | 7/2001 |
| WO | 01/78724 | 10/2001 |
| WO | 01/91750 | 12/2001 |
| WO | WO 01/97853 A1 | 12/2001 |
| WO | 02/00627 | 1/2002 |
| WO | WO 02/10125 A1 | 2/2002 |
| WO | 02/56878 | 7/2002 |
| WO | WO 02/056915 A1 | 7/2002 |
| WO | WO 02/062318 A2 | 8/2002 |
| WO | 02/102376 | 12/2002 |
| WO | WO 03 033462 A2 | 4/2003 |
| WO | WO 03/070738 A2 | 8/2003 |
| WO | WO 03/074474 A2 | 9/2003 |
| WO | WO 03/101392 A2 | 12/2003 |
| WO | WO 2004/054571 A1 | 7/2004 |
| WO | WO 2004/060347 A2 | 7/2004 |
| WO | WO 2004/078161 A1 | 9/2004 |
| WO | WO 2004/078163 | 9/2004 |
| WO | WO 2004/089313 A2 | 10/2004 |
| WO | WO 2005/023198 A2 | 3/2005 |
| WO | WO 2005/037424 A1 | 4/2005 |
| WO | 2005/053612 | 6/2005 |
| WO | WO 2005/055983 A2 | 6/2005 |
| WO | WO 2005/060968 A1 | 7/2005 |
| WO | WO 2005/077894 A1 | 8/2005 |
| WO | WO 2005/089375 A2 | 9/2005 |
| WO | WO 2005/094804 A1 | 10/2005 |
| WO | WO 2005/118577 A1 | 12/2005 |
| WO | WO 2006/024930 A1 | 3/2006 |

OTHER PUBLICATIONS

Urbina, J. et al. "Supramolecular design of inorganic/organic networks using flexible ligands with self-complementary hydrogen bonds (Abstract)" 38th Midwest Regional Meeting of the American Chemical Society in Columbia, MO., Nov. 5-7, 2003, published by the American Chemical Society, Washington, D.C.

Smith, D. et al. "Structure confirmation by single crystal X-ray diffraction of a series of new schiff bases and theoretical computations on 3-(N-2-α, α, α-triflourotoluylidene amino) tetrahydrothiophene-1, 1-dioxide (Abstract)" 216th ACS National Meeting in Boston, MA., Aug. 23-27, 1998, published by the American Chemical Society, Washington, D.C.

Desiraju, G. "Supramolecular synthons in crystal engineering—A new organic synthesis" Angew. Chem. Int. Ed. Engl., 1995, pp. 2311-2327, vol. 34.

Fritchie, C. et al. "The configuration of phenothiazine in various molecular complexes" Chem. Commun., 1968, pp. 833-834.

Ball, P. "Materials Chemistry—Scandal of Crystal Design . . .", Nature, Jun. 20, 1996, pp. 648-650, vol. 381.

Bernstein, J. et al. "Concomitant Polymorphs", Angew. Chem., Int. Ed., 1999, pp. 3440-3461, vol. 38.

Zaworotko, M. J. "Crystal Engineering of Diamondoid Networks", Chem. Soc. Rev., 1994, pp. 283-288, vol. 23.

Shattock, T. R. et al. "Hierarchy of Supramolecular Synthons: Persistent Carboxylic Acid—Pyridine Hydrogen Bonds in Cocrystals that also contain a Hydroxyl Moiety" Crystal Growth 7 Design, 2008, pp. 4533-4545, vol. 8, No. 12.

Huang, C.-M. et al. "Molecular packing modes. Part XI. Crystal structures of the 2:1 complexes of benzamide with succinic acid and furamide with oxalic acid" J. Chem. Soc. Perkins Trans. 2: Physical Organic Chemistry, 1973, pp. 503-508, vol. 5.

Jackisch, M. et al. "Structures of three related biphenyl compounds: 4,4'-biphenyldiol, 3, 3',5,5'-tetra-tert-butyl-4,4'-biphenyldiol, and 3,3',5,5'-tetra-tert-butyl-1,1'-bicyclohexa-2,5-dienylidene-4,4'-dione" Acta Cryst., 1990, pp. 919-922, vol. C46.

Kim, S. et al. "The structure of a crystalline complex containing one phenobarbital molecule and two adenine derivatives" Proc. Natl. Acad. Sci. USA, 1968, pp. 402-408, vol. 60.

Kobayashi, H. et al. "Sinusoidal structure of the 1:1 complex of phenothiazine and 7,7,8,8-tetracyanoquinodimethane, PTZ-TCNQ" Acta Cryst., 1974, pp. 1010-1017, vol. B30.

Ermer, O. et al. "Molecular recognition among alcohols and amines: super-tetrahedral crystal architectures of linear diphenol-diamine complexes and aminophenols" J. Chem. Soc. Perkins Trans. 2, 1994, pp. 925-944.

Martin, R. et al. "Polyphenal-caffeine complexation" J. Chem. Soc., Chem. Commun., 1986, pp. 105-106.

Lehn, J.-M. et al. "Molecular recognition directed self-assembly of ordered supramolecular strands by cocrystallization of complementary molecular components" Chem. Soc., Chem. Commun., 1990, pp. 479-481.

Boucher, E. et al. "Use of Hydrogen-Bonds to Control Molecular Aggregation. Behavior of Dipyridones and Pyridone-Pyrimidones Designed to Form Cyclic Triplexes", J. Org. Chem., 1995, pp. 1408-1412, vol. 60.

Chang, Y. L. et al. "An Approach to the Design of Molecular-Solids. Strategies for Controlling the Assembly of Molecules Into Two-Dimensional Layered Structures", J. Am. Chem. Soc., 1993, pp. 5991-6000, vol. 115.

Desiraju, G. R. "Crystal Gazing: Structure Prediction and Polymorphism", Science, Oct. 17, 1997, pp. 404-405, vol. 278, No. 5337.

Feynman, R. "There's Plenty of Room at the Bottom", Engineering and Science, Feb. 1960, pp. 22-36.

Moulton, B. et al. "From Molecules to Crystal Engineering: Supramolecular Isomerism and Polymorphism in Network Solids", Chem. Rev., 2001, pp. 1629-1658, vol. 101.

Lynch, D. et al. "Molecular cocrystals of carboxylic acids. XV* Preparation and characterization of heterocyclic base adducts with a series of carboxylic acids, and the crystal structures of the adducts of 2-aminopyrimidine with 2,6-dihydroxybenzoic acid, 4-aminobenzoic acid, phenoxyacetic acid, (2,4-dichlorophenoxy) acetic acid, (3,4-dichlorophenoxy)-acetic acid and salicylic acid, and 2-aminopyridmine with 2,6-dihydroxybenzoic acid" Aust. J. Chem., 1994, pp. 1097-1115, vol. 47.

McIntosh, J. et al. "Chemotherapeutic drugs in anaerobic infections of wounds" The Lancet, Jun. 26, 1943, pp. 793-795.

McIntosh, J. et al. "Zinc peroxide, proflavine and penicillin in experimental cl. welchii infections" The Lancet, Dec. 26, 1942, pp. 750-752.

Smith, G. et al. "Molecular cocrystals of carboxylic acids. XXI* The role of secondary group interactions in adduct formation between 2-aminopyramidine and substituted benzoic acids: the crystal structures of the adducts with o-phthalic acid, o-nitrobenzoic acid, o-aminobenzoic acid and m-aminobenzoic acid" Aust. J. Chem., 1995, pp. 1151-1166, vol. 48.

Weissbuch, I. et al. "Crystal morphology control with tailor-made additives; a stereochemical approach" Advances in Crystal Growth Research, 2001, pp. 381-400.

McMahon, J. et al. "Crystal engineering of the composition of pharmaceutical phases. 3[1]. Primary amide supramolecular heterosynthons and their role in the design of pharmaceutical cocrystals" Z. Kristallogr., 2005, pp. 340-350, vol. 220.

Meejoo, S. et al. "The interplay of aryl-perifluoroaryl stacking interactions and interstack hydrogen bonding in controlling the structure of a molecular cocrystal" Chemphyschem, 2003, pp. 766-769, vol. 4.

Mirmehrabi, M. et al. "Improving the filterability and solid density of ranitidine hydrochloride form 1" Journal of Pharmaceutical Sciences, Jul. 2004, pp. 1692-1700, vol. 93, No. 7.

Morris, K. et al. "Theoretical approaches to physical transformations of active pharmaceutical ingredients during manufacturing processes" Advanced Drug Delivery Reviews, 2001, pp. 91-114, vol. 48.

Nakanishi, I. et al. "X-ray structural studies on two forms of β-cyclodextrin barbital complexes" Journal of Inclusion Phenomena, 1984, pp. 689-699, vol. 2.

Nakao, S. et al. "The crystal and molecular structure of the 2:1 molecular complex of theophylline with phenobarbital" Acta Cryst., 1977, pp. 1373-1378, vol. B33.

Natarajan, S. et al. "Reinvestigation of the crystal structure of diglycine hydrochloride" Zeitschrift für Kristallographic, 1992, pp. 265-270, vol. 198.

Olenik, B. et al. "Cooperative and anticooperative effects in the cocrystals of mono- and diazanaphthalenes with meso-1, 2-diphenyl-1,2-ethanediol" Crystal Growth & Design, 2003, pp. 175-181, vol. 3, No. 2.

Olenik, B. et al. "Supramolecular synthesis by cocrystallization of oxalic and fumaric acid with diazanaphthalenes" Crystal Growth & Design, 2003, pp. 183-188, vol. 3, No. 2.

Groth, P. "d-Glucose-sodium chloride-monohydrate (glucose-sodium chloride) = $2C_6H_{12}O_6 \cdot NaCl \cdot H_2O$" Chemische Krystallographie, 1910, pp. 438-439.

Oswald, I. et al. "Rationalisation of co-crystal formation through knowledge-mining" Crystallography Reviews, 2004, pp. 57-66, vol. 10, No. 1.

Ouyang, X. et al. "Single-crystal-to-single-crystal topochemical polymerizations of a terminal diacetylene: two remarkable transformations give the same conjugated polymer" J. Am. Chem. Soc., 2003, pp. 12400-12401, vol. 125.

Patel, U. et al. "Structure of the 1:1 complex between 4-amino-N-(4,6-dimethyl-2-pyrimidinyl)-benzenesulfonamide (sulfadimidine) and 2-hydroxybenzoic acid (salicylic acid)" Acta Cryst., 1988, pp. 1264-1267, vol. C44.

Reddy, L. et al. "Phenyl-perfluorophenyl synthon mediated cocrystallization of carboxylic acids and amides" Crystal Growth & Design, 2004, pp. 89-94, vol. 4., No. 1.

Remenar, J. et al. "Crystal engineering of novel cocrystals of a triazole drug with 1,4-dicarboxylic acids" J. Am. Chem. Soc., 2003, pp. 8456-8457, vol. 125.

Schmidt, G. "Photodimerization in the solid state" Pure Appl. Chem., 1971, pp. 647-678, vol. 27.

Shan, N. et al. "Co-crystal of 4,7-phenanthroline and carboxylic acids: synthon competition and prediction" Tetrahedron Letters, 2002, pp. 8721-8725, vol. 43.

Shan, N. et al. "Crystal engineering using 4,4'-bipyridyl with di- and tricarboxylic acids" Crystal Engineering, 2002, pp. 9-24, vol. 5.

Shan, N. et al "Supramolecular synthons in the co-crystal structures of 2-aminopyrimdine with diols and carboxylic acids" Tetrahedron Letters, 2002, pp. 3101-3104, vol. 43.

McIntosh, J. et al. "Further observations on the chemotherapy of experimental gas gangrene: flavazole, marfanil, V187 and V335" British Journal of Experimental Pathology, 1946, pp. 46-54, vol. 27.

Shaviv, R. et al. "Magnetochemistry of the tetrahaloferrate (III) ions 6. Crystal structure and magnetic ordering in $[(pyH)_3Cl]$ $[FeCl_4]_2$" Inorganica Chimica Acta, 1992, pp. 613-621, vol. 198-200.

Shefter, E. "Structural studies on complexes IV: Crystal structure of a 1:1 5-chlorosalicylic acid and theophylline complex" Journal of Pharmaceutical Sciences, 1969, pp. 710-714, vol. 58.

Shimizu, N. et al. "Structure of 2,4-diamino-5-(3,4,5-trimethoxybenzyl) pyrimidine-5,5-diethylbarbituric acid (1:1)" Acta Cryst., 1982, pp. 2309- 2311, vol. B38.

Singh, N. B. et al. "Solid state reaction between 8-hydroxyquinoline and ρ-nitrobenzoic acid" Indian Journal of Chemistry, May 1988, pp. 429-432, vol. 37B.

Smith, G. et al. "The 1:1 adduct of 4-aminobenzoic acid with 4-aminobenzonitrile" Acta Cryst., 2000, pp. 1155-1156, vol. C56.

Steiner, T. "Donor and acceptor strengths in C-H•••O hydrogen bonds quantified from crystallographic data of small solvent molecules" New. J. Chem., 1998, pp. 1099-1103.

Storey, R. et al. "Automation of solid form screening procedures in the pharmaceutical industry—how to avoid the bottlenecks" Crystallography Reviews, 2004, pp. 45-56, vol. 10, No. 1.

Szafran, M. et al. "Molecular structures and hydrogen bonding in the 1:1 and 1:2 complexes of pyridine betaine with 2,6-dichloro-4-nitrophenol; an example of strongly coupled hydrogen bonds, O-H•••O=C-O-H•••O-" Journal of Molecular Structure, 1997, pp. 145-160, vol. 416.

Takeuchi, M. et al. "Synchrotron radiation SAXS/WAXS study of polymorph-dependent phase behavior of binary mixtures of saturated monoacid triacylglycerols" Crystal Growth & Design, 2003, pp. 369-374, vol. 3, No. 3.

Tang, C. P. et al. "Reaction pathways in crystalline host-guest inclusion complexes: rotation by a net 180° of the acetyl group on photoaddition of guest-acetophenone and -m-Chloroacetophenone to the atom C5 of host deoxycholic acid" J. Am. Chem. Soc., 1985, pp. 4058-4070, vol. 107.

Taylor, R. et al. "Rules governing the crystal packing of mono- and dialcohols" Acta Crystallographica Section B, Structural Science, 2001, pp. 815-827, vol. B57.

Thallapally, P. et al. "Polymorphism of 1,3,5-trinitrobenzene induced by a trisindane additive" Angew. Chem. Int. Ed., 2004, pp. 1149-1155, vol. 43.

Timmerman, P. et al. "Noncovalent Assembly of functional groups on calix[4]arene molecular boxes" Chem. Eur. J., 1997, pp. 1823-1832, vol. 3., No. 11.

Shan, N. et al. "Mechanochemistry and co-crystal formation: effect of solvent on reaction kinetics" Chem. Commun., 2002, pp. 2372-2373.

Caira, M. et al. "X-ray structure and thermal analysis of a 1:1 complex between (S)-naproxen and heptakis (2,3,6-tri-O-methyl)-β-cyclodextrin" Journal of Inclusion Phenomena and Molecular Recognition in Chemistry, 1995, pp. 277-290, vol. 20, pp. 11-15.

Trask, A. et al. "Crystal engineering of organic cocrystals by the solid-state grinding approach" Top Curr. Chem., 2005, pp. 41-70, vol. 254.

Trask, A. et al. "Pharmaceutical cocrystallization: engineering a remedy for caffeine hydration" Crystal Growth & Design, 2005, pp. 1013-1021, vol. 5, No. 3.

Trask, A. et al. "Solvent-drop grinding: green polymorph control of cocrystallisation" Chem. Commun., 2004, pp. 890-891 in addition to supplemental materials.

Trowbridge, L. et al. "Composites for nonlinear optics: Crystal growth and polymorphism" University of Sussex, Falmer Brighton UK, School of Chemistry and Molecular Sciences, pp. 272.

Uno, T. et al. "Structure of 5,5-diphenylhydantoin-1-(4-bromophenyl)-4-dimethylamino-2,3-dimethyl-3-pyrazolin-5-one (1:1)" Acta Cryst., 1980, pp. 2794-2796, vol. B36.

Van Roey, P. et al. "Structure-activity studies of non-steroidal aromatase inhibitors: the crystal and molecular structures of CGS 16949A and CGS 18320B" J. Enzyme Inhibition, 1991, pp. 119-132, vol. 5.

Van Roey, P. et al. "Structure of *cis*-1-{[4-(1-imidazolylmethyl) cyclohexyl] methyl} imidazole-succinic acid complex" *Acta Cryst.*, 1991, pp. 1015-1018, vol. C47.

Vishweshwar, P. et al. "Crystal engineering of pharmaceutical co-crystals from polymorphic active pharmaceutical ingredients" *Chem. Commun.*, 2005, pp. 4601-4603.

Vishweshwar, P. et al. "Recurrence of carboxylic acid-pyridine supramolecular synthon in the crystal structures of some pyrazinecarboxylic acids" *J. Org. Chem.*, 2002, pp. 556-565, vol. 67.

Vishweshwar, P. et al. "Supramolecular synthons based on N-H•••N and C-H•••O hydrogen bonds. Crystal engineering of a helical structure with 5,5-diethylbarbituric acid" *Chem. Commun.*, 2002, pp. 1830-1831.

Vishweshwar, P. et al. "Supramolecular synthons in phenol-isonicotinamide adducts" *Cryst. Eng. Comm.* 2003, pp. 164-168, vol. 5, No. 31.

Voet, D. et al. "The crystal and molecular structure of the intermolecular complex 9-ethyladenine-5, 5-diethylbarbituric acid" Journal of the American Chemical Society, Nov. 15, 1972, pp. 8213-8222, vol. 94, No. 23.

Voet, D. et al. "The structure of an intermolecular complex between cytosine and 5-fluorouracil" Journal of the American Chemical Society, May 21, 1969, pp. 3069-3075, vol. 91, No. 11.

Stezowski, J. J. et al. "Characterization of a 1:1 complex of an unusual structure in the phenothiazine/phenazine binary phase diagram" Zeitschrift fur Kristallographie in International Journal for Structural, Physical, Chemical Aspects of Crystalline Materials, 1983, pp. 213-215, vol. 162, No. 1-4.

Wang, A. et al. "Crystal structure of 1:1 complex of barbital with 1-methylimidazole" Journal of Pharmaceutical Sciences, Mar. 1979, pp. 361-363, vol. 68, No. 3.

Alberola, S. et al. "Crystalline and Molecular Structure of Sulfanilimide-Antipyrine" Acta Cryst., 1977, pp. 3337-3341, vol. B33.

Wood, R. A. et al. "2,5-O-methylene-D-mannitol sodium-chloride, C7 H14 O6. NaCl" Cryst. Struct. Comm., 1976, 207-210, vol. 5.

Xu, J. et al. "Effect of composition distribution on miscibility and co-crystallization phenomena in the blends of low density polyethylene with conventional and metallocene-based ethylene-butene copolymers" *Polymer*, 2001, pp. 3867-3874, vol. 42.

Yoo, J. et al. "Cocrystallization of a dinuclear platinum complex as a monomer and a one-dimensional polymer" *Polyhedron*, 2002, pp. 715-719, vol. 21.

Zaitu, S. et al. "A 2:1 molecular complex of theophylline and 5-fluorouracil as the monohydrate" *Acta Cryst.*, 1995, pp. 1857-1859, vol. C51.

Zaman, M. B. et al. "Linear hydrogen-bonded molecular tapes in the cocrystals of squaric acid with 4,4'-dipyridylacetylene and 1,2-bis(4-pyridyl) ethylene" *Acta Cryst.*, 2001, pp. 621-624, vol. C57.

Zerkowski, J. et al. "Design of organic structures in the solid state: hydrogen-bonded molecular "tapes"[1]" *J. Am. Chem. Soc.*, 1990, pp. 9025-9026, vol. 112.

Zerkowski, J. et al. "Investigations into the robustness of secondary and tertiary architecture of hydrogen-bonded crystalline tapes" *Chem. Mater.*, 1994, pp. 1250-1257, vol. 6.

Zerkowski, J. et al. "New varieties of crystalline architecture produced by small changes in molecular structure in tape complexes of melamines and barbiturates" *J. Am. Chem. Soc.*, 1994, pp. 4305-4315, vol. 116.

Zerkowski, J. et al. "Polymorphic packing arrangements in a class of engineered organic crystals" *Chem. Mater.*, 1997, pp. 1933-1941, vol. 9.

Zerkowski, J. et al. "Solid-state structures of "Rosette" and "Crinkled Tape" motifs derived from the cyanuric acid-melamine lattice" *J. Am. Chem. Soc.*, 1992, pp. 5473-5475, vol. 114.

Zhang, R. et al. "Atmospheric new particle formation enhanced by organic acids" *Science*, Jun. 4, 2004, pp. 1487-1490 with additional supporting online material, vol. 304.

Zhu, H. et al. "Influence of water activity in organic solvent + water mixtures on the nature of the crystallizing drug phase. 1. theophylline" *International Journal of Pharmaceutics*, 1996, pp. 151-160, vol. 135.

Aakeröy, C. et al. "Aromatic dicarboxylic acids as building blocks of extended hydrogen-bonded architectures" *Supramolecular Chemistry*, 1998, pp. 127-135, vol. 9.

Aakeröy, C. et al. "Assembly of 2-D inorganic/organic lamellar structures through a combination of copper (I) coordination polymers and self-complimentary hydrogen bonds" *J. Chem. Soc., Dalton Trans.*, 2000, pp. 3869-3872.

Aakeröy, C. et al. "Building organic assemblies with 2-pyridone and dicarboxylic acids: relating molecular conformation and synthon stability to crystal structure" *Crystal Engineering*, 1998, pp. 225-241, vol. 1, No. 3-4.

Aakeröy, C. et al. "The C-H•••Cl hydrogen bond: does it exist?" *New J. Chem.*, 1999, pp. 145-152.

Aakeröy, C. et al. "Crystal engineering of ionic solids" *Modular Chemistry* (ed. By Michl, J.), 1997, pp. 153-162, Kluwer Academic Publishers, The Netherlands.

Aakeröy, C. et al. "Crystal engineering: strategies and architectures" *Acta Cryst.*, 1997, pp. 569-586, vol. B53.

Aakeröy, C. et al. "Crystal engineering using intermolecular hydrogen-bonded connectors and classic coordination chemistry" *Transactions ACA*, 1998, pp. 97-103, vol. 33.

Aakeröy, C. et al. "The crystal structure of the molecular cocrystal *L*-malic acid *L*-tartaric acid (1/1)" *Supramolecular Chemistry*, 1996, pp. 153-156, vol. 7.

Aakeröy, C. et al. "Deliberate combination of coordination polymers and hydrogen bonds in a supramolecular design strategy for inorganic/organic hybrid networks" *Chem. Commun.*, 2000, pp. 935-936.

Aakeröy, C. et al. "Di-hydroxy malonic acid as a building block of hydrogen-bonded 3-dimensional architectures" *Journal of Chemical Crystallography*, 1998, pp. 111-117, vol. 28, No. 2.

Aakeröy, C. et al. "Do polymorphic compounds make good cocrystallizing agents? A structural case study that demonstrates the importance of synthon flexibility" *Crystal Growth & Design*, 2003, 159-165, vol. 3, No. 2.

Aakeröy, C. et al. "Heteromeric intermolecular interactions as synthetic tools for the formation of binary co-crystals" *Cryst. Eng. Comm.*, 2004, pp. 19-24, vol. 6, No. 5.

Aakeröy, C. et al. "A high-yielding supramolecular reaction" *J. Am. Chem. Soc.*, 2002, 14425-14432, vol. 124.

Aakeröy, C. et al. "The hydrogen bond and crystal engineering" *Chemical Society Reviews*, 1993, pp. 397-407.

Aakeröy, C. et al. "Hydrogen-bond assisted assembly of organic and organic-inorganic solids" *Crystal Engineering: From Molecules and Crystals to Materials*, 1999, pp. 89-106, Kluwer Academic Publishers, The Netherlands.

Aakeröy, C. et al. "Hydrogen-bonding in solids" *Crystal Engineering* (ed. by Seddon, K. R. et al.), 1999, pp. 303-324, Kluwer Academic Publishers, The Netherlands.

Aakeröy, C. et al. "Low-dimensional architectures of silver coordination compounds assembled via amide-amide hydrogen bonds" *Crystal Engineering*, 1998, pp. 39-49, vol. 1, No. 1.

Aakeröy, C. et al. "Molecular mechanics and crystal engineering" *Crystal Engineering* (ed. by Seddon, K. R. et al.), 1999, pp. 69-82, Kluwer Academic Publishers, The Netherlands.

Aakeröy, C. et al. "New building blocks for crystal engineering. Syntheses and crystal structures of oxime-substituted pyridines" *Cryst. Eng. Comm.*, 2000, pp. 1-6, vol. 27.

Aakeröy, C. et al. "Novel colorless composite materials for nonlinear optics" *Adv. Mater.*, 1993, pp. 364-367, vol. 5, No. 5.

Aakeröy, C. et al. "Organic assemblies of 2-pyridones with dicarboxylic acids" *Tetrahedron*, 2000, pp. 6693-6699, vol. 56.

Aakeröy, C. et al. "Pitfalls in the supramolecular assembly of silver(I) coordination compounds" *Journal of Molecular Structure*, 1999, pp. 91-101, vol. 474.

Aakeröy, C. et al. "A structural study of 2-amino-5-nitropyridine and 2-amino-3-nitropyridine: intermolecular forces and polymorphism" *J. Mater. Chem.*, 1998, pp. 1385-1389, vol. 8, No. 6.

Aakeröy, C. et al. "Supramolecular assembly of low-dimensional silver (I) architectures via amide-amide hydrogen bonds" *Chem. Commun.*, 1998, pp. 1067-1068.

Aakeröy, C. et al. "'Total synthesis' supramolecular style: design and hydrogen-bond-directed assembly of ternary supermolecules" *Angew. Chem. Int. Ed.*, 2001, pp. 3240-3242, vol. 40, No. 17.

Aakeröy, C. et al. "Two-fold interpenetration of 3-D nets assembled via three-co-ordinate silver(I) ions and amide-amide hydrogen bonds" *J. Chem. Soc., Dalton Trans.*, 1998, pp. 1943-1945.

Ahn, S. et al. "Polymorphs of a 1:1 cocrystal with tunnel and layer structures: ρ,ρ'-biphenol/dimethyl sulfoxide" *Crystal Growth & Design*, 2001, pp. 107-111, vol. 1, No. 2.

Akazome, M. et al. "Enantioselective inclusion of methyl phenyl sulfoxides and benzyl methyl sulfoxides by (R)-phenylglycyl-(R)-phenylglycine and the crystal structures of the inclusion cavities" *J. Org. Chem.*, 2000, pp. 68-76, vol. 65.

Akhtaruzzaman, M.D. et al. "One-dimensional hydrogen-bonded molecular tapes in 1, 4-bis[(4-pyridinio) ethynyl]benzene chloranilate" *Acta. Cryst.*, 2001, pp. o353-o355, vol. E57.

Allen, F. et al. "Systematic analysis of structural data as a research technique in organic chemistry" *Acc. Chem. Res.*, 1983, pp. 146-153, vol. 16.

Almarsson, Ö. et al. "Crystal engineering of the composition of pharmaceutical phases. Do pharmaceutical co-crystals represent a new path to improved medicines?" *Chem. Commun.*, 2004, pp. 1889-1896.

Amai, M. et al. "1:1 complex of octadecanoic acid and 3-pyridinecarboxamide" *Acta Cryst.*, 1998, pp. 1367-1369, vol. C54.

Anderson, N. et al. "Sulfonation with inversion by mitsunobu reaction: an improvement on the original conditions" *J. Org. Chem.*, 1996, pp. 7955-7958, vol. 61.

Aoki, K. et al. "A 1:1 complex of theophylline and p-nitrophenol" *Acta Cryst.*, 1978, pp. 2333-2336, vol. B34.

Ashton, P. et al. "Combining different hydrogen-bonding motifs to self-assemble interwoven superstructures" *Chem. Eur. J.*, 1998, pp. 577-589, vol. 4, No. 4.

Barker, P. A. et al. "Effect of crystallization temperature on the cocrystallization temperature on the cocrystallization of hydroxybutyrate/ hydroxyvalerate copolymers" *Polymer*, pp. 913-919, vol. 38, No. 4.

Berkovitch-Yellin, Z. et al. "Electron density distribution in cumulenes: an x-ray study of the complex allenedicarboxylic acid-acetamide (1:1) at -150° C." *Acta Cryst.*, 1977, pp. 3670-3677, vol. B33.

Berkovitch-Yellin, Z. et al. "The role played by C-H•••O and C-H•••N interactions in determining molecular packing and conformation" *Acta Cryst.*, 1984, pp. 159-165, vol. B40.

Berl, V. et al. "Induced fit selection of a barbiturate receptor from a dynamic structural and conformational/configurational library" *Eur. J. Org. Chem.*, 1999, pp. 3089-3094.

Bertolasi, V. et al. "Competition between hydrogen bonding and donor-acceptor interactions in co-crystals of 1,3-dimethylbarbituric acid with aromatic amines" *New J. Chem.*, 2001, pp. 408-415, vol. 25.

Bertolasi, V. et al. "General rules for the packing of hydrogen-bonded crystals as derived from the analysis of squaric acid anions: aminoaromatic nitrogen base co-crystals" *Acta Cryst.*, 2001, pp. 591-598, vol. B57.

Bettinetti, G. et al. "Structure and solid-state chemistry of anhydrous and hydrated crystal forms of the trimethoprim-sulfamethoxypyridazine 1:1 molecular complex" *Journal of Pharmaceutical Sciences*, Apr. 2000, pp. 478-489, vol. 89, No. 4.

Bettinetti, G. et al. "Thermal analysis of binary systems of the pharmaceuticals trimethoprim and benzoic acid" *Journal of Thermal Analysis*, 1983, pp. 285-294, vol. 28.

Bettis, J. et al. "Biopharmaceutics and dosage form design" *Amer. J. Hosp. Pharm.*, Mar. 1973, pp. 240-243, vol. 30.

Bolton, S. et al. "Complexes formed in solution by homologs of caffeine" *Journal of the American Pharmaceutical Association*, Jan. 1957, pp. 38-41, vol. XLVI, No. 1.

Bond, A. "*In situ* co-crystallisation as a tool for low-temperature crystal engineering" *Chem. Commun.*, 2003, pp. 250-251, vol. 2.

Bonin, M. et al. "Urotropin azelate: a rather unwilling co-crystal" *Acta Cryst.*, 2003, pp. 72-86, vol. B59.

Bosshard, C. et al. "Microscopic nonlinearities of two-component organic crystals" *J. Opt. Soc. Am. B*, Nov. 2001, pp. 1620-1626, vol. 18, No. 11.

Gluzman, M. Kh. et al. "Investigation of Eutectic Melting in Systems Composed of Organic Salts and Acids" *Journal of Physical Chemistry*, 1960, pp. 2742-2747, vol. 34.

Braga, D. et al. "Hydrogen bonding interactions between ions: a powerful tool in molecular crystal engineering" *Structure and Bonding*, 2004, pp. 1-32, vol. 111.

Brierley, C. et al. "Preparation and structure of the 1:2 π-molecular complex of phenothiazine with pyromellitic dianhydride" *J. Chem. Phys.*, Feb. 1, 1985, pp. 1522-1528, vol. 82, No. 1.

Burgi, H. et al. "Crystallisation of supramolecular materials" *Current Opinion in Solid State & Materials Science*, 1998, pp. 425-430, vol. 3.

Byrn, S. R. et al. "Solid-state pharmaceutical chemistry" *Chem. Mater.*, 1994, pp. 1148-1158, vol. 6.

Caira, M. "Molecular complexes of sulfonamides. Part 1. 1:1 complexes between sulfadimidine [4-amino-N-(4,6-dimethyl-2-pyrimidinyl) benzenesulfonamide] and 2- and 4-aminobenzoic acids" *Journal of Crystallographic and Spectroscopic Research*, 1991, pp. 641-648, vol. 21, No. 5.

Caira, M. "Molecular complexes of sulfonamides. Part 2. 1:1 complexes between drug molecules: sulfadimidine-acetylsalicylic acid and sulfadimidine-4-aminosalicylic acid" *Journal of Crystallographic and Spectroscopic Research*, 1992, pp. 193-200, vol. 22, No. 2.

Caira, M. "Molecular complexes of sulfonamides. 3. Structure of 5-methoxysulfadiazine (Form II) and its 1:1 complex with acetylsalicylic acid" *Journal of Chemical Crystallography*, 1994, pp. 695-701, vol. 24, No. 10.

Caira, M. et al. "Order-disorder enantiotropy, monotropy, and isostructurality in a tetroxoprim-sulfametrole 1:1 molecular complex: crystallographic and thermal studies" *Journal of Pharmaceutical Sciences*, Nov. 2003, pp. 2164-2176, vol. 92, No. 11.

Caira, M. et al. "Selective formation of hydrogen bonded cocrystals between a sulfonamide and aromatic carboxylic acids in the solid state" *J. Chem. Soc. Perkin Trans. 2*, 1995, pp. 2213-2216.

Caira, M. et al. "Structure of a 1:1 complex between the anthelmintic drug mebendazole and propionic acid" *Journal of Chemical Crystallography*, 1998, vol. 28, No. 1, pp. 11-15.

Camerman, A. et al. "Hydrogen bonding interaction of diphenylbarbituric acid and 9-ethyladenine. Crystal structure of a 1:1 complex" *Can. J. Chem.*, 2000, pp. 1045-1051, vol. 78.

Camerman, A. et al. "Molecular structure of acetylacetone. A crystallographic determination" *J. Am. Chem. Soc.*, 1983, pp. 1584-1586, vol. 105, No. 6.

Cannon, A. et al. "Noncovalent derivatization: green chemistry applications of crystal engineering" *Crystal Growth & Design*, 2002, pp. 255-257, vol. 2. No. 4.

Chinnakali, K. et al. "2-aminopyrimidine and p-phenylene-diacetic acid (1:1) co-crystal" *Acta Cryst.*, 1999, pp. 399-401, vol. C55.

Choi, C. et al. "Cocrystallization of melaminium levulinate monohydrate" *Acta Cryst.*, 2004, pp. o295-o296, vol. C60.

Chow, Y. P. et al. "Complexation of acetaminophen with methyl xanthines" *Journal of Pharmaceutical Sciences*, 1972, pp. 1454-1458, vol. 61.

Christian, S. et al. "Activity coefficient effects in spectral and solubility studies of molecular complex equilibria" *Journal of the American Chemical Society*, Sep. 20, 1972, pp. 6861-6862, vol. 94, No. 19, Communications to the editor.

Coll, M. et al. "Molecular structure of the complex formed between the anticancer drug cisplatin and d(pGpG): C222$_1$ crystal form" *Journal of Biomolecular Structure & Dynamics*, 1990, pp. 315-330, vol. 8, No. 2.

Copp, S. et al. "Supramolecular chemistry of [Mn(CO)$_3$(μ$_3$-OH)]$_4$: Assembly of a cubic hydrogen-bonded diamondoid network with 1,2-diamineothane" *J. Am. Chem. Soc.*, 1992, pp. 8719-8720, vol. 114.

Cordi, A. et al. "(S)-Spiro [(1, 3-diazacyclopent-1-ene)-5, 2'-(7'-methyl-1',2',3',4'-tetrahydronaphthalene)]: resolution, stereospecific synthesis, and preliminary pharmacological characterization as a partial α-adrenergic agonist" *J. Med. Chem.*, 1997, pp. 2931-2935, vol. 40.

Craven, M. et al. "The 2:1 crystal complex of 5, 5-diethylbarbituric acid (barbital) and caffeine" *Acta Cryst.*, 1974, pp. 1191-1195, vol. B30.

Craven, M. et al. "The crystal structures of two polymorphs of 5,5'-diethylbarbituric acid (barbital)" *Acta Cryst.*, 1969, pp. 1978-1993, vol. B25.

Cudney, B. et al. "Screening and optimization strategies for macromolecular crystal growth" *Acta Cryst.*, 1994, pp. 414-423, vol. D50.

Datta, S. et al. "Molecular complex formation between riboflavin and salicylate in an aqueous medium" *Bull. Chem. Soc. Jpn.*, 2003, pp. 1729-1734, vol. 76.

Davey, R. J. et al. "Crystal engineering—nucleation, the key step" *Cryst. Eng. Comm.*, 2002, pp. 257-264, vol. 4, No. 47.

Davey, R. J. et al. "Crystallisation in polymer films: control of morphology and kinetics of an organic dye in a polysilicone matrix" *J. Mater. Chem.*, 1997, pp. 237-241, vol. 7, No. 2.

DeBernardis, J. et al. "Conformationally defined adrenergic agents. 5. Resolution, absolute configuration, and pharmacological characterization of the enantiomers of 2-(5,6-dihydroxy-1,2,3,4-tetrahydro-1-naphthyl)imidazoline: a potent agonist at α-adrenoceptors" *J. Med. Chem.*, 1987, pp. 1011-1017, vol. 30.

Desiraju, G. et al. "Crystal and co-crystal" *Cryst. Eng. Comm.*, 2003, pp. 466-467, vol. 5, No. 82.

Desiraju, G. et al. "Crystal engineering: outlook and prospects" *Current Science*, Oct. 25, 2001, pp. 1038-1042, vol. 81, No. 8.

Duax, W. et al. "The structure of the crystalline complex estradiol. Urea (1:1)" *Acta Cryst.*, 1972, pp. 1864-1871, vol. B28.

Dunitz, J. "Crystal and co-crystal: a second opinion" *Cryst. Eng. Comm.*, 2003, pp. 506, vol. 5, No. 91.

Dunitz, J. "New light on an old story: the solid-state transformation on ammonium cyanate into urea" *J. Am. Chem. Soc.*, 1998, pp. 13274-13275, vol. 120.

Enright, G. et al. "Thermally programmable gas storage and release in single crystals of an organic van der Waals host" *J. Am. Chem. Soc.*, 2003, pp. 9896-9897, vol. 125.

Epstein, R. et al. "The x-ray crystal structure of the molecular complex 8-bromo-9-ethyladenine-5-allyl-5-isobutylbarbituric acid" *Acta Cryst.*, 1976, pp. 2180-2188, vol. B32.

Etter, M. "Encoding and decoding hydrogen-bond patterns of organic compounds" *Acc. Chem. Res.*, 1990, pp. 120-126, vol. 23.

Etter, M. et al. "Graph-set analysis of hydrogen-bond patterns in organic crystals" *Acta Cryst.*, 1990, pp. 256-262, vol. B46.

Etter, M. et al. "Hydrogen bond directed cocrystallization and molecular recognition properties of acyclic imides" *J. Am. Chem. Soc.*, 1991, pp. 2586-2598, vol. 113.

Etter, M. "Hydrogen bonds as design elements in organic chemistry" *J. Phys. Chem.*, 1991, pp. 4601-4610, vol. 95.

Fabian, L. et al. "Volumetric measure of isostructurality" *Acta Cryst.*, 1999, pp. 1099-1108, vol. B55.

Fallon III, L. "The crystal and molecular structure of 5-fluorouracil" *Acta Cryst.*, pp. 2549-2556, vol. B29.

Feibush, B. et al. "Chiral separation of heterocyclic drugs by HPLC: solute-stationary phase base-pair interactions" *J. Am. Chem. Soc.*, 1986, pp. 3310-3318, vol. 108.

Fifer, E. et al. "Fentanyl analogues 3. 2-(1,2,3,4-tetrahydro)-naphthyl substituted 4-anilidopiperidines" *Eur. J. Med. Chem.—Chim. Ther.*, 1984, pp. 519-524, vol. 19, No. 6.

Reck, G. et al. "Crystal structures of the carbamazepine/ammonium chloride and carbamazepine/ammonium bromide adducts and their transformation into carbamazepine dihydrate" *Pharmazie*, 1991, pp. 509-512, vol. 46, No. 7.

Foxman, B. M. et al. "Environmentally benign synthesis using crystal engineering: steric accommodation in non-covalent derivatives of hydroquinones" *Crystal Engineering*, 1998, pp. 109-118, vol. 1, No. 1.

Foxman, B. M. et al. "Noncovalent derivatives of hydroquinone: BIS-(N,N-dialkyl) bicyclo[2.2.2]octane-1,4-dicarboxamide complexes" *Crystal Engineering*, 1999, pp. 55-64, vol. 2. No. 1.

Fujii, S. et al. "Crystal and molecular structure of a 1:1 molecular complex of adenine and riboflavin" *Archives of Biochemistry and Biophysics*, 1977, pp. 363-370, vol. 181.

Gao, X. et al. "Supramolecular construction of molecular ladders in the solid state" *Angew. Chem. Int. Ed.*, 2004, pp. 232-236, vol. 43.

Gartland, G. L. et al. "Hydrogen bonding NH•••O=C of barbiturates: the (1:1) crystal complex of urea and 5,5-diethylbarbituric acid (barbital)" *Acta Cryst.*, 1974, pp. 980-987, vol. B30.

Ghosh, M. "Structure and conformation of the 1:1 molecular complex sulfaproxyline-caffeine" *Acta Cryst.*, 1991, pp. 577-580, vol. C47.

Giuseppetti, G. P. et al. "The crystal structure of a sulfamethoxazole-trimethoprim 1:1 molecular compound" *Il Farmaco—Ed. Sc.*, pp. 138-151, vol. 35.

Goswami, S. et al. "2-aminopyrimidine-fumaric acid cocrystal" *Acta Cryst.*, 1999, pp. 583-585, vol. C55.

Haynes, D. "Supramolecular synthon competition in organic sulfonates: A CSD survey" *Cryst. Eng. Comm.*, 2004, pp. 584-588, vol. 6, No. 95.

Goswami, S. et al. "1:1 Hetero-assembly of 2-amino-pyramidine and (+)-camphoric acid" *Acta Cryst.*, 2000, pp. 477-478, vol. C56.

Goswami, S. et al. "Molecular recognition induced supramolecular array of 2-aminopyrimidine with terephthalic acid, 1,4-phenylenediacetic acid and furmaric acid in solid state via H-bonding and π-stacking interactions" *Supramolecular Chemistry*, 1999, pp. 25-33, vol. 11.

Graja, A. et al. "Interplay of acceptor molecule shape, crystal structure and physical properties of a new molecular complex $C_{70}$ • 2[(Ph3P) AuCl]" *Chemical Physics Letters*, Nov. 19, 1999, pp. 725-732. vol. 313.

Haixin, L. et al. "Structure of the 1:1 complex of 6,6'-diquinolyl ether with 5,5-diethylbarbituric acid" *Acta Cryst.*, 1992, pp. 2096-2098, vol. C48.

Henck, J. et al. "Disappearing and reappearing polymorphs. The benzocaine:picric acid system" *J. Am. Chem. Soc.*, 2001, pp. 1834-1841, vol. 123.

Higuchi, T. et al. "Complexation of organic substances in aqueous solution by hydroxyaromatic acids and their salts" *J. Pharm. Sci.*, 1961, pp. 905-909, vol. 50.

Hino, T. et al. "Assessment of nicotinamide polymorphs by differential scanning calorimetry" *Thermochimica Acta*, 2001, pp. 85-92, vol. 374.

Högberg, T. et al. "Crystallographic, theoretical and molecular modelling studies on the conformations of the salicylamide, raclopride, a selective dopamine-$D_2$ antagonist" *J. Pharm. Pharmacol.*, 1987, pp. 787-796, vol. 39.

Hsu, I. et al. "The 2:1 crystal complex of 2-aminopyridine and 5,5-diethylbarbituric acid (barbital)" *Acta Cryst.*, 1974, pp. 994-997, vol. B30.

Hsu, I. et al. "The 1:1 crystal complex of N-methyl-2-pyridone and 5,5-diethylbarbituric acid (barbital)" *Acta Cryst.*, 1974, pp. 998-1001, vol. B30.

Hsu, I. et al. "The crystalline complex (1:1) of salicylamide and 5-ethyl-5-isoamylbarbituric acid (amobarbital)" *Acta Cryst.*, 1974, pp. 843-846, vol. B30.

Hsu, I. et al. "The crystal structure of the 1:1 complex of acetamide with 5,5-diethylbarbituric acid (barbital)" *Acta Cryst.*, 1974, pp. 974-979, vol. B30.

Hsu, I. et al. "The crystal structure of the triclinic 1:2 complex of hexamethylphosphoramide with 5,5-diethylbarbituric acid (barbital)" *Acta Cryst.*, 1974, pp. 1299-1304, vol. B30.

Hsu, I. et al. "Hydrogen bonding Nh . . . N of barbiturates: The 1:1 crystal complex of imidazole and 5,5-diethylbarbituric acid (barbital)" *Acta Cryst.*, 1974, pp. 988-993, vol. B30.

Ibragimov, B. "A simple correlation between the structures of different crystal modifications of a given host-guest complex and their crystallization temperatures" *Journal of Inclusion of Phenomena and Macrocyclic Chemistry*, 1999, pp. 345-353, vol. 34.

Ishida, T. et al. "Structural study of histamine $H_2$-receptor antagonists. Five 3-[2-(diamino-methyleneamino)-4-thiazolymethylthio] propionamide and -amide derivatives" *Acta Cryst.*, 1989, pp. 505-512, vol. B45.

Katakai, R. et al. "Stepwise synthesis of oligopeptides with N-carboxy-α-amino acid anhydrides. IV. Glycine NCA" *J. Org. Chem.*, 1972, pp. 327-329, vol. 37, No. 2.

Kawakami, Y. et al. "The rationale for E2020 as a potent acetylcholinesterase inhibitor" *Bioorganic & Medicinal Chemistry*, 1996, pp. 1429-1446, vol. 4, No. 9.

Kelders, H. et al. "Automated protein crystallization and a new crystal form of a subtilisin: eglin complex" *Protein Engineering*, 1987, pp. 301-303, vol. 1, No. 4.

Khalil, R. M. "Complexation of paracetamol with xanthine derivatives" *Egypt. J. Pharm. Sci.*, 1992, pp. 757-769, vol. 33, No. 5-6.

Kim, S. "Crystal structure of the 1:1 complex of 5-fluorouracil and 9-ethylhypoxanthine" *Science*, Nov. 24, 1967, pp. 1046-1048, vol. 158, No. 3804.

Kiryu, S. et al. "Crystal structure of a 1:1 aminopyrine-barbital complex" *Journal of Pharmaceutical Sciences*, May 1971, pp. 699-703, vol. 60, No. 5.

Kiryu, S. et al. "Crystal structure of a 1:1 aminopyrine-cyclobarbital complex" *Chem. Pham. Bull.*, 1974, pp. 1588-1592, vol. 22.

Klein, C. et al. "Molecular structure of two conformationally restrained fentanyl analogues: cis- and trans-isomers of $N$-{3-methyl-1-[1,2,3,4-tetrahydro)   naphthyl]-4-piperidinyl}-$N$-phenylpropanamide" *Journal of Pharmaceutical Sciences*, Nov. 1985, pp. 1147-1151, vol. 74, No. 11.

Koshima, H. et al. "Photoreactivities of two kinds of bimolecular crystals formed from acridine and phenothiazine" *J. Chem. Soc., Perkins Trans.* 2, 1997, pp. 2033-2038.

Koshima, H. et al. "Polymorphs of a cocrystal with achiral and chiral structures prepared by pseudoseeding: tryptamine/hydrocinnamic acid" *Crystal Growth & Design*, 2001, pp. 355-357, vol. 1, No. 5.

Krishnamohan Sharma, C. V. et al. "X-ray crystal structure of $C_6H_3$ $(CO_2H)_3$- 1,3,5•1.5(4,4'-bipy): a 'super trimesic acid' chicken-wire grid" *Chem. Commun.*, 1996, pp. 2655-2656.

Kuroda, R. et al. "Generation of a co-crystal phase with coloristic properties via solid state grinding procedures" *Chem. Commun.*, 2002, pp. 2848-2849.

Leiserowitz, L. et al. "The molecular packing modes and hydrogen-bonding properties of amide: dicarboxylic acid complexes" *Acta Cryst.*, 1977, pp. 2719-2733, vol. B33.

Leiserowitz, L. "Molecular packing modes. Carboxylic acids" *Acta Cryst.*, 1976, pp. 775-802, vol. B32.

Lynch, D. et al. "Molecular cocrystals of carboxylic acids. XXXI adducts of 2-aminopyrimidine and 3-amino-1,2,4-triazole with heterocyclic carboxylic acids" *Aust. J. Chem.*, 1998, pp. 403-408, vol. 51.

MacGillivray, L. et al. "Supramolecular control of reactivity in the solid state using linear molecular templates" *J. Am. Chem. Soc.*, 2000, pp. 7817-7818, vol. 122.

Mathias, J. et al. "Structural preferences of hydrogen-bonded networks in organic solution—the cyclic $CA_3$• $M_3$ 'rosette'" *J. Am. Chem. Soc.*, 1994, pp. 4316-4325, vol. 116.

Mastropaolo, D. et al. "Hydrogen bonding interaction of diphenylhydantoin and 9-ethyladenine" *Molecular Pharmacology*, 1983, pp. 273-277, vol. 23.

Maryanoff, B. "Stereochemistry in a medium-sized ring. Highly diastereoselective N-oxidation of a substituted 3-benzazonine. X-ray crystal structure of an unusual complex between an amine $N$-oxide and saccharin" *J. Org. Chem.*, 1990, pp. 760-764, vol. 55.

Martin, R. et al. "The caffeine-potassium chlorogenate molecular complex" *Phytochemistry*, 1987, pp. 273-279, vol. 26, No. 1.

Anderson, J. "Constitution of aurous compounds: Gold mirrors" *Nature*, Oct. 2, 1937, pp. 583-584, Letters to the Editor.

Robbins, A. H. et al. "The crystal structure of the 1:2 adduct of potassium triiodide and 5,5-diethylbarbituric acid (barbital)" *American Crystallographic Association—Series 2, Papers and Abstracts*, 1973, p. 87.

Beerges, P. et al. "Phenothiazine tetracyanoethylene" *Private Communication*, 1994.

Madarasz, J. et al. "Thermal, ftir and xrd study on some 1:1 molecular compounds of theophylline" *Journal of Thermal Analysis and Calorimetry*, 2002, pp. 281-290, vol. 69.

Caronna, T. et al. "Halogen bonding and π•••π stacking control reactivity in the solid state" *J. Am. Chem. Soc.*, 2004, pp. 4500-4501, vol. 126.

Zerkowski, J. et al. "Steric control of secondary, solid-state architecture in 1:1 complexes of melamines and barbiturates that crystallize as crinkled tapes" *J. Am. Chem. Soc.*, 1994, pp. 4298-4304, vol. 116.

Zaitu, S. et al. "1:1 Molecular complex of theophylline and ρ-nitroaniline" *Acta Cryst.*, 1995, pp. 2390-2392, vol. C51.

Kofler, L. et al., *Thermal micromethods for the study of organic compounds and their mixtures*, pp. 1-145, 148-351, 354-386, Innsbruck, Austria, 1980.

Quehenberger, H. "Concerning organic molecular compounds and their polymorphism" *Monatshefte für Chemie*, 1949, pp. 595-606, vol. 80, No. 5.

Wiedenfeld, H. et al. "The crystal structure of the theophylline-urea complex" *Arch. Pharm.*, 1986, pp. 654-659, vol. 319.

Bunick, G. et al. "The crystal and molecular structure of the complex 2,6-diamino-9-ethylpurine 5,5-diethylbarbituric acid" *American Crystallographic Association, Abstract Papers* Winter 1976, p. 30.

Buczak, G. et al. "Crystal structure and vibrational spectra of the 1:1 and 1:2 complexes of pyridine betaine with pentachlorophenol" *Journal of Molecular Structure*, 1997, pp. 143-151, vol. 436-437.

Tomura, M. et al. "One-dimensional zigzag chain structures with intermolecular C-H••• πand C-H•••O interactions consisted of phthalic acid and pyridine derivatives" *Chemistry Letters*, 2001, pp. 532-533.

Zerkowski, J. et al. "Design of organic structures in the solid state: molecular tapes based on the network of hydrogen bonds present in the cyanuric acid•melamine complex" *J. Am. Chem. Soc.*, 1994, pp. 2382-2391, vol. 116.

Harkema, S. et al. "The crystal structure of urea oxalic acid (2:1)" *Acta Cryst.*, 1972, pp. 1646-1648, vol. B28.

Krantz, J. et al. "Sodium theophylline glycinate" *Journal of the American Pharmaceutical Association*, 1946, pp. 248-250.

Datta, S. et al. "Crystal structures of drugs: advances in determination, prediction and engineering" *Nature*, Jan. 2004, pp. 42-57, vol. 3.

Aakeröy, C. et al. "Charge-assisted hydrogen bonds and halogen-halogen interactions in organic salts: benzylammonium benzoates and pentaflourobenzoates" *Structural Chemistry*, 1999, pp. 229-242, vol. 10, No. 3.

Childs, S. et al. "Crystal engineering approach to forming cocrystals of amine hydrochlorides with organic acids. Molecular complexes of fluoxetine hydrochloride with benzoic, succinic, and fumaric acids" *J. Am. Chem. Soc.*, 2004, pp. 13335-13342, vol. 126.

Aakeroy, C. et al. "Modular supramolecular synthesis based on a dominance hierarchy of intermolecular interactions (Abstract)" 223rd ACS National Meeting in Orlando, FL., Apr. 7-11, 2002, published by the American Chemical Society, Washington, D.C.

Helfrich, B. et al. "Polymorphism as an indication of structural versatility (Abstract)" 223rd ACS National Meeting in Orlando, FL., Apr. 7-11, 2002, published by the American Chemical Society, Washington, D.C.

Weber, E. et al. "Synthesis of new Schiff bases: reaction of monofluorobenzaldehydes with 3-aminosulfolane hydrochloride (Abstract)" 216th ACS National Meeting in Boston, MA., Aug. 23-27, 1998, published by the American Chemical Society, Washington, D.C.

Scarbrough, F. et al. "Crystal structure of a complex between lumiflavin and 2,6-diamino-9-ethylpurine: a flavin adenine dinucleotide model exhibiting charge-transfer interactions" *Proc. Natl. Acad. Sci. USA*, Nov. 1976, pp. 3807-3811, vol. 73, No. 11.

Munn, R. et al. "A Model for resonance-assisted hydrogen bonding in crystals and its graph set analysis" *J. Phys. Chem. A*, 2001, pp. 6938-6942, vol. 105.

Lynch, D. et al. "1:1 Molecular complexes of 4-amino-N-(4,6-dimethylpyrimidin-2-yl) benzene-sulfonamide (sulfamethazine) with indole-2-carboxylic acid and 2,4-dinitrobenzoic acid" *Aust. J. Chem.*, 2000, pp. 383-387, vol. 53.

Aakeroy, C. et al. "Solid state, crystal engineering and hydrogen bonds" *Comprehensive Coordination Chemistry II* (ed. By McCleverty, J. et al.), pp. 679-688, Elsevier Ltd., Oxford, UK, 2004.

Levin, B. et al. "The not-so-trivial synthesis and characterization of heterocyclic boronic acids (Abstract)" 38th Midwest Regional Meeting of the American Chemical Society in Columbia, MO., Nov. 5-7, 2003, published by the American Chemical Society, Washington, D.C.

Smith, G. et al. "Interactions of aromatic carboxylic acids with quinolin-8-ol (oxine): Synthesis and the crystal structures of the proton-transfer compounds with the nitro-substituted benzoic acids" *Aust. J. Chem.*, 2001, pp. 171-175, vol. 54.

Stalker, R. et al. "Asymmetric synthesis of two new conformationally constrained lysine derivatives" *Tetrahedron*, 2002, pp. 4837-4849, vol. 58.

Voet, D. et al. "Barbiturates and adenine derivatives. Molecular structure of a hydrogen-bonded complex" *Journal of the American Chemical Society*, Aug. 9, 1972, pp. 5888-5891, vol. 94, No. 16.

Vishweshwar, P. et al. "Molecular complexes of homologous alkanedicarboxylic acids with isonicotinamide: X-ray crystal structures, hydrogen bond synthons, and melting point alternation" *Crystal Growth & Design*, 2003, pp. 783-790, vol. 3, No. 5.

Le Jeunne, C. et al. "Comparative efficacy and safety of calcium carbasalate plus metoclopramide versus ergotamine tartrate plus caffeine in the treatment of acute migraine attacks" *Eur. Neurol.*, 1999, pp. 37-43, vol. 41.

Aakeröy, C. et al. "Hydrogen-bonded layers of hydrogentartrate anions: two-dimensional building blocks for crystal engineering" *J. Mater. Chem.*, 1993, 1129-1135, vol. 3, No. 11.

Hu, Z. et al. "Separation of 4-aminobenzoic acid by cocrystallization: Crystal structure of the complex of 4-aminobenzoic acid with (2R,3R)-tartaric acid" *Journal of Chemical Crystallography*, Dec. 2002, pp. 525-529, vol. 32, No. 12.

Guarrera, D. et al. "Molecular self-assembly in the solid state. The combined use of solid state NMR and differential scanning calorimetry for the determination of phase constitution" *Chem. Mater.*, 1994, pp. 1293-1296, vol. 6.

Doi, M. et al. "Conformational study of a potent human renin inhibitor: x-ray crystal structure of isopropyl (2R, 3S)-4-cyclohexyl-2-hydroxy-3-{N[(2R)-2-morpholinocarbonylmethyl-3-(1-naphthyl)propionyl]-L-histidylamino}butyrate (KRI-1314), a pentapeptide analogue with amino acid sequence corresponding to the cleavage site of angiotensinogen" *J. Chem. Soc. Perkin Trans. 1*, 1991, pp. 1153-1158.

Crihfield, A. et al. "Crystal engineering through halogen bonding. 2. Complexes of diacetylene-linked heterocycles with organic iodides" *Crystal Growth & Design*, 2003, pp. 313-320, vol. 3, No. 3.

Aakeröy, C. et al. "A versatile route to porous solids: organic-inorganic hybrid materials assembled through hydrogen bonds" *Angew. Chem. Int. Ed.*, 1999, pp. 1815-1819, vol. 38, No. 12.

Shefter, E. et al., ACS, Abstr. Papers (Summer), 1970, 35, compound name: sulfathiazole-theophylline complex.

Shefter, E. et al., ACS, Abstr. Papers (Summer), 1970, 35, compound name: sulfathiazole-sulfanilamide complex.

Wiedenfeld, H. et al. "Solubilization of aminophenazone" *Arch. Pharm.*, 1982, pp. 633-641, vol. 315.

Cacciapuoti, A. et al. "In vitro and in vivo activities of SCH 56592 (Posaconazole), a new triazole antifungal agent, against *Aspergillus* and *Candida*" *Antimicrobial Agents and Chemotherapy*, Aug. 2000, pp. 2017-2022, vol. 44, No. 8.

Callahan, J.C. et al. "Equilibrium moisture content of pharmaceutical excipients" *Drug Development and Industrial Pharmacy*, 1982, pp. 355-369, vol. 8, No. 3.

Dannaoui, E. et al. "Acquired itraconazole resistance in *Aspergillus fumigatus*" *Journal of Antimicrobial Chemotherapy*, 2001, pp. 333-340, vol. 47.

Denning, D. W. et al. "In vitro activity of Saperconazole (R66 905) compared with Amphotericin B and Itraconazole against *Aspergillus* species" *Eur. J. Clin. Microbial. Infect. Dis.*, 1990, pp. 693-697, vol. 9.

Dressman, J. B. et al. "Dissolution testing as a prognostic tool for oral drug absorption: immediate release dosage forms" *Pharmaceutical Research*, 1998, pp. 11-22, vol. 15, No. 1.

Ebert, W. R. "Soft elastic gelatin capsules: a unique dosage form" *Pharmaceutical Technology*, Oct. 1977, pp. 44-50, vol. 1, No. 5.

Gascon, M.-P. et al. "In vitro forecasting of drugs which may interfere with the biotransformation of midazolam" *Eur. J. Clin. Pharmacol.*, 1991, pp. 573-578, vol. 41.

Heeres, J. et al. "Antimycotic azoles. 7. Synthesis and antifungal properties of a series of novel triazol-3-ones" *J. Med. Chem.*, 1984, pp. 894-900, vol. 27.

Honig, P. K. et al. "Itraconazole affects single-dose Terfenadine pharmacokinetics and cardiac repolarization pharmacodynamics" *J. Clin. Pharmacol.*, 1993, pp. 1201-1206, vol. 33.

Imai, T. et al. "Successful treatment of cerebral Aspergillosis with a high oral dose of Itraconazole after excisional surgery" *Internal Medicine*, Oct. 1999, pp. 829-832, vol. 38, No. 10.

Kovacs, J. et al. "New type of bridged monoamino-β-cyclodextrins" *Journal of Inclusion Phenomena and Molecular Recognition in Chemistry*, 1996, pp. 53-56, vol. 25.

Lavrijsen, A. P. M. et al. "Hepatic injury associated with itraconazole" *The Lancet*, Jul. 25, 1992, pp. 251-252, vol. 340.

Neuvonen, P. J. et al. "Itraconazole drastically increases plasma concentrations of lovastatin and lovastatin acid" *Clinical Pharmacology & Therapeutics*, 1996, pp. 54-61, vol. 60, No. 1.

Nomeir, A. A. et al. "Pharmacokinetics of SCH 56592, a new azole broad-spectrum antifungal agent, in mice, rats, rabbits, dogs, and cynomolgus monkeys" *Antimicrobial Agents and Chemotherapy*, Mar. 2000, pp. 727-731, vol. 44, No. 3.

Odds, F. C. "Antifungal activity of saperconazole (R 66 905) in vitro" *Journal of Antimicrobial Chemotherapy*, 1989, pp. 533-537, vol. 24.

Saksena, A. K. et al. "Advances in the chemistry of novel broad-spectrum orally active azole antifungals: recent studies leading to the discovery of SCH 56592" in *Advances in the Chemistry of Novel Broad-Spectrum Orally Active Azole Antifungals* (Royal Soc. Chem., Cambridge), 1997, pp. 180-199.

Saksena, A. K. et al. "Concise asymmetric routes to 2,2,4-trisubstituted tetrahydrofurans via chiral titanium imide enolates: key intermediates towards synthesis of highly active azole antifungals SCH 51048 and SCH 56592" *Tetrahedron Letters*, 1996, pp. 5657-5660, vol. 37, No. 32.

Hepperle, M. et al. "Mono N-arylation of piperazine(III): metal-catalyzed N-arylation and its application to the novel preparations of the antifungal posaconazole and its advanced intermediate" *Tetrahedron Letters*, 2002, pp. 3359-3363, vol. 43.

Cutsem, J. V. et al. "Oral and parenteral therapy with saperconazole (R 66905) of invasive aspergillosis in normal and immunocompromised animals" *Antimicrobial Agents and Chemotheraphy*, Dec. 1989, pp. 2063-2068, vol. 33, No. 12.

Villa, L. A. et al. "Central nervous system paracoccidioidomycosis. Report of a case successfully treated with itraconazol" *Rev. Inst. Med. Trop. S. Paulo*, Jul.-Aug. 2000, pp. 231-234, vol. 42, No. 4.

West, A. R., "Solid Solutions" In: *Solid State Chemistry and its Applications*, 1988, p. 358, p. 365, Wiley, NY.

Aronhime, J. et al. "Crystalline forms of pharmaceuticals and characterization thereof", Oral Presentation, Mar. 8, 2005, USPTO, Alexandria, VA.

Desiraju, G. R. "Chemistry beyond the molecule" *Nature*, Jul. 26, 2001, pp. 397-400, vol. 412.

Gavezzotti, A. "Are crystal structures predictable?" *Acc. Chem. Res.*, 1994, pp. 309-314, vol. 27.

Physician's Desk Reference, 56th Ed., pp. 1800-1804, 2002.

Kim, H. et al. "High-performance liquid chromatographic analysis of the anti-fungal agent SCH 56592 in dog serum" *Journal of Chromatography B*, 2000, pp. 93-98, vol. 738.

Vippagunta, S. R. et al. "Crystalline solids" *Advanced Drug Delivery Reviews*, 2001, pp. 3-26, vol. 48.

McCrone, W. C. "Polymorphism", In: *The Physics and Chemistry of the Organic Solid State*, vol. II, Fox, D. et al. (eds.), 1965, pp. 725-767, Interscience, New York.

Leger, J.M. et al. "Crystal Structure of the 1:1 Sulfacetamide-Caffeine Complex" *Acta Cryst.*, 1977, pp. 1455-1459, vol. B33.

Simonov, Y. et al. "Structure of the caffeine-copper(II) acetate additional compound", *Izvestiya Akademii Nauk Moldayskoi SSR, Seriya Fiziko-Tekhnicheskikh i Matematicheskikh Nauk*, 1972, vol. 3, pp. 83-84.

Weissbuch, I. et al. "Understanding and control of nucleation, growth, habit, dissolution and structure of two- and three-dimensional crystals using 'tailor-made' auxiliaries" *Acta Cryst.*, 1995, B51:115-148.

Faught, E. et al. "Topiramate Dose-Ranging Trial in Refractory Partial Epilepsy", *Amer. Epilepsy Soc. Proc.*, (1995), p. 33, vol. 36, Supp. 4.

Privitera, M. et al. "Dose-Ranging Trial with Higher Doses of Topiramate in Patients with Resistant Partial Seizures", *Amer. Epilepsy Soc. Proc.*, 1995, p. 33, vol. 36, Supp. 4.

Sachdeo, S. K. et al. "Topiramate: Double-Blind Trial as Monotherapy", *Amer. Epilepsy Soc. Proc.*, 1995, p. 33, vol. 36, Supp. 4.

Press Release. "Clinical Development of Topiramate for Obesity Extended to Simplify Dosing, Improve Tolerability". http://www.orthomcneil.com/news/article020402.html (Feb. 4, 2002), N.J.

Rosenfeld, W. E. "Topiramate: A Review of Preclinical, Pharmacokinetic, and Clinical Data", *Clinical Therapeutics*, 1997, pp. 1294-1308, vol. 19, No. 6.

Physician's Desk Reference, 56th Edition, 2002, pp. 2590-2595.

Brader, M.L. et al. *Nature Biotechnol.*, 2002, 20 :800-804.

El-Nahhas, S.A. Pharmazie, 1996, 51(12):960-963.

Fleischman, S.G. et al. *Crystal Growth & Design.*, 2003, 3(6): 909-919.

Oswald, I.D.H. et al. *Acta Cryst.*, 2002, B58:1057-1066.

Reynolds, J.E.F. (ed). Martindale, The Extra Pharmacopoeia, 1993,The Pharmaceutical Press, London, England, 13th Edition, pp. 1431 (e.g., Acetaminophen, Aspirin, and Caffeine Tablets), 1465 (e.g., Aspirin plus C), 1521 (Codafen Continus), 1610 (Gaboril Complex).

Walsh, R.D. Bailey et al. *Chem. Commun.*, 2003:186-187.

Database, WPI, Section Ch, Week 197936, Derwent Publications Ltd., London, GB, Class B02, AN 1979-65538B XP002282989 & JP 54 095589 A (Sumitomo) 1979 abstract.

Davies et al., Clin. Pharmacokinet., 38: 225-242 (2000).

Fitzgerald, Garret A., "The Coxibs, Selective Inhibitors of Cyclooxygenase-2", New England Journal of Medicine, vol. 345, No. 6, Aug. 9, 2001.

Fung et al., Solvent Effects on Comparative Dissolution of Pharmaceutical Solvates, Chem. Farm. Bull., 22(2), pp. 454-458 (1974).

Rubino et al., Influence of solvent composition on the solubilities and solid-state properties of the sodium salts of some drugs, Int. J. of Pharma., 65, pp. 141-145 (1990).

Bastin, R. J. et al. "Salt Selection and Optimization Procedures for Pharmaceutical New Chemical Entities". Organic Process Research & Development, 2000, vol. 4, No. 5, p. 427-435.

Bond, A.D. et al. "On the Polymorphism of Aspirin: Crystalline Aspirin as Intergrowths of Two "Polymorphic" Domains" Angew. Chem. Int. Ed., 2007, 46:618-622.

Bond, A.D. et al. "On the Polymorphism of Aspirin" Angew. Chem. Int. Ed., 2007, 46:615-617.

Brittain, H.G. "Polymorphism in Pharmacutical Solids", 1999, Marcel Dekker, Inc., p. 183, 202-208, 219.

Davidovich, et al. "Detection of Polymorphism by Powder X-Ray Difraction: Interference by Preferred Orientation" American Pharmaceutical Review, (2004), 7(1), p. 10, 12, 14, 16, 100.

Dean, J. A. Analytical Chemistry Handbook, 1995, McGraw-Hill, Inc., p. 10.24-10.26.

Defination of solvate, The Free Dictionary, http://www.thefreedictionary.com/solvate, accessed online on Jul. 21, 2009.

De Jong et al. "Dystophic psoriatic fingernails treated with 1% 5-Flourouracil in a nail penetration-enhancing vehicle: a double-blind study". Dermatology 1999; 199: pp. 313-318.

Desiraju, G.R. Crystal Engineering: A Brief overview: J. Chem. Sci., Sep. 2010, pp. 667-675, vol. 122, No. 5.

Desiraju, G. R. "The C-H•••O Hydrogen Bond in Crystals: What Is It?" Acc. Chem. Res., 1991, pp. 290-296, vol. 24.

Doelker et al. "Crystalline Modifications and Polymorphism changes during drug manufacturing" Annales Pharmaceutiques Francaises, 2002, vol. 60, No. 3, pp. 161-176.

Doelker et al. "Physicochemical behavior or active substances. Consequences for the feasibility and stability of pharmaceutical forms" S.T.P. Pharma Practiques, 1999, vol. 9 No. 5, pp. 399-409.

Dunitz, J. "Are crystal structures predictable?" J. Roy Soc. Chem. Chem. Comm. 2003, pp. 545-548(2003).

Dvorkin et al. Crystal and Molecular Structure of a Complex of 18-crown-6 with 6-chloror-7-sulfamido-3,4-dihydro-1,2,4-benzothiadiazine-1, 1-dioxide (hypothiazide) of 1:1 Composition, 1990, Kristallagrafiya, vol. 35, No. 3, pp. 682-686 (with english abstract).

Felthouse, T. R. et al. "Maleic Anhydride, Maleic Acid and Fumaric Acid", Apr. 26, 2001, submitted for Kirk Online,http://www.huntsman.com/performance_products/media_komaleic.pdf.

Jain et al. "Polymorphisom in pharmacey" Indian Drugs, 1986, vol. 23, No. 6, pp. 315-329.

Japanese Notice of Reasons for Rejection dated Oct. 8, 2009, Japanese Application No. 2003-572946.

Kirchner, M.T. et al. "Cocrystals with Acetylene: Small is not Simple!" Chem. Eur. J. (2010) pp. 2131-2146, vol. 16.

Osorio-Lozada et al. "Synthesis and determination of the absolute stereochemistry of the enantiomers of adrafinil and modafinil" Tetrahedron: Asymmetry, 2004, vol. 15, No. 23, pp. 3811-3815 especially third complete paragraph, second column, p. 3813 ( Cited in PCT SR).

Pedireddi, V.R. et al. "Layered Structures Formed by Dinitrobenzoic Acids" Tetrahedron Letters, 1998, pp. 9831-9834, vol. 39.

Rasenack, N. et al. "Dissolution Rate Enhancement by in Situ Micronization of Poorly Water-Soluable Drugs" Pharmaceutical Research Dec. 2002, pp. 1894-1900, vol. 19, No. 12.

Remenar, et al.: "Celecoxib sodium salt: engineering crystal forms for performance" Crystengcomm, Royal Society of Chemistry, Cambridge, GB; Feb. 21, 2011., vol. 13. No. 4, pp. 1081-1089 ( EP Search Report 10193736).

Salem et al. 5,736,541, International Journal of Pharmacuetics, 141, 1996, 257-259.

Shan, N. et al. "Crystal engineering using 4,4'-bipyridyl with di- and tricarboxylic acids" Crystal Engineering, 2002, pp. 9-24, vol. 5.

Summers, M.P. et al. "The polymorphism of aspirin" J. Pharm. Pharmac,, 1970, 22:615-616.

Thayer, A.M. "Form and Function: The choice of pharmaceutical crystalline form can be used to optimize drug properties, and cocrystals are emerging as new alternatives". Chemical & Engineering News, Jun. 18, 2007, pp. 17-30, vol. 85, No. 25.

US Pharmacopia #23, 1995, p. 1843.

Wheatley, P.J. "The Crystal and Molecular Structure of Aspirin" J. Chem. Soc., 1964, 6036-6048.

Wunderlich, H.F. et al. "The Derivatives of carbamazepine with ammonium halogenides and formamide" Pharmazie, 1991, pp. 507-509, vol. 46, No. 7 ( Not in English).

Yadav, A.V. et al. "Co-Crystals: A novel approach to modify physicochemical properties of active pharmaceutical ingredients", Indian Journal of Pharmaceuatical Sciences, Jul. 2009, Vo. 71. No. 4, pp. 1-11.

Zaman, M.B. et al. "Crystal Engineering Using Anilic Acids and Dipyridyl Compounds through a New Supramolecular Synthon" J. Org. Chem., 2001, pp. 5987-5995, vol. 66.

Bustamante et al., "Partial-Solubility Parameters of Naproxen and Sodium Diclofenac", *J. Pharm. Pharmacol.*, 1998, vol. 50, p. 975-982.

Kim et al., "Characterization and Solid-State Transformations of the Pseudopolymorphic Forms of Sodium Naproxen", *Crystal Growth & Design*, 2004, vol. 4, No. 6, p. 1211-1216.

* cited by examiner

| Formulation # & Dosing | TPI-336 Form | Percent Mass with respect to TPI-336 freeacid content | | | | | | |
|---|---|---|---|---|---|---|---|---|
| | | HPC | TPGS | Avicel | Pluronic F127 | Pluronic L44 | PEG400 |
| 1 – IV | Freeacid | --- | --- | --- | --- | --- | --- |
| 2 – Oral | Freeacid | 100 | 100 | 50 | --- | --- | --- |
| 3 – Oral | Celebrex (i.e., freeacid) | --- | --- | --- | --- | --- | --- |
| 4 – Oral | Na Hydrate | 100 | 100 | --- | --- | --- | --- |
| 5 – Oral | Na Hydrate | 100 | 100 | 50 | --- | --- | --- |
| 6 – Oral | Na PG Solvate | 100 | 100 | --- | --- | --- | --- |
| 7 – Oral | Na Hydrate | 100 | --- | --- | 100 | --- | --- |
| 8 – Oral | Na Hydrate | 100 | --- | --- | 100 | 40 | --- |
| 9 – Oral | Na Hydrate | 100 | --- | --- | 100 | --- | 40 |

FIG. 5A

| Formulation ID | Route | Mean dose (mg/kg) | Cmax (ng/mL) | Tmax (hr) | AUC(I) (ng·hr/mL) | t½ (hr) | CL/F (mL/hr·kg) | F(%) |
|---|---|---|---|---|---|---|---|---|
| Celebrex[a] | Oral | 5.09 (0.05) | 654 (199) | 1.25 (0.88) | 7663 (3119) | 9.3 (3.5) | 798 (317) | 40.5 (15.45) |
| Celecoxib[a] | IV | 1.0 (0.00) | 718 (91) | NA | 3808 (933) | 8.2 (2.9) | 278 (77) | NA |
| Celecoxib free form/HPC/TPGS[b] | Oral | 5.14 (0.124) | 622 (484) | 2.7 (1.5) | 7290 (5624) | 8.5 (2.0) | 1072 (767) | 29.80 (17.14) |
| Celecoxib Na/HPC/TPGS[b] | Oral | 2.85 (0.27) | 1635 (144) | 0.4 (0.1) | 10100 (4729) | 7.7 (3.7) | 281 (107) | 103.2 (12.82) |
| Celecoxib Na/HPC/TPGS[a] | Oral | 5.05 (0.12) | 2495 (680) | 0.75 (0.27) | 17031 (4263) | 9.0 (2.7) | 311 (72) | 89.15 (9.70) |
| Celecoxib Na/HPC/TPGS[b] | Oral | 7.54 (0.24) | 3445 (646) | 0.80 (0.29) | 24994 (7596) | 7.1 (2.5) | 318 (84) | 99.43 (3.68) |
| Celecoxib Na PG/HPC/TPGS[b] | Oral | 4.89 (0.49) | 2955 (794) | 0.8 (0.3) | 22711 (4043) | 7.7 (1.2) | 225 (40.3) | 109.4 (14.92) |
| Celecoxib Na/HPC/F127[c] | Oral | 5.29 (0.07) | 2276 (272) | 1.0 (0.0) | 14669 (2496) | 6.1 (2.9) | 366 (67) | 97.82 (3.36) |
| Celecoxib Na/HPC/F127/L44[c] | Oral | 5.26 (0.03) | 3411 (529) | 0.5 (0.0) | 22365 (3448) | 9.0 (1.8) | 238 (38) | 108.9 (2.57) |
| Celecoxib Na/HPC/F127/PEG400[c] | Oral | 5.45 (0.06) | 3121 (119) | 0.5 (0.0) | 24377 (2469) | 6.5 (3.2) | 225 (25) | 95.9 (0.68) |

FIG. 5B

| Poloxamer | Physical form | a | b | Average molecular weight | Percent a | Percent b | Ratio a/b |
|---|---|---|---|---|---|---|---|
| 124 | Liquid | 12 | 20 | 2090-2360 | 0.38 | 0.63 | 0.60 |
| 188 | Solid | 80 | 27 | 7680-9510 | 0.75 | 0.25 | 2.96 |
| | | 64 | 37 | 6840-8830 | | | 1.73 |
| 338 | Solid | 141 | 44 | 12 700-17 400 | 0.76 | 0.24 | 3.20 |
| | | 101 | 56 | 9840-14 600 | | | 1.80 |

PHARMACEUTICAL COMPOSITIONS WITH IMPROVED DISSOLUTION

RELATED APPLICATIONS

This application is a 371 national stage entry of International Application No. PCT/US03/41273, filed Dec. 24, 2003, which claims priority to 60/437,516, filed Dec. 30, 2002; 60/441,335, filed Jan. 21, 2003; 60,451,213, filed Feb. 28, 2003; 60/456,027, filed Mar. 18, 2003; 60/456,608, filed Mar. 21, 2003; 60/459,501, filed Apr. 1, 2003; 10/601,092, filed Jun. 20, 2003; 60/486,713, filed Jul. 11, 2003; 60/487, 064, filed Jul. 11, 2003; and 10/660,202, filed Sep. 11, 2003, which are hereby incorporated by reference for all purposes.

FIELD OF THE INVENTION

The present invention relates to pharmaceutical compositions and methods for preparing same.

BACKGROUND OF THE INVENTION

Celecoxib (4-[5-(4-methylphenyl)-3-(trifluoromethyl)-1H-pyrazol-1-yl]benzenesulfonamide) is a substituted pyrazolylbenzenesulfonamide represented by the structure (I):

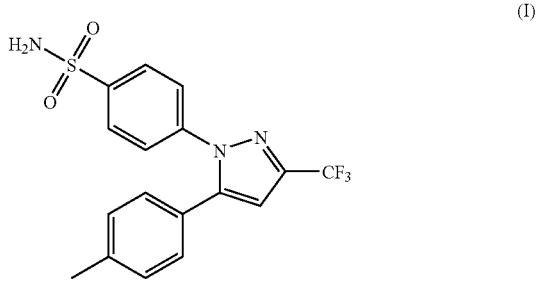 [SMILES: Cc1ccc(-c2cc(C(F)(F)F)nn2-c2ccc(S(N)(=O)=O)cc2)cc1]

Celecoxib belongs to the general class of non-steroidal anti-inflammatory drugs (NSAIDs). Unlike traditional NSAIDs, celecoxib is a selective inhibitor of cyclooxygenase II (COX-2) that causes fewer side effects when administered to a subject. The synthesis and use of celecoxib are further described in U.S. Pat. Nos. 5,466,823, 5,510,496, 5,563,165, 5,753,688, 5,760,068, 5,972,986, 6,156,781, and 6,579,895, the contents of which are incorporated by reference in their entireties. Orally deliverable liquid formulations of celecoxib are discussed in U.S. Patent Application Publication No. 2002/0107250, the contents of which are incorporated herein by reference in their entirety.

Other COX-2 inhibitory drugs are related to celecoxib, which form part of a larger group of drugs, all of which are benzene sulfonamides. These include: deracoxib, which is 4-[3-fluoro-4-methoxyphenyl)-3-difluoromethyl-1H-pyrazol-1-yl]benzene sulfonamide; valdecoxib, which is 4-[5-methyl-3-phenyl isoxazol-4-yl]benzene sulfonamide; rofecoxib, which is 3-phenyl-4-[-(methylsulfonyl)phenyl]-5H-furan-2-one; and etoricoxib, which is 5-chloro-3-(4-methylsulfonyl)phenyl-2-(2-methyl-5-pyridinyl)pyridine. These drugs are described in further detail in WO 01/78724 and WO 02/102376.

In its commercially available form, trademarked as CELEBREX, celecoxib is a neutral molecule that is essentially insoluble in water. Celecoxib typically exists as needle-like crystals, which tend to aggregate into a mass. Aggregation occurs even when celecoxib is mixed with other substances, such that a non-uniform mixture is obtained. These properties are shared by other pyrazolylbenzenesulfonamides and present significant problems in preparing pharmaceutical formulations of the drugs, particularly oral formulations.

It would be advantageous to provide new forms of drugs that have low aqueous dissolution which have improved properties, in particular as oral formulations. In particular, even where an active pharmaceutical ingredient (API) of low aqueous solubility is provided in a form which has improved aqueous solubility, there still exists a problem when dissolution of the API is required, for example after having been taken as an oral formulation where the API becomes diluted in the alimentary canal. (The terms "API" and "pharmaceutical" are used herein interchangeably.) In this situation, APIs having low aqueous solubility tend to come out of solution. When this happens, for example by a process of crystallization or precipitation, the bioavailability of the API is significantly decreased. It would therefore be desirable to improve the properties of formulations containing such APIs so as to increase the bioavailability of the API in an orally-administered form, thereby providing a more rapid onset to therapeutic effect.

SUMMARY OF THE INVENTION

It has now been found that stable, crystalline salts and co-crystals of celecoxib can be synthesized. The celecoxib compositions of the present invention have a greater solubility, dissolution, total bioavailability (area under the curve or AUC), lower $T_{max}$, the time to reach peak blood serum levels, and higher $C_{max}$, the maximum blood serum concentration, than neutral celecoxib. The celecoxib compositions of the present invention also include compounds that are less hygroscopic and more stable. The celecoxib salts of the present invention when in crystalline form convert to either an amorphous free form of celecoxib upon neutralization of the salt, which subsequently converts to a neutral metastable crystalline form or directly to a neutral metastable crystalline form. These amorphous and metastable crystalline forms of neutral celecoxib are more readily available forms of the API than is presently-marketed neutral celecoxib. Neutral crystalline celecoxib is presently-marketed as CELEBREX, and is designated as "neutral" to distinguish it from the ionized salt form of celecoxib. In addition, acidification or neutralization of a solution of the celecoxib salt in situ yields amorphous celecoxib, which subsequently converts to a metastable crystalline form or directly to a neutral metastable crystalline form of neutral celecoxib before finally converting into stable, neutral celecoxib.

An aspect of the present invention relates to methods of increasing dissolution, solubility, and or the time an API (either alone or as part of a pharmaceutical composition), can be maintained, upon dissolution, as a supersaturated solution, before precipitating out of solution. The increase in dissolution (or concentration as a function of time) results in, and thus can be represented by an increase in bioavailability, AUC, reduced time to $T_{max}$ or increased $C_{max}$. The methods comprise the steps of making a salt or co-crystal from an API (e.g. free acid) and combining the salt or co-crystal with a precipitation retardant and optionally, a precipitation retardant enhancer (referred to as enhancer hereafter). The term "precipitation" refers to either a crystalline or amorphous solid form separating or "coming out of" the solution. The salt may be amorphous or crystalline, but is preferably crystalline. Normally the salt or co-crystal form used is in a crystalline form that dissolves and then recrystallizes and precipitates out of solution, which is why the term "crystallization"

retardant may be used in place of "precipitation" for greater specificity. The term "crystallization" retardant can also be used to specify a salt or co-crystal that was in amorphous form prior to dissolution, and precipitates out of solution in crystalline form after dissolution. Crystalline salts are superior to amorphous salts as the initial compound, with an amorphous salt being superior to a neutral amorphous or crystalline form. Free acid forms are not preferred initial compounds unless first solubilized in a solubilizer resulting in a liquid formulation comprising a precipitation retardant and optional enhancer. The precipitation retardant is often a surfactant, preferably a surfactant with an ether functional group, preferably a repeating ether group, e.g., an ether group repeated at least two or three times wherein the oxygen atoms are separated by 2 carbon atoms. Further preferred surfactants have an interfacial tension of less than 10 dynes per centimeter when measured at a concentration of 0.1 percent w/w in water at 25 degrees C. and/or the surface tension of the precipitation retardant (e.g., poloxamers) is less than 42 dynes/cm when measured as a concentration of 0.1% w/w in water at 25 degrees C. The combination of salt or co-crystal, precipitation retardant and an optional enhancer (or precipitation retardant, an optional enhancer and some other form) preferably prevents or delays precipitation of a supersaturated solution by about 5, 10, 15, 20, 25, 30, 35, 40, 45, 50, 55, or 60 minutes or greater than 1 hour in an aqueous solution, preferably water or gastric fluid conditions such as the gastric fluids of an average human stomach fasted for 12 hours or simulated gastric fluid (SGF). Preferably, the solution remains supersaturated for more than 15, 20, or 30 minutes to allow the composition to move out of the stomach and into an environment with a higher pH. The SGF may be diluted by 2, 3, 4, 5, 6, 7, 8, 9, or 10 fold to represent water intake. For example, the SGF may be diluted 5 fold to represent a patient drinking a glass of water at the time a composition of the present invention is taken orally. The degree of increase in solubility, dissolution, and/or supersaturation may be specified, such as by 10, 20, 30, 40, 50, 60, 70, 80, 90, or 100%, or by 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than neutral celecoxib (e.g., free acid) in the same solution. The increase in dissolution may be further specified by the time the composition remains supersaturated.

The enhancer preferably comprises a cellulose ester such as hydroxypropylcellulose (HPC) or hydroxypropylmethylcellulose (HPMC). Thus according to the methods of the present invention, supersaturated concentrations upon which a drug may be maintained upon dissolution and/or the degree of dissolution of a drug in gastric fluid conditions (e.g., SGF) is enhanced.

Normally, the enhancer does not improve or only minimally improves (less than/equal to 10%) the length of time the API can remain supersaturated without the additional presence of the precipitation retardant. The methods of the present invention are used to make a pharmaceutical drug formulation with greater solubility, dissolution, and bioavailability, AUC, reduced time to $T_{max}$, the time to reach peak blood serum levels, and higher $C_{max}$, the maximum blood serum concentration, when compared to the neutral form or salt alone. AUC is the area under the plot of plasma concentration of drug (not logarithm of the concentration) against time after drug administration. The area is conveniently determined by the "trapezoidal rule": the data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of drugs, and in estimating total clearance of drugs ($Cl_T$). Following single intravenous doses, $AUC=D/Cl_T$, where D is the dose, for single compartment systems obeying first-order elimination kinetics; alternatively, $AUC=C_0/k_{el}$, where $k_{el}$ is the drug elimination rate constant. With routes other than the intravenous, $AUC=F \cdot D/Cl_T$, where F is the absolute bioavailability of the drug.

The invention further relates to wherein a precipitation retardant and an optional enhancer is combined with a pharmaceutical that is already in a salt or co-crystal form. The invention further relates to wherein a precipitation retardant and an optional enhancer is combined with a pharmaceutical that is a solvate, desolvate, hydrate, dehydrate, or anhydrous form of a salt or co-crystal form.

Accordingly, in a further aspect, the present invention provides a pharmaceutical composition comprising:
  (a) an API having low aqueous solubility or dissolution, preferably in gastric fluid conditions;
  (b) a precipitation retardant; and
  (c) an optional enhancer.

In a further aspect, the present invention provides a pharmaceutical composition comprising:
  (a) an API having low aqueous solubility or dissolution, preferably in gastric fluid conditions;
  (b) a precipitation retardant having an interfacial tension of less than 10 dyne/cm or a surface tension of less then 42 dyne/cm; and
  (c) an optional enhancer.

In a further aspect, the present invention provides a pharmaceutical composition comprising:
  (a) an API having low aqueous solubility or dissolution, preferably in gastric fluid conditions;
  (b) a surfactant; and
  (c) an optional enhancer.

In a further aspect, the present invention provides a pharmaceutical composition comprising:
  (a) an API having low aqueous solubility or dissolution, preferably in gastric fluid conditions;
  (b) a poloxamer having an interfacial tension of less than 10 dyne/cm or surface tension less then 42 dyne/cm; and
  (c) an optional enhancer.

In a further aspect, the present invention provides a pharmaceutical composition comprising:
  (a) an API having low aqueous solubility or dissolution, preferably in gastric fluid conditions;
  (b) a surfactant; and
  (c) a cellulose ester.

In a further aspect, the present invention provides a pharmaceutical composition comprising:
  (a) an API having low aqueous solubility or dissolution, preferably in gastric fluid conditions;
  (b) a surfactant having an interfacial tension of less than 10 dyne/cm or surface tension less then 42 dyne/cm; and
  (c) hydroxypropylcellulose (HPC) or hydroxypropylmethylcellulose (HPMC).

In a further aspect, the present invention provides a pharmaceutical composition comprising:
  (a) an API having low aqueous solubility or dissolution, preferably in gastric fluid conditions;
  (b) a poloxamer; and
  (c) hydroxypropylcellulose (HPC) or hydroxypropylmethylcellulose (HPMC).

In a further aspect, the present invention provides a pharmaceutical composition comprising:
  (a) an API having low aqueous solubility or dissolution, preferably in gastric fluid conditions;
  (b) a poloxamer having an interfacial tension of less than 10 dyne/cm or surface tension less then 42 dyne/cm; and
  (c) hydroxypropylcellulose (HPC) or hydroxypropylmethylcellulose (HPMC).

In a further aspect, the present invention provides a pharmaceutical composition comprising
  (a) celecoxib;
  (b) a poloxamer surfactant having an interfacial tension at a concentration of 0.1% of less than 10 dyne/cm or surface tension less then 42 dyne/cm; and
  (c) hydroxypropylcellulose (HPC) or hydroxypropylmethylcellulose (HPMC).

In a further aspect, the present invention provides a process for producing a pharmaceutical composition for delivering a supersaturated concentration of a drug having low aqueous dissolution, preferably in gastric fluid conditions, which comprises intimately mixing together the components of the above aspects or elsewhere herein.

In a further aspect, the surfactant is at a concentration of less than 5%, 4%, 3%, 2%, 1%, 0.9%, 0.8%, 0.7%, 0.6%, 0.5%, 0.4%, 0.3%, 0.2%, or 0.1% or at a concentration of 0.1% (w/w) upon dissolving in the dissolution medium.

The present invention further provides a process for producing a pharmaceutical composition, which comprises:
  (1) providing a plurality of containers;
  (2) providing a plurality of excipient solutions;
  (3) providing a plurality of compound solutions, each having dissolved therein a pharmaceutical compound;
  (4) dispensing into each container one of the excipient solutions with one of the compound solutions so as to form an intimate mixture, a property of each mixture being varied in different containers;
  (5) incubating the mixture;
  (6) determining onset of solid-state nucleation or precipitation;
  (7) selecting a pharmaceutical compound/excipient combination whereby onset of solid-state nucleation is retarded; and
  (8) producing a pharmaceutical composition comprising the pharmaceutical compound/excipient combination.

Applicants found that it is possible to screen mixtures containing a pharmaceutical compound and an excipient in a rapid and simple manner so as to identify which properties of the pharmaceutical compound/excipient combination retard (inhibit) solid-state nucleation. The term "solid-state nucleation" is used herein to refer to the initiation of solidification, whether amorphous or crystalline, but may be specified as being amorphous or crystalline. In this way, those excipients or other properties of the combination can be chosen for the production of a pharmaceutical composition in which the API remains in solution for a sufficient time after administration to a subject. In this way, pharmaceutical compositions which attain at least a minimum bioavailability of the API may be readily produced based on a straightforward in vitro screen.

Various properties of a pharmaceutical composition may affect the onset of solid-state nucleation or precipitation of the API. Such properties include the identity or amount of the excipient and the identity or amount of the pharmaceutical compound in the composition. Other properties may include the amount of other diluents or carriers such as salts or buffering compounds. The pharmaceutical compound itself may be screened in a variety of different forms if it is capable of polymorphism. Additionally, different salt, solvate, hydrate, co-crystal and other forms of the API may be screened in accordance with the invention.

The invention is readily applicable to screening a large variety of different excipients. Accordingly, in a preferred aspect, the present invention provides a process for producing a pharmaceutical composition, which comprises:
  (1) providing a plurality of containers;
  (2) providing a plurality of excipient solutions;
  (3) providing a plurality of compound solutions, each having dissolved therein a pharmaceutical compound;
  (4) dispensing into each container one of the excipient solutions with one of the compound solutions so as to form an intimate mixture, the excipient being varied in different containers;
  (5) incubating the mixture;
  (6) determining onset of solid-state nucleation or precipitation;
  (7) selecting an excipient which is found to retard onset of solid-state nucleation or precipitation; and
  (8) producing a pharmaceutical composition comprising the pharmaceutical compound and the selected excipient.

According to this embodiment, it is the excipient which is varied. Different excipients may be used in different containers and may be present as a single excipient or in a combination of a plurality of excipients, for example, a binary, ternary, tertiary or higher order combination.

In a further aspect, the present invention provides a pharmaceutical composition obtained by processes according to the invention. The pharmaceutical composition may comprise a further excipient, diluent or carrier. In a preferred aspect, the pharmaceutical composition is formulated for oral administration.

The invention further provides a method for assessing excipient-mediated retardation of solid-state nucleation or precipitation of a pharmaceutical compound, which method comprises:
  (1) providing a plurality of containers;
  (2) providing a plurality of excipient solutions;
  (3) providing a plurality of compound solutions, each having dissolved therein a pharmaceutical compound;
  (4) dispensing into each container one of the excipient solutions with one of the compound solutions so as to form an intimate mixture, a property of each mixture being varied in different containers;
  (5) incubating the mixture;
  (6) determining onset of solid-state nucleation or precipitation; and
  (7) ranking the property of the mixture according to time of onset of solid-state nucleation or precipitation.

In a further aspect the present invention provides a method for screening excipients that retard solid-state nucleation or precipitation of a pharmaceutical compound, which method comprises:
  (1) providing a plurality of containers;
  (2) providing a plurality of excipient solutions;
  (3) providing a plurality of compound solutions, each having dissolved therein a pharmaceutical compound;
  (4) dispensing into each container one of the excipient solutions with one of the compound solutions so as to form an intimate mixture, the excipient being varied in different containers;
  (5) incubating the mixture;
  (6) determining onset of solid-state nucleation or precipitation; and
  (7) ranking the excipient according to time of onset of solid-state nucleation or precipitation.

Generally speaking, the active pharmaceutical ingredient (API) is typically capable of existing as a supersaturated solution, preferably in an aqueous-based medium. The API may be a free acid, free base, co-crystal or salt, or a solvate, hydrate or dehydrate thereof. The invention is particularly applicable to pharmaceutical compositions comprising an API which, when in contact with a body fluid such as gastric juices or intestinal fluids, would be likely to precipitate or crystallize from solution in a nucleation event. Accordingly, the invention is particularly applicable to pharmaceutical compounds which may have relatively low solubility, or dissolution, as defined herein, when in contact with bodily fluids but possibly relatively high solubility, or dissolution, in appropriate in vitro conditions.

According to the invention, the compound solution is a solution wherein the compound is solubilized and may be a non-aqueous solution or an aqueous solution with a pH adjusted to accommodate the compound. For example, in order to achieve high solubility of the compound, a free base-type compound would be dissolved in aqueous solution at acidic pH whereas a free acid-type compound would be dissolved in an aqueous solution of basic pH. The compound solution may therefore be, and preferably is, a supersaturated solution when compared to water, gastric fluids or intestinal fluids. It would also be preferred for the excipient to be in a solution comprising water, usually deionised water, or another aqueous based solution. In one aspect, the mixture simulates gastric fluid (SGF) or intestinal fluids (SIF, 0.68% monobasic potassium phosphate, 1% pancreatin, and sodium hydroxide where the pH of the final solution is 7.5) and in this aspect it is preferred that the excipient is added in a solution simulating those body fluids. Alternatively, further additives, usually in solution, may be added to form the mixtures creating an environment appropriate for the screening to be undertaken.

One advantage of the present invention is that the plurality of containers may be presented in a multiple well plate format or block and tube format such that at least 24, 48, 96, 384, or 1536 samples are assayed in parallel. Multiple block and tubes or multiwell plates may be assayed such that at least 1000, 3000, 5000, 7000, 10000, 20000, 30000, 40000, 50000, 60000, 70000, 80000, 90000, or 100000 total samples are assayed. This is advantageous because the process may be operated in a semi-automated or automated way using existing multiple well plate format-based apparatus. At least the step of dispensing may be performed with automated liquid handling apparatus. Accordingly, it is possible to operate the process as a high throughput screen. Additionally, using a multiple well plate format, the scale of the screening is relatively low. For example, each sample may contain less than 100 mg, 50 mg, 25 mg, 10, mg, 5 mg, 750 micrograms, 500 micrograms, 250, micrograms, 100 micrograms, 75 micrograms, 50 micrograms, 25 micrograms, 10 micrograms, 1 microgram, 750 ng, 500 ng, 250 ng, 100 ng, or less than 50 ng, depending on the API, sample size, etc. This, therefore, minimizes the amount of API which is needed to identify excipients or properties of the combination of pharmaceutical compound and excipient that retard onset of nucleation. In this way, improved speed and relatively low cost are advantages.

The intimate mixture formed in the process may be achieved by any conventional method, including the use of a mixer during or after dispensing of the solutions. Once the mixture has been formed, it is generally advantageous to incubate the mixture at a constant temperature, such as approximately 37 degrees C., to simulate in vivo conditions.

Measurement of onset of solid-state nucleation or precipitation may be determined for example, by measuring the light scattering of a mixture. This may be achieved by any conventional light scattering measurement, such as the use of a nephelometer. It is also possible to include a further step in which the crystallinity of the products of the solid-state nucleation or precipitation is determined. This step is conveniently performed before selecting the pharmaceutical compound/ excipient combination for use in the pharmaceutical composition. Crystallinity may be determined, e.g., by birefringence screening.

Neither the light scattering measurement nor the birefringence screening are invasive measurement techniques. Advantageously, a portion or all of the sample solution does not need to be transferred to a second container and the containers or wells can be sealed with a transparent seal to allow use of these techniques.

In its most general aspect, the present invention relates to a pharmaceutical composition which includes an API having a low aqueous solubility or dissolution (as defined herein). Typically, low aqueous solubility in the present application refers to a compound having a solubility in water which is less than or equal to 10 mg/mL, when measured at 37 degrees C., and preferably less than or equal to 1 mg/mL. The invention relates more particularly to drugs which have a solubility of not greater than 0.1 mg/mL. The invention further relates to compounds that cannot be maintained as a supersaturated solution in gastric or intestinal fluid or in SGF or SIF. Such drugs include some sulfonamide drugs, such as the benzene sulfonamides, particularly those pyrazolylbenzenesulfonamides discussed above, which include COX-2 inhibitors. Disclosed herein are stable crystalline metal salts of pyrazolylbenzenesulfonamides such as celecoxib. Such metal salts include alkali metal or alkaline earth metal salts, preferably sodium, potassium, lithium, calcium and magnesium salts.

It is preferred that the pharmaceutical composition is formulated for oral administration. Drugs according to the invention may be prepared in a form having reduced time to onset of therapeutic effectiveness (the time when an effect for which the drug is administered can be identified or measured, e.g., the point in time when a reduction in fever or pain felt by a patient begins to occur) or increased bioavailability. The pharmaceutical compositions according to the invention are therefore particularly suitable for administration to human subjects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A and 5B show the formulations and mean pharmacokinetic parameters (and standard deviations thereof) of celecoxib in the plasma of male dogs following a single oral or single intravenous dose of celecoxib or celecoxib sodium salt.

DETAILED DESCRIPTION OF THE INVENTION

Figure 1:
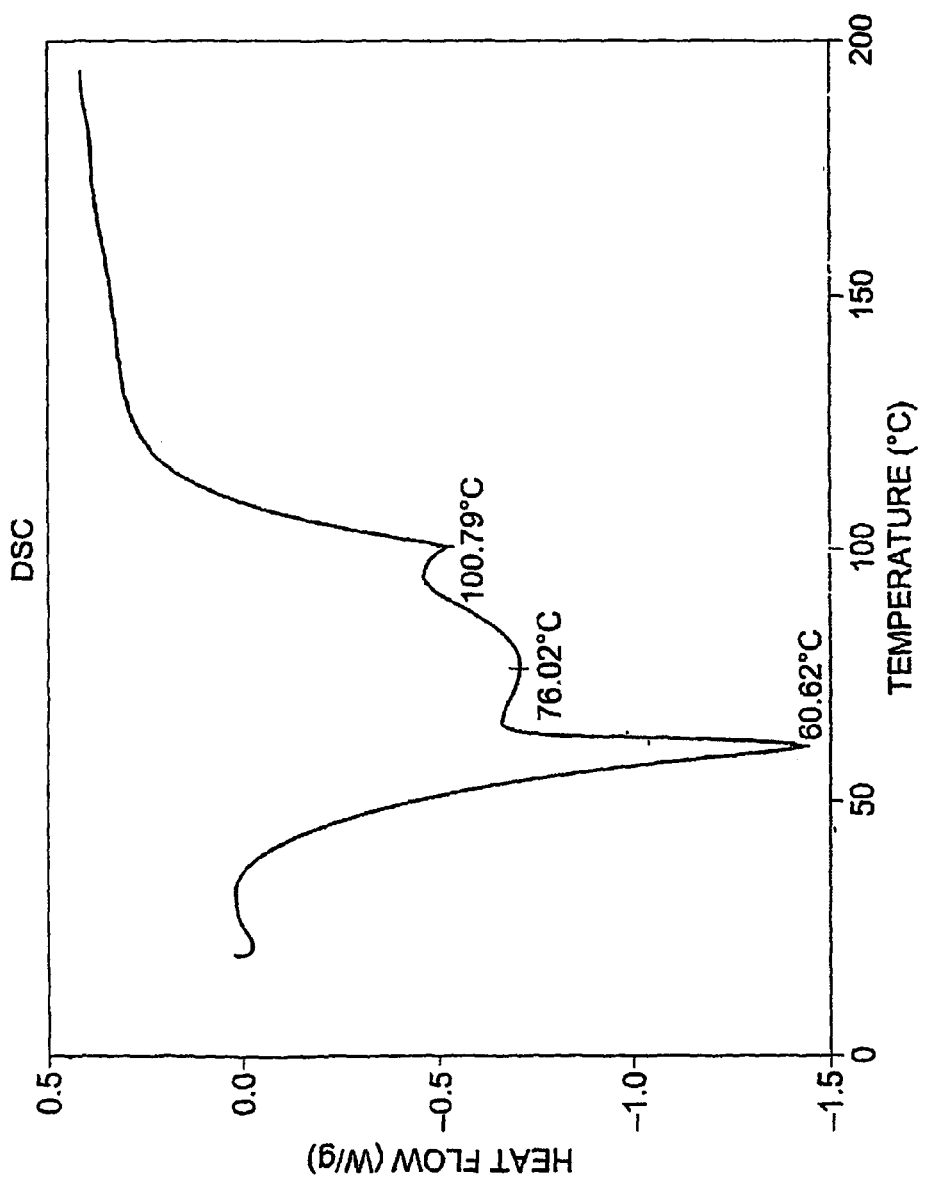
FIG. 1 shows a reproduction of a differential scanning calorimetry (DSC) thermogram of the sodium salt of celecoxib prepared by Example 1 between 50 degrees C. and 110 degrees C.

In its most general aspect, the present invention relates to a pharmaceutical composition that includes an API having a low aqueous solubility, e.g., in gastric fluid conditions. Typically, low aqueous solubility in the present application refers to a compound having a solubility in water which is less than or equal to 10 mg/mL, when measured at 37 degrees C., and preferably less than or equal to 5 mg/mL or 1 mg/mL. "Low aqueous solubility" can further be defined as less than or equal to 900, 800, 700, 600, 500, 400, 300, 200 150 100, 90, 80, 70, 60, 50, 40, 30, 20 micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 37 degrees C. Further aqueous solubility can be measured in simulated gastric fluid (SGF) rather than water. SGF (non-diluted) of the present invention is made by combining 1 g/L Triton X-100 and 2 g/L NaCl in water and adjusting the pH with 20 mM HCl to obtain a solution with a final pH=1.7. The pH of the solution may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 6, 6.5, 7, 7.5, 8, 8.5, 9, 9.5, 10, 10.5, 11, 11.5, or 12.

APIs which have a solubility of not greater than 0.1 mg/mL, including some sulfonamide drugs, such as the benzene sulfonamides, particularly those pyrazolylbenzenesulfonamides discussed above, which include COX-2 inhibitors, are included in the present invention. Disclosed herein are stable crystalline metal salts and co-crystals of pyrazolylbenzenesulfonamides such as celecoxib. Such metal salts include alkali metal or alkaline earth metal salts, preferably sodium, potassium, lithium, calcium and magnesium salts.

In one aspect of the present invention, an API with low aqueous solubility is formulated with a precipitation retardant and, optionally, with a precipitation retardant enhancer. The precipitation retardant used in the present invention can be chosen from a wide range of surfactants (see e.g., FIG. 30). Embodiments include where the surfactant is non-ionic or wherein the surfactant is ionic. In embodiments of the present invention, the interfacial tension of the precipitation retardant (e.g., poloxamers) is less than 10 dyne/cm when measured as a concentration of 0.1 percent w/w in water as compared to mineral oil at 25 degrees C. and/or the surface tension of the precipitation retardant (e.g., poloxamers) is less than 42 dyne/cm when measured as a concentration of 0.1% w/w in water. In other embodiments of the invention the interfacial tension is less than 15, 14, 13, 12, 11, 9, 8, 7, or 6 dyne/cm or the surface tension is less than 45, 44, 43, 41, 40, 39, 38, 37, 36, or 35 dyne/cm. In other embodiments, the surfactant is a poloxamer. A poloxamer comprises an ethylene oxide-propylene oxide block copolymer, which preferably has a structure $(PEG)_x\text{-}(PPG)_y\text{-}(PEG)_z$, where x, y and z are integers and x is usually equal to z. Preferred forms of poloxamers are those obtainable from BASF, as trademarked PLURONIC. The invention is not, however, limited to the PLURONIC series as similar poloxamers obtainable from other sources may be used. Examples of PLURONIC poloxamers according to the invention include PLURONIC L122, PLURONIC P123, PLURONIC F127 (Poloxamer 407), PLURONIC L72, PLURONIC P105, PLURONIC LP2, PLURONIC P104, PLURONIC F108 (Poloxamer 338), PLURONIC P103, PLURONIC L44 (Polaxamer 124), PLURONIC F68 (Poloxamer 188), and PLURONIC F87 (Poloxamer 237). A specific poloxamer and its corresponding PLURONIC, i.e., the generic and tradename, may be used interchangeably throughout.

In one embodiment, the invention provides a pharmaceutical composition comprising:
(a) an API; and
(b) a polyether block copolymer comprising an A-type linear polymeric segment joined at one end to a B-type linear polymeric segment, wherein the A-type segment is of relatively hydrophilic character, the repeating units of which contribute an average Hansch-Leo fragmental constant of about −0.4 or less and have molecular weight contributions between about 30 and about 500, wherein the B-type segment is of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage. In a preferred first embodiment, the polyether block copolymer is selected from the group consisting of polymers of formulas:

 $A - B - A'$, (i)

 $A - B$, (ii)

 $B - A - B'$, or (iii)

 $L(R^1)(R^2)(R^3)(R^4)$ (iv)

wherein A and A' are A-type linear polymeric segments, B and B' are B-type linear polymeric segments, and $R^1$, $R^2$, $R^3$ and $R^4$ are either block copolymers of formulas (i), (ii) or (iii) or hydrogen and L is a linking group, with the proviso that no more than two of $R^1$, $R^2$, $R^3$ or $R^4$ are hydrogen.

In another embodiment, the composition includes micelles of the block copolymer or forms micelles of the block copolymers during the course of administration or subsequent thereto. Preferably, at least about 0.1% of the API is incorporated in the micelles, more preferably, at least about 1% of the API, yet more preferably, at least about 5% of the API.

In another embodiment, the hydrophobic percentage of the copolymer of the composition is at least about 50% more preferably, at least about 60%, yet more preferably 70%.

In another embodiment, the hydrophobic weight of the copolymer is at least about 900, more preferably, at least about 1700, yet more preferably at least about 2000, still more preferably at least about 2300.

In other embodiments, the hydrophobic weight is at least about 2000 and the hydrophobic percentage is at least about 20%, preferably 35%; or the hydrophobic weight is at least about 2300 and the hydrophobic percentage is at least about 20%, preferably 35%.

The optional third component of the pharmaceutical composition according to the present invention comprises a precipitation retardant enhancer. An enhancer is a compound capable of increasing the effectiveness of the precipitation retardant in inhibiting, preventing or at least reducing the extent of precipitation of a drug of low aqueous solubility, usually when diluted such as following oral administration. In one embodiment the enhancer does not act as a precipitation retardant alone. In another embodiment the enhancer has no effect or a negative effect in an in vitro precipitation assay, but increases the effectiveness of the precipitation retardant in an in vivo or in vitro dissolution assay. Cellulose esters, such as hydroxypropyl cellulose, are particularly useful enhancers according to the present invention. Cellulose esters vary in the chain length of their cellulosic backbone and consequently, vary in their viscosities as measured for example at a 2% by weight concentration in water at 20 degrees C. Lower viscosities are normally preferred to higher viscosities in the present invention. In embodiments of the present invention the cellulose ester, such as HPC, has a viscosity, 2% in water, of about 100 to about 100,000 cP or about 1000 to about 15,000 cP. In other embodiments the viscosity is less than 1,500,000, 1,000,000, 500,000, 100,000, 75,000, 50,000, 35,000, 25,000, 20,000, 17,500, 15,000, 12,500. 11,000, 10,500, 9,000, 8,000, 7,000, 6,000, 5,000, 4,000, 3,000, 2,000, 1,000, 750, 500, or 250 cP, or has a viscosity in a range selected from any two preceding integers.

Enhancers are also useful in delaying the $T_{max}$ and/or increasing the amount of time the API concentration is above $\frac{1}{2}T_m$, thus acting to smooth out a curve of blood serum concentration vs. time. Preferred enhancers increase the amount of time the API concentration is above $\frac{1}{2}T_{max}$ by 25%, 50%, 75%, 100%, three fold or more than three fold. In a preferred embodiment, the composition has both a reduced time to $T_{max}$ and remains at $\frac{1}{2}T_{max}$ longer than the free acid or in the same composition except the salt or co-crystal is replaced by the free acid.

The ratio of component a:b:c (API: precipitation retardant; enhancer) as exemplified herein is approximately 1:1:1 (+/− 0.2 for the precipitation retardant and enhancer). However, the ratio can be adjusted to suit the application. For example, the amount of precipitation retardant or enhancer may need to be decreased, and even decreased below the optimum concentration in order to decrease the amount of excipients in the administered form of the composition, such as a tablet or capsule. In one embodiment the unit dosage form comprises an amount of precipitation retardant (surfactant) that is at or above an amount needed for the retardant to reach its critical micelle concentration (CMC) in $H_2O$ or SGF. It is noted the poloxamers may not form true micells but do form analogous structures which are considered micelles for the purpose of the present invention.

The composition may further comprise a pharmaceutically-acceptable diluent, excipient or carrier and such additional components are discussed in further detail below. One such additional component comprises a granulating fluid-like liquid, such as poloxamer 124, PEG 200 or PEG 400, that forms an intimate contact between the API, precipitation retardant and optional enhancer by binding or partially dissolving them. Preferably the composition remains in a solid, semi-solid or paste, although an embodiment is drawn to wherein the composition is at least 25%, 50%, 75% or nearly or fully dissolved. Any pharmaceutically acceptable liquid may be used as long as it does not cause conversion of the salt or co-crystal form to the free form in the solid state. Some non-limiting examples include methanol, ethanol, isopropanol, higher alcohols, propylene glycol, ethyl caprylate, propylene glycol laurate, PEG, diethyl glycol monoethyl ether (DGME), tetraethylene glycol dimethyl ether, triethylene glycol monoethyl ether, and polysorbate 80. The presence of the granulating fluid-like liquid increases the dissolution of the API, possibly by delaying the contact between the API and the dissolution medium until the surfactant dissolves to a significant extent, thus delaying precipitation. The use of a granulating fluid-like liquid is particularly useful when the API and precipitation retardant are solids.

As an alternative embodiment to increase supersaturation of the API, the pharmaceutical composition is in the form of a compact whereby, during the process of producing the pharmaceutical composition, the components are compacted together. Compaction may perform a similar role to that performed by the granulating fluid. Retarded dissolution or a smoothing out of the curve of blood serum concentration vs. time may be limited, if required, by using a disintegrant in the compact.

In a further embodiment the API and precipitation retardant (and optional enhancer), forms a paste or non-aqueous solution when mixed. An adherent mass of components may be produced if a paste is used, which is thought to delay dissolution of the API by allowing the surfactant to dissolve first. This is thought to promote supersaturation of the API.

Normally the compounds of the present invention are intimately associated as a pharmaceutical composition. An "intimate association" in the present context includes, for example, the pharmaceutical admixed with the precipitation retardant, the pharmaceutical embedded or incorporated in the retardant, the compound forming a coating on particles of the pharmaceutical or vice versa, and a substantially homogeneous dispersion of the pharmaceutical throughout the compounds.

Where the pharmaceutical composition includes a COX-2 inhibitor, a method of treating a subject is provided in a further aspect of the invention, in which the subject may be suffering from pain, inflammation, cancer or pre-cancer such as intestinal or colonic polyps. The method comprises administering to the subject a pharmaceutical composition as described herein.

It is preferred that the pharmaceutical composition is formulated for oral administration. Drugs according to the invention may be prepared in a form having a decreased time to onset of therapeutic effectiveness and an increased bioavailability. The pharmaceutical compositions according to the invention are particularly suitable for administration to human subjects.

The methods and compositions of the present invention relate to improving solubility, dissolution and bioavailability of pharmaceuticals. The present invention further relates to improving the performance of pharmaceutical compounds that initially dissolve but then precipitate or recrystallize in gastric fluid conditions.

Further embodiments relate to pharmaceuticals with an aminosulfonyl functional group. The term "aminosulfonyl functional group" herein refers to a functional group having the following structure (II):

Wherein the wavy line represents a bond by which the functional group is attached to the rest of the drug molecule; and R is hydrogen or a substituent that preserves ability of polyethylene glycol or a polyethylene glycol degradation product to react with the amino group adjacent to R to form an addition compound. Illustrative examples of such substituents include partially unsaturated hereocyclyl, hereoaryl, cycloalkenyl, aryl, alkylcarbonyl, formyl, halo, alkyl, haloalkyl, oxo, cyano, nitro, carboxyl, phenyl, alkoxy, aminocarbonyl, alkoxycarbonyl, carboxyalkyl, cyanoalkyl, hydroxyalkyl, hydroxyl, alkoxyalkyloxyalkyl, haloalkylsulfonyloxy, carboxyalkoxyalkyl, cycloalkylalkyl, alkynyl, heterocyclyloxy, alkylthio, cycloalkyl, heterocyclyl, cycloalkenyl, aralkyl, heterocyclylalkyl, heteroarylcarbonyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-Narylamino, aminoalkyl, alkylaminoalkyl, N-arylaminoalkyl, N-aralkylamincoalkyl, N-alkyl-N-aralkylaminoalkyl, N-alkyl-N-arylaminoalkyl, aryloxy, aralkoxy, arylthio, aralkylthio, alkylsufinyl, alkylsulfonyl, etc.

Non-limiting illustrative examples of aminosulfonyl-comprising drugs include ABT-751 of Eisai (N-(2-(4-hydroxyphenyl)amino)-3-pyridyl)-4-methoxybenzenesulfonamide); alpipride; amosulalol; amprenavir; amsacrine; argatroban; asulacrine; azosemide; BAY-38-4766 of Bayer (N-[4-[[[5-(dimethylamino)-1-naphthalenyl]sulfonyl] amino]phenyl]-3-hyrdroxy-2,2-dimethylpropanamide); bendroflumethiazide; BMS-193884 of Bristol Myers Squibb (N-(3,4-dimethyl-5-isoxazolyl)-4$^1$-(2-oxazolyl)-[1,1$^1$-biphenyl]-2-sulfonamide); bosentan; bumetide; celecoxib; chlorthalidone; delavirdine; deracoxib dofetilide; domitroban; dorzolamide; dronedarone; E-7070 of Eisai (N-(3-chloro-1H-indol-7-yl)-1,4-benzene-disulfonamide); EF-7412 of Schwartz Pharma (N-3-[4-[4-(tetrahydro-1,3-dioxo-1H-pyrrolo[1,2-c]imidazol-2(3H)-yl)butyl]-1-piperazinyl]phenyl]ethanesulfonamide); fenquizone; furosemide; glibenclamide; gliclazide; glimepiride; glipentide; glipizide; gliquidone; glisolamide; GW-8510 of Glaxo SmithKline (4-[[6,7-dihydro-7-oxo-8H-pyrrolo[2,3-g]benzothiazol-8-ylidene)methyl]amino]-N-2-pyridinylbenzenesulfonamide); GYKI-16638 of Ivax (N-[4-[2-[[2-(2,6-dimethoxyphenoxy)-1-methlethyl]methylamino]ethyl]phenyl]methanesulfonamide); HMR-1098 of Aventis (5-chloro-2-methoxy-N-[2-[4-methoxy-3-[[[(methylamino)thioxomethyl]amino] sulfonyl]phenyl]ethyl]benzamide); hydrochlorothiazide; ibutilide; indapamide; IS-741 of Ishihara (N-[2-[(ethylsulfonyl) amino]-5-(trifluoromethyl)-3-pyridinyl]cyclohexanecarboxamide); JTE-522 of Japan Tobacco (4-(4-cyclohexyl-2-methyl-5-oxazolyl)-2-fluorobenzenesulfonamide); KCB-328 of Chugai (N-[3-amino-4-[2-[[2-3,4-dimethoxyphenyl)ethyl]methylamino]ethoxy]phenyl]methanesulfonamide); KT2-962 of Kotobuki (3-[4-[[(4-chlorophenyl) sulfonyl]amino]butyl]-6-(1-methylethyl)-1-azulene sulfonic acid); levosulpiride; LY-295501 (N-[[(3,4-dichlorophyenyl)amino]carbonyl]-2,3-dihydro-5-benzofuransulfonamide) and LY-404187 (N-2-(4-(4-cyanophenyl)phenyl) propyl-2-propanesulfonamide) of Eli Lilly; metolazone; naratriptan; nimesulide; NS-49 of Nippon ((R)—N-[3-(2-amino-1-hydroxyethyl)-4-fluorophenyl]methanesulfonamide); ONO-8711 of Ono ((5Z)-6-[(2R,3S)-3-[[[(4-chloro-2-methylphenyl)sulfonyl]amino]methyl]bicyclo[2.2.2]oct-2-yl]-5-hexenoic acid); piretanide; PNU-103657 of Pharmacia (1-[5-methanesulfonamidoindol-2-ylcarbonyl]-4-(N-methyl-N-(3-(2-methylpropyl)-2-pyridinyl)amino)piperidine); polythiazide; ramatroban; RO-61-1790 of Hoffmann LaRoche (N-[6-(2-hydroxyethoxy)-5-(2-methoxyphenoxy)-2-[2-(1H-tetrazol-5-yl)-4-pyridinyl]-4-pyrimidinyl]-5-methyl-2-pyridinesulfonamide); RPR-130737 (4-hydroxy-3-[2-oxo-3(S)-[5-(3-pyridyl) thiophen-2-ylsulfonamido]pyrrolidin-1-ylmethyl]benzamide) and RPR-208707 of Aventis; S-18886 (3-[(6-(4-chlorophenylsulfonylamino)-2-methyl-5,6,7,8-tetrahydronaphth]-1-yl)propionic acid) and S-32080 (3-[6-(4-chlorophenylsulfonylamido)-2-propyl-3-(3pyridylmethyl)-5,6,7,8-tetrahydronaphthalen-1-yl]propionic acid) of Server; S-36496 of Kaken (2-sulfonyl-[N-(4-chlorophenyl)sulfonylamino-butyl-N-[(4-cyclobutylthiazol-2-yl)ethenylphenyl-3-yl-methyl]]aminobenzoic acid); sampatrilat; SB-203208 of Glaxo Smith Kline (L-phenylalanine, b-methyl-(4aR,6S,7R,7aS)-4-(aminocarbonyl)-7-[[[[[(2S,3S)-2-amino-3-methyl-1-oxopentyl]amino]sulfonyl]acetyl] amino]-7-carboxy-2,4-a,5,6,7,7a-hexahydro-2-methyl-1H-cyclopenta[c]pyridine-6yl ester, (bS)-); SE-170 of DuPont (2-(5-amidino-1H-indol-3-yl)N-[2'-(aminosulfonyl)-3-bromo(1,1'biphenyl)-4-yl]acetamide); sivelestat; SJA-6017 of Senju (N-(4-fluorophenylsulfonyl)-L-valyl-L-leucinal); SM-19712 of Sumitomo (4-chloro-N-[[(4-cyano-3-methyl-1-phenyl-1H-pyrazol-5-yl) amino]carbonyl]benzenesulfonamide); sonepiprazole; sotalol; sulfadiazine; sulfaguanole; sulfasalazine; sulpride; sulprostone; sumatriptan; T-614 of Toyama (N-[3-(formylamino)-4-oxo-6-phenoxy-4H-1-benzopyran-7-yl]-methanesulfonamide); T-138067 (2,3,4,5, 6-pentafluoro-N-(3-fluoro-4-methoxyphenyl)benzenesulfonamide) and T-900607 (2,3,4,5,6-pentafluoro-N-3-ureido-4-methoxyphenyl)benzenesulfonamide) of Tularik; TAK-661 of Takeda (2,2-dimethyl-3-[[7-(1-methylethyl)[1, 2,4]triazolo[1,5-b]pyridazin-6-yl]oxy]-1-propanesulfonamide); tamsulosin; tezosentan; tipranavir; tirofiban; torasemide; trichloromethiazide; tripamide; valdecoxib; veralipride; xipamide; Z-335 of Zeria (2-[2-(4-chlorophenylsulfonylaminomethyl)indan-5-yl]acetic acid); zafirlukast; zonisamide; and salts thereof.

In a preferred embodiment, the aminosulfonyl-comprising drug is a selective COX-2 inhibitory drug of low water solubility. Suitable selective COX-2 inhibitory drugs are compounds having the formula (III):

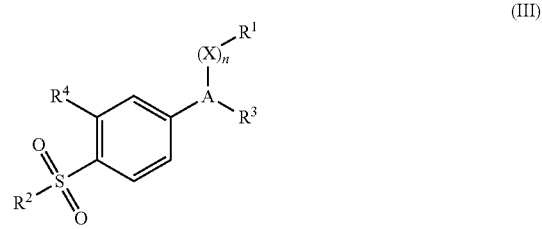

wherein:

A is a substituent selected from partially unsaturated or unsaturated heterocyclic and partially unsaturated or unsaturated carbocyclic rings, preferably a heterocyclic group selected from pyrazolyl, furanoyl, isoxazolyl, pyridinyl, cyclopentenonyl and pyridazinonyl groups;

X is O, S or $CH_2$;

n is 0 or 1;

$R^1$ is at least one substituent selected from heterocyclyl, cycloalkyl, cycloalkenyl and aryl, and is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsufinyl, halo, alkoxy and alkylthio;

$R^2$ is $NH_2$ group;

$R^3$ is one or more radicals selected from hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl, $R^3$ being optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsufinyl, halo, alkoxy and alkylthio; and $R^4$ is selected from hydrido and halo.

Particularly suitable selective COX-2 inhibitory drugs are compounds having the formula (IV):

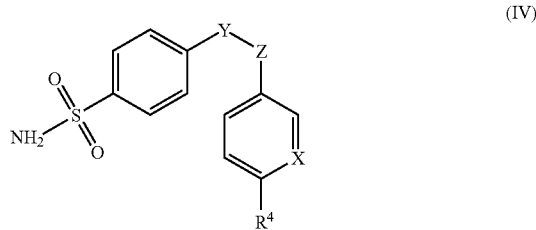

where $R^4$ is hydrogen or a $C_{1-4}$ alkyl or alkoxy group, X is N or $CR^5$ where $R^5$ is hydrogen or halogen, and Y and Z are independently carbon or nitrogen atoms defining adjacent atoms of a five-to-six-membered ring that is unsubstituted or substituted at one or more positions with oxo, halo, methyl, or halomethyl groups. Preferred such five- to six-membered rings are cyclopentenone, furanone, methylpyrazole, isoxazole and pyridine rings substituted at no more than one position.

Illustratively, compositions of the invention are suitable for celecoxib, deracoxib, valdecoxib and JTE-522, more particularly celecoxib, paracoxib and valdecoxib. Other examples of suitable compositions include Acetazolamide CAS Registry Number: 59-66-5, Acetohexamide CAS Registry Number: 968-81-0, Alpiropride CAS Registry Number: 81982-32-3, Althiazide CAS Registry Number: 5588-16-9, Ambuside CAS Registry Number: 3754-19-6, Amidephrine CAS Registry Number: 3354-67-4, Amosulalol CAS Registry Number: 85320-68-9, Amsacrine CAS Registry Number: 51264-14-3, Argatroban CAS Registry Number: 74863-84-6, Azosemide CAS Registry Number: 27589-33-9, Bendroflumethiazide CAS Registry Number: 73-48-3, Benzthiazide CAS Registry Number: 91-33-8, Benzylhydrochlorothiazide CAS Registry Number: 1824-50-6, p-(Benzylsulfonamido) benzoic Acid CAS Registry Number: 536-95-8, Bosentan CAS Registry Number: 147536-97-8, Brinzolamide CAS Registry Number: 138890-62-7 Bumetanide CAS Registry Number: 28396-03-1, Butazolamide CAS Registry Number: 16790-49-1, Buthiazide CAS Registry Number: 2043-38-1, Carbutamide CAS Registry Number: 339-43-5, Celecoxib CAS Registry Number: 169590-42-5, Chloraminophenamide CAS Registry Number: 121-30-2, Chlorothiazide CAS Registry Number: 58-94-6, Chlorpropamide CAS Registry Number: 94-20-2, Chlorthalidone CAS Registry Number: 77-36-1, Clofenamide CAS Registry Number: 671-95-4, Clopamide CAS Registry Number: 636-54-4, Clorexolone CAS Registry Number: 2127-01-7, Cyclopenthiazide CAS Registry Number: 742-20-1, Cyclothiazide CAS Registry Number: 2259-96-3, Daltroban CAS Registry Number: 79094-20-5, Delavirdine CAS Registry Number: 136817-59-9, Diazoxide CAS Registry Number: 364-98-7, Dichlorphenamide CAS Registry Number: 120-97-8, Disulfamide CAS Registry Number: 671-88-5, Dofetilide CAS Registry Number: 115256-11-6, Domitroban CAS Registry Number: 112966-96-8, Dorzolamide CAS Registry Number: 120279-96-1, Ethiazide CAS Registry Number: 1824-58-4, Ethoxzolamide CAS Registry Number: 452-35-7, Fenquizone CAS Registry Number: 20287-37-0, Flumethiazide CAS Registry Number: 148-56-1, $N^2$-Formylsulfisomidine CAS Registry Number: 795-13-1, Furosemide CAS Registry Number: 54-31-9, Glibornuride CAS Registry Number: 26944-48-9, Gliclazide CAS Registry Number: 21187-98-4, Glimepiride CAS Registry Number: 93479-97-1, Glipizide CAS Registry Number: 29094-61-9, Gliquidone CAS Registry Number: 33342-05-1, Glisoxepid CAS Registry Number: 25046-79-1, $N^4$-Beta-D-Glucosylsulfanilamide CAS Registry Number: 53274-53-6, Glyburide CAS Registry Number: 10238-21-8, Glybuthiazol(e) CAS Registry Number: 535-65-9, Glybuzole CAS Registry Number: 1492-02-0, Glyhexamide CAS Registry Number: 451-71-8, Glymidine CAS Registry Number: 339-44-6, Glypinamide CAS Registry Number: 1228-19-9, Hydrochlorothiazide CAS Registry Number: 58-93-5, Hydroflumethiazide CAS Registry Number: 135-09-1, Ibutilide CAS Registry Number: 122647-31-8, Indapamide CAS Registry Number: 26807-65-8, Mafenide CAS Registry Number: 138-39-6, Mefruside CAS Registry Number: 7195-27-9, Methazolamide CAS Registry Number: 554-57-4, Methyclothiazide CAS Registry Number: 135-07-9, Metolazone CAS Registry Number: 17560-51-9, Naratriptan CAS Registry Number: 121679-13-8, Nimesulide CAS Registry Number: 51803-78-2, Noprylsulfamide CAS Registry Number: 576-97-6, Paraflutizide CAS Registry Number: 1580-83-2, Phenbutamide CAS Registry Number: 3149-00-6, Phenosulfazole CAS Registry Number: 515-54-8, Phthalylsulfacetamide CAS Registry Number: 131-69-1, Phthalylsulfathiazole CAS Registry Number: 85-73-4, Sulfacetamide CAS Registry Number: 144-80-9, Sulfachlorpyridazine CAS Registry Number: 80-32-0, Sulfachrysoidine CAS Registry Number: 485-41-6, Sulfacytine CAS Registry Number: 17784-12-2, Sulfadiazine CAS Registry Number: 68-35-9, Sulfadicramide CAS Registry Number: 115-68-4, Sulfadimethoxine CAS Registry Number: 122-11-2, Sulfadoxine CAS Registry Number: 2447-57-6, Piretanide CAS Registry Number: 55837-27-9, Polythiazide CAS Registry Number: 346-18-9, Quinethazone CAS Registry Number: 73-49-4 Ramatroban CAS Registry Number: 116649-85-5, Salazosulfadimidine CAS Registry Number: 2315-08-4, Sampatrilat CAS Registry Number: 129981-36-8, Sematilide CAS Registry Number: 101526-83-4, Sivelestat CAS Registry Number: 127373-66-4, Sotalol CAS Registry Number: 3930-20-9, Soterenol CAS Registry Number: 13642-52-9, Succinylsulfathiazole CAS Registry Number: 116-43-8, Suclofenide CAS Registry Number: 30279-49-3, Sulfabenzamide CAS Registry Number: 127-71-9, Sulfaethidole CAS Registry Number: 94-19-9, Sulfaguanole CAS Registry Number: 27031-08-9, Sulfalene CAS Registry Number: 152-47-6, Sulfaloxic Acid CAS Registry Number: 14376-16-O, Sulfamerazine CAS Registry Number: 127-79-7, Sulfameter CAS Registry Number: 651-06-9, Sulfamethazine CAS Registry Number: 57-68-1, Sulfamethizole CAS Registry Number: 144-82-1, Sulfamethomidine CAS Registry Number: 3772-76-7, Sulfamethoxazole CAS Registry Number: 723-46-6, Sulfamethoxypyridazine CAS Registry Number: 80-35-3, Sulfametrole CAS Registry Number: 32909-92-5, Sulfamidochrysoidine CAS Registry Number: 103-12-8, Sulfamoxole CAS Registry Number: 729-99-7, Sulfanilamide CAS Registry Number: 63-74-1,4-Sulfanilamidosalicylic Acid CAS Registry Number: 6202-21-7, $N^4$-Sulfanilylsulfanilamide CAS Registry Number: 547-52-4, Sulfanilylurea CAS Registry Number: 547-44-4, N-Sulfanilyl-3,4-xylamide CAS Registry Number: 120-34-3, Sulfaperine CAS Registry Number: 599-88-2, Sulfaphenazole CAS Registry Number: 526-08-9, Sulfaproxyline CAS Registry Number: 116-42-7, Sulfapyrazine CAS Registry Number: 116-44-9, Sulfapyridine CAS Registry Number: 144-83-2, Sulfarside CAS Registry Number: 1134-98-1, Sulfasalazine, CAS Registry Number: 599-79-1, Sulfasomizole CAS Registry Number: 632-00-8, Sulfasymazine CAS Registry Number: 1984-94-7, Sulfathiazole CAS Registry Number: 72-14-O, Sulfathiourea CAS Registry Number: 515-49-1, Sulfisomidine CAS Registry Number: 515-64-O, Sulfisoxazole CAS Registry Number: 127-69-5, Sulpiride CAS Registry Number: 15676-16-1, Sulprostone CAS Registry Number: 60325-46-4, Sulthiame CAS Registry Number: 61-56-3, Sumatriptan CAS Registry Number: 103628-46-2, Tamsulosin CAS Registry Number: 106133-20-4, Taurolidine CAS Registry Number: 19388-87-5, Teclothiazide CAS Registry Number: 4267-05-4, Tevenel® CAS Registry Number: 4302-95-8, Tirofiban CAS Registry Number: 144494-65-5,
Tolazamide CAS Registry Number: 1156-19-0, Tolbutamide CAS Registry Number: 64-77-7, Tolcyclamide CAS Registry Number: 664-95-9, Torsemide CAS Registry Number: 56211-40-6, Trichlormethiazide CAS Registry Number: 133-67-5, Tripamide CAS Registry Number: 73803-48-2, Veralipride CAS Registry Number: 66644-81-3, Xipamide CAS Registry Number: 14293-44-8, Zafirlukast CAS Registry Number: 107753-78-6, Zonisamide CAS Registry Number: 68291-97-4.

In a particularly preferred embodiment, the pharmaceutical compositions of the present invention comprise a salt of celecoxib, (e.g., sodium, lithium, potassium, magnesium, or calcium salt). The salt may be significantly more soluble in water than presently-marketed neutral celecoxib. Due to the high $pK_a$ of celecoxib (approximately 11), salts only form under strongly basic conditions. Typically, more than about one equivalent of a base is required to convert celecoxib to its salt form. A suitable aqueous solution for converting celecoxib to a salt has a pH of about 11.0 or greater, about 11.5 or greater, about 12 or greater, or about 13 or greater. Typically, the pH of such a solution is about 12 to about 13. Although celecoxib is a preferred embodiment, the invention includes other pharmaceutical drugs with a $pK_a$ greater than 9, 9.5, 10, 10.5, 11, 11.5, 12, 12.5, or 13. The drug may normally be in a neutral form or a salt form may already exist.

Salts of the pharmaceutical, such as celecoxib, are formed by reaction of the pharmaceutical with an acceptable base. Acceptable bases include, but are not limited to, metal hydroxides and alkoxides. Metals include alkali metals (sodium, potassium, lithium, cesium), alkaline earth metals (magnesium, calcium), zinc, aluminum, and bismuth. Alkoxides include methoxide, ethoxide, n-propoxide, isopropoxide and t-butoxide. Additional bases include arginine, procaine, and other molecules having amino or guanidinium moieties with sufficiently high $pK_a$'s (e.g., $pK_a$'s greater than about 11, $pK_a$'s greater than about 11.5, or $pK_a$'s greater than about 12), along with compounds having a carbon-alkali metal bond (e.g., t-butyl lithium). Sodium hydroxide and sodium ethoxide are preferred bases. The amount of base used to form a salt is typically about one or more, about two or more, about three or more, about four or more, about five or more, or about ten or more equivalents relative to the pharmaceutical. Preferably, about three to about five equivalents of one or more bases are reacted with the pharmaceutical to form a salt.

A pharmaceutical salt can be transformed into a second pharmaceutical salt by transmetallation or another process that replaces the cation of the first pharmaceutical salt. In one example, a sodium salt of the pharmaceutical is prepared and is subsequently reacted with a second salt such as an alkaline earth metal halide (e.g., $MgBr_2$, $MgCl_2$, $CaCl_2$, $CaBr_2$), an alkaline earth metal sulfate or nitrate (e.g., $Mg(NO_3)_2$, $Mg(SO_4)_2$, $Ca(NO_3)_2$, $Ca(SO_4)_2$), or an alkaline metal salt of an organic acid (e.g. calcium formate, magnesium formate, calcium acetate, magnesium acetate, calcium propionate, magnesium propionate) to form an alkaline earth metal salt of the pharmaceutical.

In a preferred embodiment of the present invention, the pharmaceutical salts are substantially pure. A salt that is substantially pure can be greater than about 80% pure, greater than about 85% pure, greater than about 90% pure, greater than about 95% pure, greater than about 98% pure, or greater than about 99% pure. Purity of a salt can be measured with respect to the amount of salt (as opposed to unreacted neutral pharmaceutical or base) or can be measured with respect to a specific polymorph, co-crystal, solvate, desolvate, hydrate, dehydrate, or anhydrous form of a salt.

A pharmaceutical salt as described herein may be significantly more soluble in water than the existing neutral form, such as the free acid alone or the presently-marketed neutral celecoxib (CELEBREX), and is typically at least about twice, at least about three times, at least about five times, at least about ten times, at least about twenty times, at least about fifty times, or at least about one hundred times more soluble in water or SGF than the neutral form. CELEBREX is marketed by Pfizer Inc. and G. D. Searle & Co. (Pharmacia Corporation), and described on pages 2676-2680 and 2780-2784 of the 2002 edition of the Physicians Desk Reference (also referred to herein as presently-marketed celecoxib). The reference compounds to the present invention herein can refer to the free acid neutral celecoxib, either crystalline or amorphous, or CELEBREX. The solubility depends on whether the salt is tested alone, or as a formulation further comprising the precipitation retardants and enhancers of the invention.

After dissolution, typically in an aqueous or partially-aqueous solution (e.g., where one or more polar organic solvents are a co-solvent), the salt can be neutralized by an acid or by dissolved gases such as carbon dioxide. Typically, the pH of such a solution is 11 or less, 10 or less, or 9 or less. Neutralizing the salt results in precipitation of an amorphous or metastable crystalline form of neutral celecoxib. Typically, neutralizing a pharmaceutical salt includes protonating the majority of negatively charged anions. For celecoxib, protonation results in the formation of amorphous and/or metastable crystalline celecoxib, which are "neutral" (i.e., predominantly uncharged). Preferably, the neutral pharmaceutical (including amorphous and/or metastable crystalline forms thereof, such as celecoxib) comprises 10% mol or less of charged molecules. For example, at about pH 2 (e.g., about the pH of the stomach interior), solutions of the sodium salt of celecoxib precipitate immediately as an amorphous form of neutral celecoxib. The amorphous form converts to a neutral metastable crystalline form, which subsequently becomes the stable, needle-like, insoluble form of neutral celecoxib. For example, amorphous neutral celecoxib formed from the salts of the present invention, e.g., the sodium salt of Example 1, converts to metastable crystalline neutral celecoxib over about 5 to about 10 minutes. Amorphous neutral celecoxib can be characterized by a lack of regular crystal structure, while metastable crystalline neutral celecoxib can be distinguished from typical crystalline neutral celecoxib by the PXRD pattern of isolated material.

Amorphous and metastable crystalline forms of neutral celecoxib are more soluble and likely more readily absorbed by a subject than stable crystalline forms of neutral celecoxib, because the energy required for a drug molecule to escape from a stable crystal is greater than the energy required for the same drug molecule to escape from a non-crystalline, amorphous form or a metastable crystalline form. However, the instability of neutral amorphous and neutral metastable crystalline forms makes them difficult to formulate as pharmaceutical compositions. As is described in U.S. Publication No. 2002/0006951, the teachings of which are incorporated herein by reference in their entirety, without stabilization by a crystallization inhibitor, such as a polymer, amorphous neutral celecoxib converts back to a stable, insoluble crystalline form of free neutral celecoxib. These teachings are incomplete and fall far short of the present invention however, as we have surprisingly found that far superior formulations can be made from the combination of a salt or co-crystal, precipitation retardant, and an optional enhancer. Whereas others have focused on the initial solubilization of celecoxib, the present invention is equally concerned with dissolution and precipitation of the drug (See e.g., WO 02/102376 and WO 01/78724). Moreover, until now, no one has disclosed a salt of celecoxib and the vital role it plays in dissolution and precipitation. Further, no one has taught the addition of an enhancer to a precipitation retardant.

Further aspects of the invention relate to liquid formulations of compounds of the present invention (e.g. celecoxib). In these aspects, the drug is solubilized either directly with the precipitation retardant or with a solubilizer or solvent. Preferred solubilizers are polyethylene oxides. More preferably, the polyethylene oxide is a surfactant. Preferred ethylene oxides comprise the functional group —$(C_2H_4O)_n$— where $n \geq 2$. Other preferred polyethylene oxides are poloxamers having the general formula $HO(C_2H_4O)_a(C_3H_6O)_b(C_2H_4O)_a H$ where $a \geq 2$, where $a \geq 3$, where $a \geq 2$ and $b \geq 30$, where $a \geq 2$ and $b \geq 4$, where $a \geq 2$ and $b \geq 50$, where $a \geq 2$ and $b \geq 60$.

An aminosulfonyl containing API (celecoxib) was crystallized with molecules comprising at least two oxygen atoms (e.g., ether groups) to examine the physical interactions involved in precipitation retardation by the precipitation retardant. From these results, in one aspect of the present invention the precipitation retardant compounds, preferably surfactants, have the following physical properties or characteristics: The retardant molecule comprises at least one, preferably two, 10, 25, 40, 50, 60, 80, 100 or more functional interacting groups, wherein a functional interacting group comprises two oxygen atoms, with each of the two oxygen atoms interacting (e.g., hydrogen bonding) with the API. Preferably the two oxygen atoms interact with the aminosulfonyl group of the API. Preferably the aminosulfonyl group is —$SO_2NH_2$. The two interacting oxygen atoms are preferably separated by between about 3.6 angstroms to about 5.8 angstroms, about 3.9 angstroms to about 5.5 angstroms, 4.3 to about 5.2 angstroms, 4.6 to about 5.0 angstroms, or about 4.7 to about 4.9 angstroms. In one embodiment, the two oxygen atoms are separated by at least three atoms. In another embodiment, the two oxygen atoms are separated by 5 atoms. In one embodiment of a 5 atom separation, the two oxygen atoms are separated by 4 carbons and one oxygen atom. In a more specific 5 atom separation embodiment, the order of the 5 atoms is —C—C—O—C—C—, whereby a single unit of the functional interacting group (including the two interacting oxygen atoms), is —O—C—C—O—C—C—O—.

Glycol ethers can also be used as solubilizers of neutral or other forms of celecoxib including those that conform with the formula:

$$R^1\text{—}O\text{—}((CH_2)_mO)_n\text{—}R^2 \qquad (V)$$

Wherein $R^1$ and $R^2$ are independently hydrogen or $C_{1-6}$ alkyl, $C_{1-6}$ alkenyl, phenyl or benzyl groups, but no more than one of $R^1$ and $R^2$ is hydrogen; m is an integer of 2 to about 5; and n is an integer of 1 to about 20. It is preferred that one of $R^1$ and $R^2$ is a $C_{1-4}$ alkyl group and the other is hydrogen or a $C_{1-4}$ alkyl group; more preferably at least one of $R^1$ and $R^2$ is a methyl or ethyl group. It is preferred that m is 2. It is preferred that n is an integer of 1 to about 4, more preferably 2. Non-surfactant glycol ethers, or more specifically glycol ethers of formula (V) and above, can also be specifically excluded from the present invention. Preferably, the glycol ethers are surfactants.

Compositions of the present invention optionally comprise one or more pharmaceutically acceptable co-solvents. Non-limiting examples of co-solvents suitable for use in compositions of the present invention include any glycol ether listed above; alcohols, for example ethanol and n-butanol; glycols not listed above; for example propylene glycol, 1,3-butanediol and polyethylene glycol such as PEG-400; oleic and linoleic acid triglycerides, for example soybean oil; caprylic/capric triglycerides, for example Miglyol™ 812 of Huls; caprylic/capric mono- and diglycerides, for example Capmul™ MCM of Abitec; polyoxyethylene caprylic/capric glycerides such as polyoxyethylene caprylic/capric mono- and diglycerides, for example Labrasol™ of Gattefosse; propylene glycol fatty acid esters, for example propylene glycol laurate; polyoxyethylene castor oil, for example Cremophor™ EL of BASF; polyoxyethylene glyceryl trioleate, for example Tagat™ TO of Goldschmidt; and lower alkyl esters of fatty acids, for example ethyl butyrate, ethyl caprylate and ethyl oleate.

Celecoxib salts are preferred because they are stable, such that they can be formulated as pharmaceutical compositions and stored before administration to a subject. Only after dissolution and subsequent neutralization do the celecoxib salts precipitate as or transform into substantially amorphous neutral and then substantially metastable crystalline neutral forms. Preferably, dissolution and neutralization of celecoxib salts occur in situ in the gastrointestinal tract of a subject (e.g., stomach, duodenum, ileum), such that a maximal amount of amorphous and/or metastable crystalline neutral celecoxib is present with a maximum amount of celecoxib in solution after administration (e.g., in vivo), rather than before administration.

The salts, hydrates, and solvates of the present invention are non-limiting examples of species which can be solubilized more effectively in water, SGF, and/or SIF than their respective free forms. For example, celecoxib sodium is more soluble in water than celecoxib free acid. A "spring" is defined as a high energy species that drives supersaturation of the API. Such a high energy species is less stable and, therefore, more soluble than an analogous relatively more stable form (e.g., free form, polymorph, etc.). The intrinsic solubility of a high energy species can be 1.5, 2, 3, 4, 5, 6, 7, 8, 9, 10, 25, 50, 75, 100 or more times greater than for an analogous more stable form. A spring can be in the form of, for example, a free acid, a free base, a salt, a liquid, a hydrate, a solvate, a co-crystal, etc. In this example, the sodium salt acts as a "spring" to drive the supersaturation of the API. One embodiment of the present invention provides for an API in a form with improved aqueous solubility. Once dissolution takes place, inhibition of precipitation becomes important. The inhibition of precipitation acts as a "parachute" to slow the rate of API precipitating from solution. Another embodiment of the present invention provides for an API in a formulation which inhibits precipitation upon initial dissolution. Both aspects are of great importance in a pharmaceutical composition. The ability of a pharmaceutical composition to solubilize an API and to maintain the API in solution for a duration long enough to cause the desired therapeutic effect is vital.

Dissolution Modulation:

In another aspect of the present invention, the dissolution profile of the API is modulated whereby the aqueous dissolution rate or the dissolution rate in simulated gastric fluid or in simulated intestinal fluid, or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is dissolution. Because of a limited residence time at the absorption site, APIs that are not dissolved before they are removed from the intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process.

$$\text{Dissolution rate} = KS(C_s - C)$$

where K is the dissolution rate constant, S is the surface area, $C_s$ is the apparent solubility (saturated concentration), and C is the concentration of API in the dissolution media. For rapid API absorption, $C_s - C$ is approximately equal to $C_s$. The dissolution rate of APIs may be measured by conventional means known in the art.

The increase in the dissolution rate of a composition of the present invention, as compared to the neutral free form, may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the free form in the same solution. Conditions under which the dissolution rate is measured are discussed above. The increase in dissolution may be further specified by the time the composition remains supersaturated.

Examples of above embodiments include: compositions with a dissolution rate, at 37 degrees C. and a pH of 7.0, that is increased at least 5 fold over the neutral free form, compositions with a dissolution rate in SGF that is increased at least 5 fold over the neutral free form, compositions with a dissolution rate in SIF that is increased at least 5 fold over the neutral free form.

The present invention demonstrates that the length of time in which celecoxib or other APIs remain in solution can be increased to a surprising high degree by using a salt or co-crystal form with the presence of a precipitation retardant, normally a surfactant (e.g., poloxamer, TPGS, SDS, etc.) and an optional enhancer (e.g., hydroxypropyl cellulose) as discussed herein. The presence of these agents allows the formation of a supersaturated solution of the API and a relatively high concentration of API will remain in solution for an extended period of time (as compared to the neutral free acid). The presence of these components does not preclude the presence of other further agents, including further surfactants such as, polyethylene glycol and polyoxyethylene sorbitan esters. The additional presence of other suitable surfactants is also not precluded and these are listed herein. Further additional agents which might slow the rate of precipitation such as polyvinylpyrrolidone are also not precluded. Neutral free celecoxib, for example, has a solubility in water of less than 1 microgram/mL and cannot be maintained as a supersaturated solution for any appreciable time. The present invention has drawn compositions that can be maintained for a period of time (e.g., 15, 30, 45, 60 minutes and longer) as supersaturated solutions at concentrations 2, 3, 5, 7, 10, 20, 30, 40, 50, 60, 70, 80, 90, or 100% greater, or solubilities increased by 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold over the neutral free form in the same solution (e.g., water or SGF).

The amount of precipitation inhibitor or enhancer may each or together be less than 1, 2, 3, 4, 5, 6, 7, 8, 9, 10, 15, 20, 25, 30, 35, 40, 45, 50, 55, 60, 70, 80, or 90 percent w/w of the formulated pharmaceutical. The percent w/w for either or both precipitation inhibitor and enhancer may also be in a range represented by any two integers of 1, 2, 3, 4, 5, 6, 7, 8, 9, 10, 15, 20, 25, 30, 35, 40, 45, 50, 55, 60, 70, 80, or 90.

Celecoxib salts of the present invention are typically stable (i.e., more than 90% of the celecoxib salt does not change in composition or crystalline structure) for at least about one week, at least about one month, at least about two months, at least about three months, at least about six months, at least about nine months, at least about one year, or at least about two years at room temperature in the absence of moisture. Room temperature typically ranges from about 15 degrees C. to about 30 degrees C. The absence of moisture, as defined herein, refers to celecoxib salts not contacting quantities of liquid, particularly water or alcohols. For purposes of the present invention, gases such as water vapor are not considered to be moisture.

The compositions of the present invention, including the active pharmaceutical ingredient (API) and formulations comprising the API, are suitably stable for pharmaceutical use. Preferably, the API or formulations thereof of the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient (RH), 75% (RH), or as any single integer between 1 to 99% (RH).

Bioavailability Modulation:

The methods of the present invention are used to make a pharmaceutical API formulation with greater solubility, dissolution, bioavailability, AUC, reduced time to $T_{max}$, the average time from administration to reach peak blood serum levels, higher $C_{max}$, the average maximum blood serum concentration of API following administration, and longer $T_{1/2}$, the average terminal half-life of API blood serum concentration following $T_{max}$, when compared to the neutral free form.

AUC is the area under the curve of plasma concentration of API (not logarithm of the concentration) against time after API administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, $AUC = D/Cl_T$, for single compartment systems obeying first-order elimination kinetics Alternatively, $AUC=C_0/k_{el}$. With routes other than the intravenous, $AUC=F \cdot D/Cl_T$, where F is the absolute bioavailability of the API.

Thus, in a further aspect, the present invention provides a process for modulating the bioavailability of an API when administered in its normal and effective dose range, whereby the AUC is increased, the time to $T_{max}$ is reduced, or $C_{max}$ is increased, which process comprises:

(1) forming a salt or co-crystal of an API;

(2) combining the salt or co-crystal with a precipitation retardant, and optionally, further with an enhancer.

Examples of the above embodiments include: compositions with a time to $T_{max}$ that is reduced by at least 10% as compared to the neutral free form, compositions with a time to $T_{max}$ that is reduced by at least 20% over the free form, compositions with a time to $T_{max}$ that is reduced by at least 40% over the free form, compositions with a time to $T_{max}$ that is reduced by at least 50% over the free form, compositions with a $T_{max}$ that is reduced by at least 60% over the free form, compositions with a $T_{max}$ that is reduced by at least 70% over the free form, compositions with a $T_{max}$ that is reduced by at least 80% over the free form, compositions with a $C_{max}$ that is increased by at least 20% over the free form, compositions with a $C_{max}$ that is increased by at least 30% over the free form, compositions with a $C_{max}$ that is increased by at least 40% over the free form, compositions with a $C_{max}$ that is increased by at least 50% over the free form, compositions with a $C_{max}$ that is increased by at least 60% over the free form, compositions with a $C_{max}$ that is increased by at least 70% over the free form, compositions with a $C_{max}$ that is increased by at least 80% over the free form, compositions with an AUC that is increased by at least 10% over the free form, compositions with an AUC that is increased by at least 20% over the free form, compositions with an AUC that is increased by at least 30% over the free form, compositions with an AUC that is increased by at least 40% over the free form, compositions with an AUC that is increased by at least 50% over the free form, compositions with an AUC that is increased by at least 60% over the free form, compositions with an AUC that is increased by at least 70% over the free form, or compositions with an AUC that is increased by at least 80% over the free form.

The uptake of a drug by a subject can also be assessed in terms of maximum blood serum concentration and time to reach maximum blood serum concentration. Pharmaceutical compositions with a more rapid onset to therapeutic effect typically reach a higher maximum blood serum concentration ($C_{max}$) a shorter time after oral administration ($T_{max}$). Preferably, compositions, preferably including salts, of the present invention have a higher $C_{max}$ and/or a shorter $T_{max}$ than presently-marketed celecoxib. The $T_{max}$ for the compositions of the present invention occurs within about 60 minutes, 55 minutes, 50 minutes, 45 minutes, 40 minutes, 35 minutes, 30 minutes, 25 minutes, 20 minutes, 15 minutes, 10 minutes, or within about 5 minutes of administration (e.g., oral administration). Even more preferably, the therapeutic effects of compositions of the present invention begin to occur within about 60 minutes, 55 minutes, 50 minutes, 45 minutes, 40 minutes, 35 minutes, 30 minutes, within about 25 minutes, within about 20 minutes, within about 15 minutes, within about 10 minutes, or within about 5 minutes of administration (e.g., oral administration). In U.S. Pat. No. 6,579,895, Karim et al. report about a 2.5-fold increase in $C_{max}$ over that of presently-marketed celecoxib (CELEBREX) by the suspension of neutral free form celecoxib particles in an aqueous liquid. The present invention produces an increase in $C_{max}$ of about four-fold over that of the presently-marketed drug. In addition, the present invention yields an increase in the AUC of at least about two-fold over that of presently-marketed celecoxib.

Compositions of the present invention have a bioavailability greater than neutral celecoxib and currently-marketed CELEBREX. In several embodiments, the compositions of the present invention have a bioavailability of at least 50%, 60%, 65%, 70%, 75%, 80%, 85%, 87%, 90%, 91%, 92%, 93%, 94%, 95%, 96%, 97%, 98%, or 99% greater than that of neutral celecoxib and currently-marketed CELEBREX.

Administration of the present invention to a subject may result in effective pain relief. The desired therapeutic effect calls for inter alia an appropriate blood serum concentration of the API. Effective blood serum concentrations of celecoxib can range based on many factors (e.g., age, weight, etc.) but generally are about 10 ng/mL to about 500 ng/mL, or about 25 ng/mL to 400 ng/mL, or about 50 ng/mL to about 300 ng/mL. Specifically, about 250 ng/mL is often suitable for effective pain relief. In general, an effective dosage of celecoxib will be found in the range of about 1 mg/kg to about 6 mg/kg body weight. For an average 75 kg subject, this range equates to a celecoxib dose of about 75 mg to about 450 mg. This is particularly in view of the extensive binding of celecoxib to plasma albinum which was known to occur following oral administration (Davies et al., *Clin. Pharmacokinet.* 38:225-242, 2000 and U.S. Pat. No. 6,579,895 are herein incorporated as references in their entirety). Thus, one could not have predicted that a particular blood serum concentration would produce analgesia.

An "effective pain-relieving concentration" or "effective pain-relieving blood serum concentration" as used herein is intended to mean a blood serum level in a patient which when tested in a standardized test involving patient scoring of the severity of pain, achieves a mean score indicating pain relief. In one such test as described herein below, patients score pain on a scale of from 0 (no reduction in severity of pain) to 4 (complete relief of pain) and a mean score equal to or greater than a given value is deemed to constitute effective pain-relief. A mean score of 0.5 or greater and, more preferably, 1.0 or greater in such a test, as exemplified herein, is deemed to constitute effective pain relief. The skilled artisan will appreciate, however, that other approaches can be used to assess the severity of pain and relief from such pain.

Thus, one aspect of the present invention involves a therapeutic method for analgesia in which a composition comprising a celecoxib salt or co-crystal is administered orally to a subject, in a formulation that provides detectable pain relief not later than about 30 minutes after oral administration. By "detectable pain relief", it is meant that the formulation produces effective pain relief that is measurable by a standard method such as that described above. For example, a formulation, which achieves a mean score of 0.5 or greater and, more preferably, 1.0 or greater on a scale of from 0 to 4 in a testing system as described above, is deemed to provide detectable pain relief. The invention is not limited to use of any particular type of formulation, so long as it exhibits the pharmacokinetic profile defined herein. Examples of suitable formulation types are described below.

Protocols for conducting human pharmacokinetic studies are well known in the art and any standard protocol can be used to determine whether a particular celecoxib formulation satisfies the pharmacokinetic criteria set out herein. An example of a suitable protocol is described below.

An advantage of the present invention is that relief of pain, even intense pain as can occur, for example, following oral, general or orthopedic surgery, is achieved significantly faster, i.e., in a significantly shorter time after administration, than is achievable with standard formulations of celecoxib.

Any standard pharmacokinetic protocol can be used to determine blood serum concentration profile in humans following oral administration of a celecoxib formulation, and thereby establish whether that formulation meets the pharmacokinetic criteria set out herein.

Illustratively, a randomized single-dose crossover study can be performed using a group of healthy adult human subjects. The number of subjects is sufficient to provide adequate control of variation in a statistical analysis, and is typically about 10 or greater, although for certain purposes a smaller group can suffice. Each subject receives, by oral administration at time zero, a single dose (e.g., 200 mg) of a test formulation of celecoxib, normally at around 8 am following an overnight fast. The subject continues to fast and remains in an upright position for about 4 hours after administration of the celecoxib formulation. Blood samples are collected from each subject before administration (e.g., 15 minutes prior to administration) and at several intervals after administration. For the present purpose it is preferred to take several samples within the first hour, and to sample less frequently thereafter. Illustratively, blood samples can be collected 15, 30, 45, 60 and 90 minutes after administration, then every hour from 2 to 10 hours after administration. Optionally additional blood samples can be taken later, for example 12 and 24 hours after administration. If the same subjects are to be used for study of a second test formulation, a period of at least 7 days is allowed to elapse before administration of the second formulation. Plasma is separated from the blood samples by centrifugation and the separated plasma is analyzed for celecoxib by a validated high performance liquid chromatography (HPLC) procedure with a lower limit of detection of 10 ng/mL (see for example, Paulson et al., Drug Metab. Dispos. 27:1133-1142, 1999; Paulson et al., Drug Metab. Dispos. 28:308-314, 2000; Davies et al). Blood serum concentrations of celecoxib referenced herein are intended to mean total celecoxib concentrations including both free and bound celecoxib as determined upon extraction from the plasma sample and HPLC detection according to methods known in the art such as those identified above. Ailments treatable with celecoxib and salts thereof of the present invention are discussed below. Treatment of chronic pain is a preferred embodiment of the present invention.

Dose Response Modulation:

In a further aspect the present invention provides a process for improving the dose response of an API by making a composition of the present invention.

Dose response is the quantitative relationship between the magnitude of response and the dose inducing the response and may be measured by conventional means known in the art. The curve relating effect (dependent variable) to dose (independent variable) for an API-cell system is the "dose-response curve". Typically, the dose-response curve is the measured response to an API plotted against the dose of the API (mg/kg) given. The dose response curve can also be a curve of AUC against the dose of the API given.

The dose-response curve for presently-marketed celecoxib is nonlinear. Preferably, the dose-response curve for celecoxib salt and co-crystal compositions of the present invention is linear or contains a larger linear region than presently-marketed celecoxib. Also, the absorption or uptake of presently-marketed celecoxib depends in part on food effects, such that uptake of celecoxib increases when taken with food, especially fatty food. Preferably, uptake of celecoxib salts of the present invention exhibits a decreased dependence on food, such that the difference in uptake of celecoxib salts when taken with food and when not taken with food is less than the difference in uptake of presently-marketed celecoxib.

Decreasing Hygroscopicity:

In a still further aspect the present invention provides for APIs with decreased hygroscopicity and a method for decreasing the hygroscopicity of an API by making the same. An aspect of the present invention provides a pharmaceutical composition of an API that is less hygroscopic than amorphous or crystalline free form. Hygroscopicity can be assessed by dynamic vapor sorption analysis, in which 5-50 mg of the compound is suspended from a Calm microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until equilibrium criteria are met. Typical equilibrium criteria include weight changes of less than 0.01% change over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous above 75% RH but below 95% RH, the experiment should be repeated with a fresh sample and the relative humidity range for the cycling should be narrowed to 5-75% RH or 10-75% RH instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or more preferably, 0.5% weight at 25 degrees C. when cycled between 10 and 75% RH (relative humidity at 25 degrees C.). The non-hygroscopic molecule more preferably should not gain or lose more than 1.0%, or more preferably, 0.5% weight when cycled between 5 and 95% RH at 25 degrees C., or 0.25% of its weight between 10 and 75% RH. Most preferably, a non-hygroscopic molecule will not gain or lose more than 0.25% of its weight when cycled between 5 and 95% RH.

Alternatively, for purposes of the present invention, hygroscopicity can be defined using the parameters of Callaghan et al., Equilibrium Moisture Content of Pharmaceutical Excipients, in API Dev. Ind. Pharm., Vol. 8, pp. 335-369 (1982). Callaghan et al. classified the degree of hygroscopicity into four classes.

| | |
|---|---|
| Class 1: Non-hygroscopic | Essentially no moisture increases occur at relative humidities below 90%. |
| Class 2: Slightly hygroscopic | Essentially no moisture increases occur at relative humidities below 80%. |
| Class 3: Moderately hygroscopic | Moisture content does not increase more than 5% after storage for 1 week at relative humidities below 60%. |

| | |
|---|---|
| Class 4: Very hygroscopic | Moisture content increase may occur at relative humidities as low as 40 to 50%. |

Alternatively, for purposes of the present invention, hygroscopicity can be defined using the parameters of the European Pharmacopoeia Technical Guide (1999, p. 86) which has defined hygroscopicity, based on the static method, after storage at 25 degrees C. for 24 h at 80% RH:

Slightly hygroscopic: Increase in mass is less than 2% m/m and equal to or greater than 0.2% m/m.

Hygroscopic: Increase in mass is less than 15% m/m and equal to or greater than 0.2% m/m.

Very Hygroscopic: Increase in mass is equal to or greater than 15% m/m.

Deliquescent: Sufficient water is absorbed to form a liquid.

Compositions of the present invention can be set forth as being in Class 1, Class 2, or Class 3, or as being Slightly hygroscopic, Hygroscopic, or Very Hygroscopic. Compositions of the present invention can also be set forth based on their ability to reduce hygroscopicity. Thus, preferred compositions of the present invention are less hygroscopic than the neutral free form. Further included in the present invention are compositions that do not gain or lose more than 1.0% weight at 25 degrees C. when cycled between 10 and 75% RH, wherein the reference compound gains or loses more than 1.0% weight under the same conditions. Further included in the present invention are compositions that do not gain or lose more than 0.5% weight at 25 degrees C. when cycled between 10 and 75% RH, wherein the reference compound gains or loses more than 0.5% or more than 1.0% weight under the same conditions. Further included in the present invention are compositions that do not gain or lose more than 1.0% weight at 25 degrees C. when cycled between 5 and 95% RH, wherein the reference compound gains or loses more than 1.0% weight under the same conditions. Further included in the present invention are compositions that do not gain or lose more than 0.5% weight at 25 degrees C. when cycled between 5 and 95% RH, wherein the reference compound gains or loses more than 0.5% or more than 1.0% weight under the same conditions. Further included in the present invention are compositions that do not gain or lose more than 0.25% weight at 25 degrees C. when cycled between 5 and 95% RH, wherein the reference compound gains or loses more than 0.5% or more than 1.0% weight under the same conditions.

Further included in the present invention are compositions that have a hygroscopicity (according to Callaghan et al.) that is at least one class lower than the reference compound or at least two classes lower than the reference compound. Included are a Class 1 composition of a Class 2 reference compound, a Class 2 composition of a Class 3 reference compound, a Class 3 composition of a Class 4 reference compound, a Class 1 composition of a Class 3 reference compound, a Class 1 composition of a Class 4 reference compound, or a Class 2 composition of a Class 4 reference compound.

Further included in the present invention are compositions that have a hygroscopicity (according to the European Pharmacopoeia Technical Guide) that is at least one class lower than the reference compound or at least two classes lower than the reference compound. Non-limiting examples include a Slightly hygroscopic composition of a Hygroscopic reference compound, a Hygroscopic composition of a Very Hygroscopic reference compound, a Very Hygroscopic composition of a Deliquescent reference compound, a Slightly hygroscopic composition of a Very Hygroscopic reference compound, a Slightly hygroscopic composition of a Deliquescent reference compound, a Hygroscopic composition of a Deliquescent reference compound.

In another aspect of the present invention, a correlation exists between in vivo dissolution and in vitro dissolution. For example, dissolution of celecoxib sodium hydrate formulations in SGF at 37 degrees C. is comparable to the pharmacokinetic data obtained in dogs in Example 7. For instance, the magnitude of $C_{max}$ in the pharmacokinetic study correlates with the $C_{max}$ obtained with in vitro studies completed with PLURONIC F127 and HPC at equal weight ratios to celecoxib free acid. Other pharmacokinetic parameters such as, for example, $T_{max}$ and AUC, can also be closely related between both types of experiments.

Celecoxib salts can be characterized by differential scanning calorimetry (DSC). The sodium salt of celecoxib prepared in Example 1 is characterized by at least 3 overlapping endothermic transitions between 50 degrees C. and 110 degrees C. (FIG. 1). Conditions for DSC can be found in the Exemplification.

Figure 2:
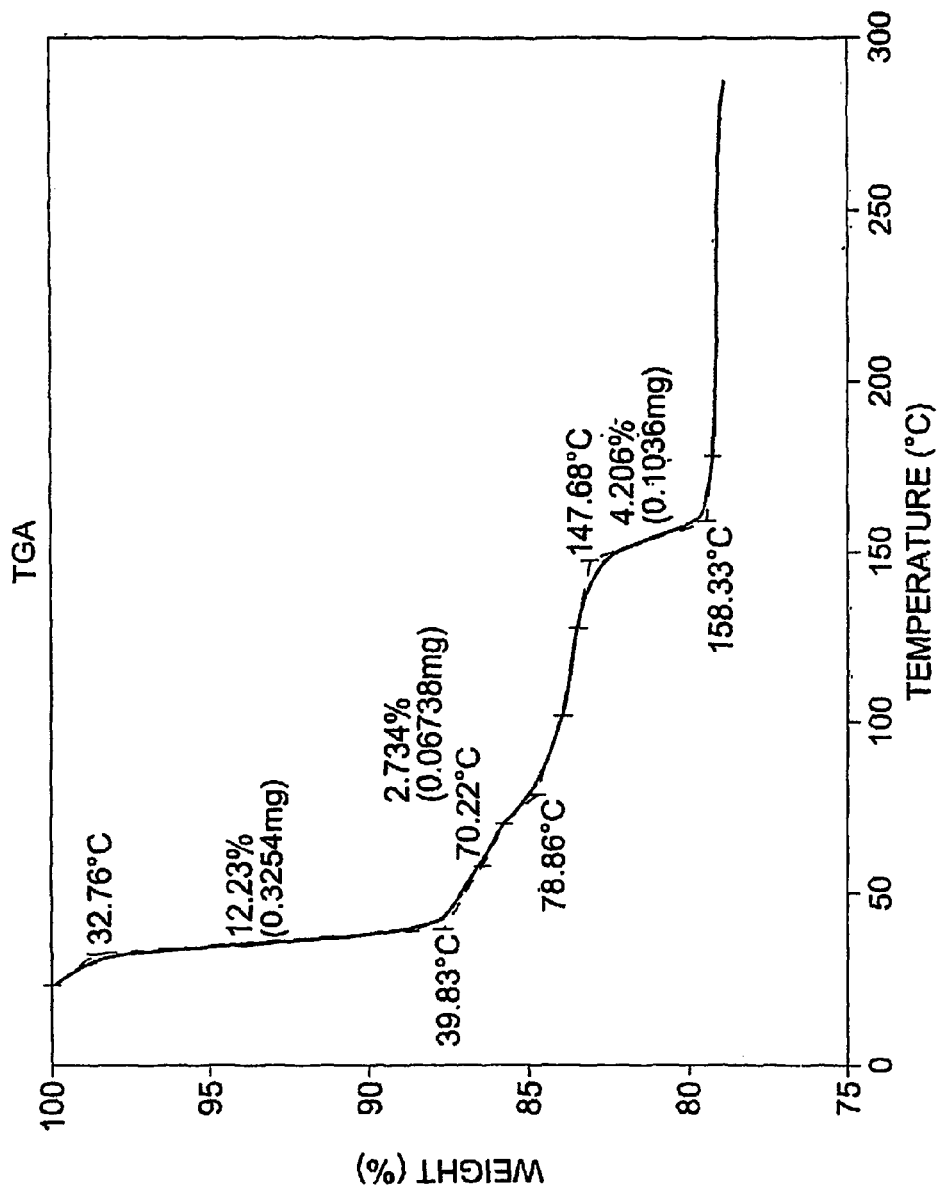
FIG. 2 shows a reproduction of a thermogravimetric analysis (TGA) thermogram of the sodium salt of celecoxib prepared by Example 1, which was conducted from about 30 degrees C. to about 160 degrees C.

Celecoxib salts can be characterized by thermogravimetric analysis (TGA). The sodium salt product prepared by Example 1 was characterized by TGA, and was determined to have about 3 loosely bound equivalents of water that evaporated between about 30 degrees C. and about 40 degrees C., one more tightly bound equivalent of water that evaporated between about 40 degrees C. and about 100 degrees C., and one very tightly bound equivalent of water that evaporated between about 140 degrees C. and about 160 degrees C. (FIG. 2). As described herein however, the sodium salt can exist at different states of hydration depending on the humidity, temperature, and other conditions. Conditions for TGA can be found in the Exemplification section.

Figure 3:
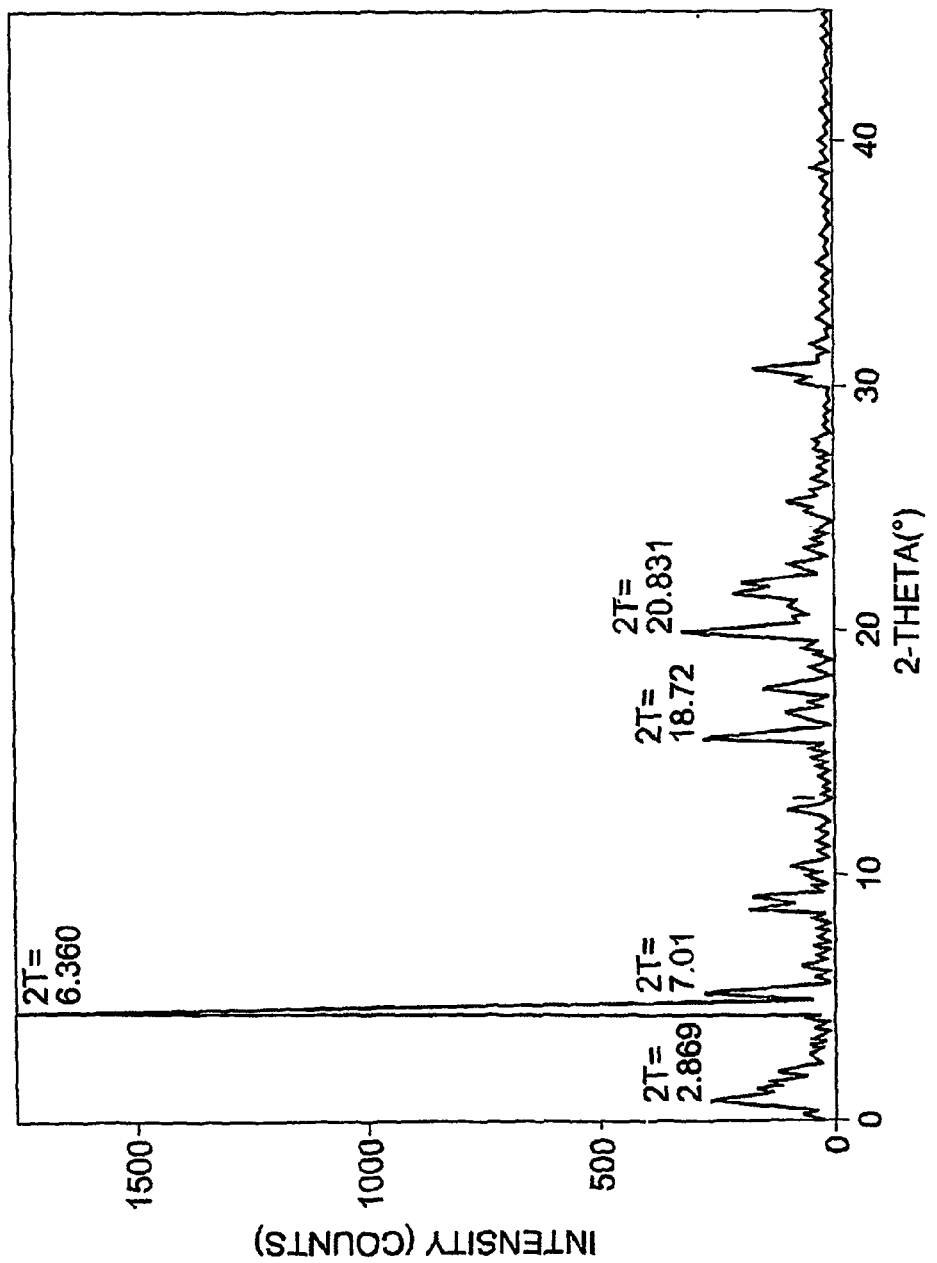
FIG. 3 shows a reproduction of a PXRD diffractogram of the sodium salt of celecoxib prepared by Example 1.

Celecoxib salts of the present invention can also be characterized by powder X-ray diffraction (PXRD). The sodium salt of celecoxib prepared by Example 1 had an intense reflection or peak at a 2-theta angle of 6.36 degrees, and other reflections or peaks at 7.01, 16.72, and 20.93 degrees (FIG. 3). Conditions for PXRD can be found in the Exemplification.

In one embodiment of the present invention, a solid form of celecoxib shows a characteristic absence of a Raman scattering peak at 906 cm$^{-1}$ (e.g., salts, solvates, etc.). The Raman scattering spectrum of celecoxib free acid comprises a peak at this position.

Celecoxib salts may comprise solvate molecules and can occur in a variety of solvation states, also known as solvates. Thus, celecoxib salts can exist as crystalline polymorphs. Polymorphs are different crystalline forms of the same drug substance, and in the present use of the term include solvates and hydrates. For example, different polymorphs of a celecoxib salt can be obtained by varying the method of preparation (compare Examples). Crystalline polymorphs typically have different solubilities, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

Suitable solvate molecules include water, alcohols, other polar organic solvents, and combinations thereof. Alcohols include methanol, ethanol, n-propanol, isopropanol, n-butanol, isobutanol, propylene glycol and t-butanol. Propylene glycol solvates are particularly preferred because they are more stable and less hygroscopic than other forms. Alcohols also include polymerized alcohols such as polyalkylene glycols (e.g., polyethylene glycol, polypropylene glycol). In an embodiment, water is the solvent. In embodiments of the invention, a celecoxib salt contains about 0.0%, less than 0.5%, 0.5, less than 1.0%, 1.0, less than 1.5%, 1.5, less than 2.0%, 2.0, 2.5, 3.0, 3.5, 4.0, 4.5, 5.0, 5.5 or about 6.0 equivalents, or about 1.0 to about 6.0, 2.0 to about 5.0, 3.0 to about 6.0, 3.0 to about 5.0, 1.0 to about 4.0, 2.0 to about 4.0, 1.0 to about 3.0, 2.0 to about 3.0, 0.0 to about 3.0, 0.5 to about 3.0, 0.0 to about 2.0, 0.5 to about 2.0, 0.0 to about 1.5, 0.5 to about 1.5, 1.0 to about 1.5, or 0.5 to about 1.0 equivalents of water per equivalent of salt. The amount of water equivalents in the above hydrates is primarily affected by the experimental conditions (e.g., temperature). Solvate molecules can be removed from a crystalline salt, such that the salt is either a partial or complete desolvate. If the solvate molecule is water (forming a hydrate), then a desolvated salt is said to be a dehydrate. A salt with all water removed is anhydrous. Solvate molecules can be removed from a salt by methods such as heating, treating under vacuum or reduced pressure, blowing dry air over a salt, or a combination thereof. Following desolvation, there are typically about one to about five equivalents, about one to about four equivalents, about one to about three equivalents, or about one to about two equivalents of solvent per equivalent of salt in a crystal.

Pharmaceuticals including celecoxib, can co-crystallize with one or more other substances. The term "co-crystal" as used herein means a crystalline material comprised of two or more unique solids at room temperature, each containing distinctive physical characteristics, such as structure, melting point and heats of fusion. Solvates of API compounds that do not further comprise a co-crystal forming compound are not co-crystals according to the present invention. The co-crystals may however, include one or more solvent molecules in the crystalline lattice. That is, solvates of co-crystals, or a co-crystal further comprising a solvent or compound that is a liquid at room temperature, is included in the present invention, but crystalline material comprised of only one solid and one or more liquids (at room temperature) are not included by the term "co-crystal". The co-crystals may include a co-crystal former and a salt of an API, but the API and the co-crystal former of the present invention are constructed or bonded together through hydrogen bonds. Other modes of molecular recognition may also be present including, π-stacking, guest-host complexation and van der Waals interactions. Of the interactions listed above, hydrogen-bonding is the dominant interaction in the formation of the co-crystal, whereby a non-covalent bond is formed between a hydrogen bond donor of one of the moieties and a hydrogen bond acceptor of the other. An alternative embodiment provides for a co-crystal wherein the co-crystal former is a second API. In another embodiment, the co-crystal former is not an API.

In several embodiments of the present invention, the composition is a co-crystal. In other embodiments the co-crystal formers are selected from one or two (for ternary co-crystals) of the following: saccharin, nicotinamide, pyridoxine (4-pyridoxic acid), acesulfame, glycine, arginine, asparagine, cysteine, glutamine, histidine, isoleucine, lysine, methionine, phenylalanine, proline, threonine, tyrosine, valine, aspartic acid, glutamic acid, tryptophan, adenine, acetohydroxamic acid, alanine, allopurinaol, 4-aminobenzoic acid, cyclamic acid, 4-ethoxyphenyl urea, 4-aminopyridine, leucine, nicotinic acid, serine, tris, vitamin k5, xylito, succinic acid, tartaric acid, pyridoxamine, ascorbic acid, hydroquinone, salicylic acid, benzoic acid, caffeine, benzenesulfonic acid, 4-chlorobenzene-sulfonic acid, citric acid, fumaric acid, gluconic acid, glutaric acid, glycolic acid, hippuric acid, maleic acid, malic acid, mandelic acid, malonic acid, 1,5-napthalene-disulfonic acid (armstrong's acid), clemizole, imidazole, glucosamine, piperazine, procaine, or urea.

In another embodiment of the present invention, a solid form of celecoxib can give rise to a distinct PXRD diffractogram. This can be caused by polymorphism, a variable hydrate, a different environmental condition, etc. In one embodiment, the propylene glycol solvate of celecoxib sodium salt can yield a PXRD pattern with theabsence or presence of a peak at 8.21 degrees 2-theta. In another embodiment, the propylene glycol solvate of celecoxib sodium salt can yield a PXRD pattern with theabsence or presence of a peak at 8.79 degrees 2-theta.

In another embodiment, a trihydrate of the propylene glycol solvate of celecoxib sodium salt is observed under 10 to 60 percent relative humidity (RH). In another embodiment, an anhydrous form of the propylene glycol solvate of celecoxib sodium salt is observed under 0 percent relative humidity (RH). In another embodiment, a dihydrate of the propylene glycol solvate of celecoxib sodium salt is observed under 40 to 60 percent relative humidity (RH). In another embodiment, a monohydrate of the celecoxib sodium salt is observed under 10 to 20 percent relative humidity (RH). In another embodiment, a trihydrate of the celecoxib sodium salt is observed under 40 to 70 percent relative humidity (RH). In another embodiment, an anhydrous form of the propylene glycol solvate of celecoxib potassium salt is observed under 0 to 40 percent relative humidity (RH).

Celecoxib salts may be prepared by contacting celecoxib with a solvent. Suitable solvents include water, alcohols, other polar organic solvents, and combinations thereof. Water and isopropanol are preferred solvents. Celecoxib is reacted with a base, where suitable bases are listed above, such that celecoxib forms a salt and preferably dissolves. Bases can be added to celecoxib with the solvent (i.e., dissolved in the solvent), such that celecoxib is solvated and deprotonated essentially simultaneously, or bases can be added after the celecoxib has been contacted with solvent (e.g., see Examples). In the latter scenario, bases can either be dissolved in a solvent, which can be either the solvent already contacting celecoxib or a different solvent, can be added as a neat solid or liquid, or a combination thereof. Sodium hydroxide and sodium ethoxide are preferred bases. The amount of base required is discussed above. The solvent can be evaporated to obtain crystals of the celecoxib salt, or the celecoxib salt may precipitate and/or crystallize independent of evaporation. Crystals of a celecoxib salt can be filtered to remove bulk solvent. Methods of removing solvated solvent molecules are discussed above.

Excipients employed in pharmaceutical compositions of the present invention can be solids, semi-solids, liquids or combinations thereof. Preferably, excipients are solids. Compositions of the invention containing excipients can be prepared by any known technique of pharmacy that comprises admixing an excipient with a drug or therapeutic agent. A pharmaceutical composition of the invention contains a desired amount of celecoxib per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the drug, such as tablets or capsules.

Non-limiting examples of excipients that can be used to prepare pharmaceutical compositions of the invention follow.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (e.g., Avicel™ PH (of FMC)), either individually or in combination, are preferred diluents. These diluents are chemically compatible with celecoxib. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also further prevent or inhibit crystallization or recrystallization/precipitation of a celecoxib salt of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the celecoxib in close association with water, a condition that is believed to improve bioavailability of the composition. Such wetting agents can also be useful in solubilizing or increasing the solubility of metal salts of celecoxib.

Non-limiting examples of surfactants that can be used as wetting agents (not necessarily as the precipitation retardant) in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred. Other excipients such as colorants, flavors and sweeteners are known in the pharmaceutical arts and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the celecoxib in an aqueous medium. Without being bound by theory, it is believed that the effervescent agent is effective to accelerate dispersion of celecoxib from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10% by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid organic acids useful in the invention include citric acid, tartaric acid (as D-, L-, or D/L-tartaric acid), malic acid, maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of celecoxib typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of a metal salt of celecoxib; about 10% to about 50%, about 25% to about 50%, about 30% to about 45%, or about 30% to about 35% by weight of an excipient which inhibits precipitation; and about 5% to about 50%, about 10% to about 40%, about 15% to about 35%, or about 30% to about 35% by weight of a binding agent. In one example, the weight ratio of the metal salt of celecoxib to the excipient which inhibits precipitation to binding agent is about 1 to 1 to 1.

The resulting formulations described above are both physically and chemically stable. The present invention can be prepared in solid dosage form well in advance (e.g., months) of oral administration without the risk of premature neutralization or precipitation of the API. Liquid suspensions of celecoxib particles can suffer from a tendency of the particles to agglomerate and/or increase in size by crystal growth after only several minutes of standing. This crystal growth can significantly reduce the bioavailability and therapeutic effect of the drug.

Solid dosage forms of the invention can be prepared by any suitable process, and are not limited to processes described herein. An illustrative process comprises (i) a step of blending a celecoxib salt of the invention with one or more excipients to form a blend, and (ii) a step of tableting or encapsulating the blend to form tablets or capsules, respectively.

In a preferred process, solid dosage forms are prepared by a process comprising (a) a step of blending the celecoxib salt to form a blend, (b) a step of granulating the blend to form a granulate, and (c) a step of tableting or encapsulating the blend to form tablets or capsules respectively. Step (b) can be accomplished by any dry or wet granulation technique known in the art. A celecoxib salt is advantageously granulated to form particles of about 10 micrometer to about 1000 micrometer, about 25 micrometer to about 500 micrometer, or about 50 micrometer to about 300 micrometer. More specifically, particles of about 100 micrometers in diameter are well suited to yield the desired therapeutic effect. One or more diluents, one or more disintegrants and one or more binding agents may be added, for example in the blending step, a wetting agent can optionally be added, for example in the granulating step, and one or more disintegrants may be added after granulating but before tableting or encapsulating. A lubricant may be added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein a celecoxib salt is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Celecoxib dosage forms of the invention preferably comprise celecoxib in a daily dosage amount of about 10 mg to about 1000 mg, more preferably about 50 mg to about 100 mg, about 100 mg to about 150 mg, 150 mg to about 200 mg, 200 mg to about 250 mg, 250 mg to about 300 mg, 300 mg to about 350 mg, 350 mg to about 400 mg, 400 mg to about 450 mg 450 mg to about 500 mg, 500 mg to about 550 mg, 550 mg to about 600 mg, 600 mg to about 700 mg, and 700 mg to about 800 mg.

Pharmaceutical compositions of the invention comprise one or more orally deliverable dose units. Each dose unit comprises celecoxib in a therapeutically effective amount that is preferably those listed. The term "dose unit" herein means a portion of a pharmaceutical composition that contains an amount of a therapeutic or prophylactic agent, in the present case celecoxib, suitable for a single oral administration to provide a therapeutic effect. Typically one dose unit, or a small plurality (up to about 4) of dose units, in a single administration provides a dose comprising a sufficient amount of the agent to result in the desired effect. Administration of such doses can be repeated as required, typically at a dosage frequency of 1, 2, 3, or 4 times per day.

It will be understood that a therapeutically effective amount of celecoxib for a subject is dependent inter alia on the body weight of the subject. A "subject" to which a celecoxib salt or a pharmaceutical composition thereof can be administered includes a human subject of either sex and of any age, and also includes any nonhuman animal, particularly a warm-blooded animal, more particularly a domestic or companion animal, illustratively a cat, dog or horse. When the subject is a child or a small animal (e.g., a dog), for example, an amount of celecoxib (measured as the neutral form of celecoxib, that is, not including counterions in a salt or water in a hydrate) relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib is likely to require dose units containing a relatively greater amount of celecoxib.

Typical dose units in a pharmaceutical composition of the invention contain about 10, 20, 25, 37.5, 50, 75, 100, 125, 150, 175, 200, 250, 300, 350, or 400 mg of celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg. Other doses that are not in current use for CELEBREX may become preferred, if the bioavailability is changed with a novel formulation. For instance, 300 mg may become a preferred dose for certain indications.

A dose unit containing a particular amount of celecoxib can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

For pain management, pharmaceutical compositions of the present invention can be used to provide a daily dosage of celecoxib of about 50 mg to about 1000 mg, preferably about 100 mg to about 600 mg, more preferably about 150 mg to about 500 mg, and still more preferably about 175 mg to about 400 mg, for example about 200 mg. A daily dose of celecoxib of about 0.7 to about 13 mg/kg body weight, preferably about 1.3 to about 8 mg/kg body weight, more preferably about 2 to about 6.7 mg/kg body weight, and still more preferably about 2.3 to about 5.3 mg/kg body weight, for example about 2.7 mg/kg body weight, is generally appropriate when administered in a pharmaceutical composition of the invention. The daily dose can be administered in one to about four doses per day. Administration at a rate of one 50 mg dose unit four times a day, one 100 mg dose unit or two 50 mg dose units twice a day, or one 200 mg dose unit, two 100 mg dose units or four 50 mg dose units once a day is preferred.

The term "oral administration" herein includes any form of delivery of a therapeutic agent or a composition thereof to a subject wherein the agent or composition is placed in the mouth of the subject, whether or not the agent or composition is immediately swallowed, although each are embodiments of the invention. Thus, "oral administration" includes buccal and sublingual as well as esophageal administration. Absorption of the agent can occur in any part or parts of the gastrointestinal tract including the mouth, esophagus, stomach, duodenum, ileum and colon. The term "orally deliverable" herein means suitable for oral administration.

In a particular embodiment of the present invention, multiple pellets can be incorporated into the formulation, each with a distinct coating thickness. This will allow each pellet to dissolve at an exclusive, predetermined time interval following administration. The result is an increased duration of the desired therapeutic effect. Such a controlled-release (CR) formulation can reduce the frequency at which a pharmaceutical must be administered to a patient, thereby decreasing the total amount of drug intake. Improvements such as reduced side effects, reduced drug accumulation, and reduced fluctuations in blood serum level are some advantages of controlled-release formulations. A further embodiment allows the formulation to include more than one therapeutic agent. Pellets of two or more APIs can be incorporated, each with distinct coating thicknesses, thereby resulting in binary, tertiary, or higher order pharmaceuticals (Chemg-ju Kim, Controlled Release Dosage Form Design).

An important aspect of the administration of drugs in conventional forms is the fluctuation between high and low blood serum concentration of the drug in the period between the administration of two successive doses. In fact, if the drug is too rapidly absorbed, excessive plasma levels may be attained, leading to undesirable and even toxic side effects. On the other hand, drugs possessing a short half-life are eliminated too rapidly and require therefore frequent administrations. In both cases the patient must be careful because particular attention and constancy in the administration is required during therapy and such conditions cannot always be easily obtained. Many efforts have been made to formulate pharmaceutical preparations able to protract in time the activity of the drug in the body at optimum plasma levels, reducing the number of administrations and thus improving the response of the patient to the treatment.

The preparation of pharmaceutical compositions intended to supply a gradual and controlled release in time of the active ingredient is well known in the pharmaceutical technology field. Systems are known comprising tablets, capsules, microcapsules, microspheres and formulations in general, in which the active ingredient is released gradually by various means including the following. Particles containing the API can be coated with individual specific external coatings so that the release of active medicament from the inner core is separated by sequential intervals. The number of defined pulses of drug released by a formulation can range from about 1 to about 10, or more specifically from about 1 to about 5. When applicable, a drug-free lag time can be instituted before the release of first dosage of the active medicament. This drug-free lag time is accomplished by delaying the first pulse-release.

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the API in desired areas of the gastro-intestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the API is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described in detail in U.S. Pat. Nos. 5,273,760 and 5,286,493, and are hereby incorporated by reference in their entirety. Other examples of sustained release formulations and coatings which may be used in accordance with the present invention include U.S. Pat. Nos. 5,324,351, 5,356,467, and 5,472,712, also hereby incorporated by reference in their entirety.

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat®(FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate co-polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

When a hydrophobic material is used to coat inert pharmaceutical beads, a plurality of the resultant solid controlled release beads may thereafter be placed in a gelatin capsule in an amount sufficient to provide an effective controlled release dose when ingested and contacted by an environmental fluid, e.g., gastric fluid or dissolution media.

The controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the hydrophobic material, altering the manner in which the plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, using a Wuster insert. Optionally; additional ingredients are also added prior to coating the beads in order to assist the binding of the API to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined controlled release of said therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

The present invention may include dual-release compositions whereby a celecoxib salt is formulated so as to contain both a fast acting component and a sustained release component of drug delivery. This formulation allows for both relatively fast and prolonged therapeutic effects while minimizing administration frequency. Dual-release compositions are further described in WO 01/45706 A1, the contents of which are herein incorporated by reference in their entirety.

A variety of known controlled- or extended-release dosage forms, formulations, and devices can be adapted for use with the celecoxib salts and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of celecoxib and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable salt of celecoxib (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g., celecoxib salt) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Because celecoxib salts and complexes of this invention (e.g., celecoxib sodium) are far more soluble in water than celecoxib itself, they are well suited for osmotic-based delivery to patients. This invention does, however, encompass the incorporation of celecoxib, and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a salt of celecoxib, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of celecoxib, or a polymorph, solvate, hydrate, dehydrate, co-crystal, anhydrous, or amorphous form thereof. See U.S. Pat. No. 6,342,249, the entirety of which is incorporated herein by reference.

Celecoxib compositions useful in methods of the present invention can be used in combination therapies with opioids and other analgesics. The compound to be administered in combination with a celecoxib composition useful in methods of the invention can be formulated separately from said composition or co-formulated with said composition. Where a celecoxib composition is co-formulated with a second drug, for example an opioid drug, the second drug can be formulated in immediate-release, rapid-onset, sustained-release or dual-release form. In a specific embodiment of the present invention, celecoxib can be combined with an anti-platelet drug for example, but not limited to, tirofiban, aspirin, dipyridamole, anagrelide, epoprostenol, eptifibatide, clopidogrel, cilostazol, abciximab, or ticlopidine.

In another embodiment of the present invention, a formulation comprises a celecoxib salt (e.g., celecoxib sodium salt) and the free acid form. This combination allows for both a fast onset and a delayed response following administration to a subject. In another embodiment, the combination of a celecoxib salt and the free acid also comprises any one, any two, any three, any four, or any five or more excipients listed herein (e.g., precipitation retardants, enhancers, etc.).

Pharmaceutical compositions of the invention are useful in treatment and prevention of a very wide range of disorders mediated by COX-2, including but not restricted to disorders characterized by inflammation, pain and/or fever. Such pharmaceutical compositions are especially useful as anti-inflammatory agents, such as in treatment of arthritis, with the additional benefit of having significantly less harmful side effects than compositions of conventional non-steroidal anti-inflammatory drugs (NSAIDs) that lack selectivity for COX-2 over COX-1. In particular, pharmaceutical compositions of the invention have reduced the potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions of the invention are particularly useful as an alternative to conventional NSAIDs where such NSAIDs are contraindicated, for example in subjects with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems, kidney disease, or in subjects prior to surgery or subjects taking anticoagulants.

Contemplated pharmaceutical compositions are useful to treat a variety of arthritic disorders, including but not limited to rheumatoid arthritis, spondyloarthropathies, gouty arthritis, osteoarthritis, systemic lupus erythematosus and juvenile arthritis.

Such pharmaceutical compositions are useful in treatment of asthma, bronchitis, menstrual cramps, preterm labor, tendonitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Pharmaceutical compositions of the present invention are useful to treat gastrointestinal conditions such as, but not limited to, inflammatory bowel disease, Crohn's disease, gastritis, irritable bowel syndrome and ulcerative colitis.

Such pharmaceutical compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

In addition, these pharmaceutical compositions are useful in treatment of ophthalmic diseases, such as retinitis, conjunctivitis, retinopathies, uveitis, ocular photophobia, and of acute injury to the eye tissue.

Also, such pharmaceutical compositions are useful in treatment of pulmonary inflammation, such as that associated with viral infections and cystic fibrosis, and in bone resorption such as that associated with osteoporosis.

The pharmaceutical compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such pharmaceutical compositions are useful in treatment of allergic rhinitis, respiratory distress syndrome, endotoxin shock syndrome and liver disease.

Further, pharmaceutical compositions of the present invention are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, bums, and trauma following surgical and dental procedures.

The present invention is further directed to a therapeutic method of treating a condition or disorder where treatment with a COX-2 inhibitory drug is indicated, the method comprising oral administration of a pharmaceutical composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above. The present pharmaceutical compositions can be used in combination with other therapies or therapeutic agents, including but not limited to, therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, GABA active agents, norexin neuropeptide modulators, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylori, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, alpha-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, modafinil, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papavereturn, paranyline, parsahnide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, topiramate, tramadol, tropesin, viminol, xenbucin, ximoprofen, zaltoprofen and zomepirac (see The Merck Index, 12th Edition, Therapeutic Category and Biological Activity Index, ed. S. Budavari (1996), pp. Ther-2 to Ther-3 and Ther-12 (Analgesic (D)ental), Analgesic (Narcotic), Analgesic (Non-narcotic), Anti-inflammatory (Non-steroidal)).

Pharmaceutical compositions of the present invention are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

These pharmaceutical compositions are also useful in treatment of angiogenesis-related disorders in a subject, for example to inhibit tumor angiogenesis. Such pharmaceutical compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Moreover, pharmaceutical compositions of the present invention are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreatic cancer, ovarian cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such pharmaceutical compositions can also be used to treat fibrosis that occurs with radiation therapy. These pharmaceutical compositions can be used to treat subjects having adenomatous polyps, including those with familial adenomatous polyposis (FAP). Additionally, pharmaceutical compositions of the present invention can be used to prevent polyps from forming in subjects at risk of FAP.

Also, the pharmaceutical compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for pharmaceutical compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention. A particular preferred use is for rapid pain management, such as when a celecoxib salt or a pharmaceutical composition thereof is effective in treating pain within about 30 minutes or less.

Besides being useful for human treatment, pharmaceutical compositions of the invention are useful for veterinary treatment of companion animals, exotic animals, farm animals, and the like, particularly mammals. More particularly, pharmaceutical compositions of the invention are useful for treatment of COX-2 mediated disorders in horses, dogs, and cats.

EXEMPLIFICATION

Below are standard procedures for acquiring Raman, PXRD, DSC and TGA data herein. These procedures will be followed for each respective method of analysis herein unless otherwise indicated.

Procedure for Raman Acquisition

Acquisition

The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-4495) system fitted with a 785 nm laser source. The sample was manually brought into focus using the microscope portion of the apparatus with a 10× power objective (unless otherwise noted), thus directing the laser onto the surface of the sample. The spectrum was acquired using the parameters outlined in Table 1. (Exposure times and number of exposures may vary; changes to parameters will be indicated for each acquisition.) Unless otherwise noted, all Raman scattering peaks are +/−5 $cm^{-1}$.

TABLE 1

Raman Spectral acquisition parameters

| Parameter | Setting Used |
|---|---|
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range ($cm^{-1}$) | 104-3428 |
| Grating position | Single |
| Temperature at acquisition (degrees C.) | 24.0 |

Procedure for Powder X-Ray Diffraction (PXRD)

All powder x-ray diffraction patterns were obtained using the D/Max Rapid X-ray Diffractometer (D/Max Rapid, Contact Rigaku/MSC, 9009 New Trails Drive, The Woodlands, Tex., USA 77381-5209) equipped with a copper source (Cu/ $K_\alpha$. 1.5406 angstroms), manual x-y stage, and 0.3 mm collimator (unless otherwise indicated). The sample was loaded into a 0.3 mm boron rich glass capillary tube (e.g., Charles Supper Company, 15 Tech Circle, Natick, Mass. 01760-1024) by sectioning off one end of the tube and tapping the open, sectioned end into a bed of the powdered sample or into the sediment of a slurried precipitate. Note, precipitate can be amorphous or crystalline. The loaded capillary was mounted in a holder that was secured into the x-y stage. A diffractogram was acquired (e.g., Control software: RINT Rapid Control Software, Rigaku Rapid/XRD, version 1.0.0, © 1999 Rigaku Co.) under ambient conditions at a power setting of 46 kV at 40 mA in reflection mode, while oscillating about the omega-axis from 0-5 degrees at 1 degree/s and spinning about the phi-axis at 2 degrees/s. The exposure time was 15 minutes unless otherwise specified. The diffractogram obtained was integrated over 2-theta from 2-60 degrees and chi (1 segment) from 0-360 degrees at a step size of 0.02 degrees using the cyllnt utility in the RINT Rapid display software (Analysis software: RINT Rapid display software, version 1.18, Rigaku/MSC.) provided by Rigaku with the instrument. The dark counts value was set to 8 as per the system calibration (System set-up and calibration by Rigaku); normalization was set to average; the omega offset was set to 180°; and no chi or phi offsets were used for the integration. The analysis software JADE XRD Pattern Processing, versions 5.0 and 6.0 ([8]1995-2002, Materials Data, Inc.) was also used.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator. The above limitations result in a PXRD error of +/−0.2 degrees 2-theta for each diffraction peak.

Procedure for Differential Scanning Calorimetry (DSC)

An aliquot of the sample was weighed into an aluminum sample pan. (e.g., Pan part #900786.091; lid part #900779.901; TA Instruments, 109 Lukens Drive, New Castle, Del. 19720) The sample pan was sealed either by crimping for dry samples or press fitting for wet samples (e.g., hydrated or solvated samples). The sample pan was loaded into the apparatus (DSC: ☐1000 Differential Scanning calorimeter, TA Instruments, 109 Lukens Drive, New Castle, Del. 19720), which is equipped with an autosampler, and a thermogram was obtained by individually heating the sample (e.g., Control software: Advantage for QW—Series, version 1.0.0.78, Thermal Advantage Release 2.0, © 2001 TA instruments—Water LLC) at a rate of 10 degrees C./min from $T_{min}$ (typically 20 degrees C.) to $T_{max}$ (typically 300 degrees C.) (Heating rate and temperature range may vary, changes to these parameters will be indicated for each sample) using an empty aluminum pan as a reference. Dry nitrogen (e.g., Compressed nitrogen, grade 4.8, BOC Gases, 575 Mountain Avenue, Murray Hill, N.J. 07974-2082) was used as a sample purge gas and was set at a flow rate of 50 mL/min. Thermal transitions were viewed and analyzed using the analysis software (Analysis Software: Universal Analysis 2000 for Windows 95/95/2000/NT, version 3.1E; Build 3.1.0.40, © 1991-2001TA instruments—Water LLC) provided with the instrument.

Procedure for Thermogravimetric Analysis (TGA)

An aliquot of the sample was transferred into a platinum sample pan. (Pan part #952019.906; TA Instruments, 109 Lukens Drive, New Castle, Del. 19720) The pan was placed on the loading platform and was then automatically loaded into the apparatus (TGA: Q500 Thermogravimetric Analyzer, TA Instruments, 109 Lukens Drive, New Castle, Del. 19720) using the control software (Control software: Advantage for QW-Series, version 1.0.0.78, Thermal Advantage Release 2.0, 2001 TA instruments—Water LLC). Thermograms were obtained by individually heating the sample at 10 degrees C./min from 25 degrees C. to 300 degrees C. (Heating rate and temperature range may vary, changes in parameters will be indicated for each sample) under flowing dry nitrogen (e.g., Compressed nitrogen, grade 4.8, BOC Gases, 575 Mountain Avenue, Murray Hill, N.J. 07974-2082), with a sample purge flow rate of 60 mL/min and a balance purge flow rate of 40 mL/min. Thermal transitions (e.g. weight changes) were viewed and analyzed using the analysis software (Analysis Software: Universal Analysis 2000 for Windows 95/95/2000/NT, version 3.1E; Build 3.1.0.40, © 1991-2001TA instruments—Water LLC) provided with the instrument.

Example 1

Celecoxib Sodium Salt from Aqueous Solution

To 77.3 mg of commercially-available celecoxib was added 1.0 mL distilled water, followed by 0.220 mL of 1 M NaOH. The mixture was heated with stirring to 60 degrees C., whereupon an additional 1.0 mL distilled water was added. Solid NaOH (22 mg) was added, and the solid NaOH and celecoxib dissolved. The mixture was heated again at 60 degrees C. to evaporate water. About 15 mL reagent-grade ethanol was added, while the mixture was stirred and heated at 60 degrees C. with air blowing over the solution. Heating continued until the solution was dry. The resulting material was analyzed by differential scanning calorimetry (DSC), thermogravimetric analysis (TGA), and powder x-ray diffraction (PXRD), the results of which are seen in FIGS. 1-3. The product was found to contain about 4.1 equivalents of water per equivalent of salt, although most of all of the water could be contained in the NaOH that co-precipitated with the salt.

For the DSC analysis, the purge gas used was dry nitrogen, the reference material was an empty, aluminum pan that was crimped, and the sample purge was 50 mL/minute. DSC analysis of the sample was performed by placing 2.594 mg of sample in an aluminum pan with a crimped pan closure. The starting temperature was 20 degrees C. with a heating rate of 10 degrees C./minute, and the ending temperature was 200 degrees C. A reproduction of the resulting DSC analysis is shown in FIG. 1. The transitions observed include a melt/dehydration process between about 40 and about 70 degrees C., another transition between about 70 and about 100 degrees C. possibly resulting from a recrystallization/precipitation event and a second melt/dehydration transition between about 100 and about 110 degrees C.

TGA of the sample was performed by placing 2.460 mg of sample in a platinum pan. The starting temperature was 20 degrees C. with a heating rate of 10 degrees C./minute, and the ending temperature was 300 degrees C. A reproduction of the resulting TGA analysis is shown in FIG. 2. The TGA shows a mass loss of about 12.5 percent between about 30 and about 50 degrees C., attributed to the loss of about 2.8 equivalents of water. A second mass loss of about 2.5 percent between about 71 and 85 degrees C., attributed to the loss of about 0.5 equivalents of water. Finally, a mass loss of about 4.0 percent between about 148 and 170° C. attributed to either the loss of about 1 equivalent of water or some decomposition of the drug compound. The hydration state of the salt can vary depending on the humidity, temperature and other conditions, as discussed in Examples 24, 25, and 30.

A reproduction of the PXRD pattern for the compound prepared above is shown in FIG. 3. In the diffractogram of FIG. 3, the background has been removed. The PXRD pattern has characteristic peaks that can be used to characterize the salt comprising any one, or any combination of any two, any three, any four, or any five peaks or any other combination of peaks at a 2-theta angle of FIG. 3 including for example, the peaks at 2.87, 6.36, 7.01, 16.72, and 20.83 degrees 2-theta.

Example 2

Celecoxib Sodium Salt from 2-propanol Solution

To 126.3 mg of celecoxib was added a 1.0 mL aliquot of isopropanol, and the mixture was heated to dissolve the celecoxib. Sodium ethoxide was added as a solution (21%) in ethanol (0.124 mL solution, $3.31 \times 10^4$ mol sodium ethoxide). An additional 1.0 mL of isopropanol was added. The mixture was stirred to obtain a slurry of white crystalline solids that appeared as fine birefringent needles by polarized light microscopy.

Figure 62:
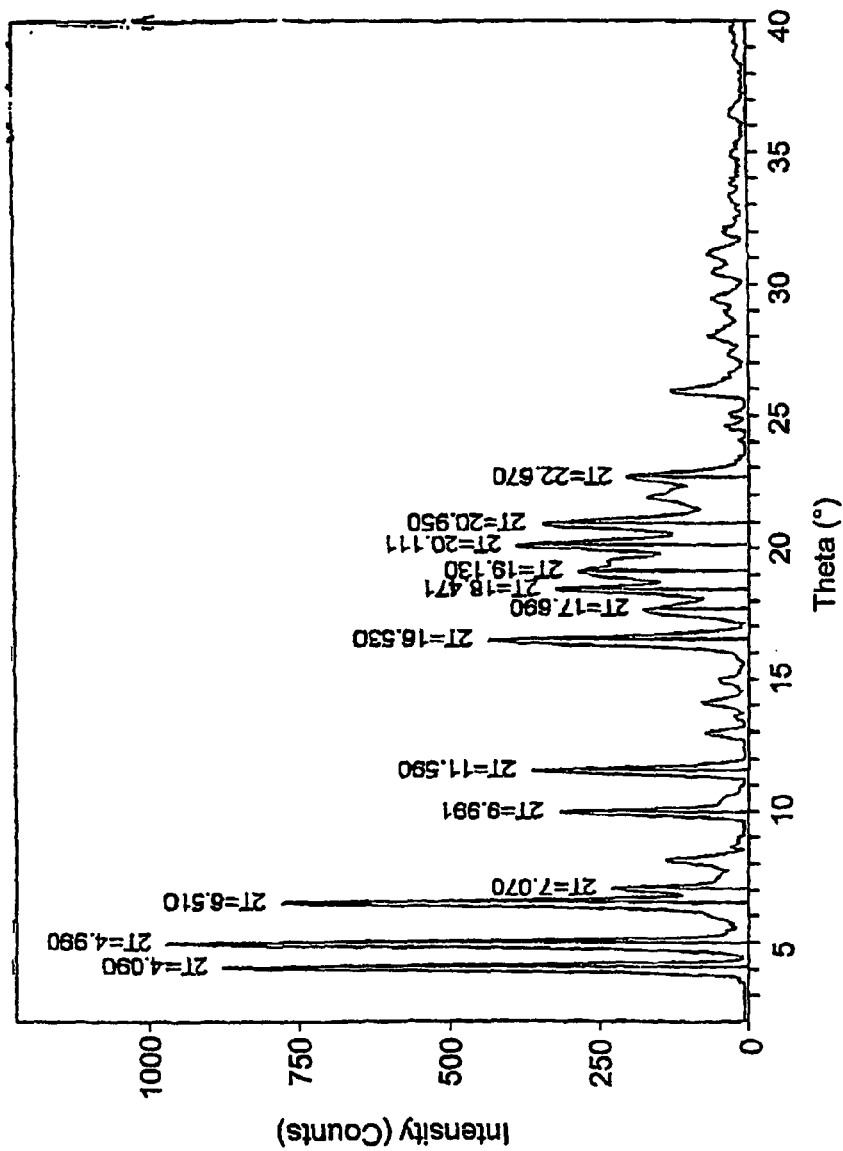
FIG. 62 shows a PXRD diffractogram of celecoxib sodium salt prepared by Example 2.
Figure 101:
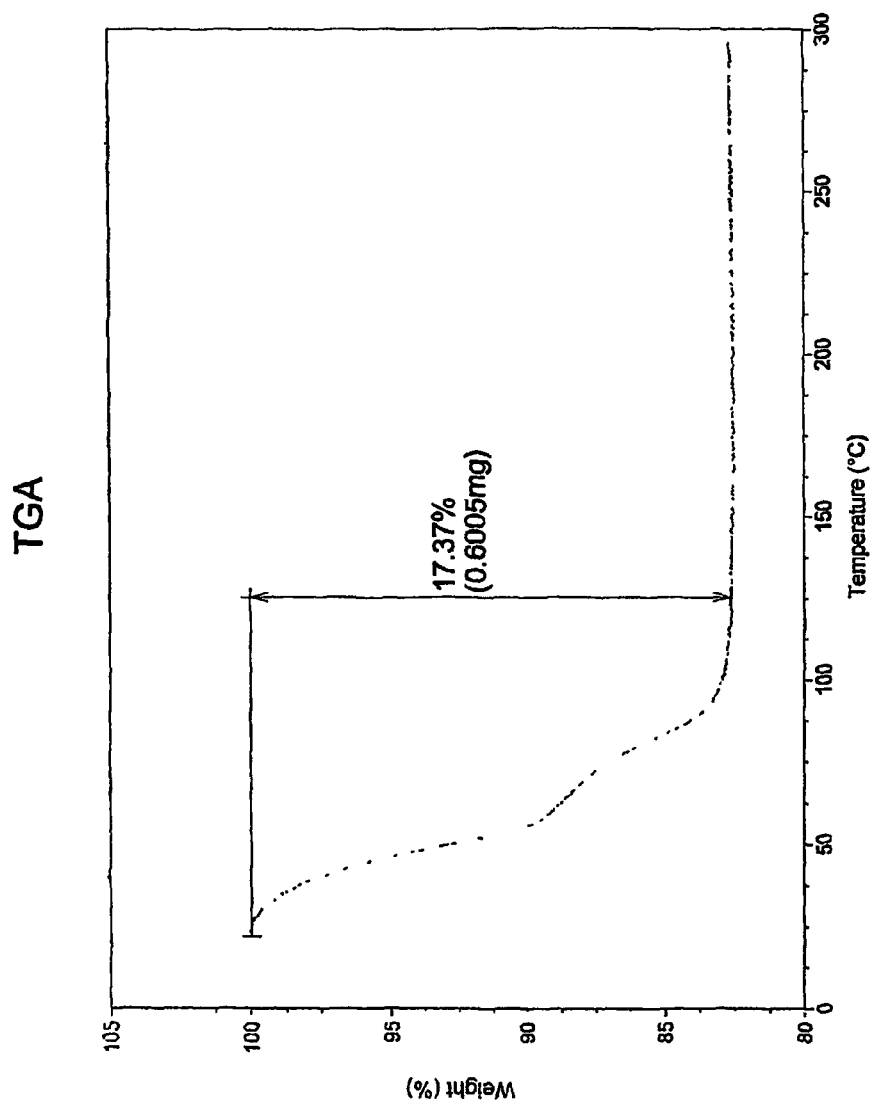
FIG. 101 shows a TGA thermogram of celecoxib sodium salt synthesized from 2-propanol.
Figure 102:
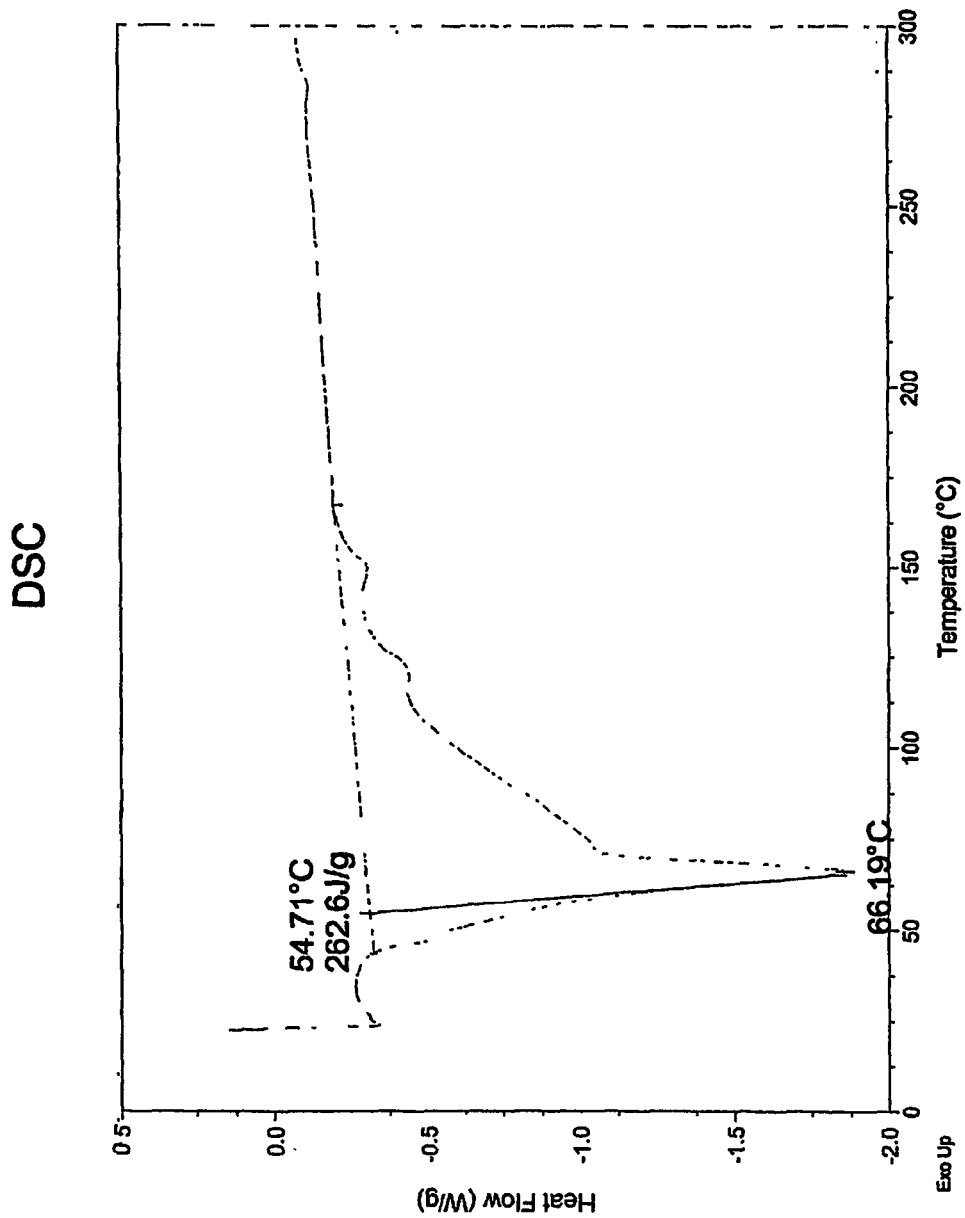
FIG. 102 shows a DSC thermogram of celecoxib sodium salt synthesized from 2-propanol.

The slurry was filtered by suction filtration and rinsed with 2 mL of isopropanol. The solid was allowed to air dry before being gently ground to a powder. The product was analyzed by PXRD, DSC, and TGA as in Example 1, but a 0.5 mm capillary was used to hold the sample in the PXRD experiment. The compound lost 17.37% weight between room temperature and 120 degrees C. (See FIG. 101). The DSC thermogram shows a broad endothermic region, which is consistent with a loss of volatile components with increasing temperature (See FIG. 102). The endotherm peaks at 66 degrees C. The PXRD pattern peaks that can be used to characterize the salt include any one or combination comprising any two, any three, any four, any five, any six, any seven, any eight, any nine, any ten, any eleven, any twelve, or all thirteen 2-theta angles of 4.09, 4.99, 6.51, 7.07, 9.99, 11.59, 16.53, 17.69, 18.47, 19.13, 20.11, 20.95, 22.67 degrees, or any one or combination of 2, 3, 4, 5, 6, 7, 8, 9, 10, 11, 12, or 13 peaks of FIG. 62.

Example 3

Celecoxib Sodium Salt from Aqueous Solution

Synthesis 1: To a vial was added 29.64 mg celecoxib and 3.00 mL of 1 M sodium hydroxide. The celecoxib dissolved. After a time, celecoxib sodium salt precipitated from solution.

Synthesis 2: To a vial was added 7.10 mg celecoxib and 3.00 mL of 1 M sodium hydroxide. The celecoxib dissolved. Overnight, celecoxib sodium salt precipitated and formed white, needle-like crystals.

Synthesis 3: To a vial was added 17.6 mg celecoxib and 10 mL of 1 M sodium hydroxide. The celecoxib dissolved. The vial was placed in a beaker wrapped in aluminum foil and filled with a large tissue for insulation. The beaker was left and celecoxib sodium salt crystals formed within about 12-36 hours.

Analysis: The product solids from syntheses 1 and 2 were combined and analyzed by PXRD, DSC, and TGA as in example 1, but a 0.5 mm capillary was used to hold the sample in the PXRD experiment. The product salt was found to contain about 4 equivalents of water per equivalent of salt, although as stated herein the hydration state of the salt can vary depending on humidity, temperature, and other conditions. TGA showed a weight loss of 14.9 percent as the temperature was increased from room temperature to 100 degrees C. at 10 degrees C./min. DSC analysis showed a large endothermic transition at 74+/−1.0 degrees C. and a second broad and noisy endothermic transition at about 130+/−5.0 degrees C. The PXRD pattern has peaks that can be used to characterize the salt by including any one or a combination comprising any two, any three, any four, any five, or all six 2-theta angle peaks of 3.6, 8.9, 9.6, 10.8, 11.4, and 20.0 degrees.

Example 4

Pharmacokinetic Studies in Rats

Figure 4A:
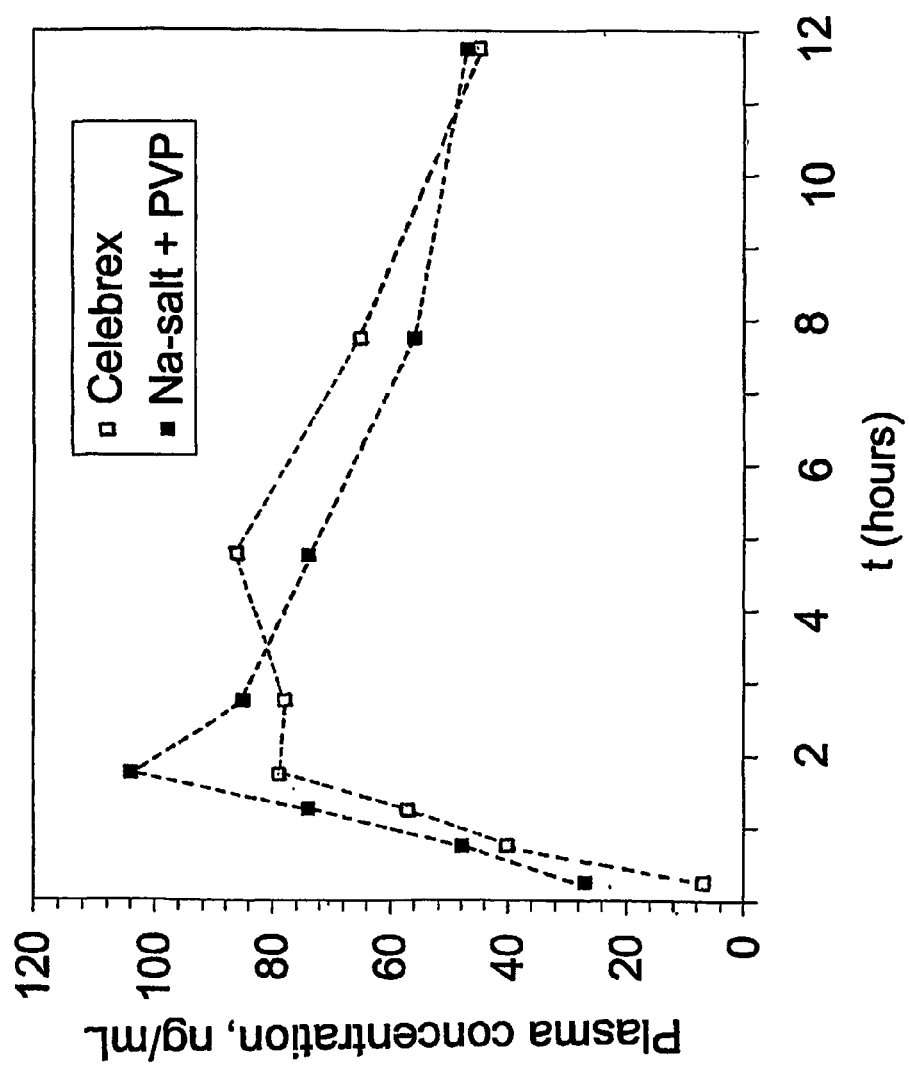
FIGS. 4A and 4B show pharmacokinetics in male Sprague-Dawley rats after 5 mg/kg oral doses of the celecoxib crystal form used in the marketed formulations and the sodium salt of 4-[5-(4-methylphenyl)-3-(trifluoromethyl)-1H-pyrazol-1-yl]benzenesulfonamide, as obtained following the protocol described in Example 4.
Figure 4B:
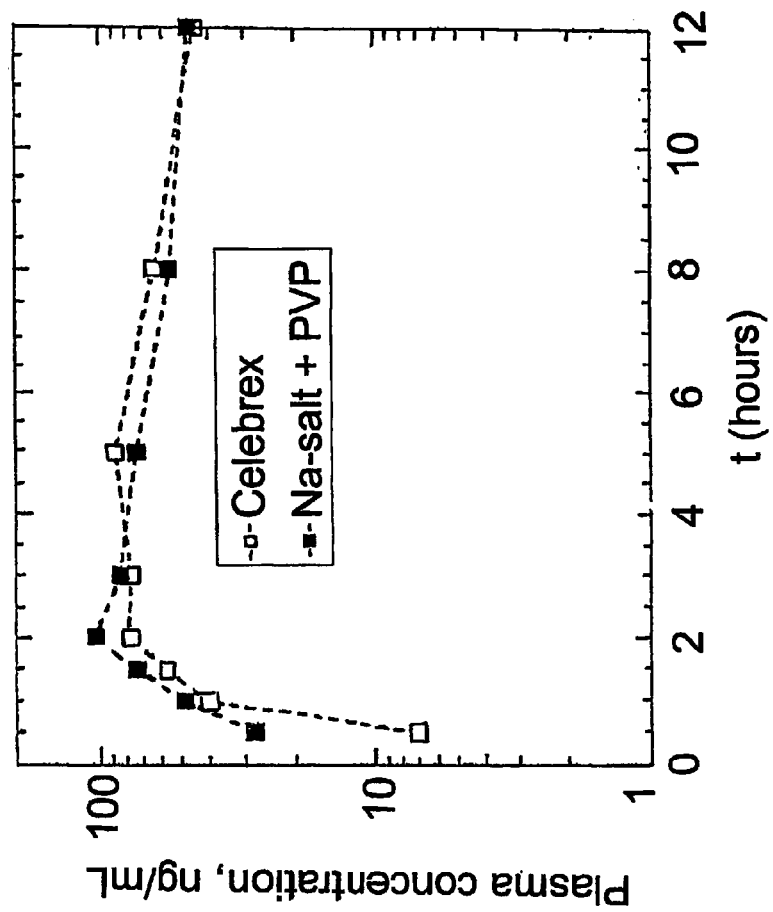

The sodium salt form (from Example 6) was compared with CELEBREX powder in terms of absorption in rats (FIGS. 4A and 4B).

Pharmacokinetics in male Sprague-Dawley rats after 5 mg/kg oral doses of the celecoxib crystal form used in the marketed formulations and the sodium salt form are shown in FIGS. 4A and 4B. Solids were placed in size 9 gelatin capsules (Torpac) and dosed via gavage needle, followed by oral gavage of 1 mL water. CELEBREX granulation was transferred from commercial 200 mg capsules. The sodium salt was blended with polyvinylpyrrolidone (e.g. PovidoneK30) in a 1:4 mixture. The plots are averages of plasma levels at each of the time points from plasma of 5 rats.

The pharmacokinetics at 5 mg/kg doses of the celecoxib sodium salt demonstrate a faster peak level of the drug in plasma. Early timepoints show higher levels of celecoxib in plasma from the sodium salt relative to CELEBREX (in particular, see FIG. 4A).

Example 5

Solubility of Celecoxib Sodium Salt in the Presence of Polyvinylpyrrolidone

Water was added to a 1:4 mixture of celecoxib sodium salt and polyvinylpyrrolidone (PVP) to obtain a clear solution. The solution was stable for at least 15 minutes, after which time, crystals of neutral celecoxib began to form.

Crystalline neutral celecoxib did not dissolve when added to aqueous polyvinylpyrrolidone or when water was added to a dry blend of neutral crystalline celecoxib and polyvinylpyrrolidone.

Example 6

Preparation of Celecoxib Sodium Salt

The free acid of celecoxib (5.027 g; 13.16 mmol) was suspended in a 1 M aqueous solution of NaOH (13.18 mL; 13.18 mmol). The suspension was gently heated at 60 degrees C. for 1 minute to dissolve the remaining solid. The mixture was allowed to cool to room temperature, which yielded no solid. Further cooling in an ice bath for 1 hour yielded crystallization of the product. The resulting suspension was filtered and allowed to air dry.

Figure 13A:
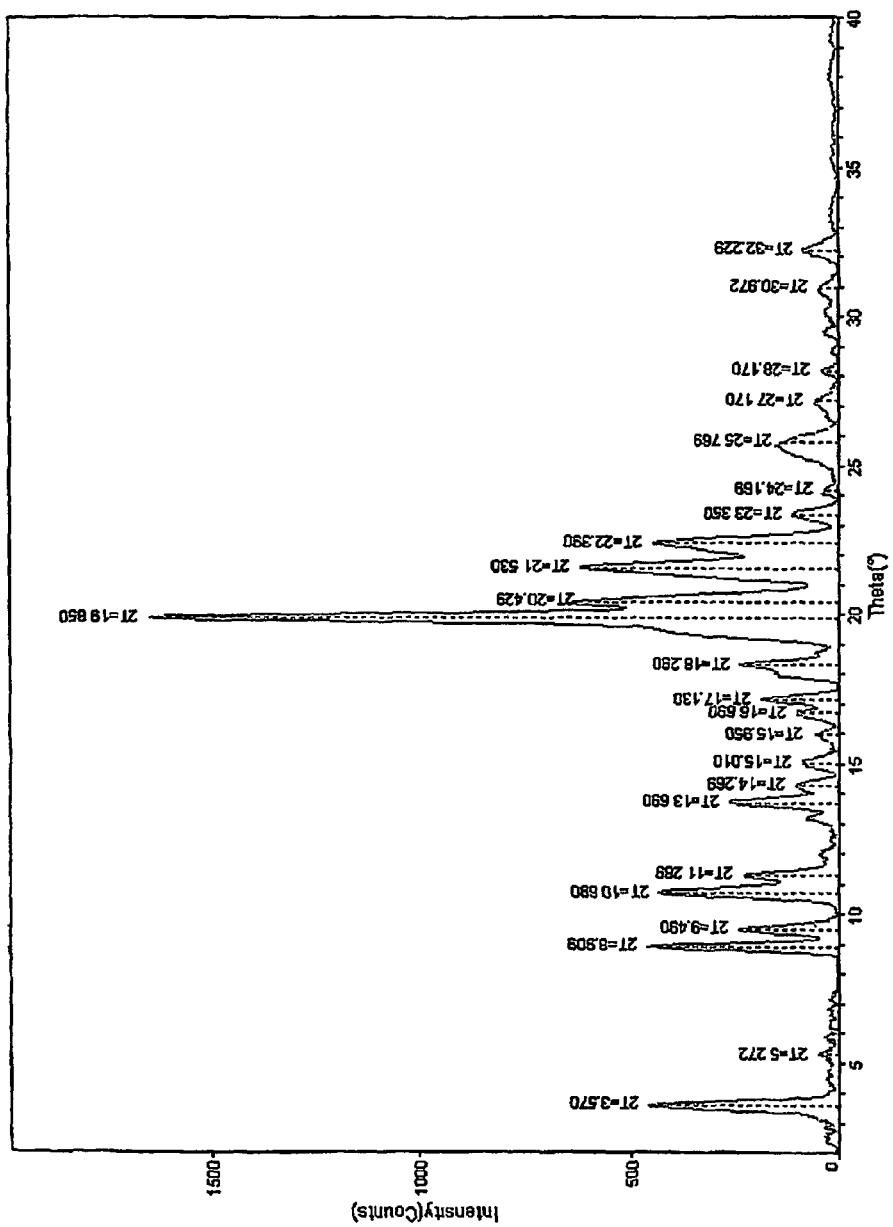
FIGS. 13A and 13B show the PXRD diffractogram and Raman spectrum, respectively, of the sodium salt of celecoxib prepared by the method of Example 6.
Figure 13B:
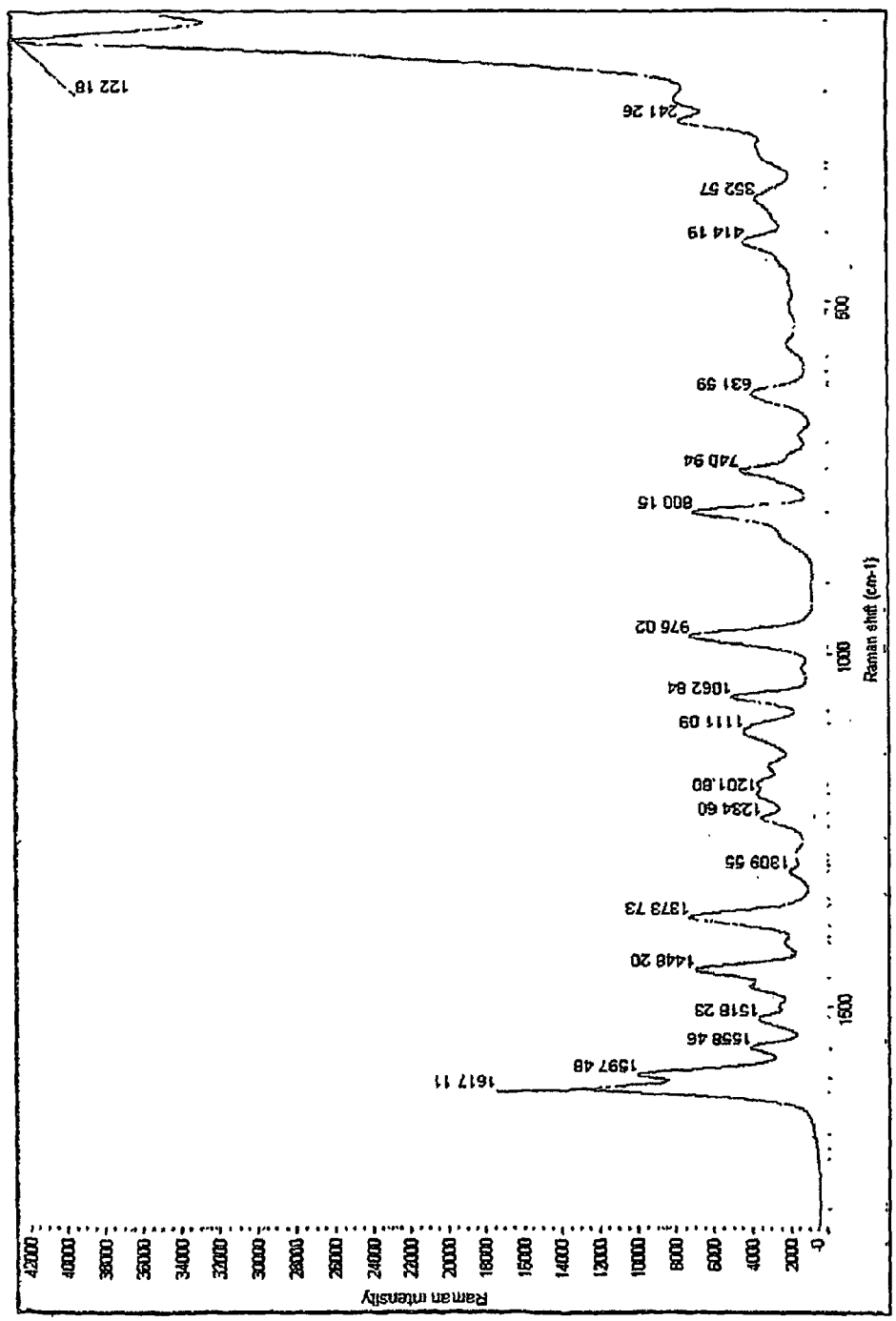

Characterization of the product has been achieved via TGA, DSC, PXRD, and Raman spectroscopy. The TGA shows a weight loss of 6.67 wt % from 25 degrees C. to 105 degrees C. This weight loss indicates some level of hydration or residual water. The DSC shows a large endotherm centered at 100 degrees C. The PXRD pattern has characteristic peaks as shown in FIG. 13A. An intense peak can be seen at 19.85 with other peaks at 2-theta angles including but not limited to, 3.57, 10.69, 13.69, 20.43, 21.53 and 22.39 degrees. The crystal can be characterized by any one, any two, any three, any four, any five, or all six of the peaks above, or any one or combination of any number of 2-theta angles of FIG. 13A. Results of Raman spectroscopy can be seen in FIG. 13B. Raman shift ($cm^{-1}$) peaks occur at positions including, but not limited to, any one, any two, any three, any four, all five of 1617, 1446, 1374, 975 and 800 $cm^{-1}$, or any combinations of 2, 3, 4, 5 or more peaks of FIG. 13B.

Example 7

Administration of Celecoxib Compositions to Dogs

The celecoxib salt of Example 6 was administered to dogs and compared to administration of commercially available celecoxib. Six male beagle dogs aged 2-4 years old and weighing 8-12 kg were food-deprived overnight, but were given water. Each of the dogs was administered 3 test doses as described below and allowed a one week washout period between doses. The test doses included: (1) commercially available celecoxib in the form of CELEBREX at 1 milligram per kilogram (mpk) combined with PEG 400:water (70:30) which was administered intravenously, (2) an oral dose of commercially available celecoxib in the form of CELEBREX at 5 mpk adjusted for each dog's weight in size 4 gelatin capsules, and (3) an oral dose of the sodium salt of the present invention as prepared according to Example 6 at 5 mpk adjusted for each dog's weight in size 4 gelatin capsules. Details regarding formulations of the intravenous and oral doses can be found in FIG. 5A. Blood samples of approximately 2 mL in sodium heparin were obtained by jugular venipuncture at 0.25, 0.5, 1, 3, 4, 6, 8, 12, and 24 hours post-dose. Additional samples were obtained predose and at 0.08 hr for the IV study. Blood samples were immediately placed on ice and centrifuged within 30 minutes of collection. Plasma samples (~1.0 mL) were harvested and stored in 4 aliquots of 0.25 mL at –20 degrees C. Plasma samples were analyzed for celecoxib using an LC-MS/MS assay with a lower limit of quantitation of 5 ng/mL. Pharmacokinetic profiles of celecoxib in plasma were analyzed using the PhAST software Program (Version 2.3, Pheonix Life Sciences, Inc.). The absolute bioavailability (F) is reported for oral doses relative to the IV dose.

Figure 5C:
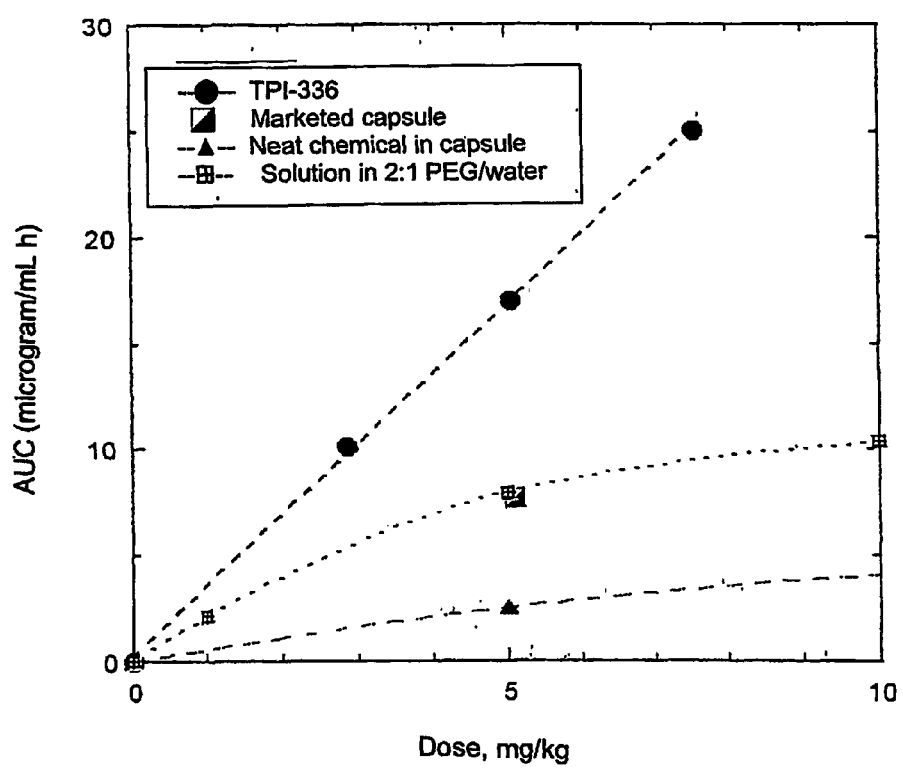
FIG. 5C shows a linear dose response with a plot of AUC versus dose.
Figure 6:
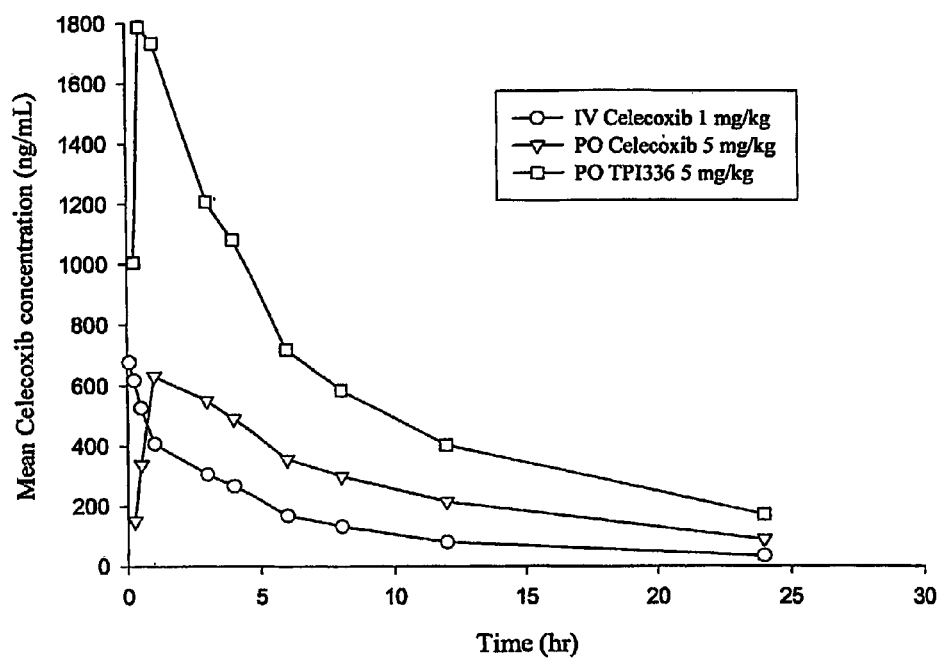
FIG. 6 shows the mean concentrations of celecoxib in plasma following the administration of a single oral dose of celecoxib or celecoxib sodium or a single intravenous dose of celecoxib in male dogs.

FIG. 5B shows the mean pharmacokinetic parameters (and standard deviations thereof) of celecoxib in the plasma of male dogs following a single oral or single intravenous dose of celecoxib or celecoxib sodium salt. The maximum blood serum concentration and bioavailability of orally-administered celecoxib sodium salt was about three- and two-fold greater, respectively, than a roughly equal dose of orally-administered celecoxib, and the maximum blood serum concentration of celecoxib sodium was reached 40% faster than for celecoxib. FIG. 6 shows the dissolution of celecoxib in the plasma of male dogs following a single oral or single intravenous dose of celecoxib or celecoxib sodium salt.

All novel combinations of form and formulation performed significantly better than the commercial product, Celebrex. The supporting data for this conclusion are detailed in FIG. 5B and are summarized as follows: (1) The formulations were fully bioavailable versus only 40 percent bioavailable for Celebrex; (2) The formulations had pharmacokinetics that were linear with dose, as shown in FIG. 5C, which was not the case with Celebrex; and (3) A half dose of the formulations (i.e., 2.5 mg/kg) exhibited a mean celecoxib plasma level that was 5-fold greater that a full dose of Celebrex (5 mg/kg) in the first 15 minutes post dosing. The last observation, illustrated in FIG. 5B, indicates an improved rate of therapeutic onset for the formulations of the present invention.

FIG. 5B shows mean pharmacokinetic parameters of celecoxib in plasma following administration of IV and oral doses. Definitions of the parameters are as follows: (a) Cmax: peak concentration; observed value; (b) Tmax: Time to Cmax; observed value; (c) AUC(I): The area under the plasma concentration versus time curve from time zero to infinity; (d) $t_{1/2}$: Terminal phase half-life; (e) F: Relative oral bioavailability; and (f) CL/F: Plasma clearance of the absorbed fraction. The number of beagles used per formulation are identified by the superscript next to the formulation name, where (i) a refers to n=6; (ii) b refers to n=3; and (iii) c refers to n=2.

Example 8

Celecoxib Lithium Salt Preparation Method: MO-116-49B

Figure 14:
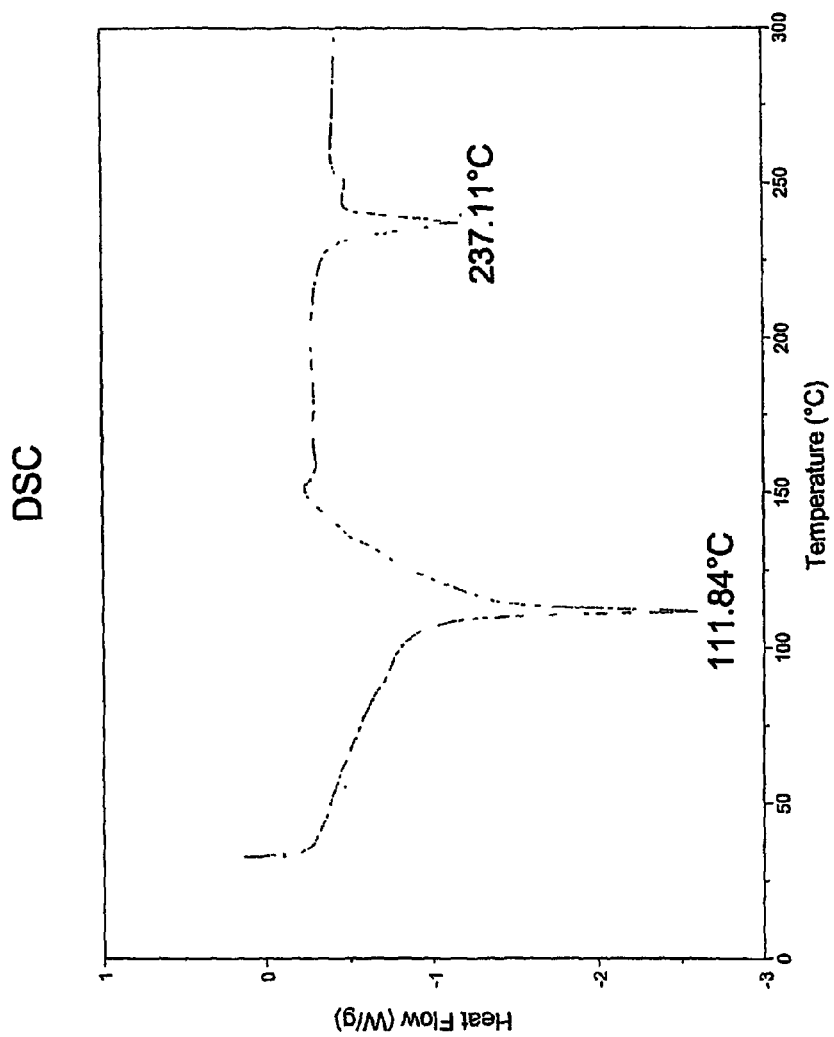
FIG. 14 shows a differential scanning calorimetry (DSC) thermogram of celecoxib lithium salt MO-116-49B.
Figure 15:
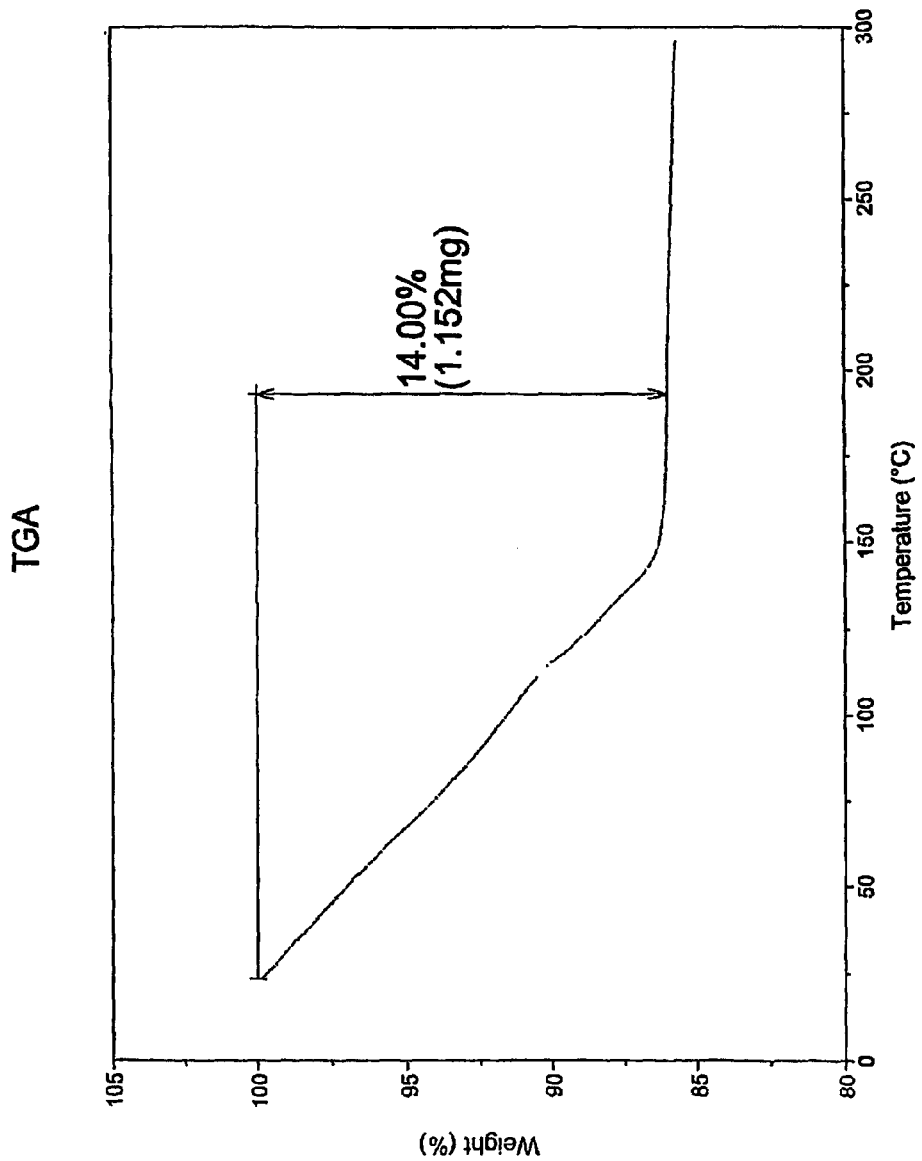
FIG. 15 shows a thermogravimetric analysis (TGA) thermogram of celecoxib lithium salt MO-116-49B.
Figure 16:
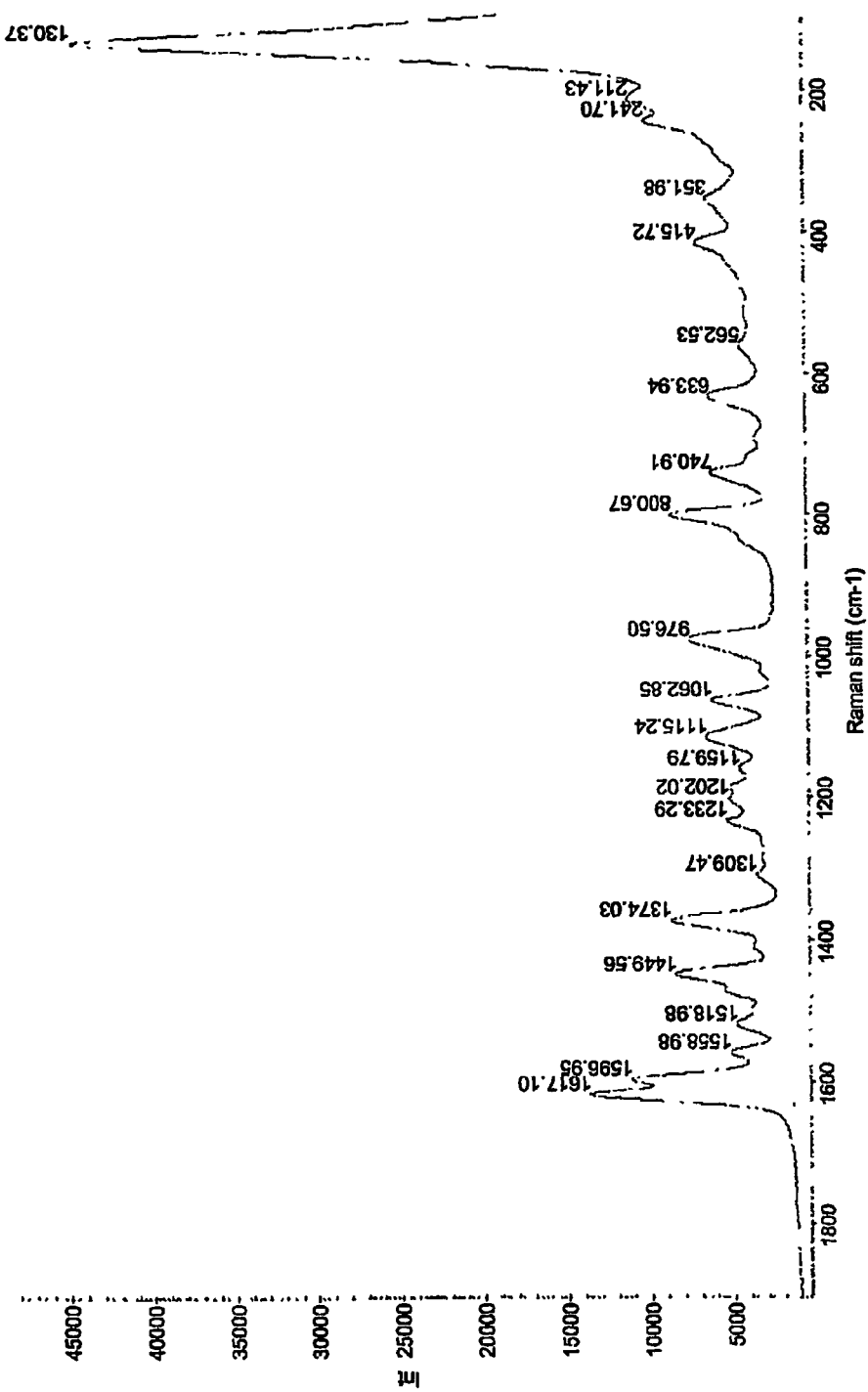
FIG. 16 shows the RAMAN spectrum of celecoxib lithium salt MO-116-49B.

To celecoxib (101.4 mg; 0.2656 mmol) was added an aqueous solution of LiOH (0.35 M; 1.05 mL; 0.37 mmol). The mixture was gently heated during dissolution with occasional swirling until the solid dissolved. The water was evaporated with flowing nitrogen gas to yield a white crystalline solid. Characterization of the product mixture was achieved via DSC (FIG. 14), TGA (FIG. 15), Raman spectroscopy (FIG. 16) and PXRD (FIG. 17) and showed the presence of celecoxib Li salt. Further purification of the drug to remove the excess base can be achieved via recrystallization.

Figure 17:
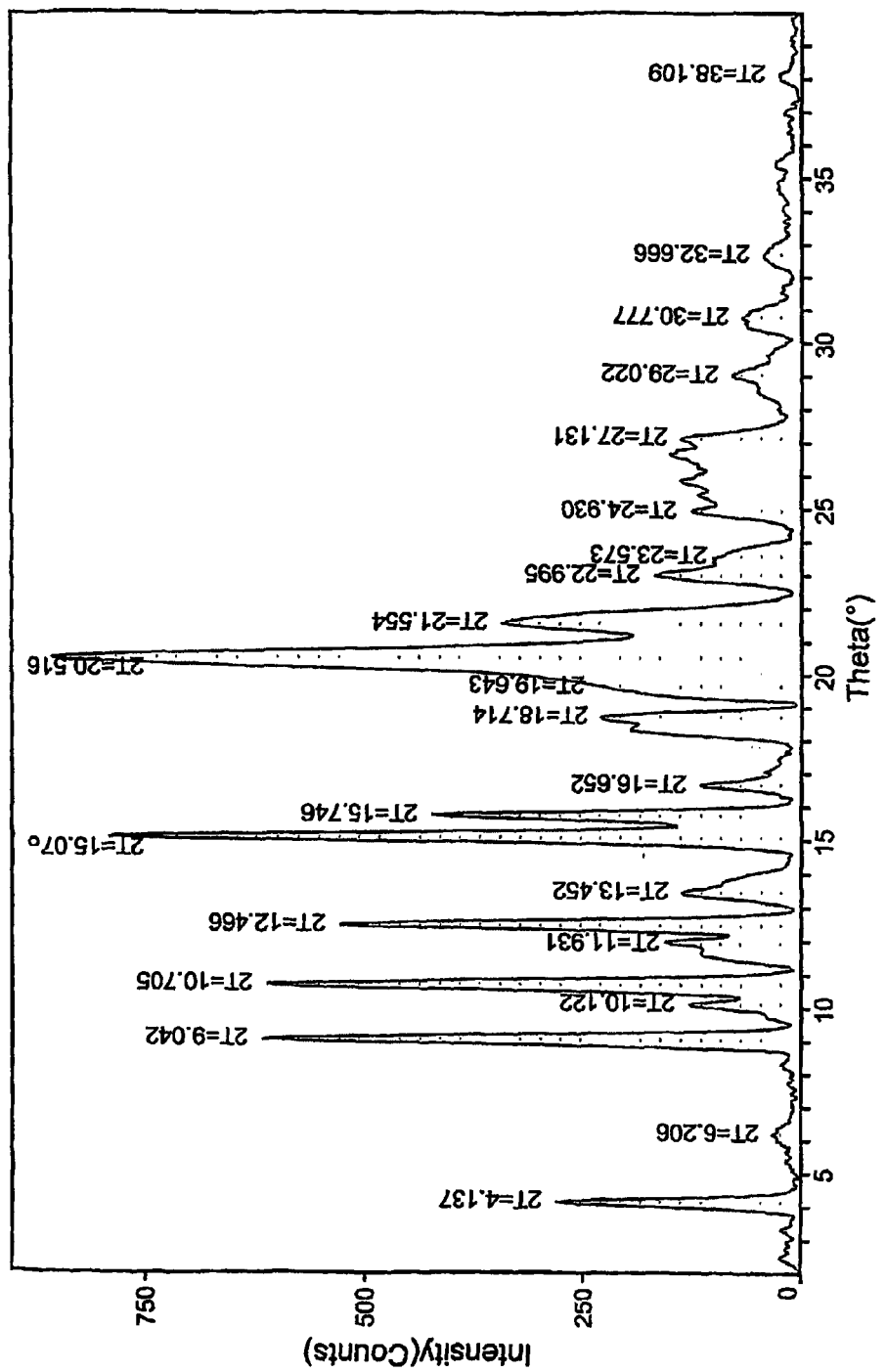
FIG. 17 shows the PXRD diffractogram of celecoxib lithium salt MO-116-49B.

Results of the DSC thermogram (FIG. 14) show an endotherm at 111.84 degrees C. and a second endotherm at 237.11 degrees C. Results of the TGA (FIG. 15) demonstrated a 14% weight loss between about 25 degrees C. and 190 degrees C. Results of Raman spectroscopy show multiple spectral peaks that can be used to characterize the salt. These include any one, any two, any three, any four, any five, any six, any seven, any eight, any nine, any ten, or any other combination of peaks of FIG. 16, e.g., 1617, 1597, 1450, 1374, 1115, 1063, 976, 801, 741 and 634 $cm^1$. The PXRD pattern has characteristic peaks as shown in FIG. 17. PXRD peaks that can be used to characterize the salt include any one, or combination of any two, any three, any four, any five, any six, any seven, any eight, any nine, any ten, any eleven, or any other combination of 2-theta angles from FIG. 17, e.g., 4.14, 9.04, 10.705, 12.47, 15.08, 15.75, 18.71, 19.64, 20.52, 21.55 and 23.00 degrees. A 0.8 mm collimator was used during acquisition of the diffractogram.

Example 9

Celecoxib Potassium Salt: Preparation Method MO-116-49A

To celecoxib (100.7 mg; 0.2637 mmol) was added an aqueous solution of KOH (0.35 M; 1.15 ml; 0.40 mmol). The mixture was gently heated during dissolution with occasional swirling until the solid dissolved. The water was subsequently evaporated with flowing nitrogen gas to yield a white crystalline solid. Characterization of the resulting mixture was performed via DSC (FIG. 18) TGA (FIG. 19), Raman spectroscopy (FIG. 20) and PXRD (FIG. 21) and verified the presence of celecoxib K salt. Further purification of the drug to remove the excess base could be achieved via recrystallization.

Figure 18:
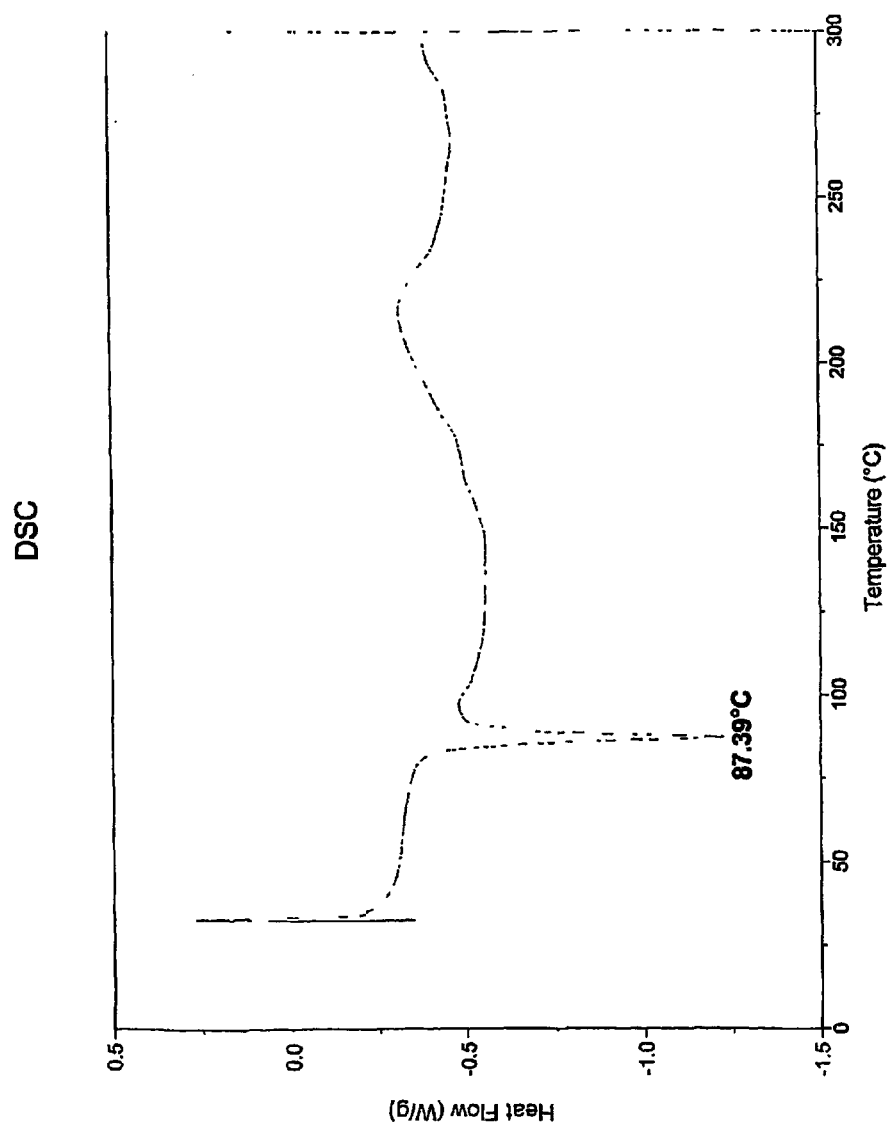
FIG. 18 shows a differential scanning calorimetry (DSC) thermogram of celecoxib potassium salt MO-116-49A.
Figure 19:
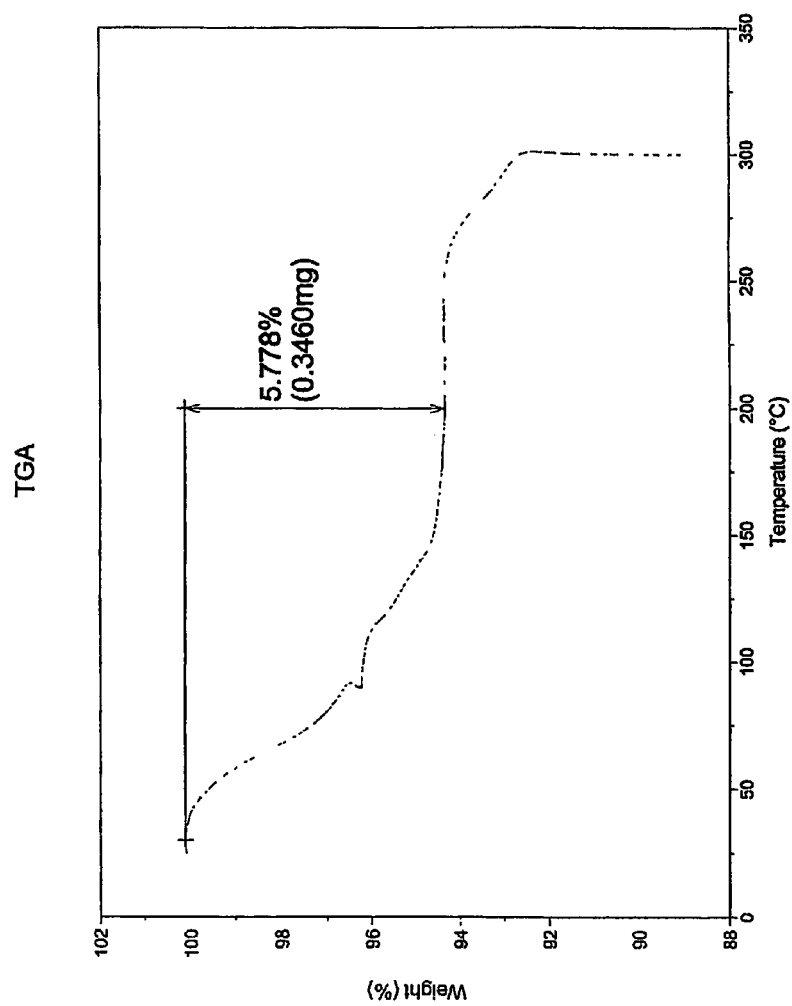
FIG. 19 shows a thermogravimetric analysis (TGA) thermogram of celecoxib potassium salt MO-116-49A.
Figure 20:
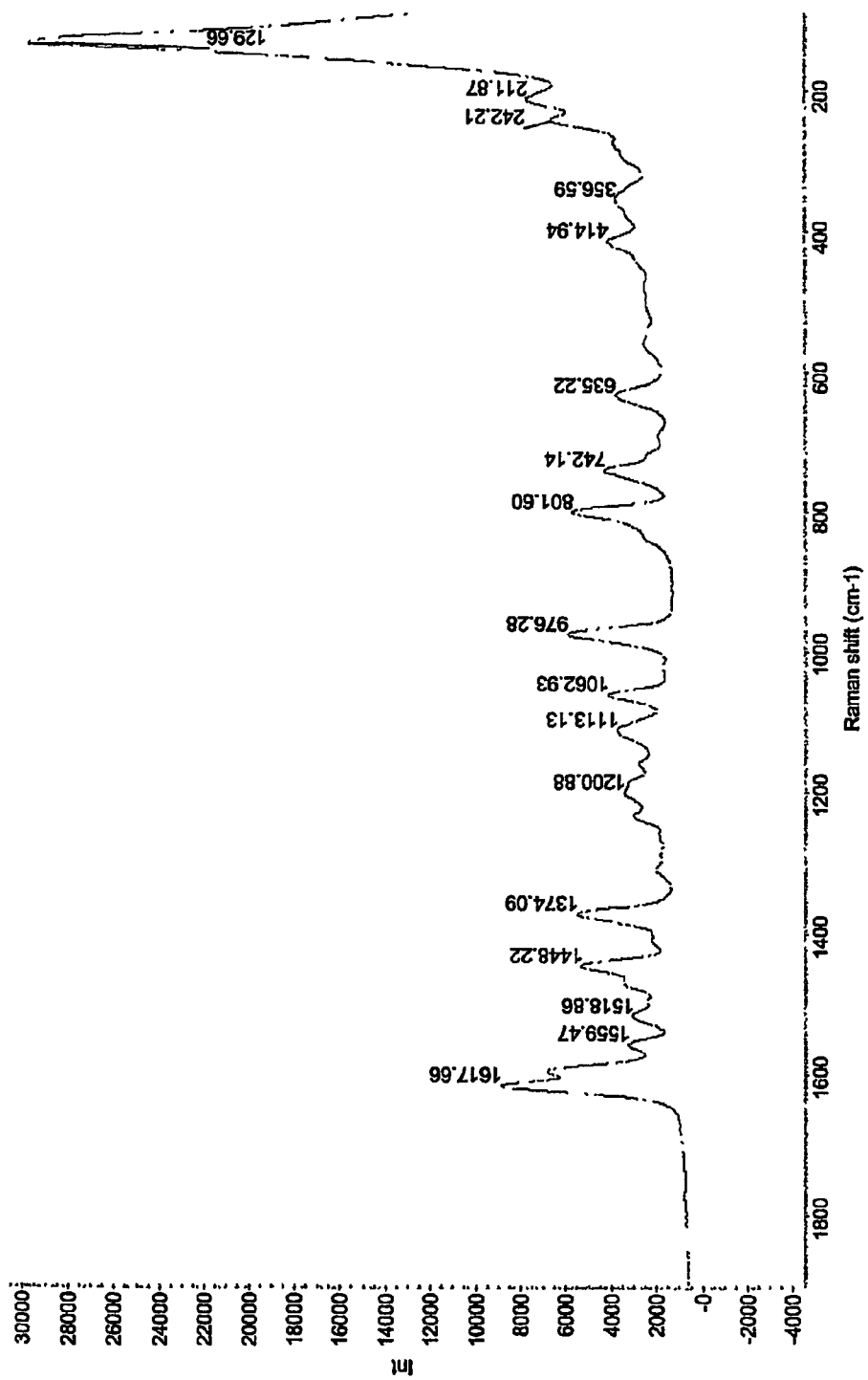
FIG. 20 shows the RAMAN spectrum of celecoxib potassium salt MO-116-49A.
Figure 21:
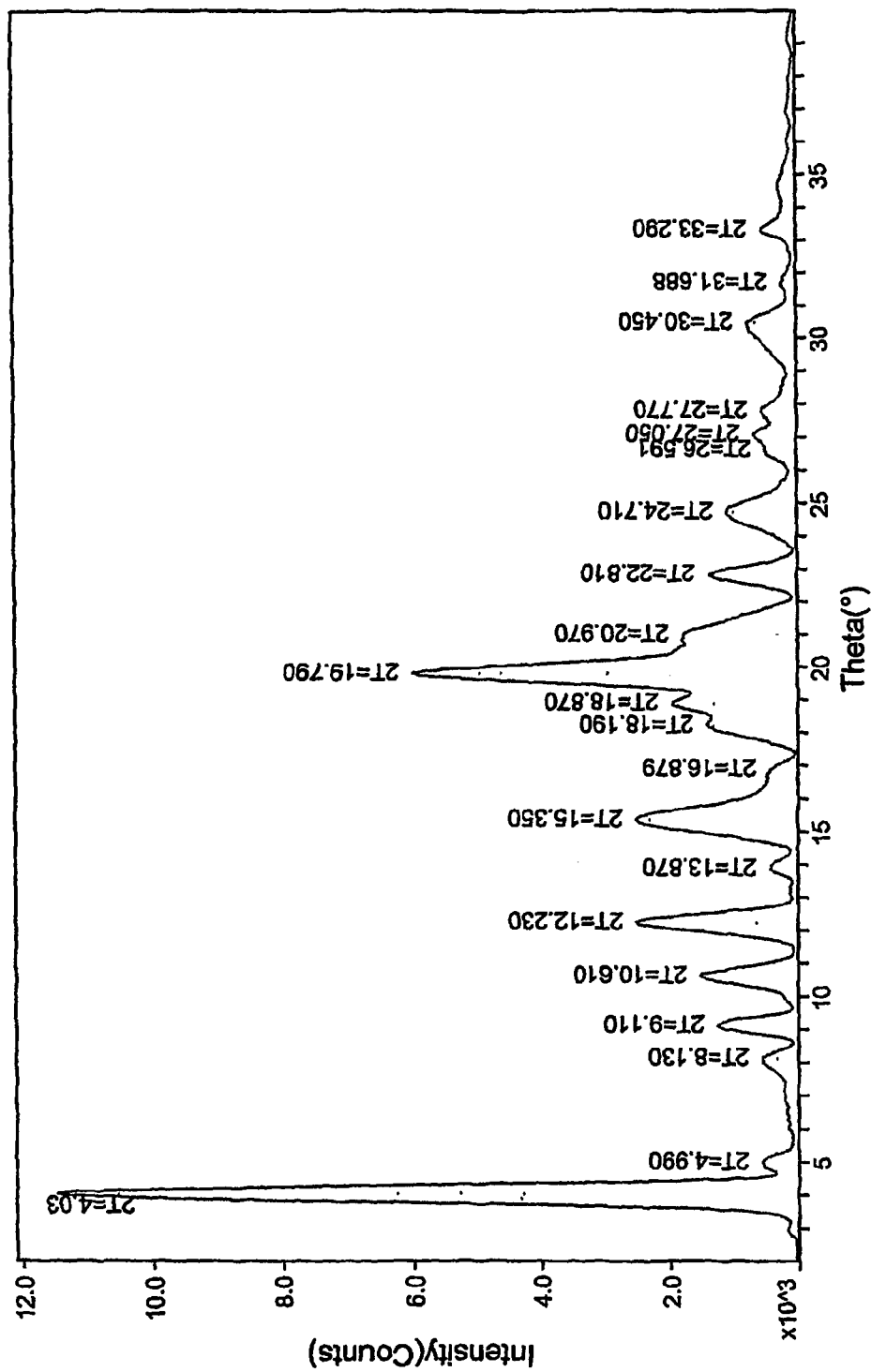
FIG. 21 shows the PXRD diffractogram of celecoxib potassium salt MO-116-49A.

The results of the DSC analysis are depicted in the graph of FIG. 18 and show that the mixture has an endotherm at 87.4 degrees C. The results of the TGA are depicted in FIG. 19 and show a 5.8 wt % loss between 25 and 200 degrees C. A shoulder in the data is seen at 80 degrees C. The Raman spectrum is depicted in FIG. 20 and show characteristic Raman shift ($cm^{-1}$) peaks at positions including, but not limited to any one or combination of any two, any three, any, four, or all five of the peaks: 1618, 1448, 1374, 976, and 801 $cm^{-1}$, or any combinations of 1, 2, 3, 4, 5, or more peaks of FIG. 20. The PXRD pattern has characteristic peaks as shown in FIG. 21. Peaks can be seen at 2-theta angles including, but not limited to, 4.03, 9.11, 12.23, 15.35, 18.87, 19.79, 20.97, and 22.81 degrees. The crystal can be characterized by any one or combination of any two, any three, any four, any five, any six, any seven, or all eight of the above angles or any one or any number combination of 2-theta angles of FIG. 21. A 0.8 mm collimator was used during acquisition of the diffractogram.

Example 10

Celecoxib Potassium Salt: Preparation Method MO-116-55D

Figure 23:
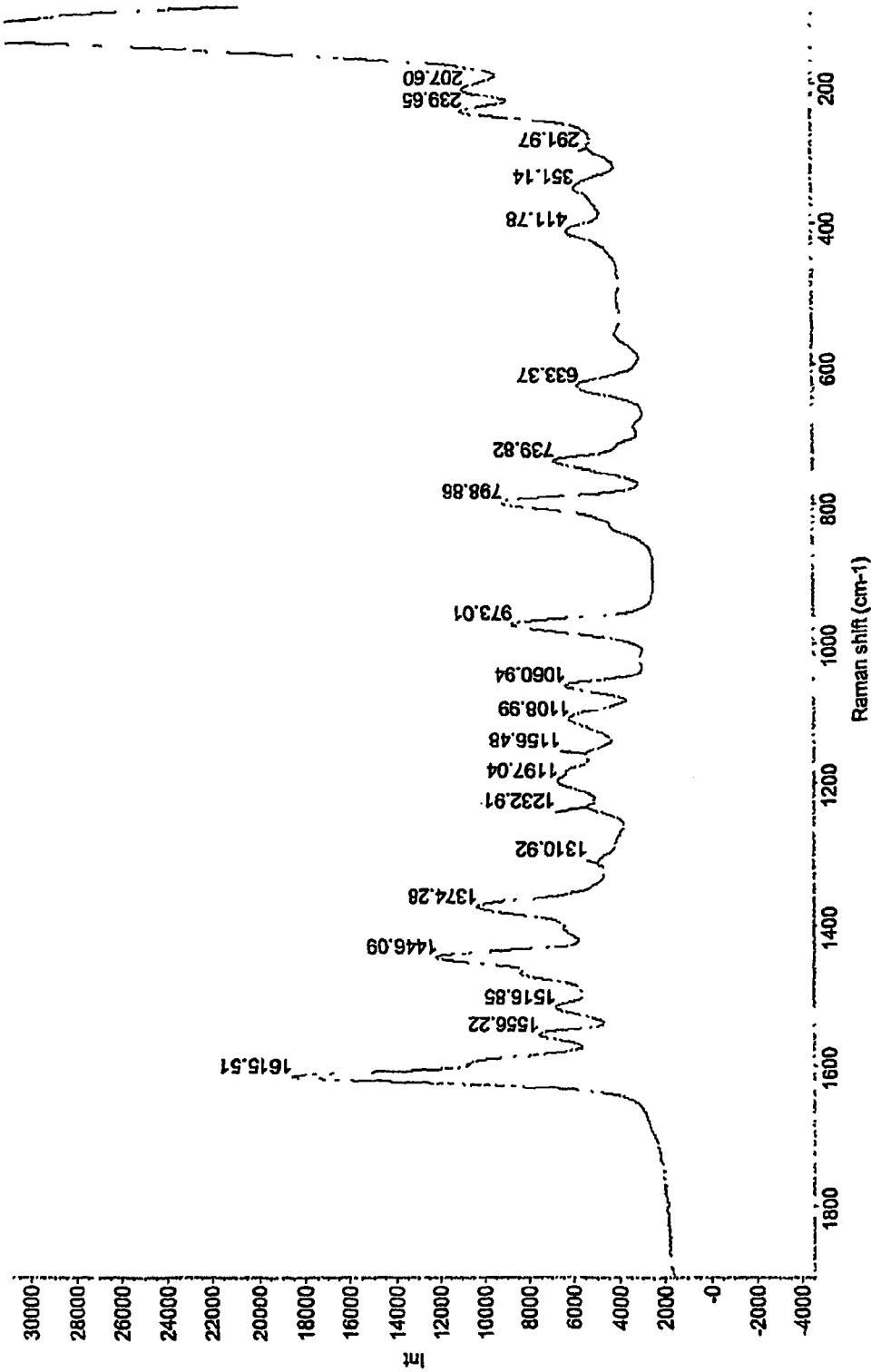
FIG. 23 shows the RAMAN spectrum of celecoxib potassium salt MO-116-55D.
Figure 24:
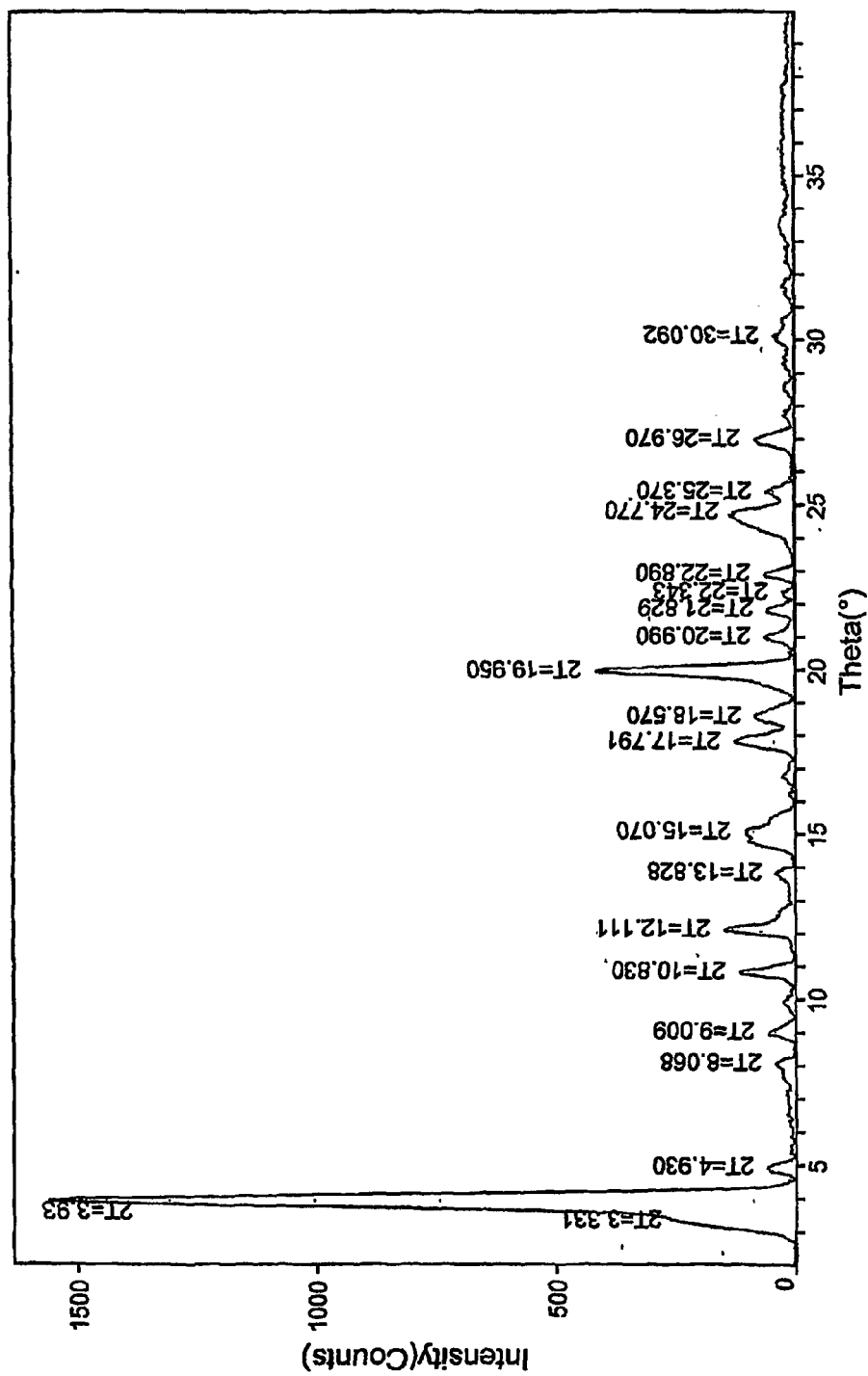
FIG. 24 shows the PXRD diffractogram of celecoxib potassium salt MO-116-55D.

A suspension of celecoxib (100.2 mg; 0.2627 mmol) in toluene (2.2 mL) and methanol (0.1 mL) was gently warmed to yield a solution. To the solution was added 3M aqueous KOH (0.090 ml; 0.027 mmol). After the resulting phase separation, the aqueous phase was removed and dried by flowing nitrogen gas. The resulting crystalline solid was characterized via TGA (FIG. 22), Raman spectroscopy (FIG. 23), and PXRD (FIG. 24).

Figure 22:
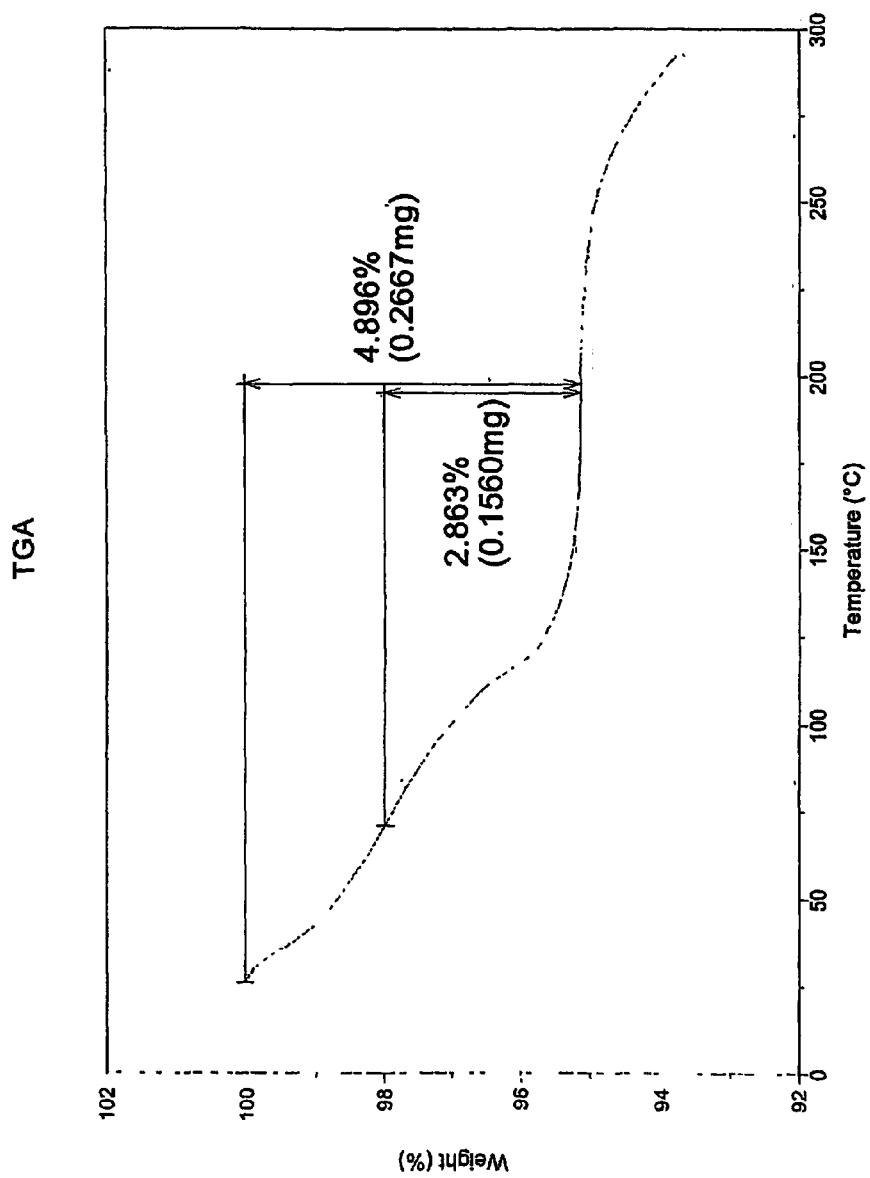
FIG. 22 shows a thermogravimetric analysis (TGA) thermogram of celecoxib potassium salt MO-116-55D.

The TGA sample was heated at 10 degrees C./min to 90 degrees C., held for 10 minutes, ramped 10 degrees C./min to 300 degrees C., and held for 10 minutes with 40 mL/min nitrogen purge gas. The results are depicted in FIG. 22 and show a weight loss of about 4.9 wt % from 25 degrees C. to 200 degrees C. and 2.9 wt % at a shoulder from about 70 degrees C. to 200 degrees C. This weight loss may indicate some level of solvation or residual solvent. The Raman spectrum of the solid is depicted in FIG. 23 and shows characteristic Raman shift ($cm^{-1}$) peaks at positions including, but not limited to any one or a combination of any two, any three, any four, any five, any six, any seven, any eight, any nine, any ten, or all eleven of the peaks 1616, 1446, 1374, 1233, 1197, 1109, 1061, 973, 799, 740, or 633 $cm^{-1}$, or any one or combinations of 2, 3, 4, 5, 6, 7, 8, 9, 10, 11, 12, 13, 14 or more peaks of FIG. 23. The PXRD pattern is depicted in FIG. 24 and shows characteristic peaks at 2-theta angles of 3.93, 10.83, 12.11, 15.07, 17.79, 18.57, 19.95, 24.77, and 26.97 degrees. Any one, any two, any three, any four, any five, any six, any seven, any eight, any nine, or more of these peaks or those listed in FIG. 24 may be used to characterize celecoxib potassium salt.

Example 11

Celecoxib Calcium Salt: Preparation Method MO-116-62A

Figure 25:
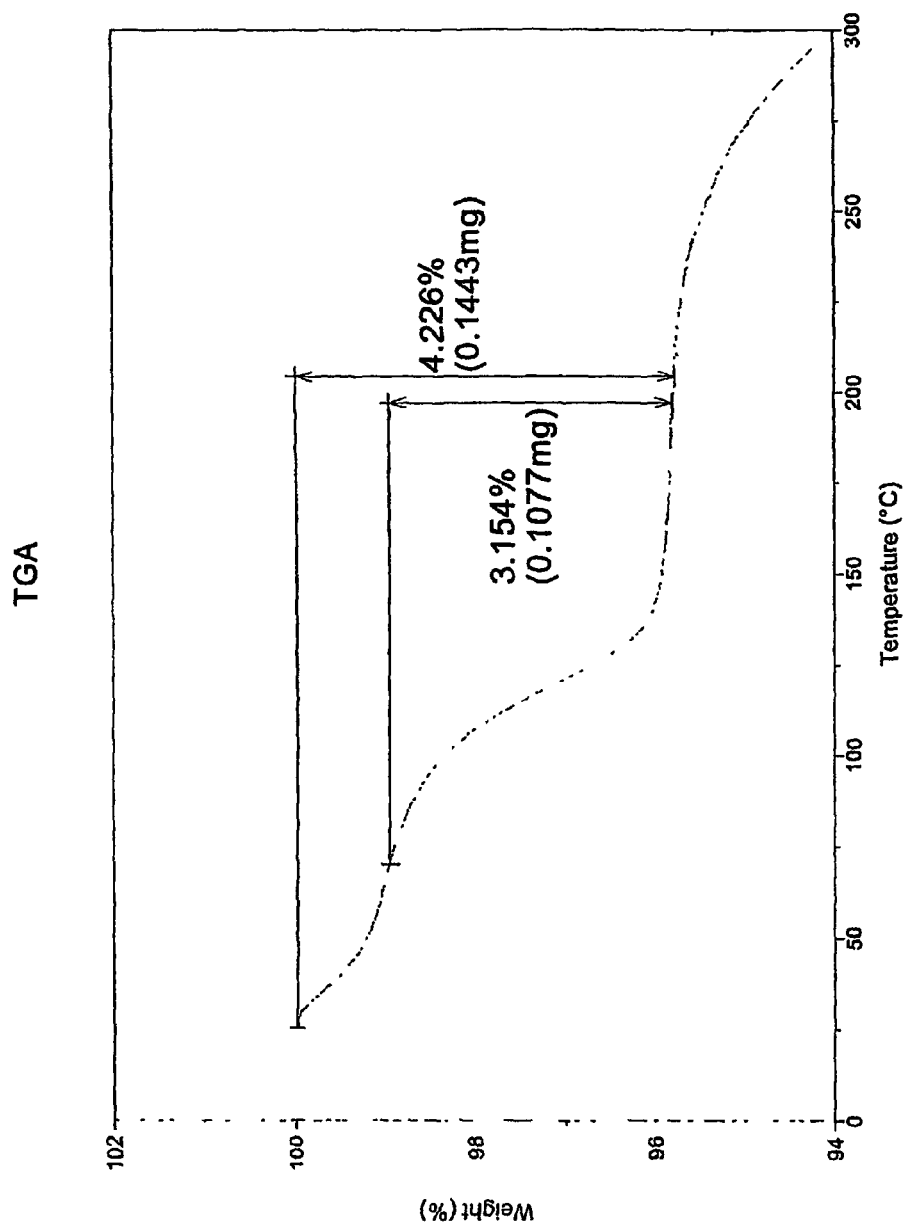
FIG. 25 shows a thermogravimetric analysis (TGA) thermogram of celecoxib calcium salt MO-116-62A.
Figure 26:
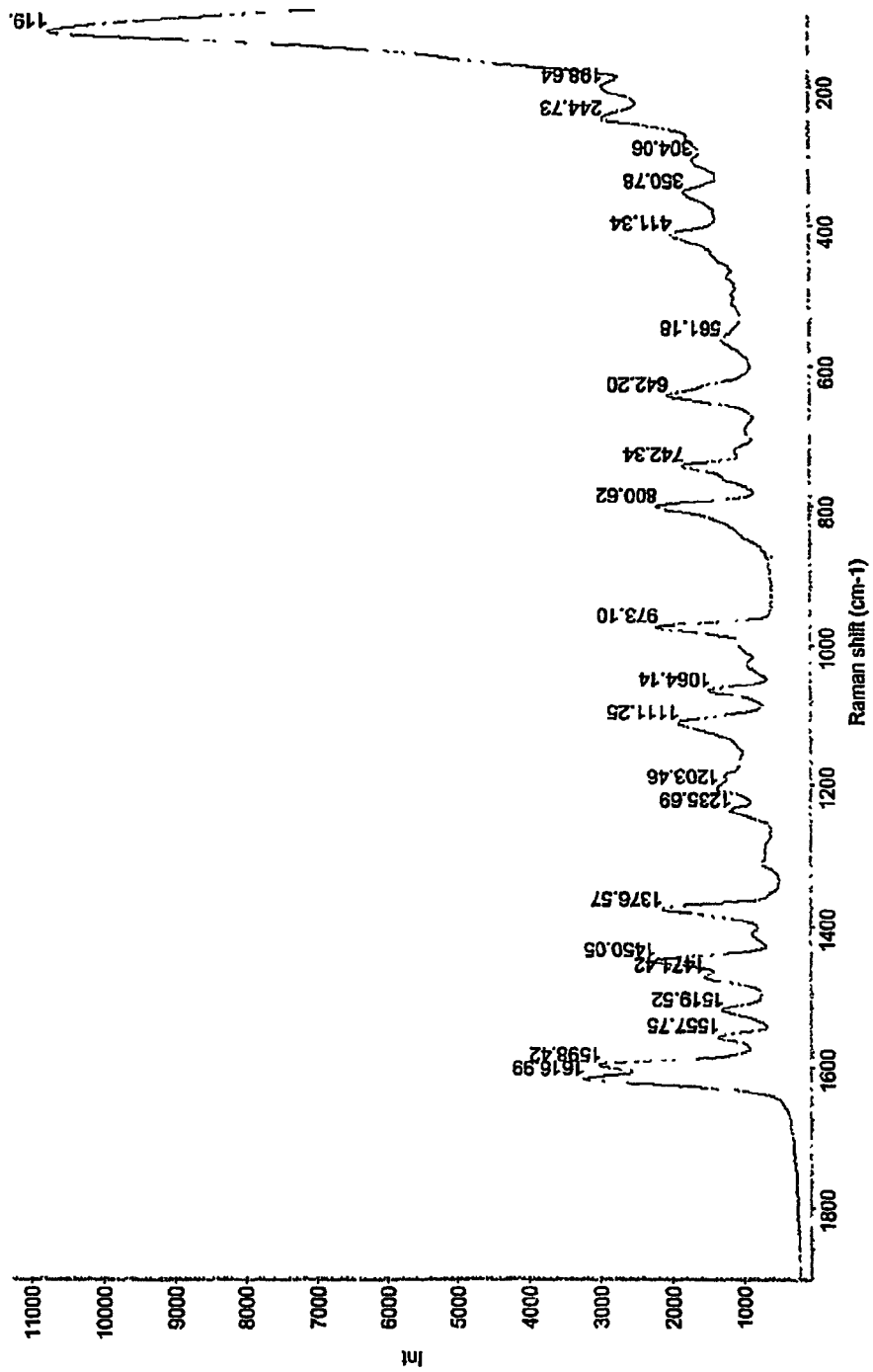
FIG. 26 shows the RAMAN spectrum of celecoxib calcium salt MO-116-62A.
Figure 27:
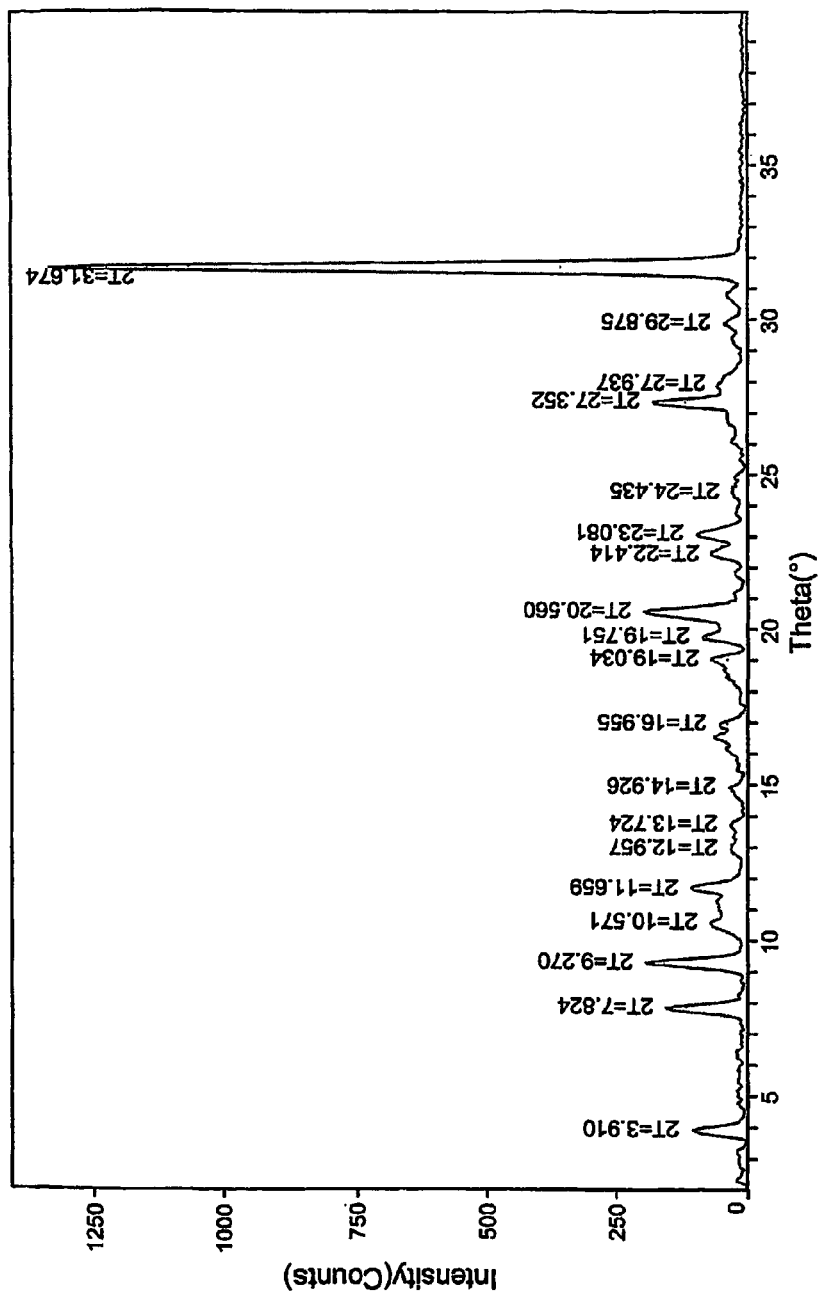
FIG. 27 shows the PXRD diffractogram of celecoxib calcium salt MO-116-62A.

To celecoxib (100 mg; 0.262 mmol) was added a solution of 1 M NaOH in methanol (0.29 mL; 0.29 mmol). The mixture was gently warmed with occasional swirling until all the solids were dissolved resulting in a colorless solution. To the solution was added a 3 M $CaCl_2$ solution in methanol (0.131 mL; 0.393 mmol). A solid formed within minutes. The precipitate was filtered and the powder was dried overnight with flowing nitrogen gas. Characterization of the product mixture was achieved via TGA (FIG. 25), Raman spectroscopy (FIG. 26), and PXRD (FIG. 27) and showed the presence of celecoxib Ca salt and NaCl.

Results of the TGA (FIG. 25) show a total loss of 4.2 wt % between 25 and 200 degrees C. The Raman spectrum shows characteristic Raman shift ($cm^-$) peaks at positions including, but not limited to, any one, any two, any three, any four, any five, any six, or all seven of the peaks 1617, 1598, 1450, 1377, 973, 801, 642, or any combinations of 2, 3, 4, 5, 6, 7 or more peaks of FIG. 26. The PXRD pattern shows 2-theta angles at 3.91, 7.82, 9.27, 11.66, 20.56, and 23.08 degrees. Any one or a combination of 2, 3, 4, 5, or more of the preceding peaks can be used to characterize the salt, as well as, any 1, 2, 3, 4, 5, 6, or more peaks of FIG. 27. The peaks at 27.35 and 31.67 degrees 2-theta are due to NaCl.

Example 12

Comparative Analysis of Neutral Celecoxib

Figure 28:
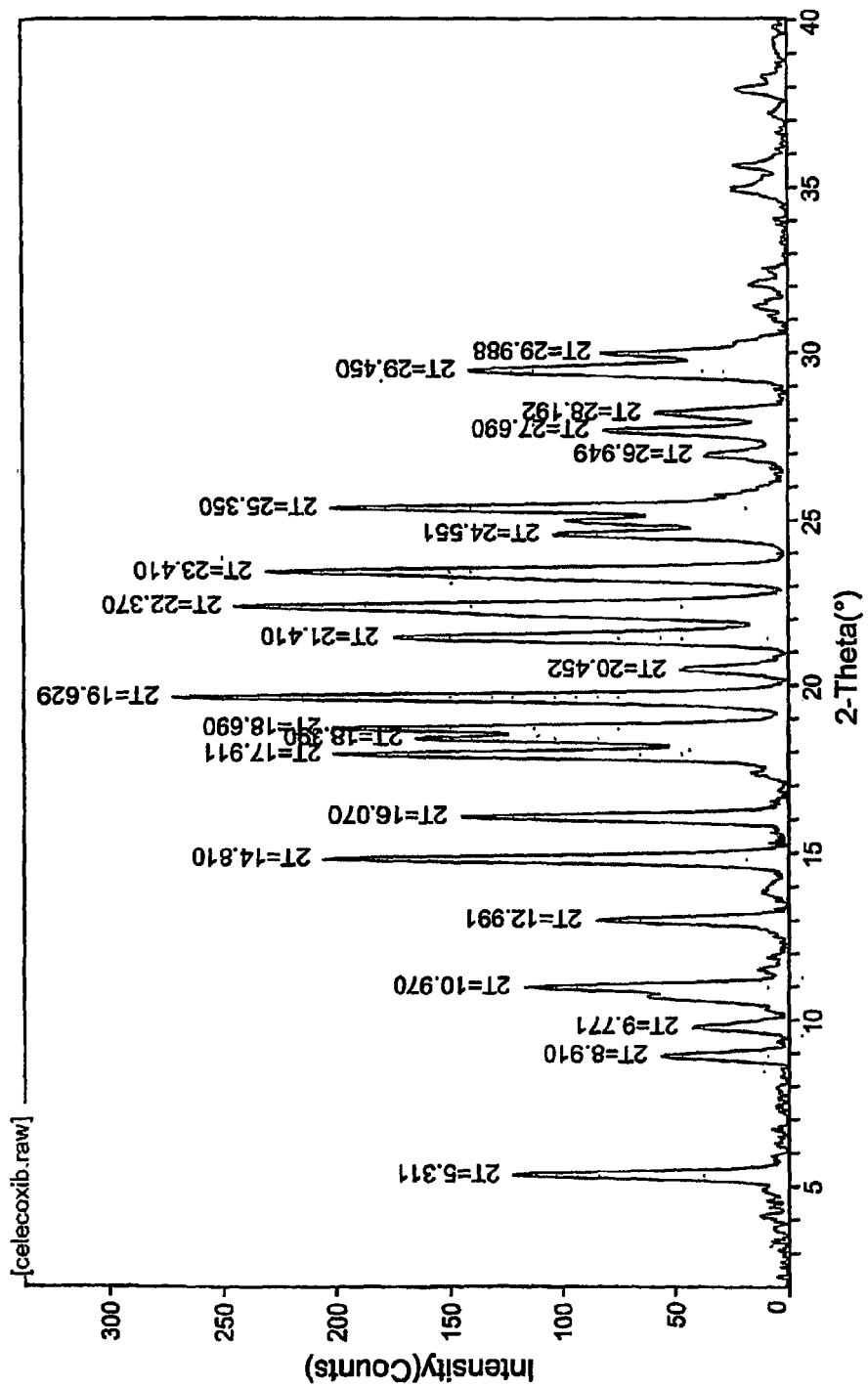
FIG. 28 shows the PXRD diffractogram of commercially-available celecoxib.

To aid in the analysis of some of the data retrieved, commercially available celecoxib was subjected to the same analytical techniques of powder X-ray diffraction (PXRD) and Raman spectroscopy. The results were used as a comparison for the salts of the present invention.
Comparison Data: Celecoxib (PXRD)
A small amount of commercially available celecoxib was placed in a 0.3 mm glass PXRD tube. The tube was placed in Rigaku D/Max Rapid PXRD set to Cu; 46 kV/40 mA; Collimator: 0.5 mm; Omega-axis oscillation, Pos(deg) 0-5, speed 1; Phi-axis spin, Pos 360, Speed 2; Collection time was 15 minutes. The results are depicted in FIG. 28.

Figure 29:
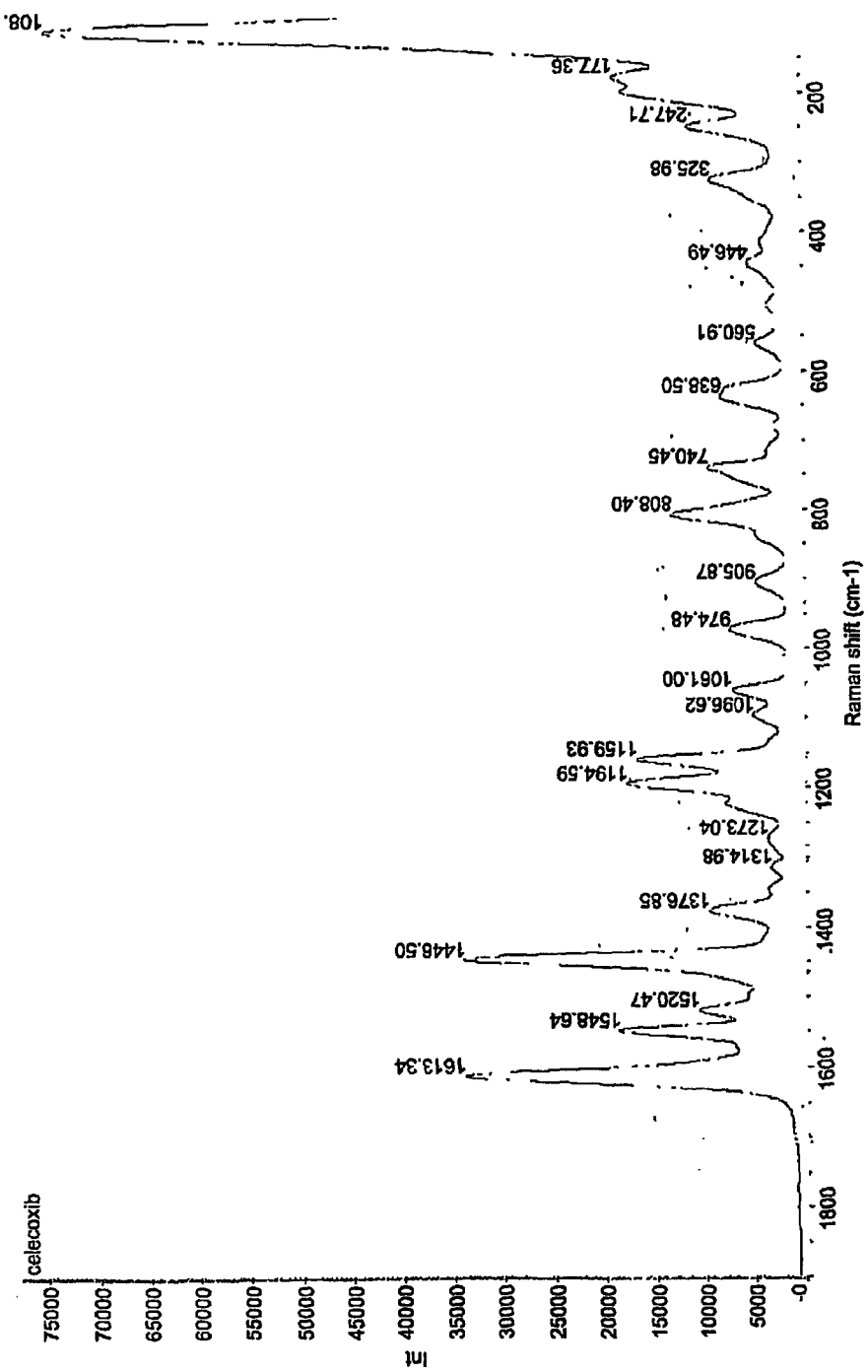
FIG. 29 shows the RAMAN spectrum of commercially-available celecoxib.

Some of the peaks of the free acid may also be found in the compositions of the present invention. As a further means of characterizing the compositions of the present invention, the peaks characteristic of the free acid, as shown in FIG. 28, may also be specifically excluded from compositions of the present invention.
Comparison Data: Celecoxib (Raman)
A small quantity of commercially available celecoxib was placed on a glass slide and mounted in the Thermo Nicolet Almega Dispersive Raman spectrometer. The sample capture was set to 6 background scans and 12 sample collection scans. The results are depicted in FIG. 29. An important feature in the Raman spectrum of celecoxib free acid is a peak near 906 $cm^{-1}$. This peak is not found in the Raman spectra of the sodium, potassium, lithium, and calcium salts of the present invention.

Example 13

Solid-state Formulations of Celecoxib Sodium Salt Hydrate

Solid-state formulations based on selected PLURONIC excipients in combination with hydroxypropylcellulose (HPC) and the crystalline celecoxib sodium hydrate salt, prepared using traditional mortar and pestle technique, showed enhanced dissolution of the celecoxib salt in simulated gastric fluid.

This example demonstrates that related solid-state formulations enhance the dissolution and retard the precipitation of celecoxib salts as compared to the celecoxib neutral free acid compound. The processes used to identify and test the preferred excipients in these examples are two-fold: (1) A "precipitation retardation assay" was used to identify excipients that supersaturate celecoxib in solution; and (2) In-vitro dissolution studies were performed on selected excipients to verify the "precipitation retardation assay" results.

Example 14

Precipitation Retardation Assay

Precipitation Retardation Assay—Method 1. 58 excipients according to Table 2 were prepared at a concentration of 1.8 mg/mL (0.18% by weight) in simulated gastric fluid (SGF) having 200 mM hydrochloric acid and dispensed in quadruplicate in 96-well plates at a volume of 150 microliters. SGF without excipients was used as a negative control. The composition of SGF was 2 g/L sodium chloride, 1 g/L Triton X-100, and 200 mM HCl in deionized water.

TABLE 2

Excipients used in Precipitation Retardation Assay

| | | |
|---|---|---|
| Alkamus 719 | Polyethyleneglycol Monooleate (Mapeg 400-MO) | PLURONIC P123 |
| Alkamus EL 620 | Polyethyleneglycol 300 | PLURONIC P85 |
| Alkamus EL 719 | PLURONIC 17R2 | Poloxamer 188 |
| Benzyl Alcohol | PLURONIC F108 | Poloxamer 338 |
| Cremophor EL | PLURONIC F127 | Polypropyl 52 |
| Cremophor RH40 | PLURONIC F38 | Polysorbate 40 |
| Crillet 1 HP | PLURONIC F68 | Polysorbate 80 |
| Crovol A-70 | PLURONIC F77 | Propylene Glycol |
| Ethosperse G-26 | PLURONIC F87 | Polyvinylpyrrolidone 10K |
| Ethylene Glycol | PLURONIC F88 | Polyvinylpyrrolidone 360K |
| Glycerin | PLURONIC F98 | Polyvinylpyrrolidone 55K |
| HEC 250K | 2-Ethoxyethanol | Saccharin |
| Hydroxypropylcellulose (HPC) | PLURONIC L31 | Sodium lauryl sulphate |
| Isopropanolamine | PLURONIC L43 | Tagat O2 |
| Myrj 52 | PLURONIC L44 | Transcutol P |
| Polyethyleneglycol 1000 | PLURONIC L92 | Triacetin |
| Polyethyleneglycol 200 | PLURONIC P103 | Triethanol amine |
| Polyethyleneglycol 400 | PLURONIC P104 | Vitamin E TPGS |
| Polyethyleneglycol 600 | PLURONIC P105 | Vitamin E TPGS & HPC |

2. The 96-well plates were sealed, and incubated to a temperature of 40 degrees C. for 20 minutes. After incubation, the plate seals were removed.
3. Celecoxib, pre-dissolved in potassium hydroxide at 5.5 mg/mL, was dispensed in 15 microliter aliquots to each well and immediately mixed to give a final celecoxib concentration of 0.5 mg/mL per well. The final excipient concentration was 1.8 mg/mL. The assay plate was sealed using an optically clear seal.
4. A nephelometer (Nephelostar Galaxy, BMG Technologies, Durham, N.C.), with a chamber preheated to 37 degrees C., was used to analyze the ability of the excipients to retard the crystallization/precipitation of supersaturated celecoxib via light scatter measurements.

Figure 30:
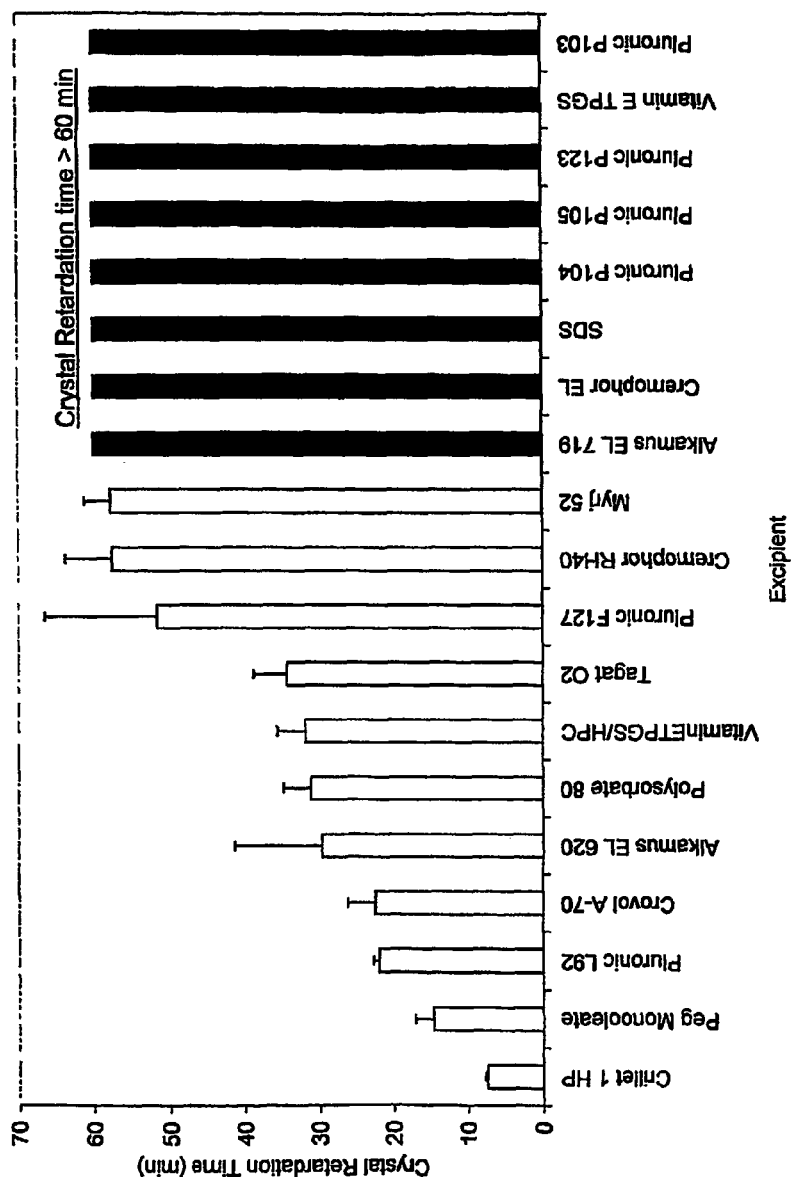
FIG. 30 shows crystal retardation time for celecoxib as a function of excipient in simulated gastric fluid (SGF).

Precipitation Retardation Assay—Results:

FIG. 30 shows precipitation retardation time for celecoxib as a function of excipient in simulated gastric fluid (SGF). Final concentration of celecoxib was 0.5 mg/mL. Black bars indicate precipitation retardation time that may be greater than 60 min. Excipients listed in Table 8, but excluded from FIG. 30 did not show any appreciable precipitation retardation time (i.e., greater than 1.5 minutes). Nineteen of 58 excipients were found to retard recrystallization/precipitation of celecoxib.

The presence of six PLURONIC (poloxamer) excipients among successful precipitation retardants prompted further study of these compounds. PLURONICs are ethylene oxide—propylene oxide block copolymers, whose properties can be significantly altered (e.g., melting point, cloud point, molecular weight, HLB number, critical micelle concentration, surface tension, interfacial tension, etc.) by adjusting the ratio of copolymer blocks. Further examination of these properties showed that the surface tension of these copolymers at a 0.1% concentration in water correlates with the ability to retard the crystallization/precipitation of celecoxib. PLURONIC excipients having low interfacial tension (i.e., less than about 10 dyne/cm) or having a surface tension less then about 42 dyne/cm were more effective at keeping celecoxib in solution than PLURONIC excipients having high interfacial tension or surface tension. This observation is illustrated in FIG. 31A, along with interfacial data for PLURONICs that were not tested.

Figure 31A:
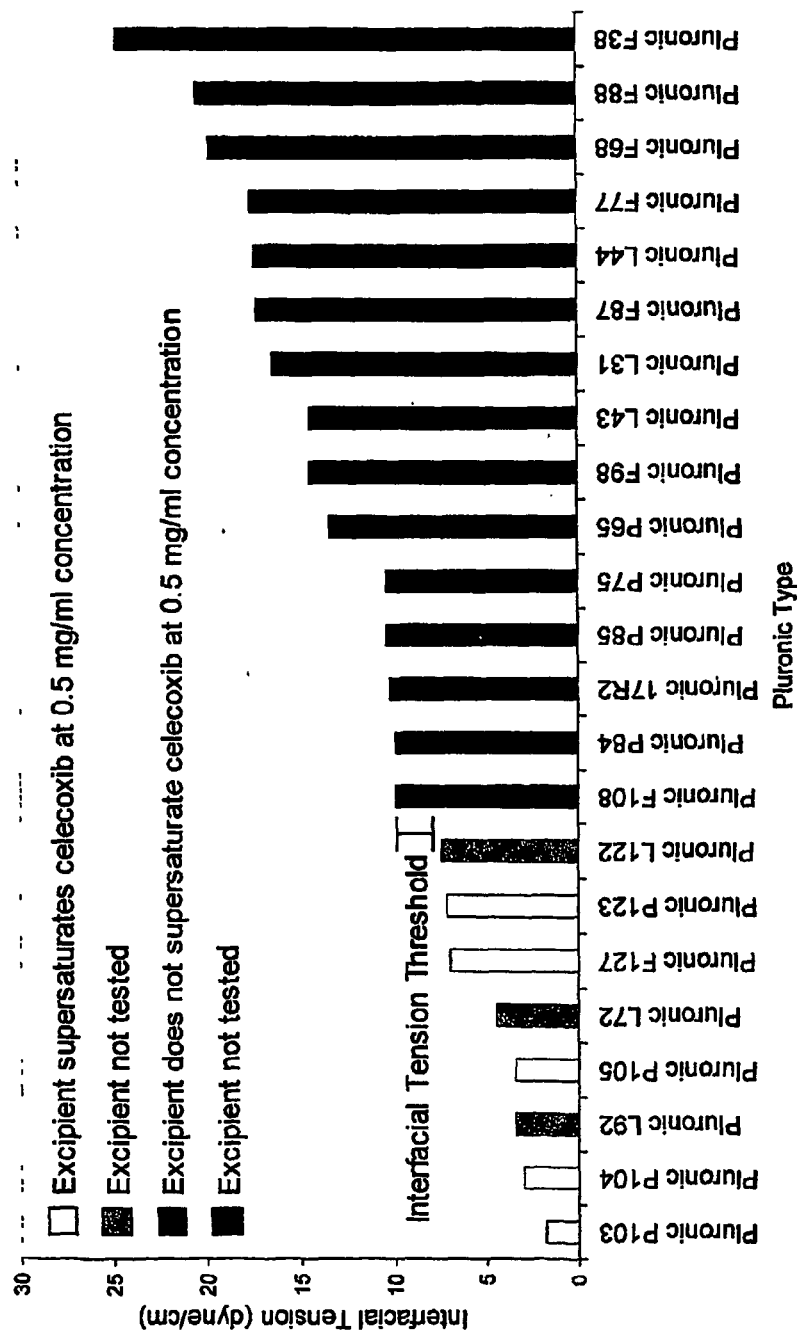
FIG. 31A shows interfacial tension of selected PLURONIC excipients in water.

FIG. 31A shows interfacial tension values of selected PLURONIC excipients in water. PLURONIC excipients having low interfacial tension correlated with excipients that retarded crystallization/precipitation of celecoxib in simulated gastric fluid. An interfacial tension threshold for precipitation retardation was loosely defined as less than about 9 or 10 dyne/cm. The excipient concentration in the assay was 0.18%; celecoxib concentration was 0.5 mg/mL. Interfacial data obtained from BASF at 0.1% concentration in water versus mineral oil at 25 degrees C. (PLURONIC is a trademark of BASF). It is important to emphasize that the Pluronics were used at a 1.8 mg/mL concentration in this assay. It is suggested that a higher interfacial and surface tension threshold will correlate with the ability to prevent celecoxib precipitation when the Pluronics are used at a higher concentration.

Figure 31B:
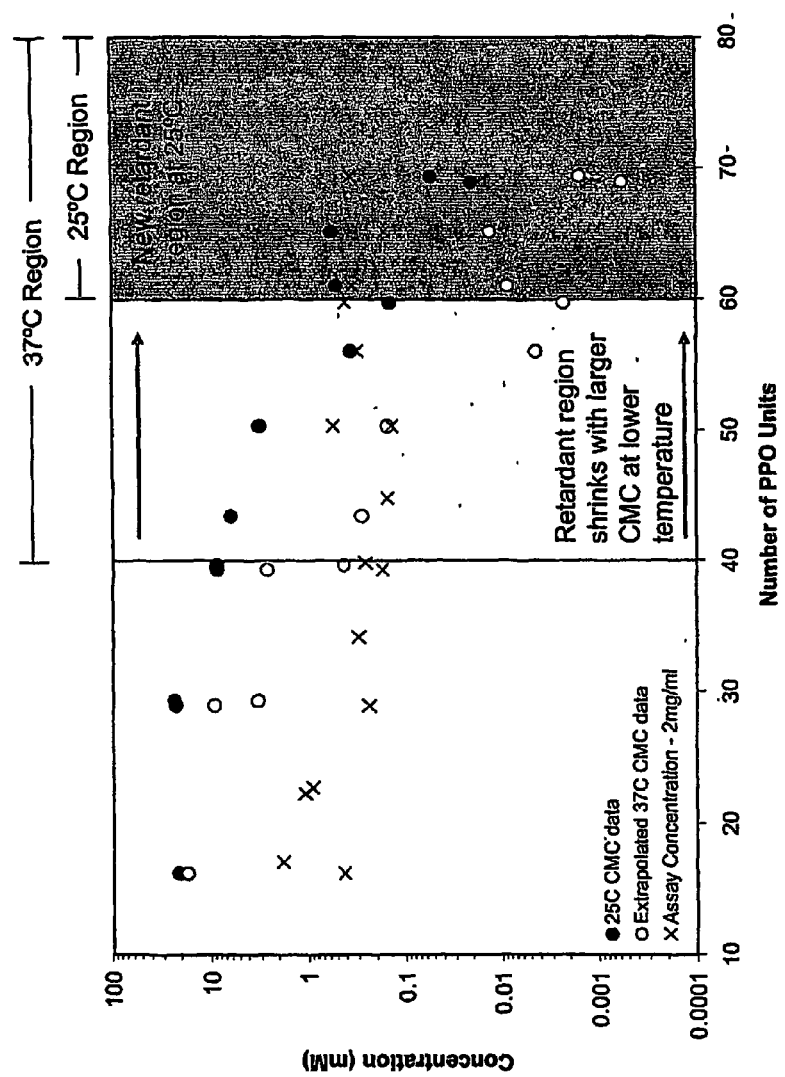
FIG. 31B shows that Pluronic concentrations greater than or equal to the CMC are preferred for effective precipitation inhibition.

The precipitation retardation data obtained using the Pluronic excipients was further correlated to critical micelle concentration (CMC) values as a function of temperature. In this analysis, the dependence of CMC values as a function of propylene oxide content (i.e., PPO units) at both 25 and 37 degrees is illustrated in FIG. 31B, where the concentration values of the Pluronic excipients used in the screen are overlayed for comparison. As shown in FIG. 31, effective retardants at 37 degrees C. had a propylene oxide content greater than 40 PPO because the retardants were used at a concentration higher than the CMC value. At 25 degrees C., the number of effective retardants became smaller because the use level of the Pluronic compounds fell below the CMC value at this temperature. A concentration of Pluronic excipients greater than the CMC is thus preferred for preventing immediate precipitation of celecoxib. The reported CMC data was obtained from V. M. Nace, in Nonionic Surfactants (V. M. Nace, Ed.), Marcel Dekker, New York, 1996, pp 78-80.

Example 15

In Vitro Dissolution Studies of PLURONIC Excipients

In Vitro Dissolution Studies of PLURONIC Excipients—Method

1. Celecoxib Preparation
   a. Fresh celecoxib sodium salt hydrate was prepared and analyzed to be approximately 90 percent free acid vs. sodium content.
   b. The celecoxib salt was ground using mortar and pestle until fine powder was formed. The fine powder was sieved using a 105 micrometer pore size mesh and stored in a 20 mL scintillation vial at room temperature.
2. Formulation Preparation
   a. Fresh PLURONIC excipient was dispensed into a mortar. If initially a solid at room temperature, the PLURONIC was ground until a smooth powder was formed.
   b. If hydroxypropylcellulose (HPC) was to be added, it was dispensed after the PLURONIC excipient. The HPC was combined with the PLURONIC and the two were ground together using a pestle and mixed with a spatula for 1 minute.
   c. 105 micrometer sieved celecoxib salt was added to mortar and the mixture was ground and mixed for several minutes.
   d. If needed, a liquid excipient such as Poloxamer 124, PEG 200, or PEG 400 was added to the mortar as a granulating fluid-like liquid to form an intimate contact between drug and excipient. The mixture was ground and mixed until a uniform consistency was observed in the solid-state mixture.
3. Dissolution Assay
   a. A water bath was set up at 37 degrees C.
   b. Simulated gastric fluid in the fasted state (SGF) was prepared at pH 1.7 and diluted by a factor of five with deionized water. The final pH was approximately 2.4. The simulated gastric fluid was diluted by a factor of five to simulate the effect of drinking a glass of water with the medication. The SGF was pre-heated to 37 degrees C.
   c. The formulation was placed in a 20 mL scintillation vial.
   d. A 10 mm×3 mm stir bar was added.
   e. Diluted SGF was added to the formulation. The volume added was set to satisfy a 2 mg/mL dose of celecoxib free acid.
   f. The vial was placed in the water bath and allowed to stir.
   g. At each time point, 0.9 mL of solution was extracted and filtered through a 0.2 micrometer polyvinylflouridine filter. The first ⅔ of filtrate was discarded as waste and the last ⅓ was collected into an eppendorf tube. 0.1 mL of the collected filtrate was immediately transferred to an autosampler vial and diluted by a factor of ten with 0.9 mL of methanol. The autosampler vials were crimp sealed and submitted for content analysis using high performance liquid chromatography with ultraviolet detection.

Figure 32:
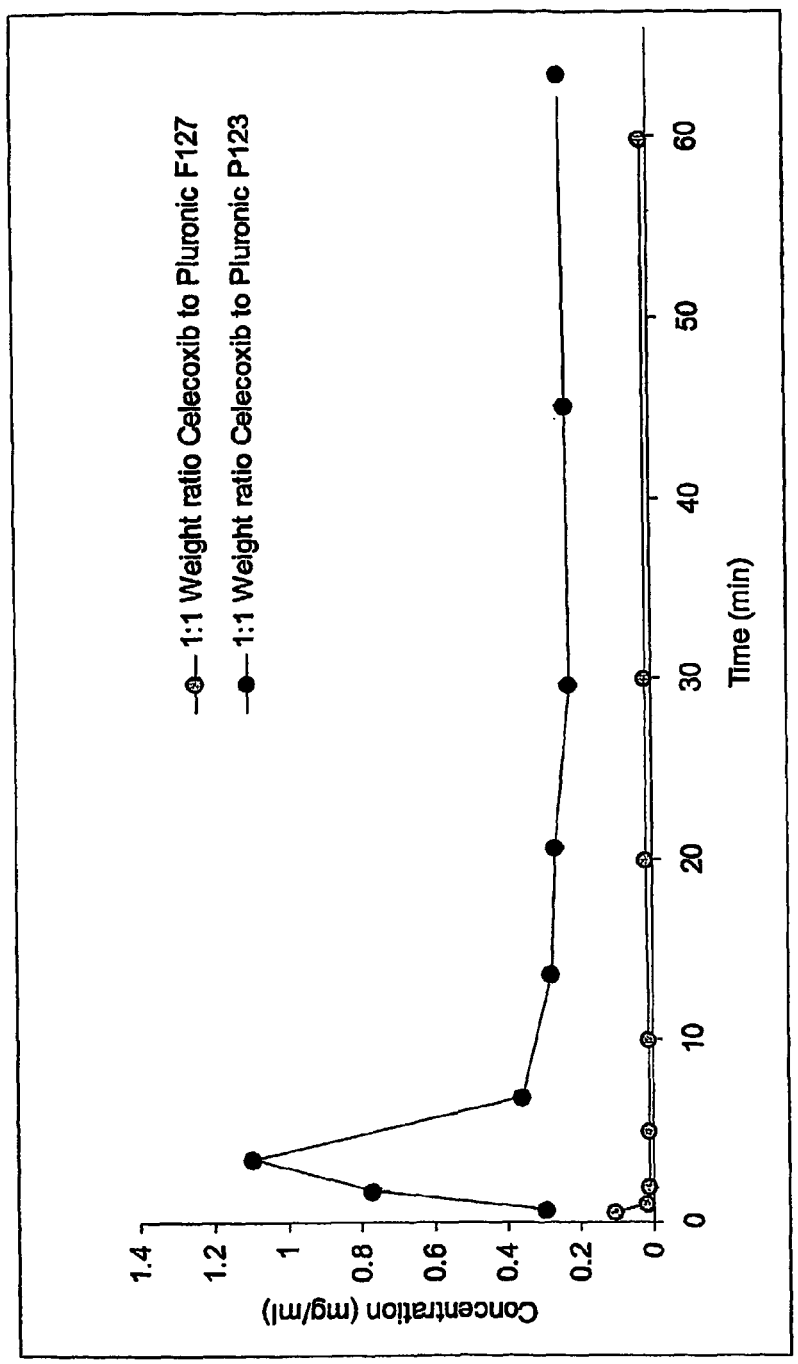
FIG. 32 shows dissolution of celecoxib sodium hydrate from compositions containing PLURONIC P123 and F127.

In Vitro Dissolution Studies of PLURONIC Excipients—Results:

1. Dissolution of two PLURONIC excipients that had low interfacial tension: PLURONIC P123 and F127. PLURONIC P123 was a paste at room temperature, and resulted in a sticky formulation of celecoxib salt. PLURONIC F127 was a solid at room temperature and formed a flowable powder solid-state mixture with the celecoxib salt. The dissolution results for these mixtures at equal weight concentrations of excipient to celecoxib free acid content are shown in FIG. 32. (Weight ratios for the dissolution studies were based on the molar mass of celecoxib free acid.) PLURONIC P123 gave enhanced dissolution of celecoxib salt, while PLURONIC F127 did not. The poor performance of PLURONIC F127 in enhancing celecoxib dissolution was due to the slow dissolution of the excipient. In contrast, PLURONIC P123 was intimately bound with the celecoxib salt in a "sticky" waxy mass, which delayed the dissolution of celecoxib. This allowed the excipient to dissolve to a greater extent prior to the full dissolution of the celecoxib salt form.

Figure 33:
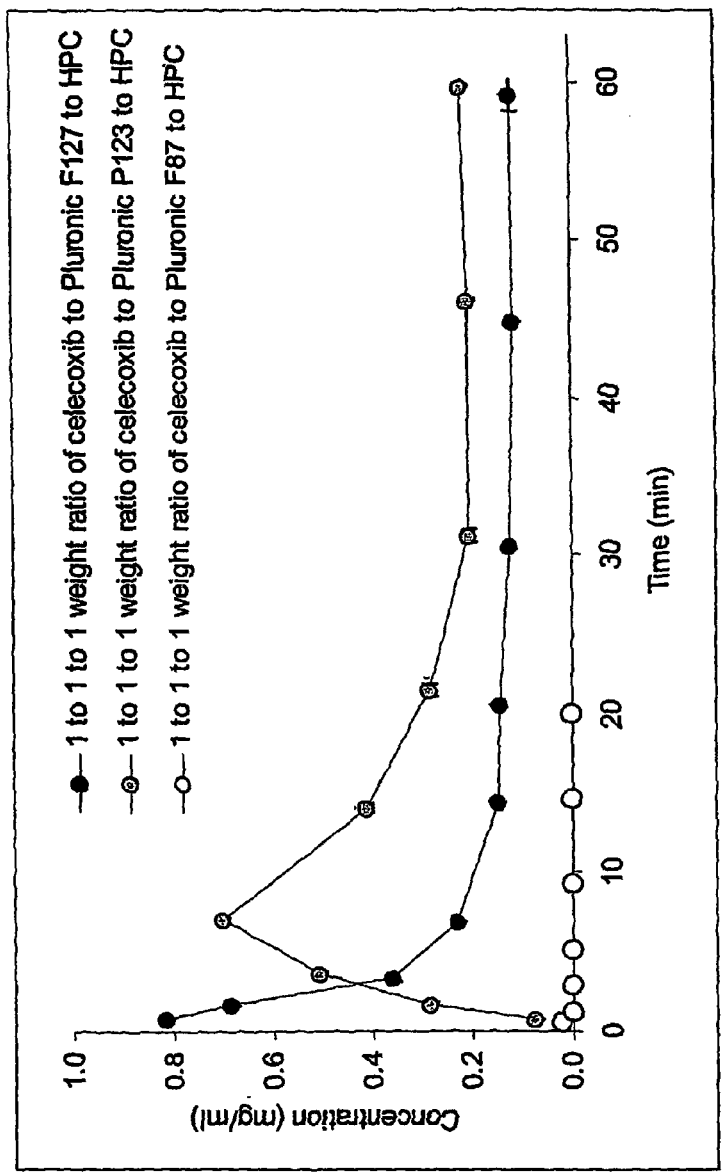
FIG. 33 shows dissolution of celecoxib sodium hydrate from PLURONIC P123, F127 and F87, in the presence of HPC.

2. Dissolution of celecoxib sodium hydrate was performed in the presence of HPC using PLURONIC P123, PLURONIC F127, and PLURONIC F87. PLURONIC F87 has a high interfacial tension value. Equal weight concentrations of PLURONIC and HPC to celecoxib free acid content were used in the formulations. The PLURONIC P123 formulation was sticky due to the pasty nature of the excipient. The PLURONIC F127 and F87 formulation were flowable since these excipients are solids at room temperature. Dissolution data for these formulations are shown in FIG. 33. The data showed that addition of HPC in the PLURONIC P123 formulation produced a widening of the dissolution profile. In the PLURONIC F127 formulation, HPC enhanced the initial dissolution component of the profile (i.e. <10 minutes). In contrast, no dissolution profile was observed in the PLURONIC F87 formulation. Since PLURONIC F87 has a high interfacial tension (17.4 dyne/cm), the resulting data supports the correlation of precipitation retardants with interfacial tension. Since the PLURONIC P123 formulation (i.e., sticky) showed a dissolution profile that was enhanced to a greater extent than the PLURONIC F127 formulation (i.e., loose powder) in terms of time to recrystallization/precipitation, it was hypothesized that the addition of an excipient that physically binds the components of the PLURONIC F127 formulation will result in further dissolution enhancement.

Figure 34:
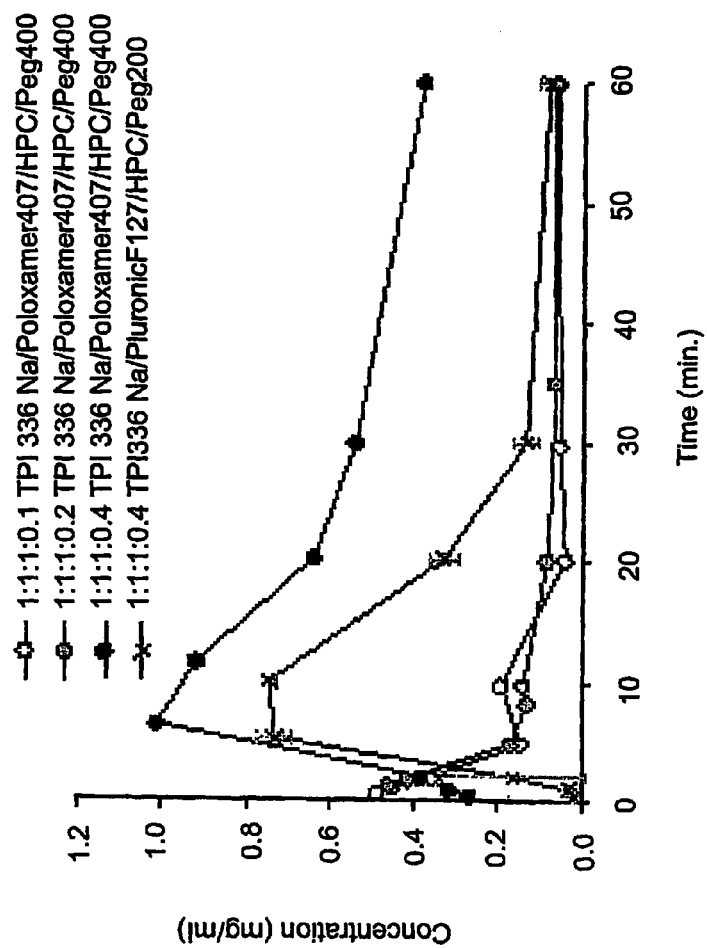
FIG. 34 shows dissolution of celecoxib sodium hydrate using PLURONIC F127, HPC and a granulating fluid.
Figure 35A:
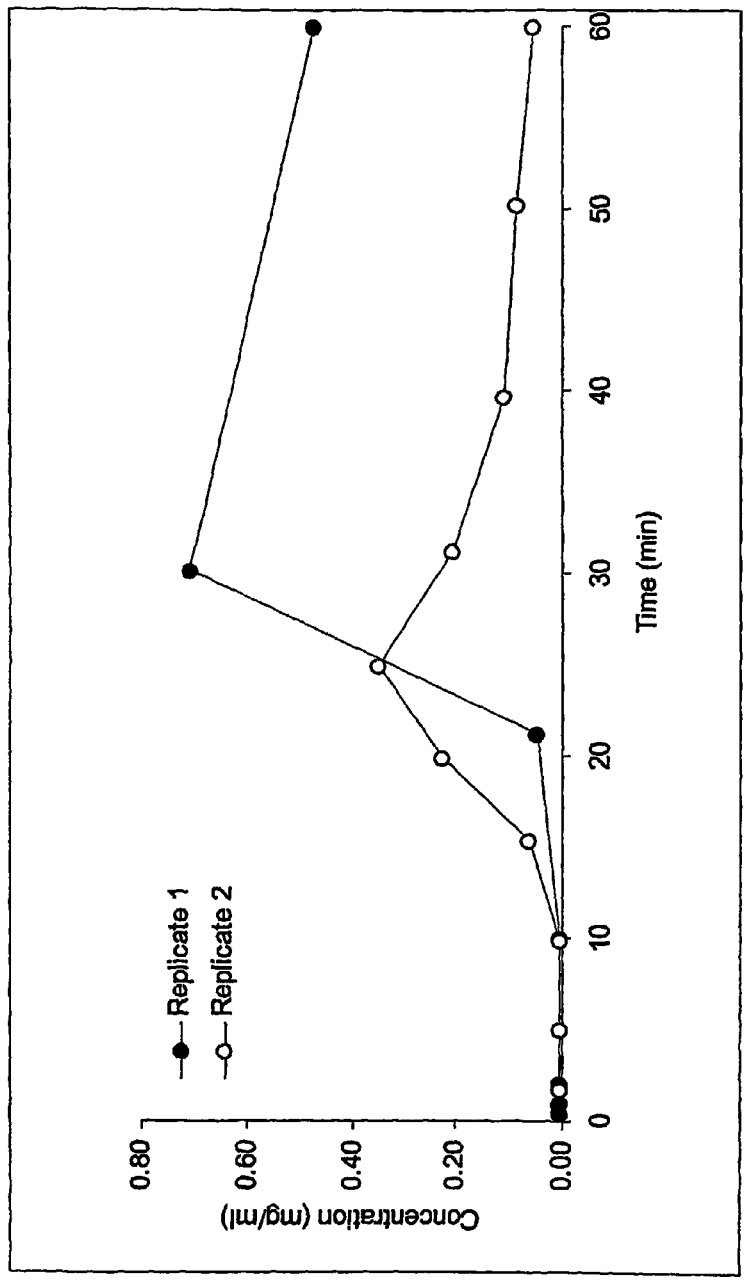
FIG. 35A shows dissolution of celecoxib sodium hydrate using PLURONIC F127 and HPC in a compact formulation.

3. Dissolution of celecoxib sodium hydrate using PLURONIC F127 and HPC was performed using a granulated fluid-like liquid to bind the solid-state mixture. Three granulating fluid-like liquids were chosen: PEG 200, PEG 400, and Poloxamer 124. Equal weight ratios of celecoxib free acid content, PLURONIC F127, and HPC were formulated with 40-45% celecoxib free acid weight of granulating fluid. The effect of these formulations on dissolution is shown in FIG. 34. The granulating fluid-like liquids increased the dissolution of celecoxib, possibly by delaying the contact between the celecoxib salt and the dissolution media until PLURONIC F127 had been dissolved to a significant extent. Dissolution of celecoxib sodium hydrate was then measured from a compacted formulation containing PLURONIC F127 and HPC excipients. Formulations containing equal weight ratios of celecoxib free acid content, PLURONIC F127, and HPC were mixed and compacted into 6 mm discs at 4900 psi. Dissolution results, shown in FIG. 35A, indicated enhanced dissolution with onset retarded by approximately 15-20 minutes. The compaction process produced a similar effect on dissolution to that observed by the addition of a granulating fluid (see FIG. 34) with the addition of a delayed release mechanism. The delayed release characteristic of the profile can be modulated by selecting HPC or HPMC with varying grades of viscosity and the addition of disintegrants into the compact. Compacts are attractive formulations due to their lower production cost and fewer processing steps. FIG. 31B shows the concentration of PLURONIC excipients as a function of polypropylene oxide (PPO) units. This figure shows that PLURONIC concentrations greater than the CMC are preferred for effectively inhibiting precipitation.

Figure 35B:
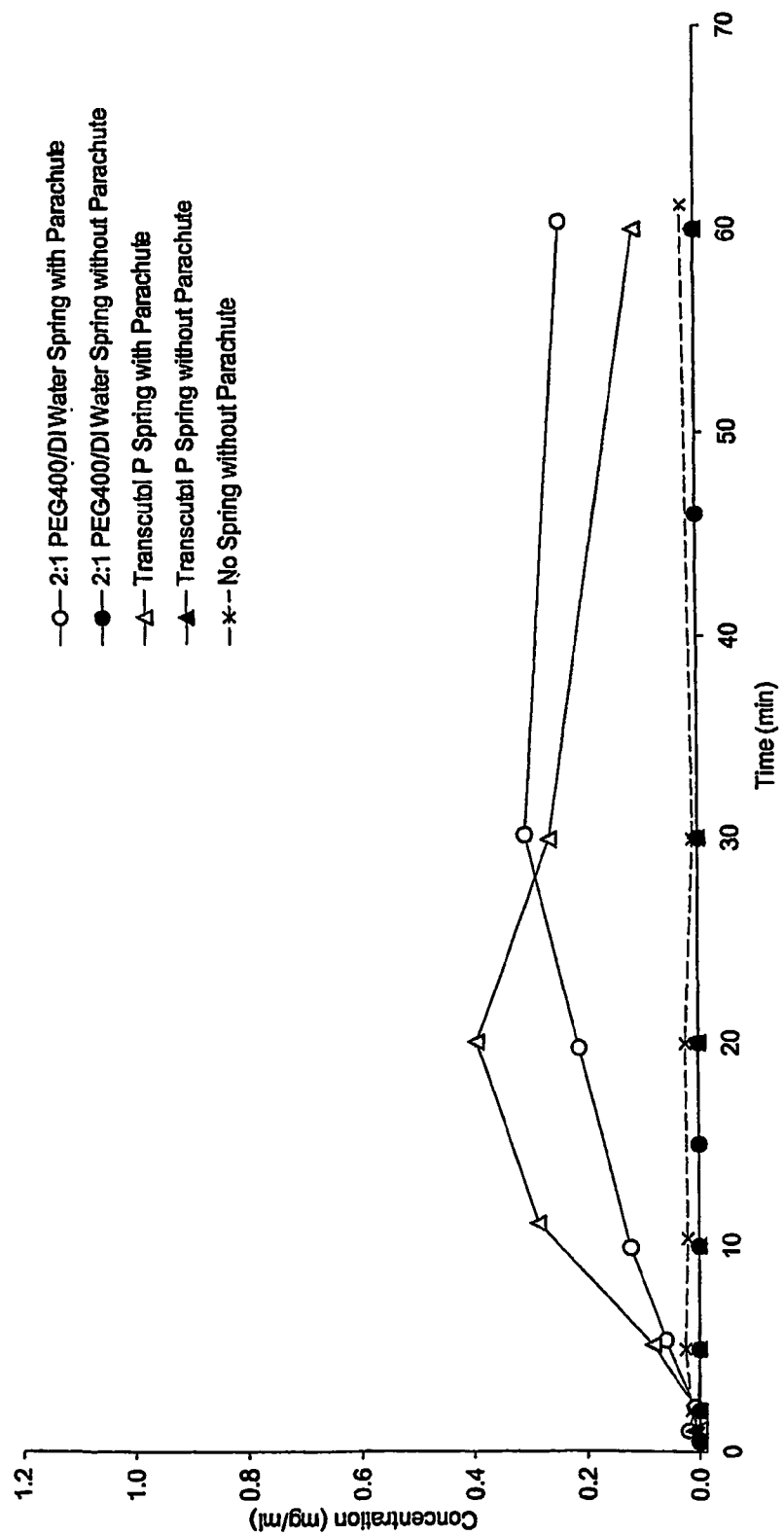
FIG. 35B shows a dissolution profile of springs with and without parachutes.

The data collected thus far, assumped that both initial solubilization and precipitation inhibition were needed to achieve enhanced dissolution of celecoxib. To confirm this assumption, free acid celecoxib was tested in the selected precipitation inhibition excipients: Pluronic F127 and HPC. As shown in FIG. 35B, the dissolution of celecoxib did not show a supersaturation component. The small but measurable increased dissolution over the commercial formulation (i.e., Celebrex) reflects the enhanced thermodynamic solubility of the celecoxib free form in the excipient solution. These data highlight the importance of a novel form to serve as a "spring" and provide a good driving force for supersaturation to occur. In the precipitation inhibition screen the driving force was pre-solubilized celecoxib freeacid in 1 M potassium hydroxide.

FIG. 35B shows the dose of celecoxib free acid in the dissolution medium was 2 mg/ml. The parachute component was comprised of a surfactant, Pluronic F127, and an enhancer, 100,000 MW hydroxypropylcellulose (HPC) at equal mass ratios of celecoxib free acid. "Springs" refer to celecoxib free acid dissolved in either 2:1 PEG400:DI Water or Transcutol P. "No spring" refers to neat celecoxib free acid. DI=deionized, Transcutol P=diethylene glycol monoethyl ether. Dissolution was performed at 37 degrees C.

To test if the "parachute" concept (i.e., surfactant or surfactant plus enhancer) enhances the dissolution of these springs, we decided to co-formulate several species with Pluronic F127 and HPC. The dissolution data obtained with these "springs", FIG. 35B, strongly suggest a "parachute" (surfactant or surfactant plus enhancer) is needed for any appreciable dissolution. Addition of "parachutes", such as of Pluronic F127 and HPC, enabled the dissolution.

Dissolution was performed on a selection of celecoxib "springs" to generalize the concept that the "parachutes" function independently of "spring" type. In these experiments, it was assumed that the selected "springs" were "strong enough" to drive the compound of interest into solution. Once in solution, the "spring" component is theoretically exhausted and the "parachute" component takes an active role in retarding precipitation. The following celecoxib "springs" were compared: (i) freeacid; (ii) sodium hydrate; (iii) sodium propylene glycol solvate; (iv) n-methylpyrolidone (NMP) solvate; and (v) celecoxib:nicotinamide co-crystal. The parachute(s) used in the comparison was a combination surfactant and enhancer, Pluronic F127 and HPC, at same celecoxib free acid mass concentrations. A granulating agent such as Pluronic L44 or PEG400 was added to some of the samples for the purpose of determining its effect on the dissolution profile. The results shown in FIG. 35C confirm that the "parachute" maintained supersaturated levels of celecoxib when a spring was used. The free acid sample, which represents a spring with zero strength, showed concentration levels that were below those concentrations obtained for the other springs.

Figure 35C:
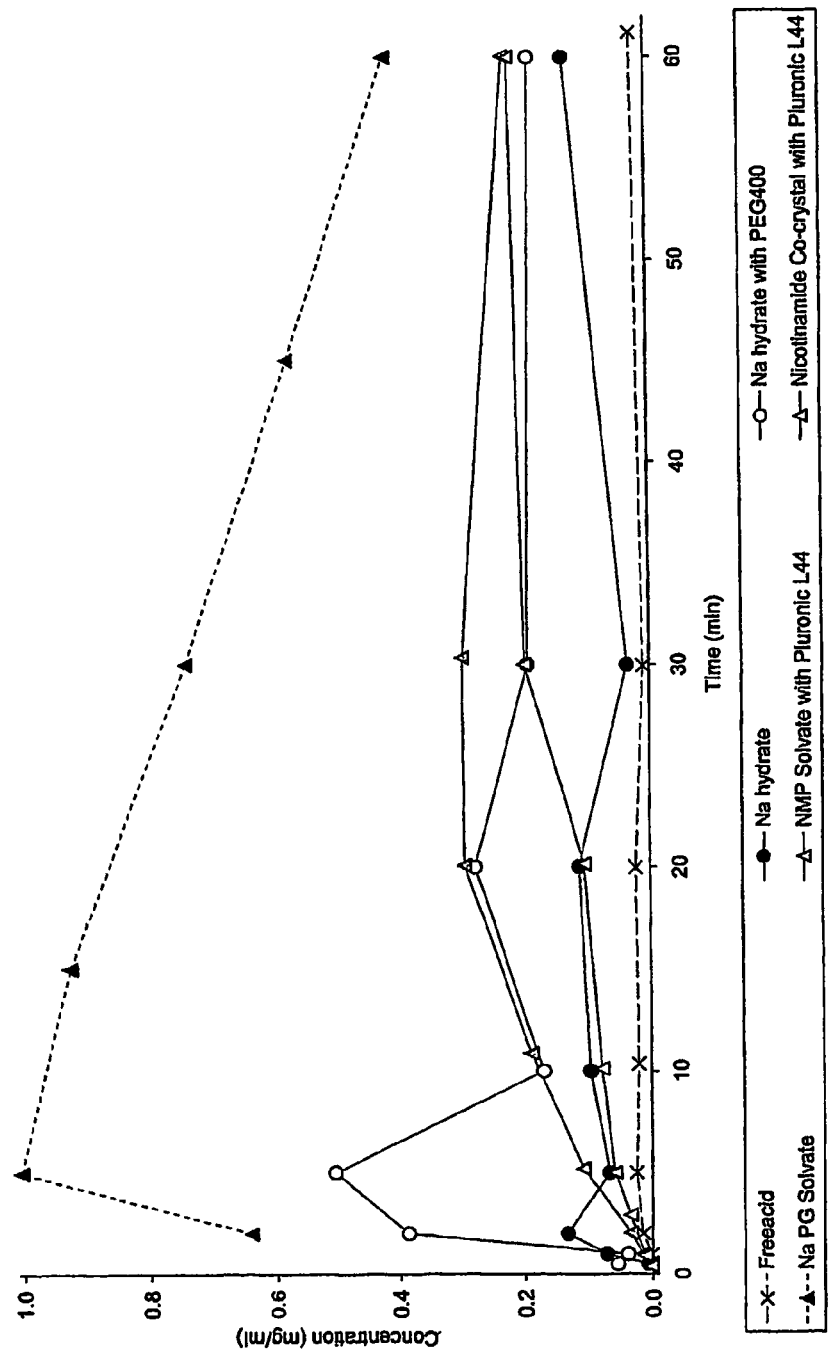

FIG. 35C shows spring enhanced celecoxib dissolution in presence of parachute. The dose of celecoxib free acid in the dissolution media was 2 mg/ml. The implied parachute in all samples was the combined surfactant and enhancer, Pluronic F127 and 100,000 MW HPC, at equal mass ratios of celecoxib free acid. PG=propylene glycol, NMP=n-methylpyrolidone, PEG400=polyethylene glycol with an average molecular weight of 400 Da. Dissolution was performed at 37 degrees C.

Example 16

General Method of Precipitation Retardation Assay

Figure 36:
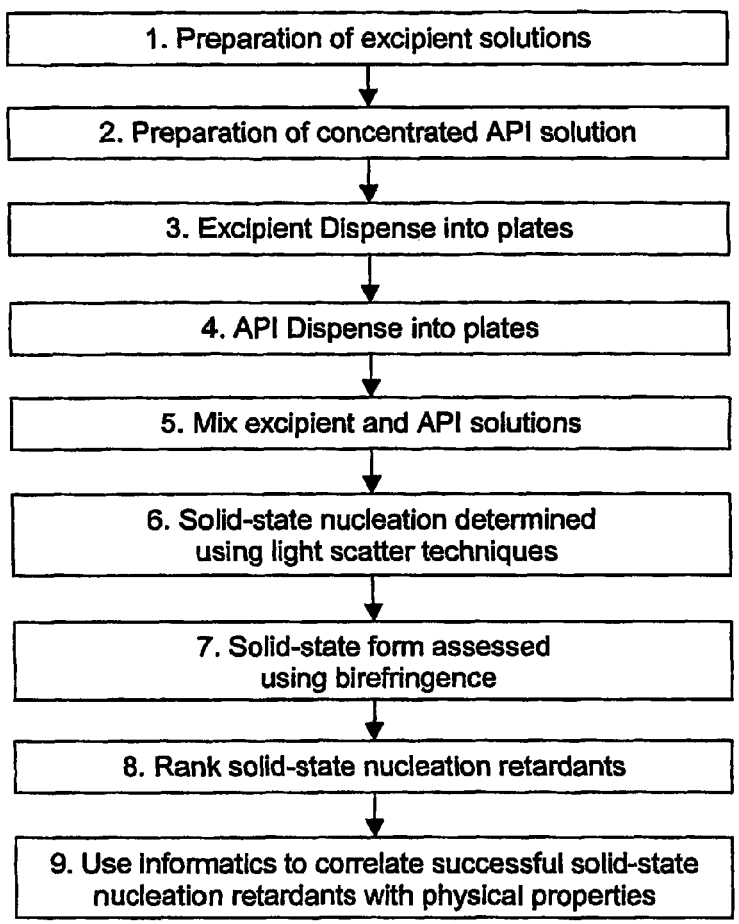
FIG. 36 shows a flowchart outlining a process according to the invention.

The methods described above are specific examples of general methods of the present invention aimed at identifying excipients that retard the nucleation of solid-state API, their derivatives, and other non-pharmaceutical compounds of marketable interest from a solution supersaturated with API. The method is outlined in FIG. 36 and is described as follows:
1. Excipients are dissolved to a desired concentration in de-ionized (DI) water or other media (i.e., simulated gastric or intestinal fluids).
2. API is dissolved in a suitable solvent in which it has high solubility (i.e., acidic pH environment for free base type API; and basic pH environment for free acid type API).
3. The excipient solutions are dispensed into an assay plate (i.e., 96-well or 384-well optically clear plate) either manually, or using automated liquid handling equipment. The excipients can be added as single, binary, ternary, or higher order excipient combinations into each well. An example of a liquid handling instrument is the Tecan Genesis (Tecan U.S. Inc, Research Triangle Park, N.C.).
4. The API solution is dispensed into the assay plate. The API solution can be dispensed one well at a time, by rows, or columns using the Tecan Genesis instrument or simultaneously into all wells using the Tecan Genmate instrument. The volume of API solution added is restricted to a small size to avoid causing any shifts in the properties of the excipient solution.
5. The solutions are mixed to uniformly distribute the API throughout the excipient solution. The plate is sealed and incubated at a desired temperature.
6. Onset of solid-state nucleation is determined using an instrument capable of measuring scattered light. Examples of scattered light measurement capable instruments are the NepheloStar nephelometer (BMG Technologies, Durham, N.C.) and the SPECTRAmax PLUS plate reader (Molecular Devices Corp, Sunnyvale, Calif.). Temperature is maintained at a constant pre-defined set point by the incubation features of the instruments.
7. Birefringence screening, PXRD, etc. may be performed to determine if precipitated API is amorphous or crystalline. If the API is crystalline, crystal habit and particle size can be recorded.
8. The data are analyzed and the excipients are ranked according to their respective retardation times.

Informatics may be used to correlate successful excipients that retard nucleation with physical property information.

Example 17

Illustration of Resulting Precipitation Retardation Data

Goal: Identify excipients that retard the solid-state nucleation of Compound A in Fluid F at a temperature of 37 degrees C.
Method:
1. 24 excipient solutions were prepared at a concentration of 16 mg/mL in de-ionized water.

Figure 37:
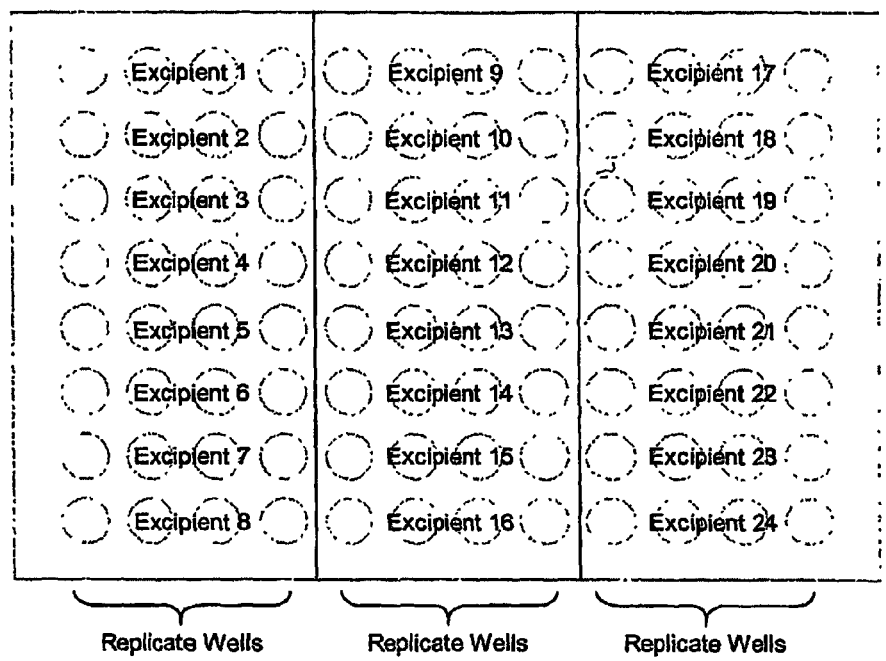
FIG. 37 shows a platemap for an automated liquid dispenser.
Figure 38:
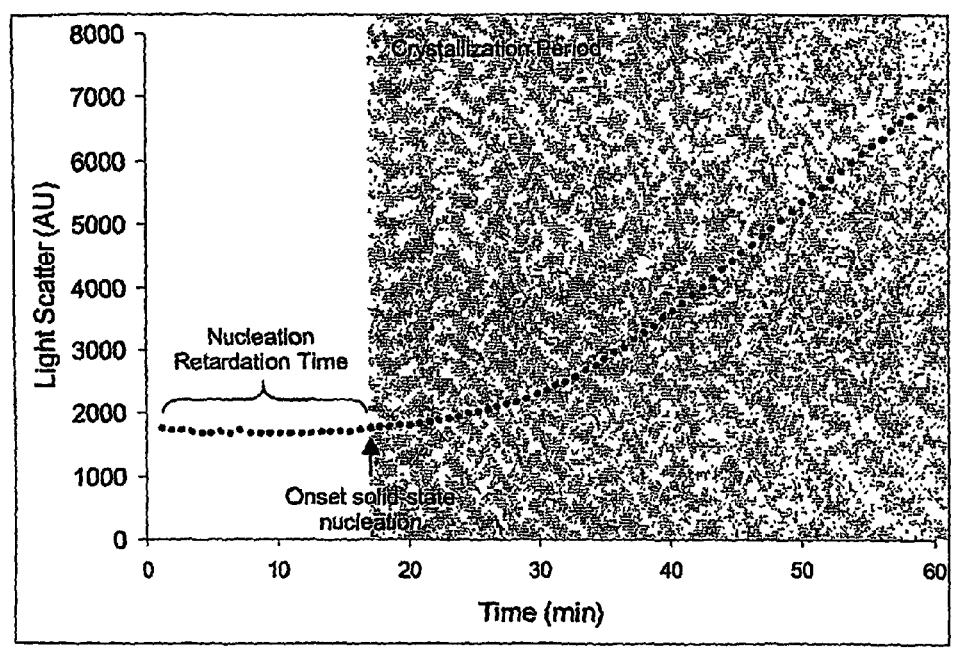
FIG. 38 shows a trace of light scatter against time in an assay according to the invention.

2. Fluid F was prepared in de-ionized H$_2$O by mixing ingredients at twice the desired final concentration.
3. API solution was prepared at a concentration of 5.5 mg/mL in Fluid C.
4. The Tecan Genesis instrument was used to dispense a combination of 75 microliters Fluid F, 18.75 microliters excipient solution, and 56.25 microliters de-ionized H$_2$O into each well of a 96-well plate. The final concentration of excipient in each well was 2 mg/mL in Fluid F. The total fluid volume per well was 150 microliters. Four replicate wells were used for each single excipient solution. An example of the layout is shown in FIG. 37.
5. The plate was sealed using a transparent seal and incubated at 40 degrees C. for 20 minutes.
6. The seal was removed and 15 microliters of API solution was dispensed simultaneously into all 96-wells. The final concentration of API in each well was 0.5 mg/mL. (Note: The time dependence for solid-state nucleation began as soon as the API solution was added.)
7. The well contents were mixed and sealed using the transparent seal.
8. The plate was placed on the Nephelostar instrument to collect light scatter data over a 1 hour time period. The Nephelostar incubated the plate at 37 degrees C. as specified in the goal of the assay.
9. At the end of the assay, the data were analyzed using Microsoft Excel® and retardation times were calculated. An example of collected light scatter data is shown in FIG. 38. Onset of solid-state nucleation is defined as the time when the light scatter signal increases above the baseline signal. The threshold limit for the increase of the light scatter signal used to define a precipitation/crystallization event is usually set at three times the standard deviation of the baseline signal to take into account background noise. The threshold can be set however, to a different value depending on the sensitivity of the assay and the desired limit of precipitation/crystallization.
10. The retardation times (if any) for the excipient solutions were ranked. FIG. 30 shows a graphical representation of the ranking.

Non-limiting examples of alternatives to this general method include:
1. Retardation time can be measured as a function of excipient concentration.
2. Retardation time can be measured as a function of API salt or co-crystal concentration.
3. API can be concentrated in a non-aqueous medium prior to assay.
4. Temperature can be varied and controlled according to a desired specification.

Example 18

Propylene Glycol Solvate of Celecoxib Sodium Salt

A propylene glycol solvate of the sodium salt of celecoxib was prepared. To a solution of celecoxib (312 mg; 0.818 mmol) in diethyl ether (6 mL) was added propylene glycol (0.127 mL, 1.73 mmol). To the clear solution was added sodium ethoxide in ethanol (21%, 0.275 mL, 0.817 mmol). After 1 minute, crystals began to form. After 5 minutes, the solid had completely crystallized. The solid was collected by filtration and was washed with additional diethyl ether (10 mL). The off-white solid was then air-dried and collected. The crystalline salt form was identified as a 1:1 solvate of propylene glycol. The solid was characterized by TGA and PXRD. The results are depicted in FIGS. 39 and 40A.

Figure 39:
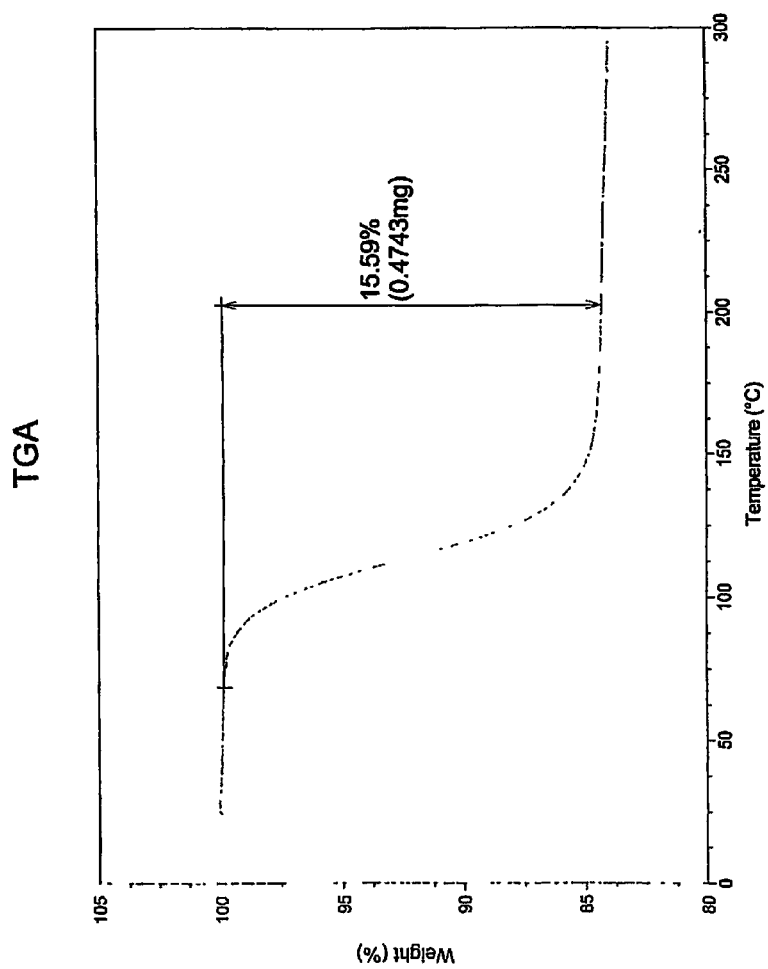
FIG. 39 shows a thermogravimetric analysis (TGA) thermogram of a propylene glycol solvate of a celecoxib sodium salt.
Figure 40A:
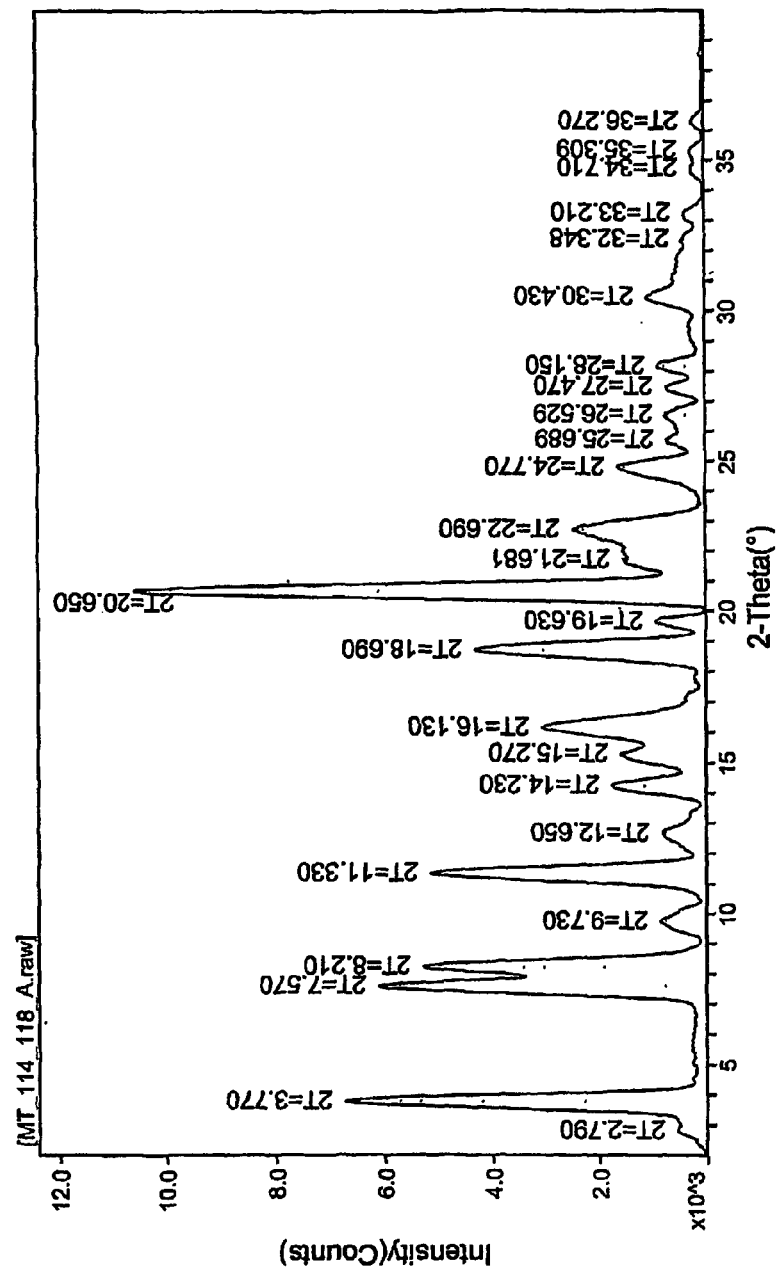
FIGS. 40A-D show the PXRD diffractograms of a propylene glycol solvate of a celecoxib sodium salt.

FIG. 39 shows the results of TGA. A weight loss of about 15.6% was observed between about 65 and 200 degrees C. which represents 1 molar equivalent of propylene glycol to celecoxib Na salt. FIG. 40A shows the results of PXRD. Peaks, in 2-theta angles, that can be used to characterize the solvate include any 1, 2, 3, 4, 5, 6, 7, 8, 9, or 10 of the following: 3.77, 7.57, 8.21, 11.33, 14.23, 16.13, 18.69, 20.65, 22.69 and 24.77 degrees or any one or any combination of 1, 2, 3, 4, 5, 6, 7, 8, 9, 10, or more peaks of FIG. 40A. The TGA thermogram or PXRD diffractogram data may be used alone or in any combination to characterize the solvate. A 0.8 mm collimator was used during acquisition of the diffractogram.

Figure 40B:
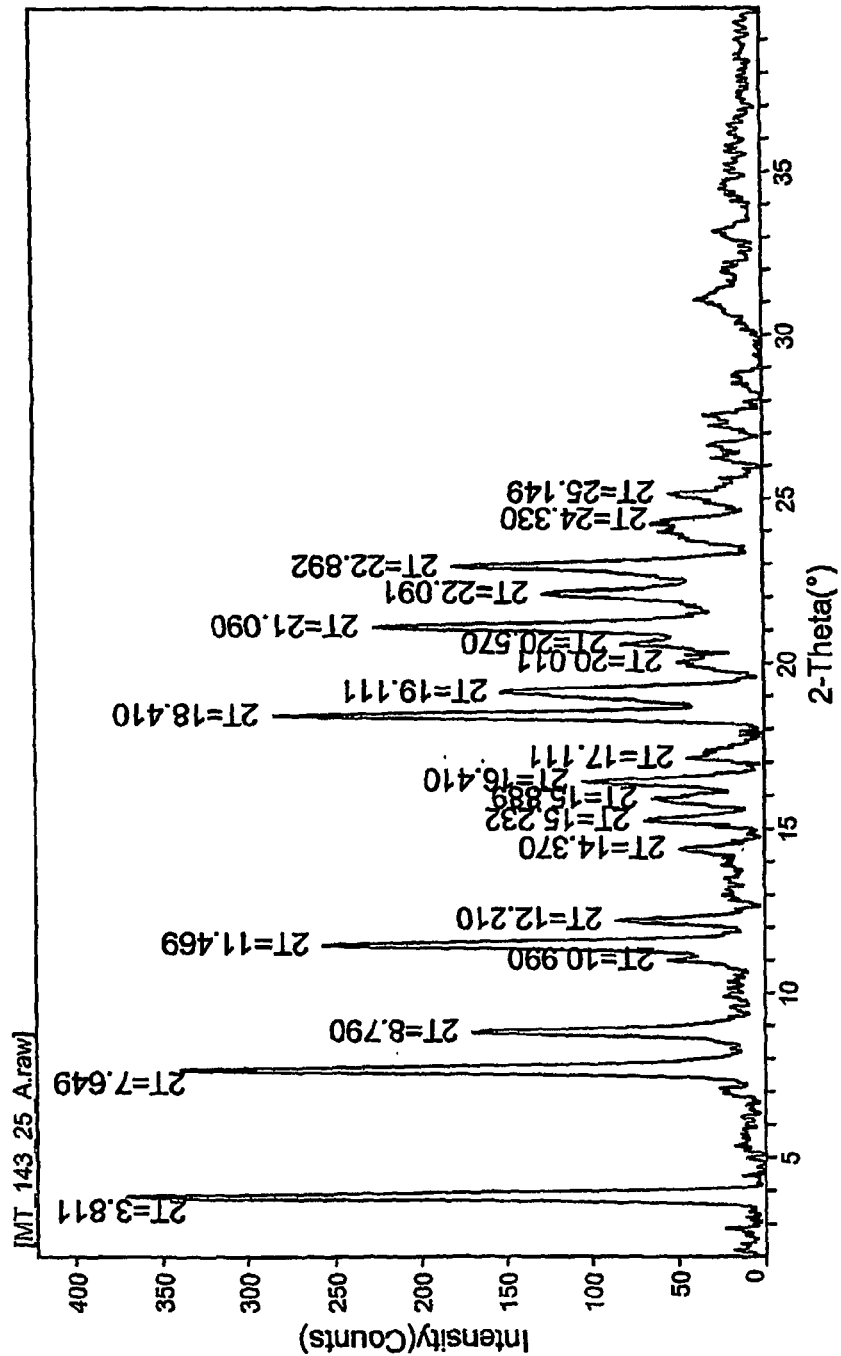
Figure 40C:
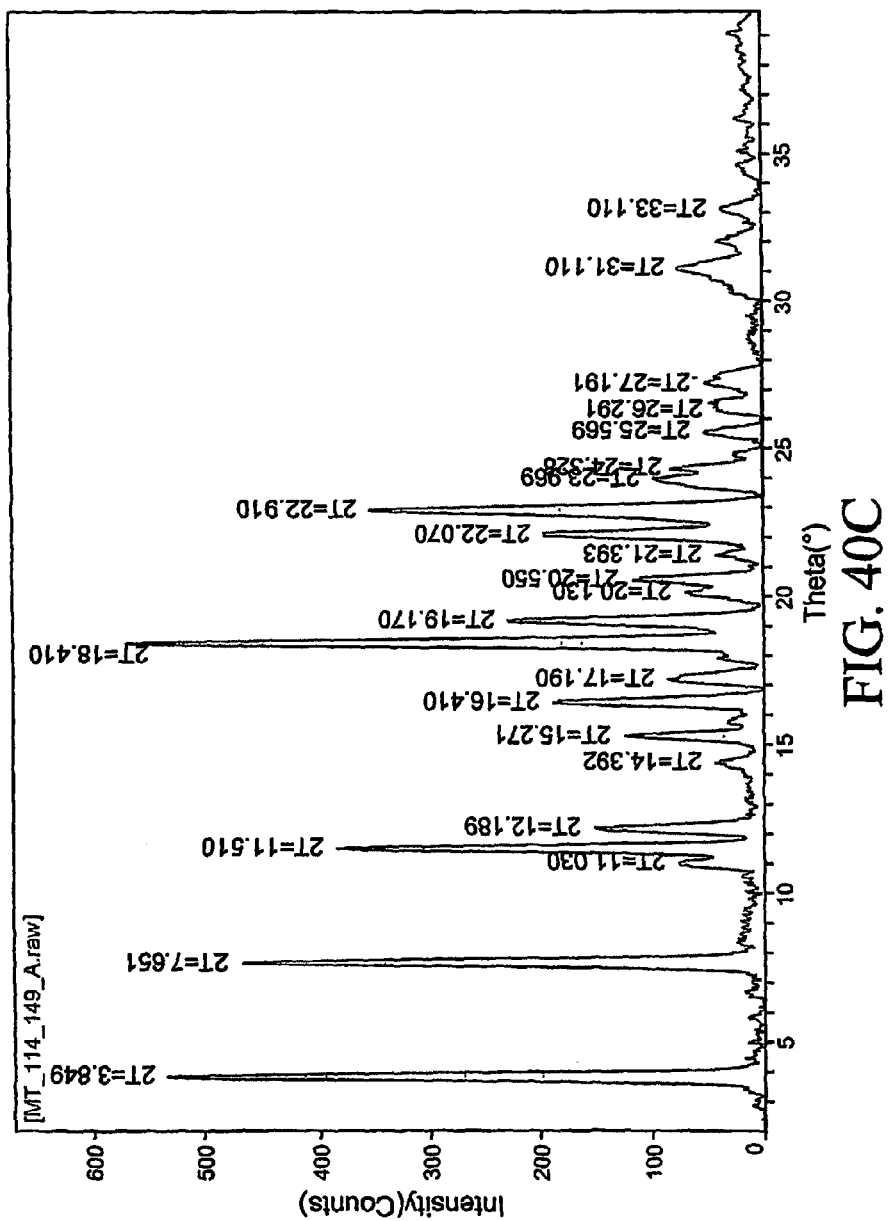
Figure 40D:
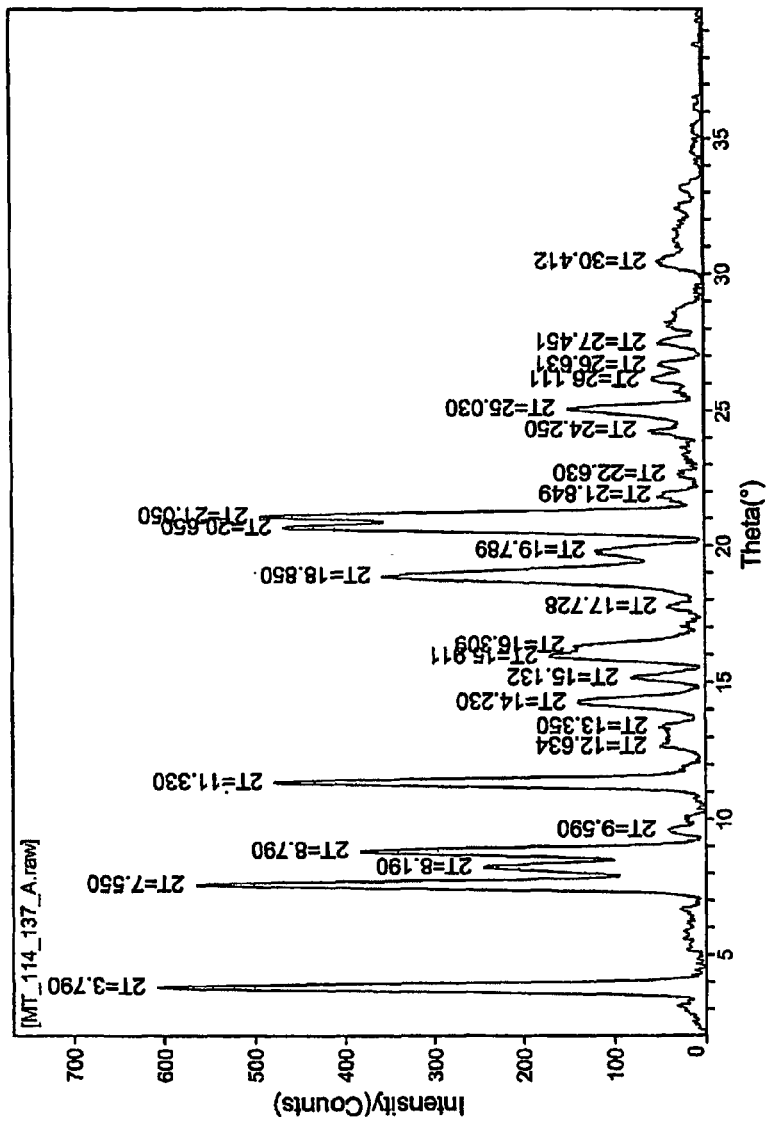

Several closely related, yet distinguishable, PXRD diffractograms have been obtained by performing the above synthesis several times. FIGS. 40B, 40C, and 40D are additional diffractograms of the propylene glycol solvate of celecoxib sodium salt. A comparison of these diffractograms yields a number of noticeable differences. For example, the peak at 8.21 degrees 2-theta in FIG. 40A is not present in FIG. 40B or 40C. Another peak at 8.79 degrees 2-theta, present in FIGS. 40B and 40D, is not found in FIG. 40A or 40C. Other distinctions can also be found between the four diffractograms. Such distinctions in otherwise similar diffractograms suggest the existence of polymorphism or perhaps a variable hydrate.

Example 19

Propylene Glycol Solvate of Celecoxib Potassium Salt

A propylene glycol solvate of the potassium salt of celecoxib was prepared. To a solution of celecoxib (253 mg, 0.664 mmol) in diethyl ether (6 mL) was added propylene glycol (0.075 mL, 1.02 mmol). To the clear solution was added potassium t-butoxide in tetrahydrofuran (THF) (1 M, 0.66 mL, 0.66 mmol). Crystals immediately began to form. After 5 minutes, the solid had completely crystallized. The solid was collected by filtration and was washed with additional diethyl ether (10 mL). The white solid was then air-dried and collected. The crystalline salt form was found to be a 1:1 propylene glycol solvate of celecoxib K salt. The solid was characterized by TGA and PXRD. The results are depicted in FIGS. 41 and 42.

Figure 41:
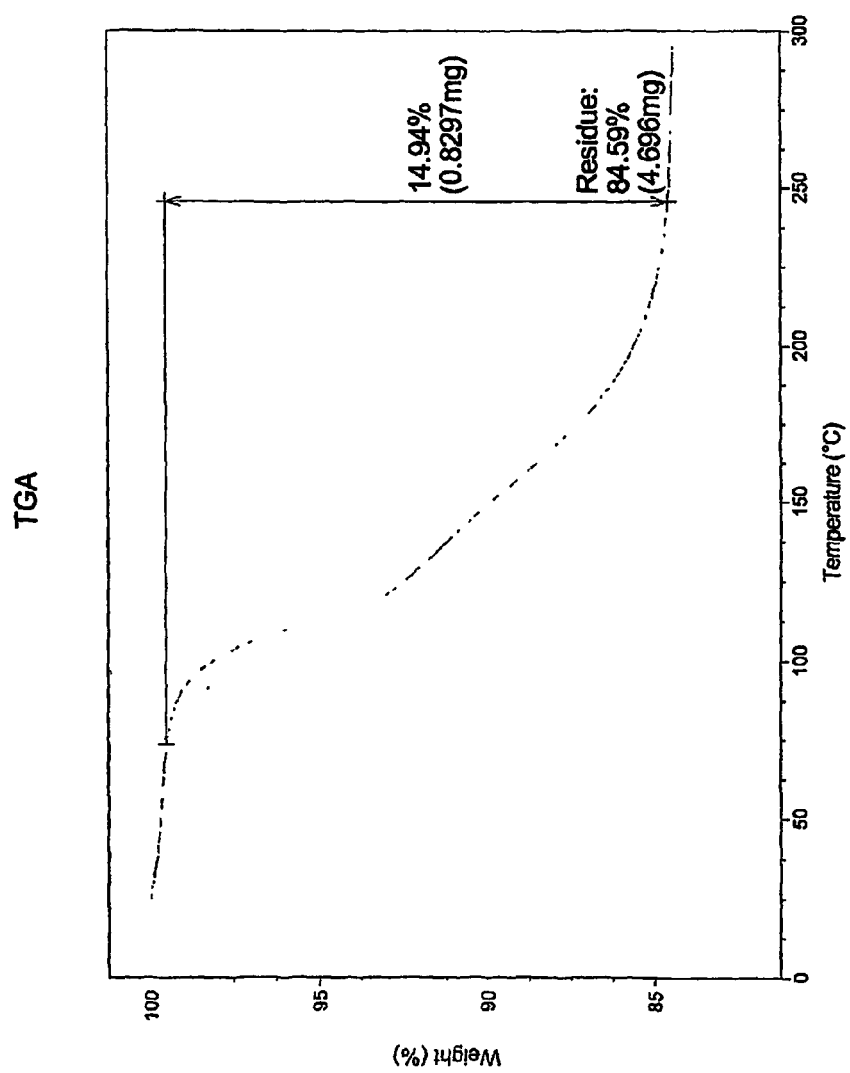
FIG. 41 shows a thermogravimetric analysis (TGA) thermogram of a propylene glycol solvate of a celecoxib potassium salt.
Figure 42:
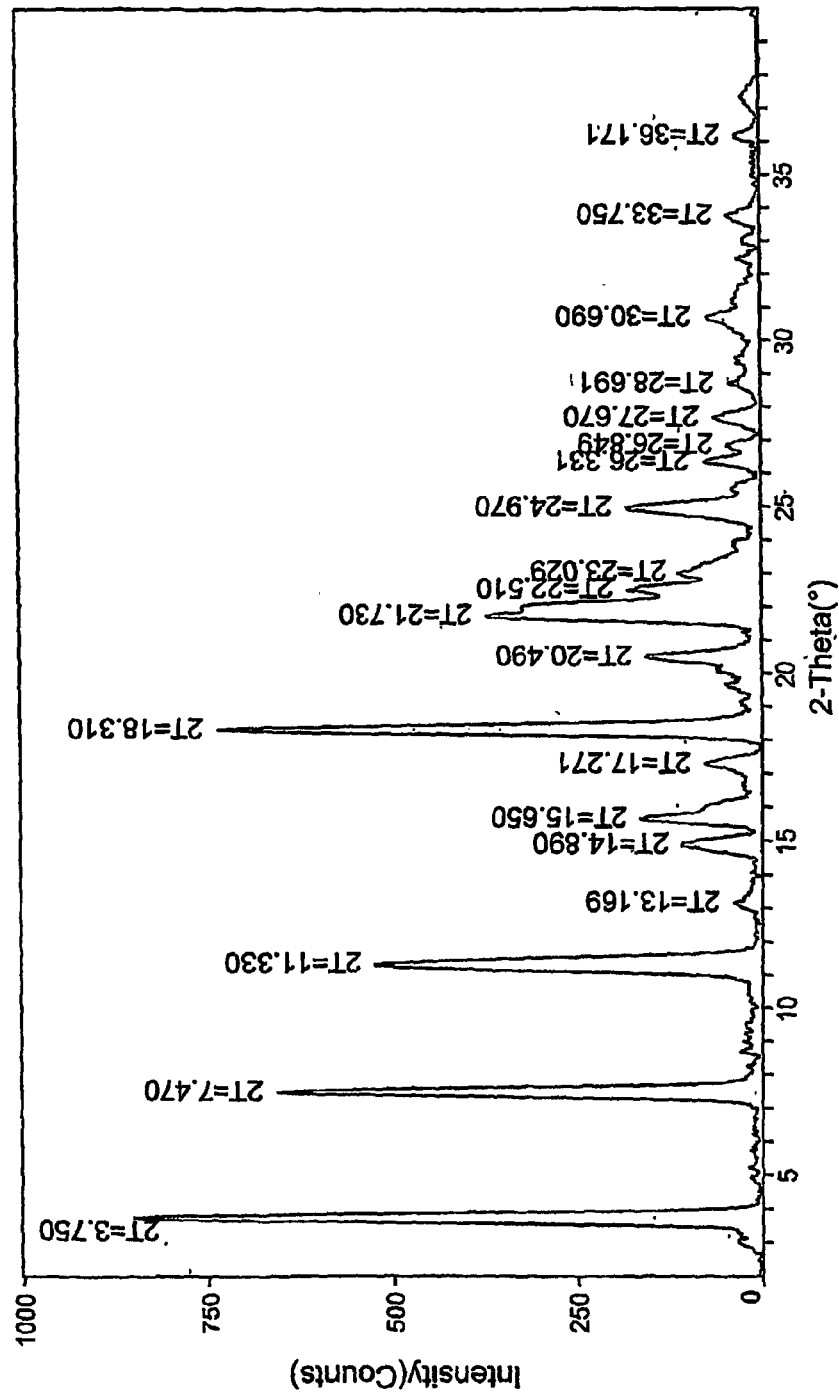
FIG. 42 shows the PXRD diffractogram of a propylene glycol solvate of a celecoxib potassium salt.

FIG. 41 shows the results of TGA. A weight loss of about 14.94% was observed between about 65 and about 250 degrees C. which is consistent with 1 molar equivalent of propylene glycol to celecoxib K. FIG. 42 shows the results of PXRD. Peaks, in 2-theta angles, that can be used to, characterize the solvate include any 1, 2, 3, 4, 5, 6, 7, 8, 9, or 10 of the following: 3.75, 7.47, 11.33, 14.89, 15.65, 18.31, 20.49, 21.73, 22.51, and 24.97 degrees or any one or any combination of 1, 2, 3, 4, 5, 6, 7, 8, 9, 10, or more peaks of FIG. 42.

Example 20

Propylene Glycol Solvate of Celecoxib Lithium Salt

A propylene glycol solvate of the lithium salt of celecoxib was prepared. To a solution of celecoxib (264 mg, 0.693 mmol) in diethyl ether Et$_2$O (8 mL) was added propylene glycol (0.075 mL, 1.02 mmol). To the clear solution was added t-butyl lithium in pentane (1.7 M, 0.40 mL, 0.68 mmol). A brown solid formed immediately but dissolved within one minute which subsequently yielded a white fluffy solid. The white solid crystallized completely after 10 minutes. The solid was collected by filtration and was washed with additional diethyl ether (10 mL). The white solid was then air-dried and collected. The crystalline salt form was found to be a 1:1 propylene glycol solvate of celecoxib Li. The solid was characterized by TGA and PXRD.

Figure 43:
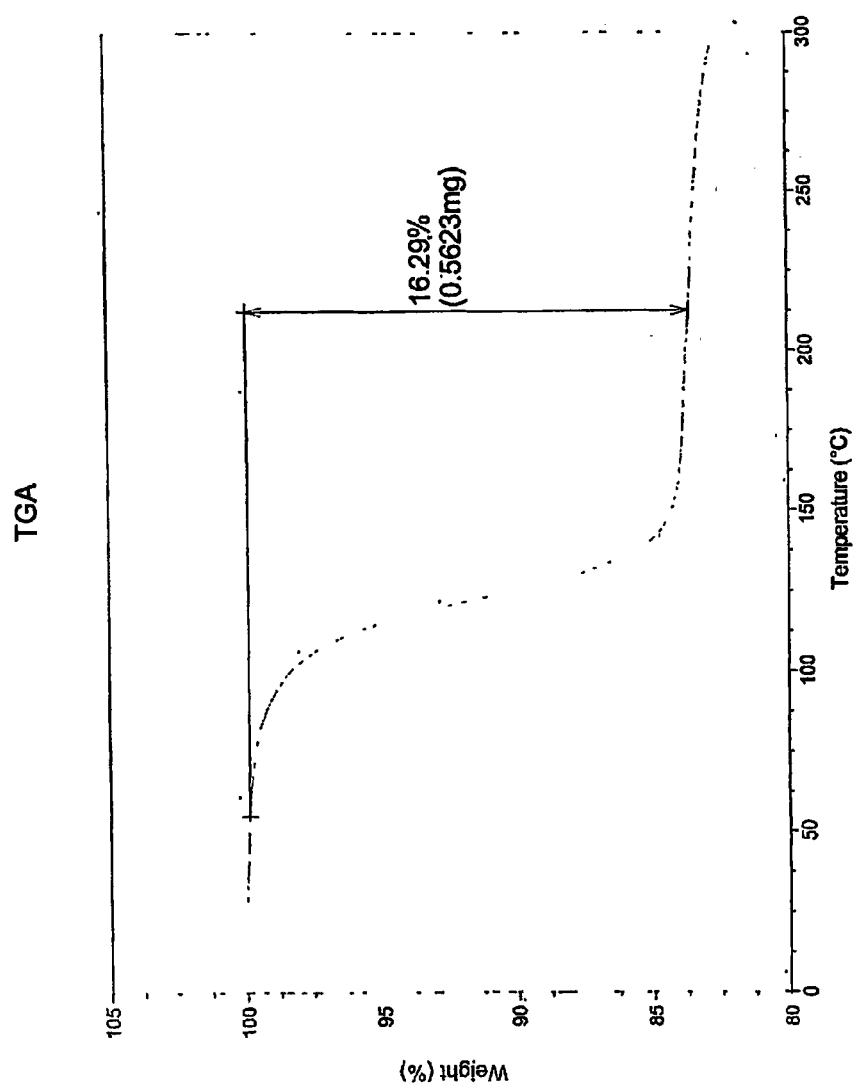
FIG. 43 shows a thermogravimetric analysis (TGA) thermogram of a propylene glycol solvate of a celecoxib lithium salt.
Figure 51:
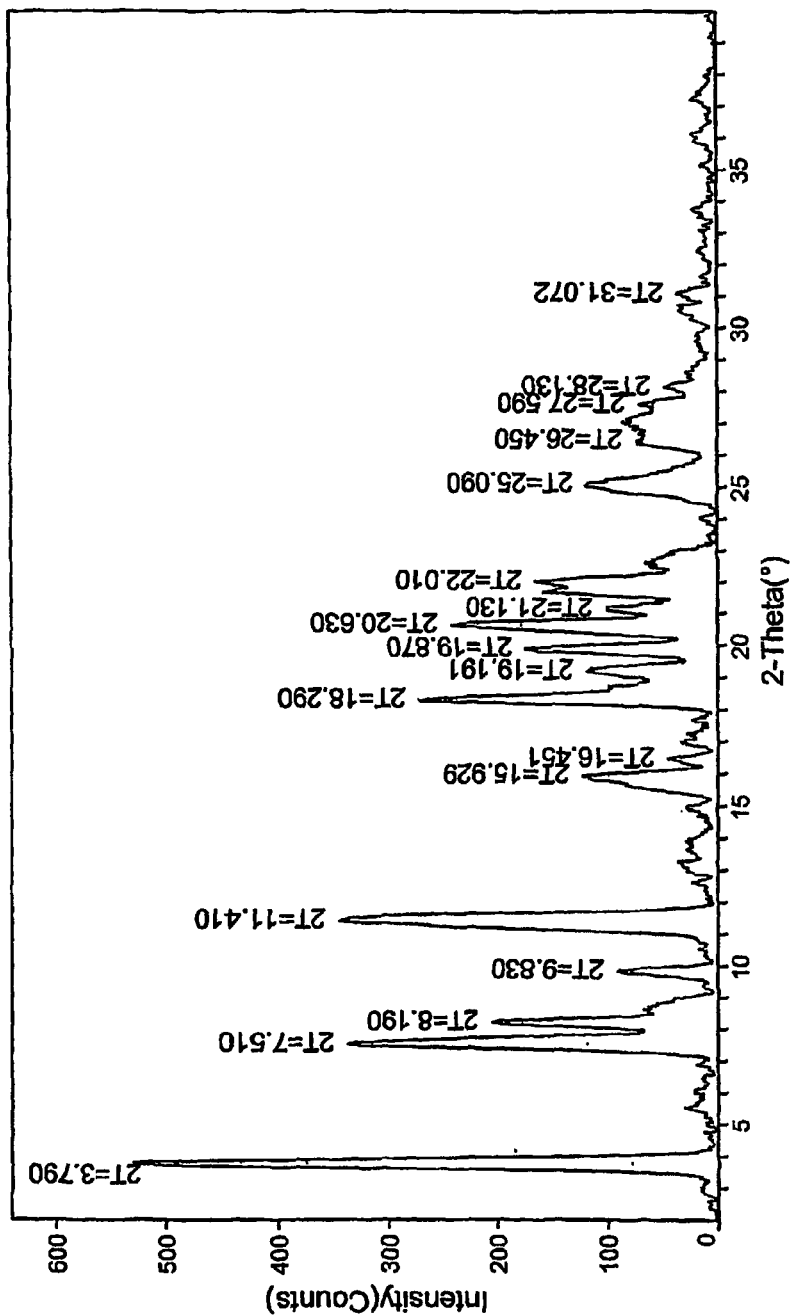
FIG. 51 shows a PXRD diffractogram of the propylene glycol solvate of celecoxib lithium salt prepared by Example 20.

The results of TGA are depicted in FIG. 43 and show a weight loss of about 16.3% between 50 degrees C. and 210 degrees C. which is consistent with 1 molar equivalent of propylene glycol to celecoxib Li. The results of PXRD are shown in FIG. 51. Characteristic peaks of 2-theta angles that can be used to characterize the salt include any one, or combination of any 2, 3, 4, 5, 6, 7, 8, 9, 10, 11, or 12 of 3.79, 7.51, 8.19, 9.83, 11.41, 15.93, 18.29, 19.19, 19.87, 20.63, 22.01, or 25.09 degrees or any one or any combination of peaks of FIG. 51.

Example 21

Propylene Glycol Solvate of Celecoxib Sodium Trihydrate

Preparation:
Celecoxib Na propylene glycol trihydrate was formed by allowing the celecoxib sodium salt propylene glycol solvate to sit at 60% RH and 20 degrees C. for 3 days. (Note: Formation of the trihydrate at 75% and 40 degrees C. occurs as well). The trihydrate begins to form somewhere between 31 and 40% RH at room temperature.

Figure 44:
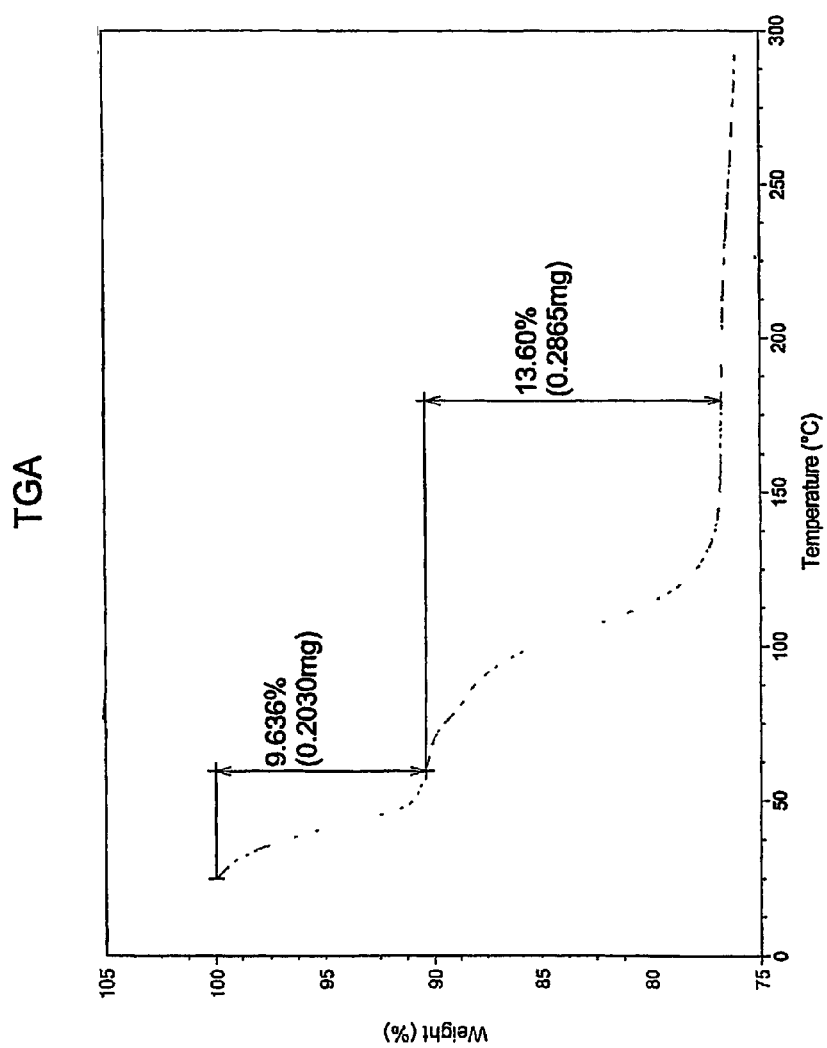
FIG. 44 shows a thermogravimetric analysis (TGA) thermogram of the sodium salt propylene glycol trihydrate of celecoxib prepared by Example 21.
Figure 45:
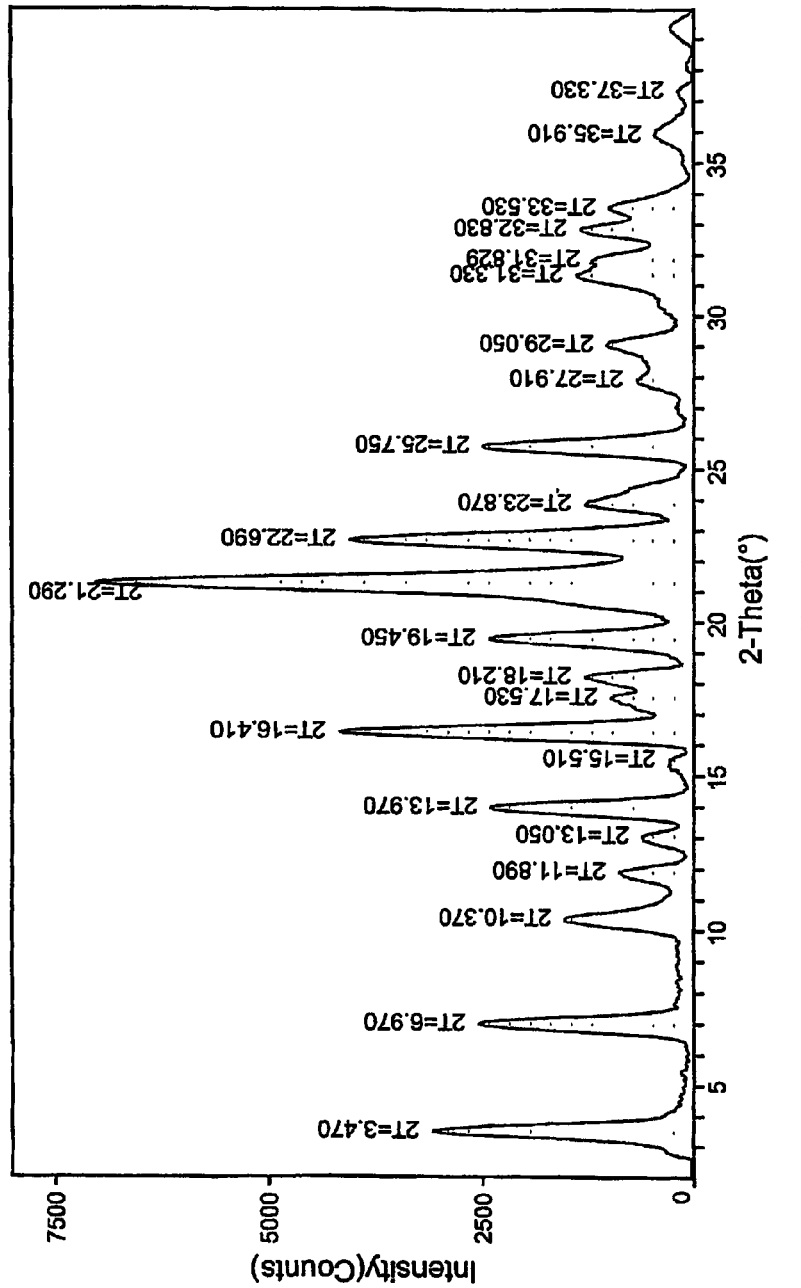
FIG. 45 shows a PXRD diffractogram of the sodium salt propylene glycol trihydrate of celecoxib prepared by Example 21.

The solid was characterized by TGA and PXRD, which are shown in FIGS. 44 and 45, respectively. FIG. 44 shows the results of the TGA where 9.64% weight loss was observed between room temperature and 60 degrees C. and 13.6% weight loss was observed between 60 degrees C. and 175 degrees C. The PXRD pattern has characteristic peaks at 2-theta angles shown in FIG. 45. Any 1, 2, 3, 4, 5, 6, 7, 8, 9, 10, or more peaks can be used to characterize the trihydrate, including for example, peaks at 3.47, 6.97, 10.37, 13.97, 16.41, 19.45, 21.29, 22.69, 23.87, and 25.75 degrees.

The trihydrate can also be formed by crystallization of celecoxib Na propylene glycol solvate in the presence of $H_2O$. To a solution of celecoxib (136.2 mg; 0.357 mmol) in diethyl ether (6.0 mL), water (0.025 mL; 1.39 mmol), and propylene glycol (0.030 mL; 0.408 mmol) was added sodium ethoxide in ethanol (21 wt. %; 0.135 mL; 0.362 mmol). A solid formed within one minute and was isolated via filtration. The solid was then washed with additional diethyl ether (2.0 mL) and allowed to air dry. This procedure gives essentially the same PXRD pattern but there is a slight excess of water, which is probably surface water.

Figure 46:
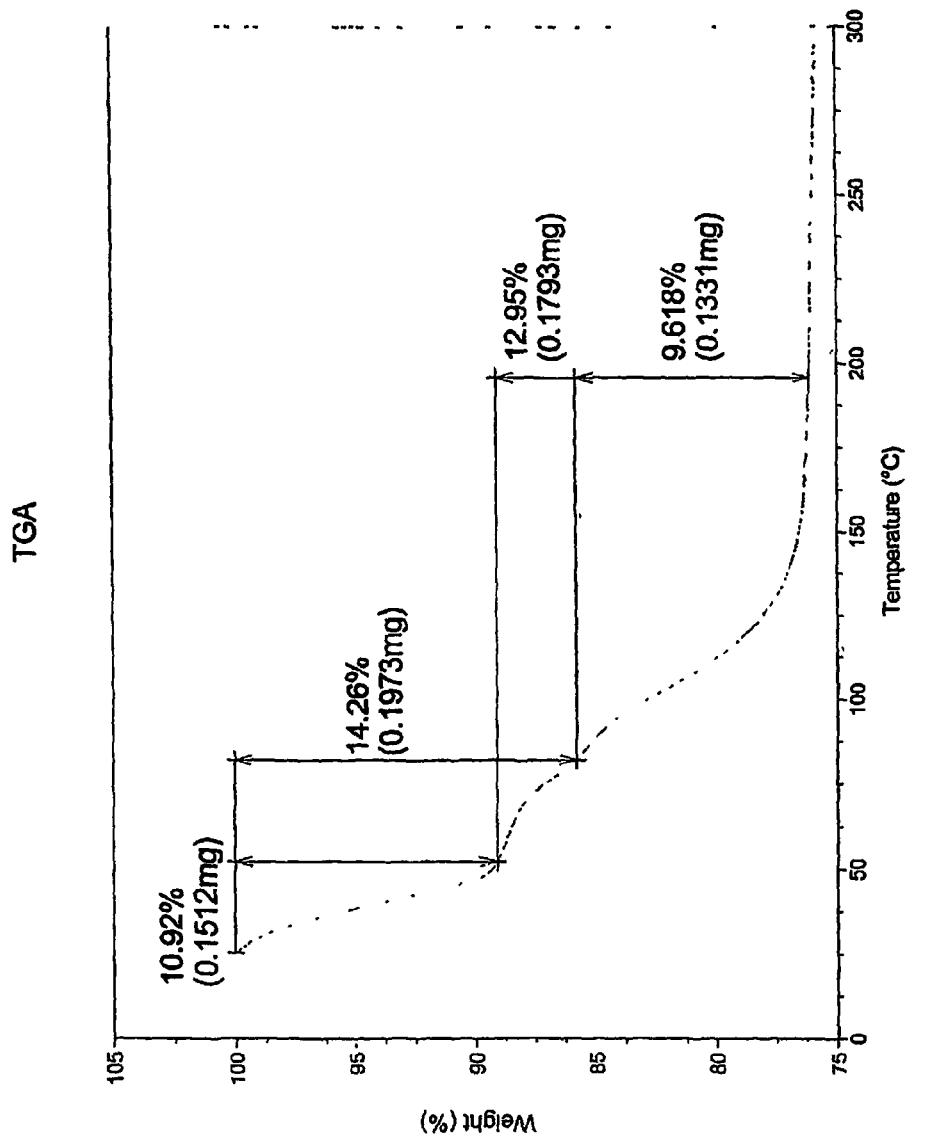
FIG. 46 shows a thermogravimetric analysis (TGA) thermogram of the sodium salt propylene glycoltrihydrate of celecoxib prepared by Example 21.
Figure 47:
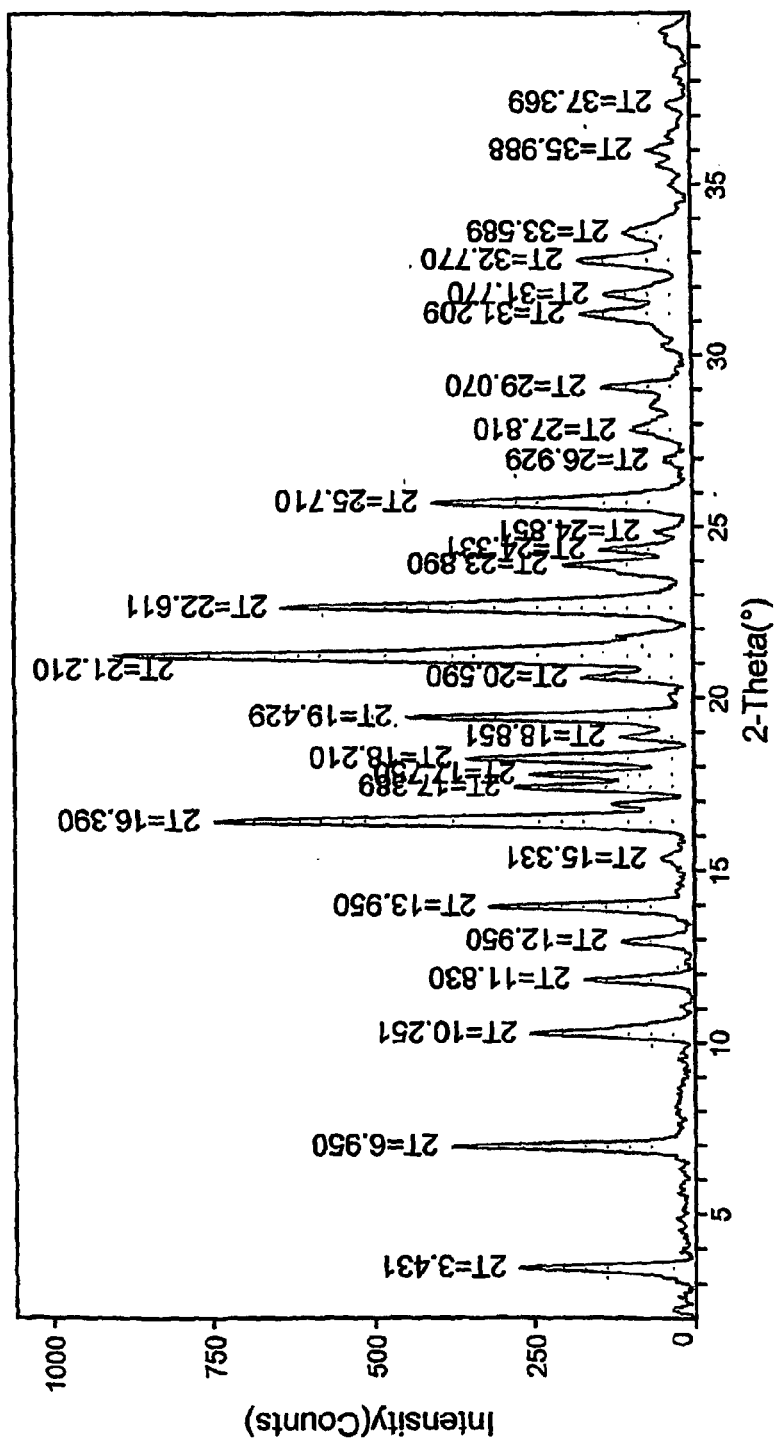
FIG. 47 shows a PXRD diffractogram of the sodium salt propylene glycol trihydrate of celecoxib prepared by Example 21.

The solid was characterized by TGA and PXRD, which are shown in FIGS. 46 and 47, respectively. FIG. 46 shows the results of TGA where 10.92% weight loss was observed between room temperature and 50 degrees C. and 12.95% weight loss was observed between 50 degrees C. and 195 degrees C. The PXRD pattern has characteristic peaks at 2-theta angles shown in FIG. 47. Any 1, 2, 3, 4, 5, 6, 7, 8, 9, 10, 11, 12, or more peaks can be used to characterize the trihydrate, including for example, peaks at 3.43, 6.95, 10.25, 13.95, 16.39, 17.39, 17.75, 18.21, 19.43, 21.21, 22.61, and 25.71 degrees. A 0.8 mm collimator was used during acquisition of the diffractogram.

Example 22

Isopropyl Alcohol Solvate of Celecoxib Sodium Salt

To a solution of celecoxib (204.2 mg; 0.5354 mmol) in diethyl ether (6.0 mL) was added isopropanol (0.070 mL). To the colorless solution was added a solution of sodium methoxide (0.5 M; 2.52 mL; 6.75 mmol) in methanol followed by hexanes (3.0 mL). The volatiles were reduced under flowing nitrogen gas. A white solid formed and was collected via filtration. After drying, the solid was found to be an isopropanol solvate (1.5:1 isopropanol:celecoxib) via TGA and PXRD.

Figure 48:
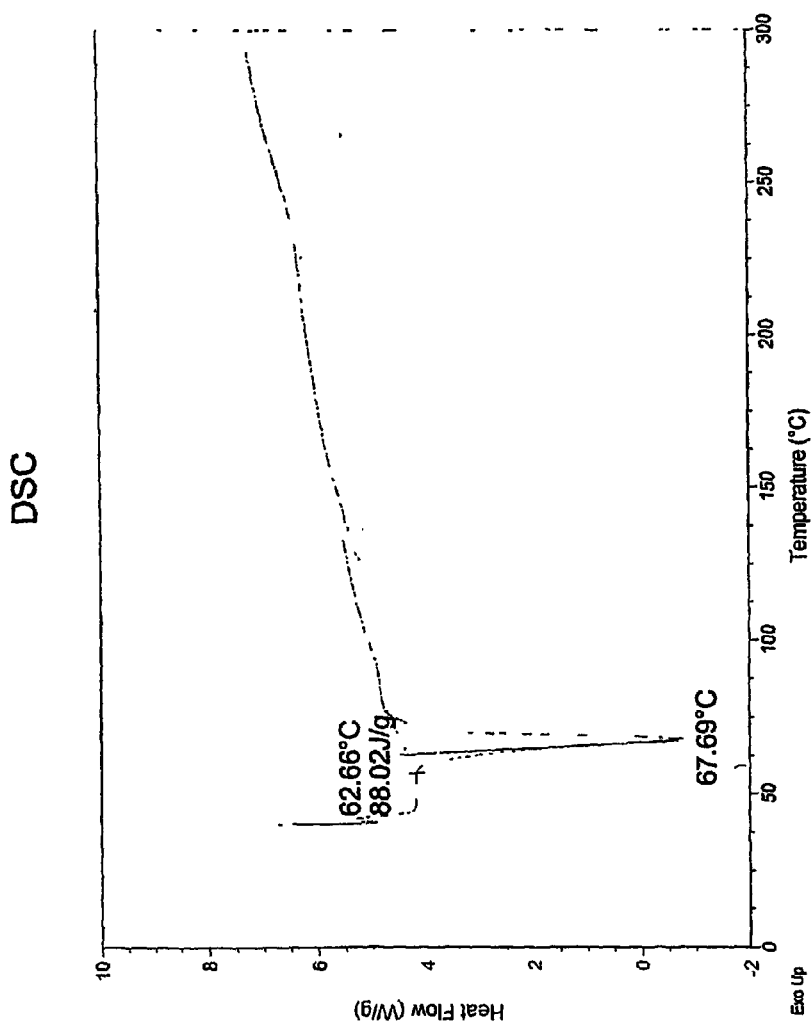
FIG. 48 shows a differential scanning calorimetry (DSC) thermogram of the sodium salt isopropyl alcohol solvate of celecoxib prepared by Example 22.
Figure 49:
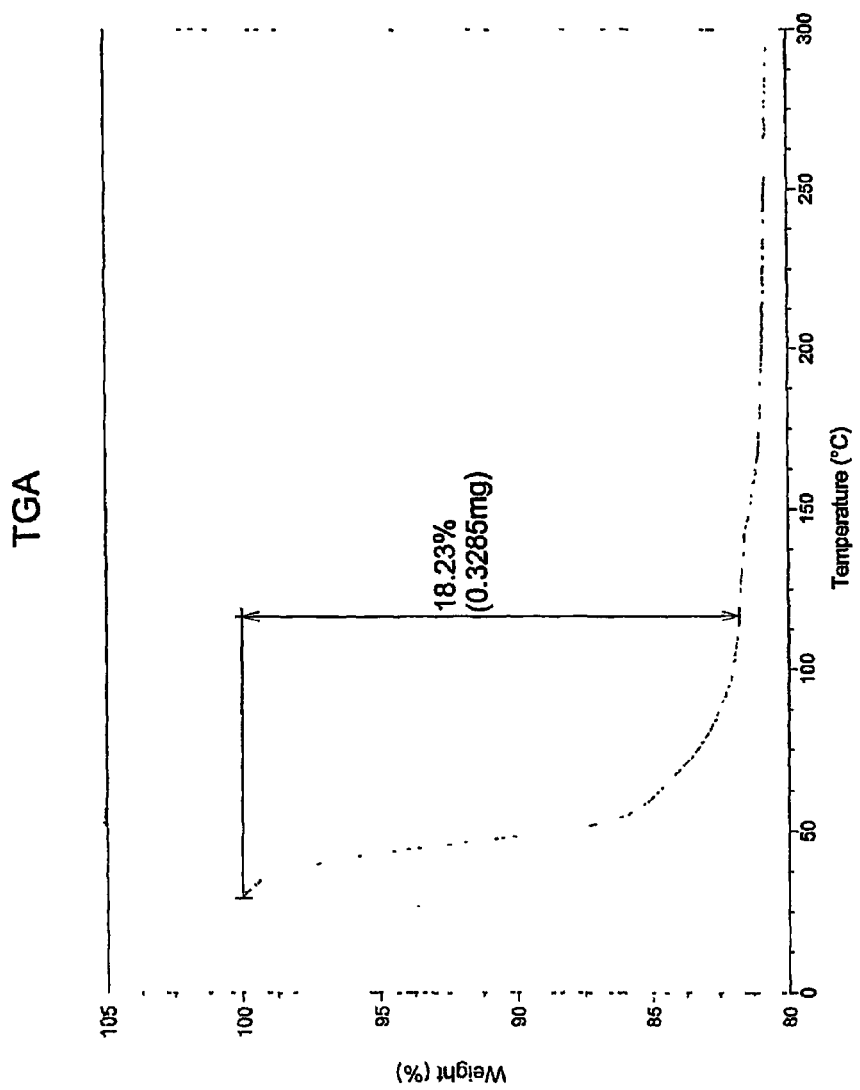
FIG. 49 shows a thermogravimetric analysis (TGA) thermogram of the sodium salt isopropyl alcohol solvate of celecoxib prepared by Example 22, which was conducted from about 30° to about 160 degrees C.
Figure 50:
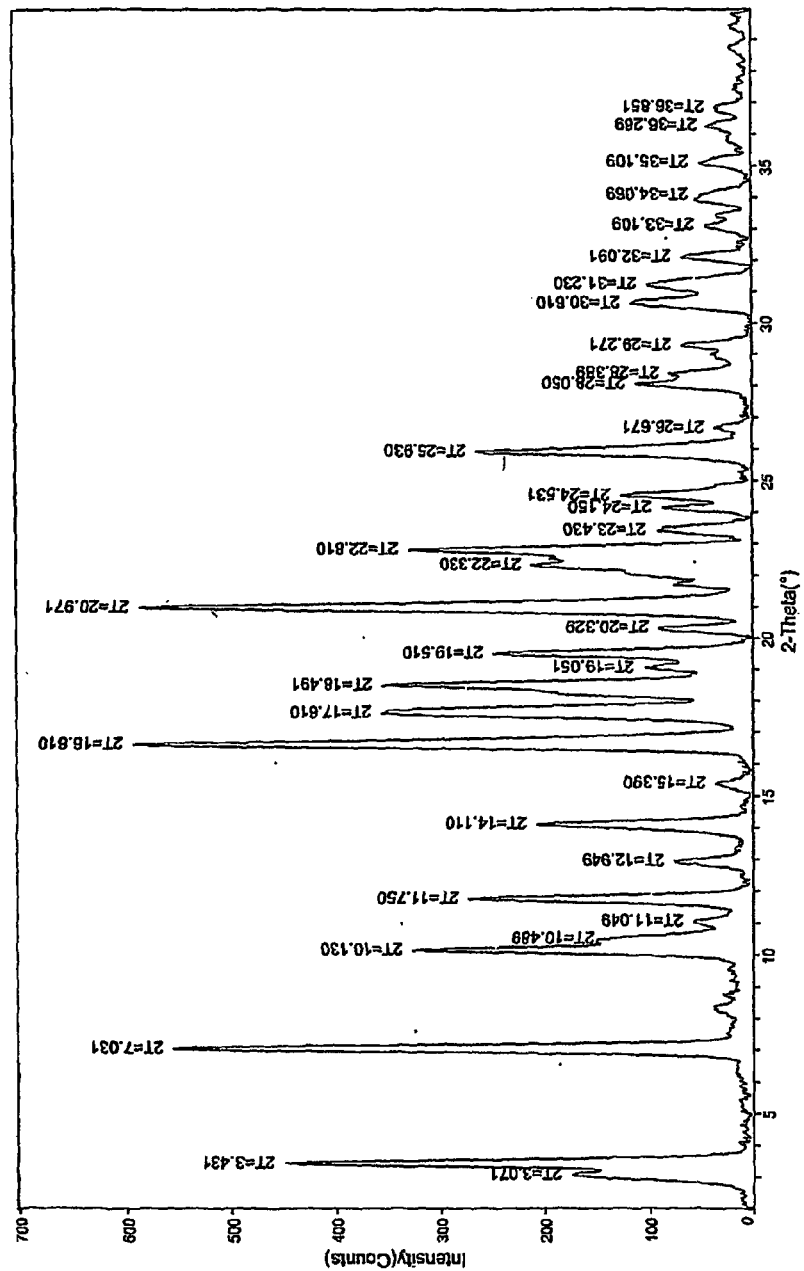
FIG. 50 shows a PXRD diffractogram of the isopropyl alcohol solvate of celecoxib sodium salt prepared by Example 22.

The results of DSC, TGA and PXRD analysis are shown in FIGS. 48-50. FIG. 48 shows the results of DSC analysis where an endotherm was observed at 67.69 degrees C. The results of TGA, as shown in FIG. 49, revealed a weight loss of about 18.23% from about room temperature to about 120 degrees C. which represents a 1.5 molar equivalent of isopropanol to celecoxib Na. The PXRD pattern has characteristic peaks at 2-theta angles shown in FIG. 50. Any 1, 2, 3, 4, 5, 6, 7, 8, 9, 10, 11, 12, 13, or more peaks can be used to characterize the solvate, including for example, peaks at 3.43, 7.03, 10.13, 11.75, 14.11, 16.61, 17.61, 18.49, 19.51, 20.97, 22.33, 22.81, and 25.93 degrees 2-theta.

Example 23

1:1 Celecoxib:Nicotinamide Co-crystals

Figure 52:
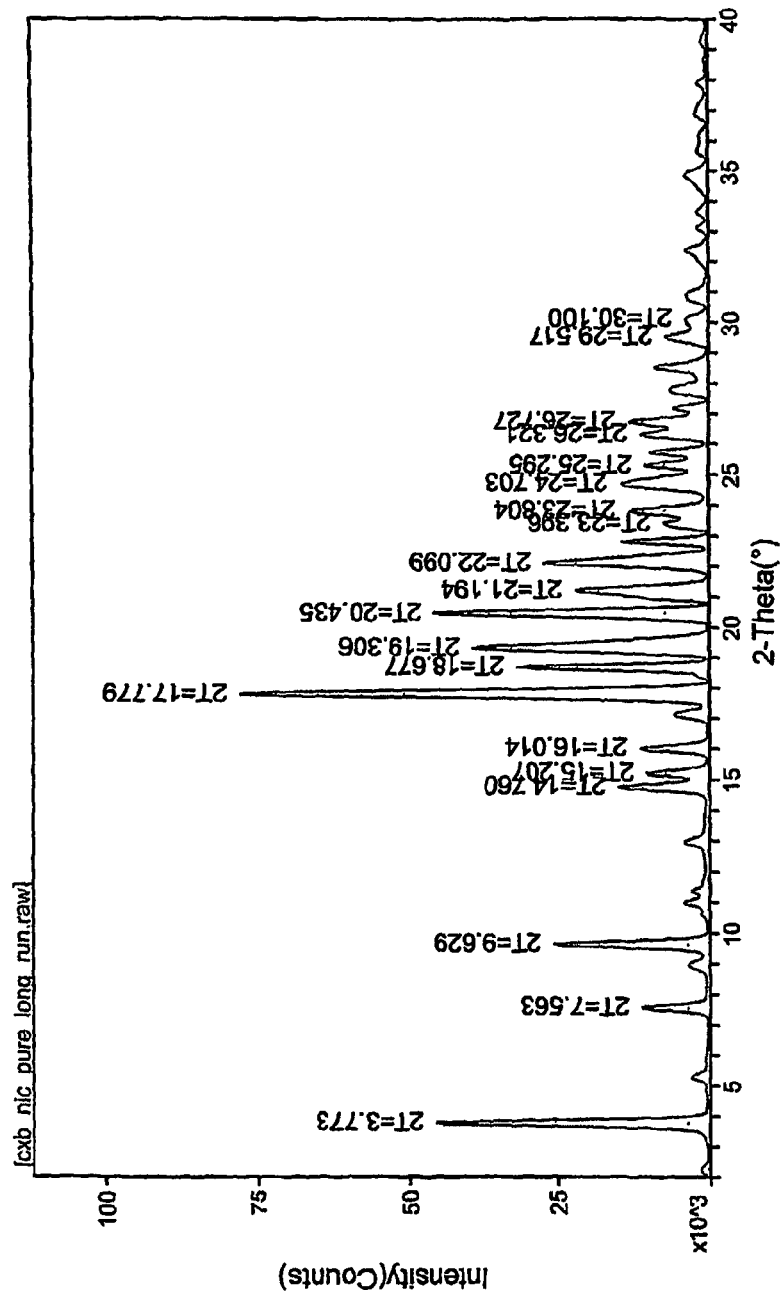
FIG. 52 shows a PXRD diffractogram of the celecoxib: nicotinamide co-crystals prepared by Example 23.
Figure 53:
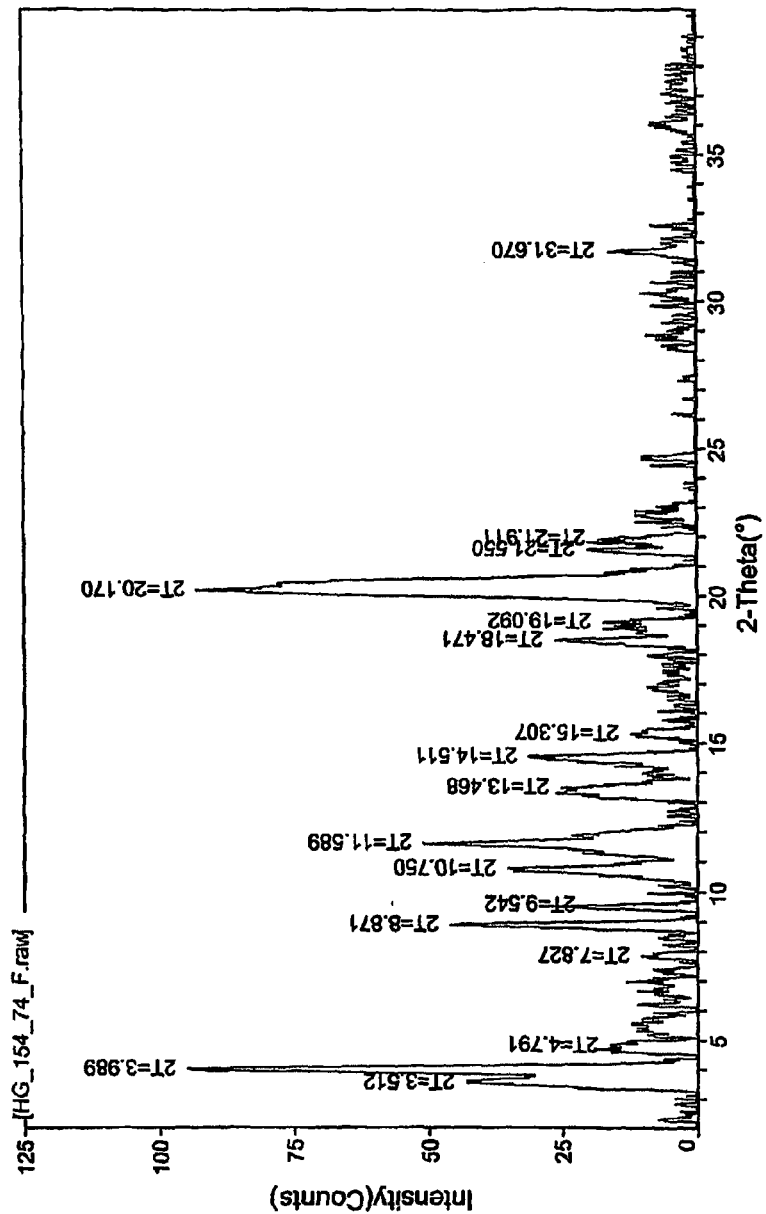
FIG. 53 shows a PXRD diffractogram of the hydrate of celecoxib sodium salt under 17% RH prepared by Example 24.
Figure 54:
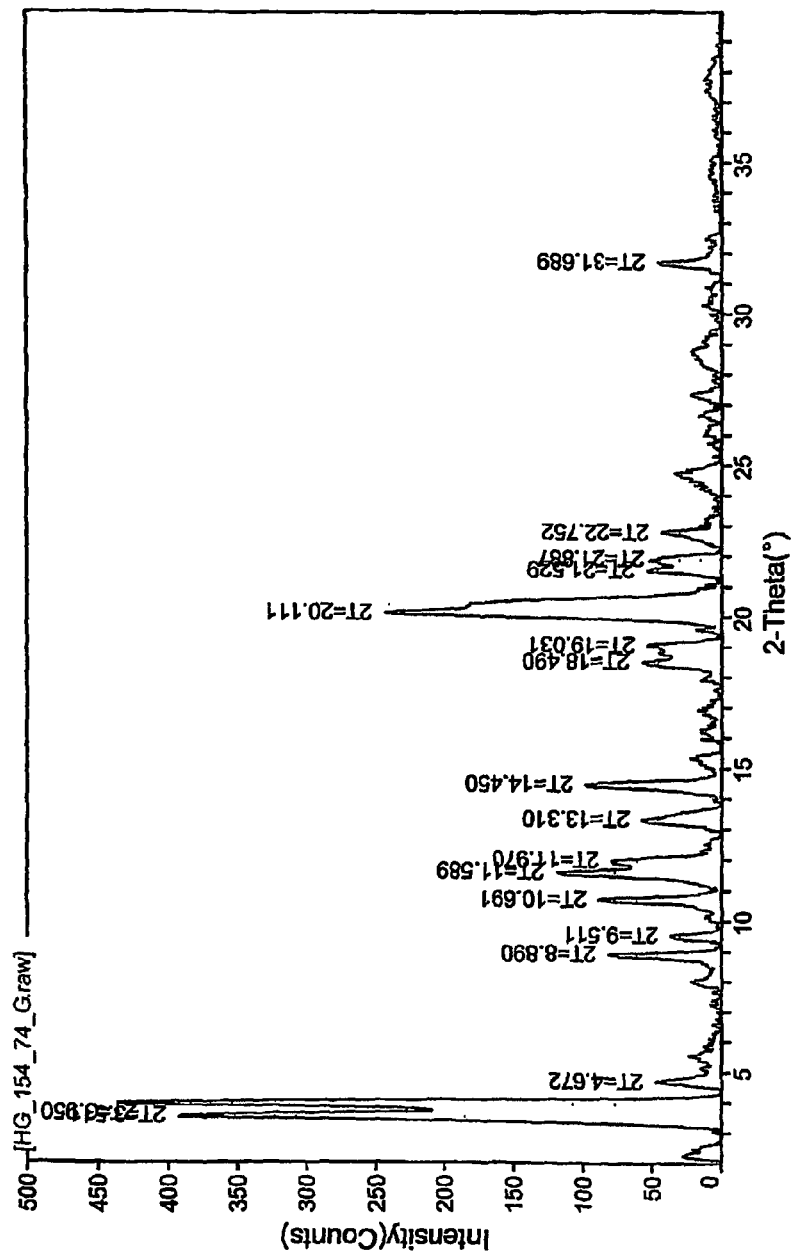
FIG. 54 shows a PXRD diffractogram of the hydrate of celecoxib sodium salt under 31% RH prepared by Example 24.
Figure 55:
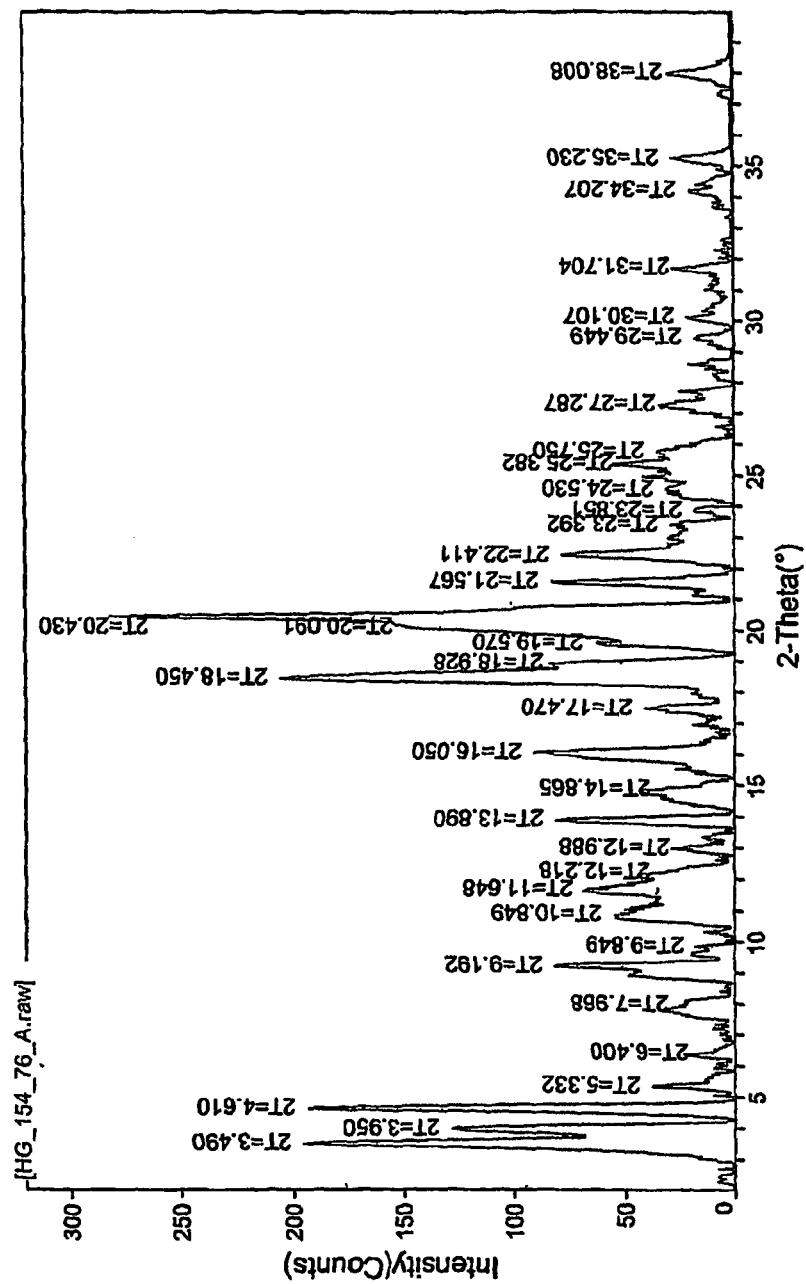
FIG. 55 shows a PXRD diffractogram of the hydrate of celecoxib sodium salt under 59% RH prepared by Example 24.
Figure 56:
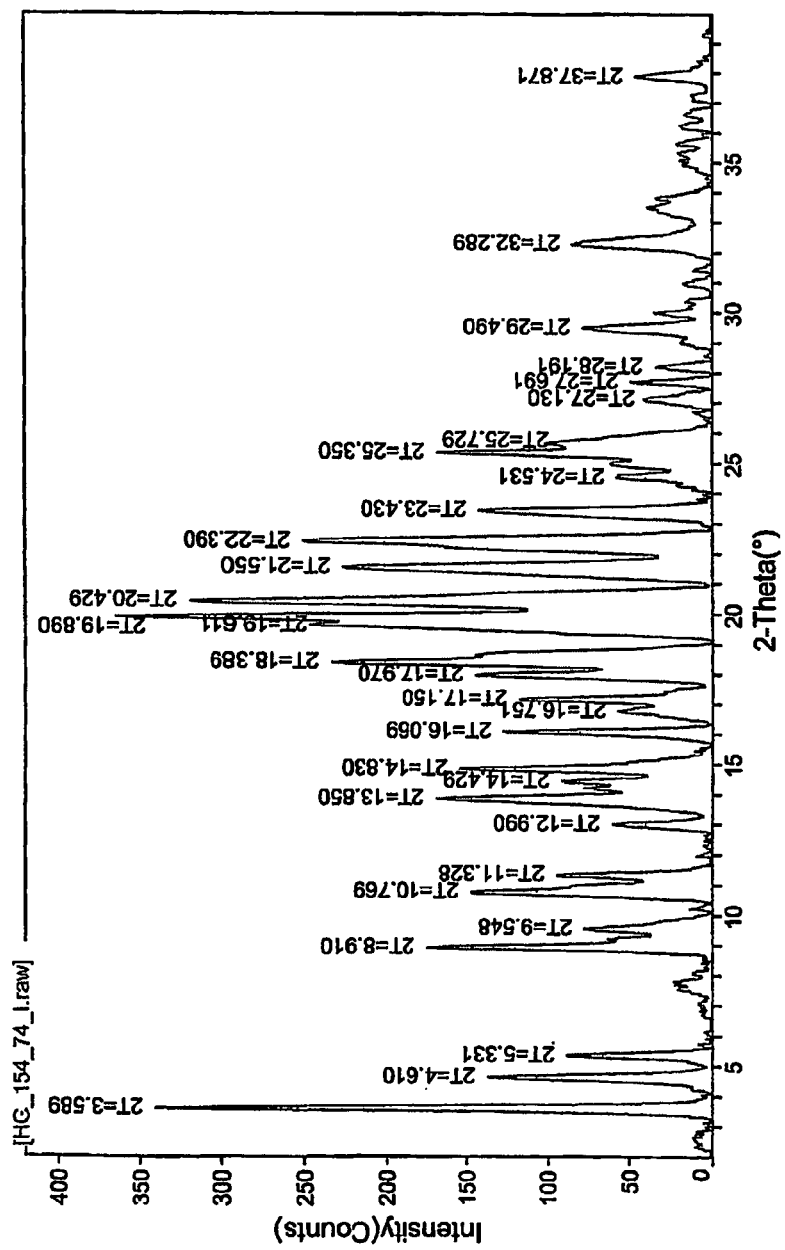
FIG. 56 shows a PXRD diffractogram of the hydrate of celecoxib sodium salt under 74% RH prepared by Example 24.
Figure 57:
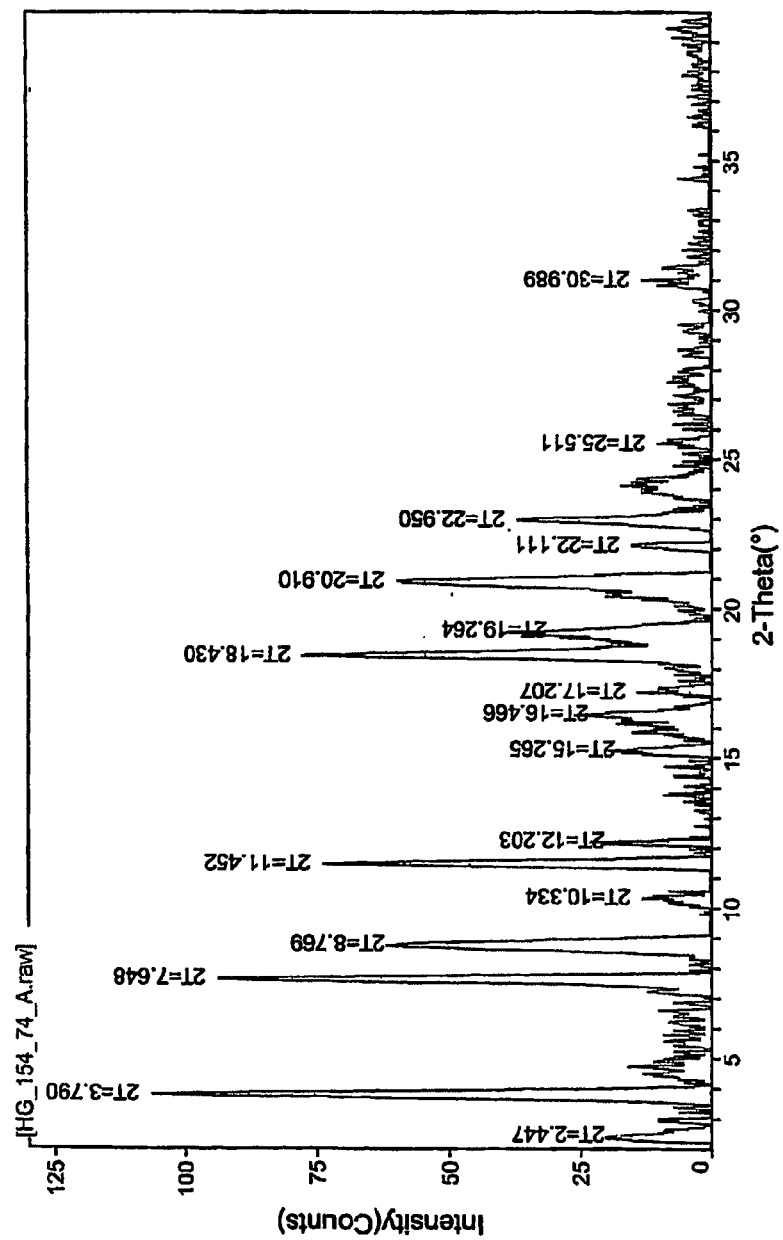
FIG. 57 shows a PXRD diffractogram of the hydrate of the propylene glycol solvate of celecoxib sodium salt under 17% RH prepared by Example 24.
Figure 58:
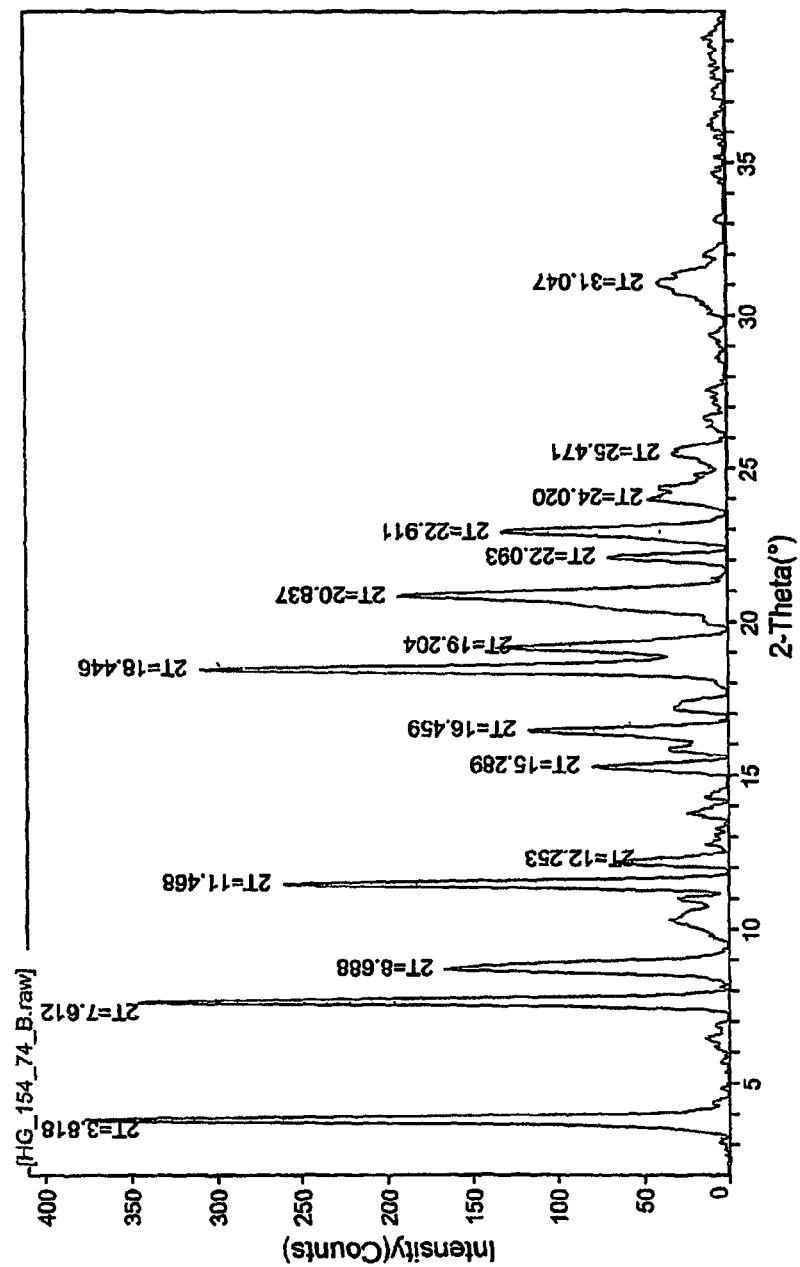
FIG. 58 shows a PXRD diffractogram of the hydrate of the propylene glycol solvate of celecoxib sodium salt under 31% RH prepared by Example 24.
Figure 59:
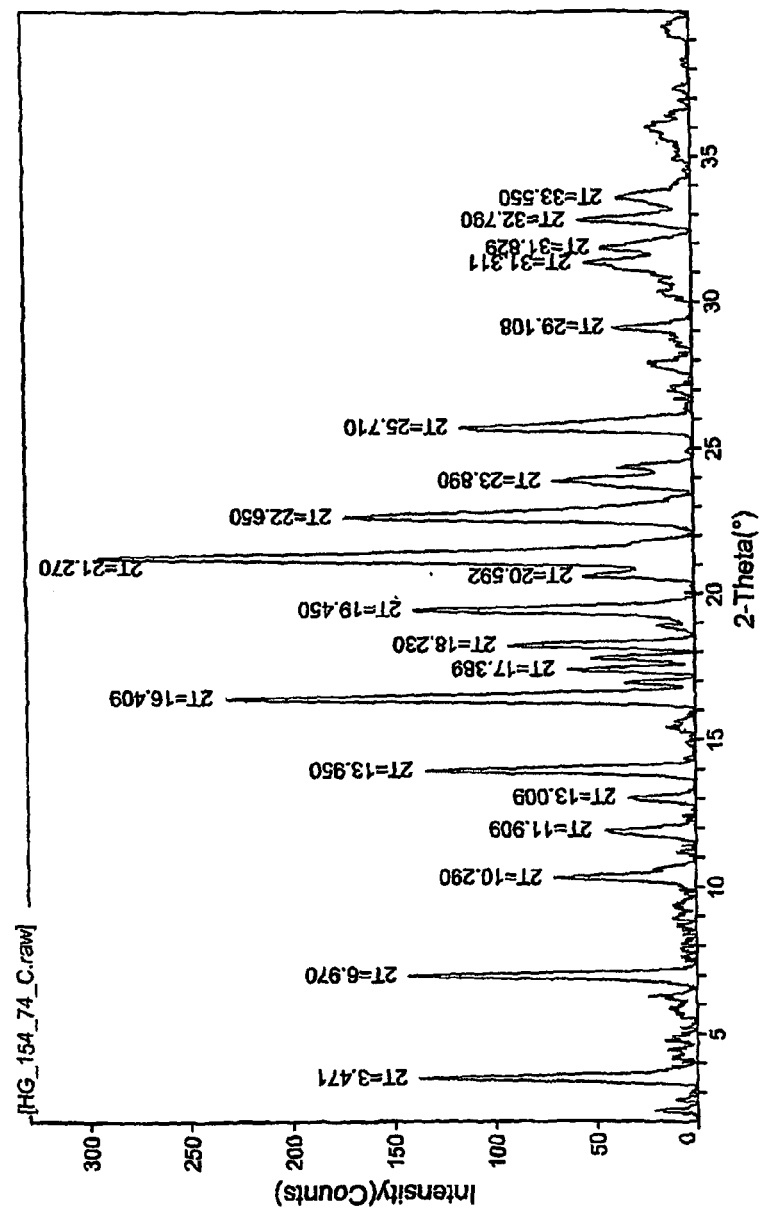
FIG. 59 shows a PXRD diffractogram of the hydrate of the propylene glycol solvate of celecoxib sodium salt under 59% RH prepared by Example 24.
Figure 60:
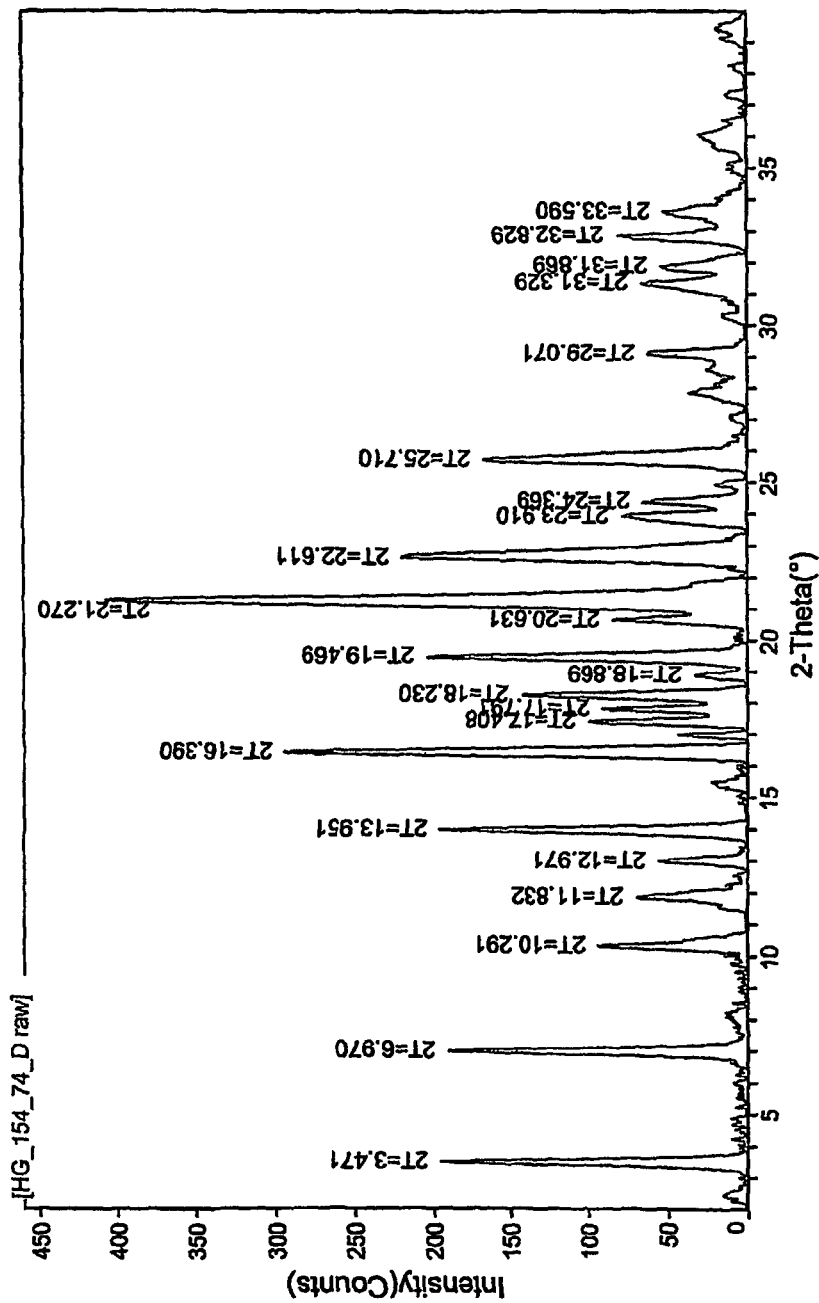
FIG. 60 shows a PXRD diffractogram of the hydrate of the propylene glycol solvate of celecoxib sodium salt under 74% RH prepared by Example 24.

Celecoxib (100 mg, 0.26 mmol) and nicotinamide (32.0 mg, 0.26 mmol) were each dissolved in acetone (2 mL). The two solutions were mixed and the resulting mixture was allowed to evaporate slowly overnight. The precipitated solid was collected and characterized. Detailed characterization of the co-crystal was performed using DSC, TGA and PXRD. The results of DSC showed two phase transitions at 117.2 and 118.8 degrees C. and a sharp endotherm at 129.7 degrees C. The results of TGA showed decomposition beginning at about 150 degrees C. The results of PXRD are shown in FIG. 52. Characteristic peaks that can be used to characterize the co-crystal include any one, or any combination of any 2, 3, 4, 5, 6, 7, 8, 9, 10, 11, 12, 13, 14, 15, of the peaks at 3.77, 7.56, 9.63, 14.76, 16.01, 17.78, 18.68, 19.31, 20.435, 21.19, 22.10, 23.80, 24.70, 25.295, and 26.73 degrees 2-theta, or any combination of peaks in FIG. 52.

Example 24

Hydrates of Celecoxib Sodium Salt and Celecoxib Sodium Propylene Glycol Solvate

Celecoxib sodium is a variable hydrate. To analyze the affect of hydration on crystal structure, celecoxib sodium salt and celecoxib sodium salt propylene glycol solvate were analyzed by PXRD under 17 percent, 31 percent, 59 percent and 74 percent constant relative humidity (RH) at room temperature. An analysis of celecoxib sodium hydrate and celecoxib sodium propylene glycol solvate was performed by incubating the samples at the above relative humidity levels at room temperature for 48 hours. The following table lists PXRD 2-theta angle (degrees) peaks at the different relative humidities.

TABLE 3

Celecoxib Sodium Salt and Celecoxib Sodium Propylene Glycol Solvate PXRD Data

| Celecoxib Sodium | | | | Celecoxib Sodium Propylene Glycol | | | |
|---|---|---|---|---|---|---|---|
| 17% | 31% | 59% | 74% | 17% | 31% | 59% | 74% |
| 3.51 | 3.51 | 3.49 | 3.59 | 3.79 | 3.82 | 3.47 | 3.47 |
| 3.99 | 3.95 | 3.95 | 4.61 | 7.65 | 7.61 | 6.97 | 6.97 |
| 8.87 | 8.91 | 4.61 | 5.35 | 8.75 | 8.69 | 10.29 | 10.29 |

TABLE 3-continued

Celecoxib Sodium Salt and Celecoxib Sodium Propylene Glycol Solvate PXRD Data

| Celecoxib Sodium | | | | Celecoxib Sodium Propylene Glycol | | | |
|---|---|---|---|---|---|---|---|
| 17% | 31% | 59% | 74% | 17% | 31% | 59% | 74% |
| 9.51 | 10.71 | 5.35 | 8.91 | 11.45 | 11.44 | 11.91 | 11.85 |
| 10.75 | 11.59 | 7.83 | 9.51 | 12.19 | 12.19 | 13.03 | 12.97 |
| 11.59 | 11.97 | 8.91 | 10.71 | 16.47 | 15.29 | 13.95 | 13.97 |
| 13.39 | 13.31 | 9.19 | 11.29 | 18.43 | 15.88 | 16.41 | 16.41 |
| 18.47 | 14.45 | 11.65 | 12.99 | 19.21 | 16.43 | 17.39 | 17.39 |
| 19.09 | 18.49 | 12.21 | 13.85 | 20.91 | 17.19 | 17.79 | 17.79 |
| 20.17 | 19.07 | 12.97 | 14.43 | 22.13 | 18.45 | 18.23 | 18.23 |
| 21.55 | 20.13 | 13.87 | 14.83 | 22.95 | 19.17 | 19.45 | 19.45 |
| 21.91 | 20.47 | 14.79 | 16.07 | | 20.84 | 20.59 | 20.63 |
| 31.67 | 21.53 | 16.05 | 16.75 | | 22.09 | 21.27 | 21.27 |
| | 21.85 | 17.47 | 17.13 | | 22.95 | 22.67 | 22.63 |
| | 22.77 | 18.43 | 17.97 | | 23.99 | 23.91 | 23.91 |
| | 31.69 | 18.89 | 18.39 | | 25.47 | 24.37 | 24.35 |
| | | 19.57 | 18.71 | | 31.05 | 25.71 | 25.71 |
| | | 20.13 | 19.63 | | | 29.09 | 27.83 |
| | | 20.43 | 19.89 | | | 31.33 | 29.11 |
| | | 21.57 | 20.43 | | | 31.83 | 31.31 |
| | | 22.41 | 21.55 | | | 32.79 | 31.87 |
| | | 24.53 | 22.39 | | | 33.55 | 32.83 |
| | | 25.37 | 23.43 | | | | 33.59 |
| | | 25.75 | 24.55 | | | | |
| | | 27.23 | 25.35 | | | | |
| | | 27.69 | 25.71 | | | | |
| | | 29.49 | 27.17 | | | | |
| | | 30.11 | 27.69 | | | | |
| | | 31.70 | 28.19 | | | | |
| | | 35.23 | 29.49 | | | | |
| | | 37.95 | 29.99 | | | | |
| | | | 32.29 | | | | |
| | | | 37.87 | | | | |

The composition can be characterized by any one or combination of any 2, 3, 4, 5, 6, 7, 8, 9, 10, 11, 12, 13, 14, 15, 16, 17, 18, 19, 20, 21, 22, 23, 24, 25, 26, 27, 28, 29, 30, or more peaks listed in Table 3 or any one or combination of any 2, 3, 4, 5, 6, 7, 8, 9, 10, 11, 12, 13, 14, 15, 16, 17, 18, 19, 20, 21, 22, 23, 24, 25, 26, 27, 28, 29, 30, or more peaks of any one of FIGS. 53-60. FIGS. 53-56 are PXRD diffractograms of celecoxib sodium hydrates at 17 percent, 31 percent, 59 percent, and 74 percent RH, respectively. FIGS. 57-60 are PXRD diffractograms of celecoxib sodium propylene glycol hydrates at 17 percent, 31 percent, 59 percent, and 74 percent RH, respectively.

Figure 69:
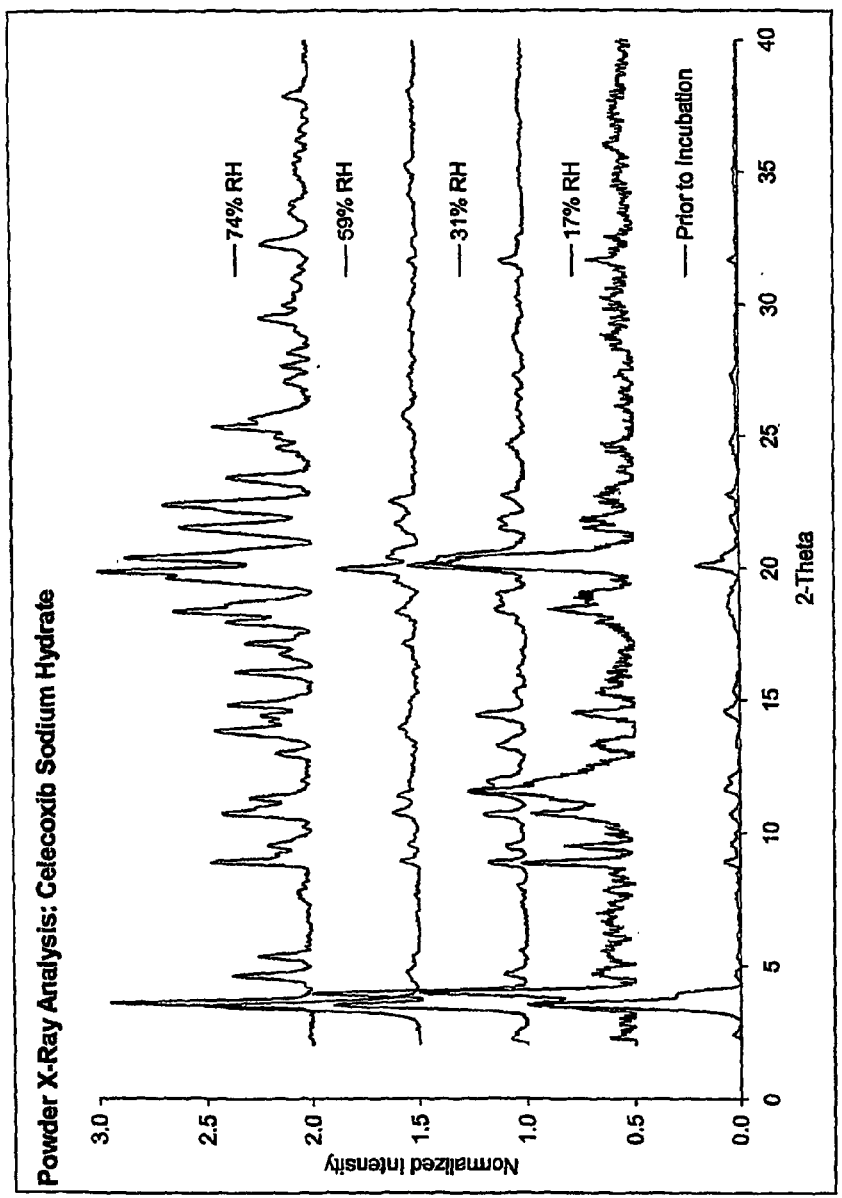
FIG. 69 shows changes in the PXRD diffractogram of celecoxib sodium hydrate as the ambient relative humidity is changed.
Figure 70:
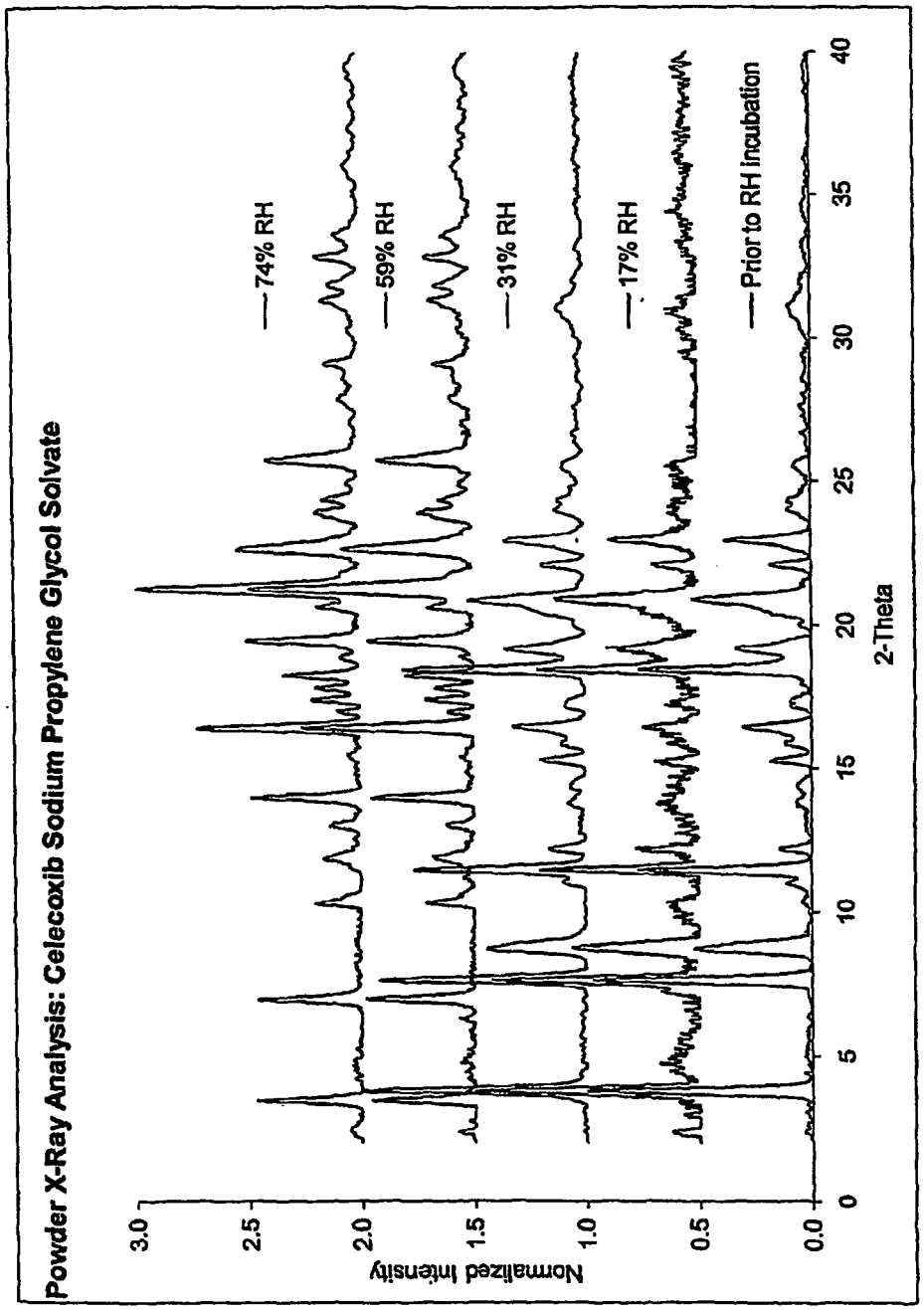
FIG. 70 shows changes in the PXRD diffractogram of celecoxib sodium propylene glycol solvate as the ambient relative humidity is changed.

PXRD analysis of celecoxib sodium hydrate shows that crystal packing changes as water is absorbed. (See FIG. 69 and dynamic moisture sorption data in Example 30.) PXRD analysis of celecoxib sodium propylene glycol solvate indicates the presence of two unique crystal forms when exposed to varying amounts of humidity. (See FIG. 70 and dynamic moisture sorption data in Example 30.) Form I is present at 31 percent RH and below, while Form II is present at 59 percent RH and above.

Example 25

Various Hydrates of Celecoxib Sodium Salt

Figure 61:
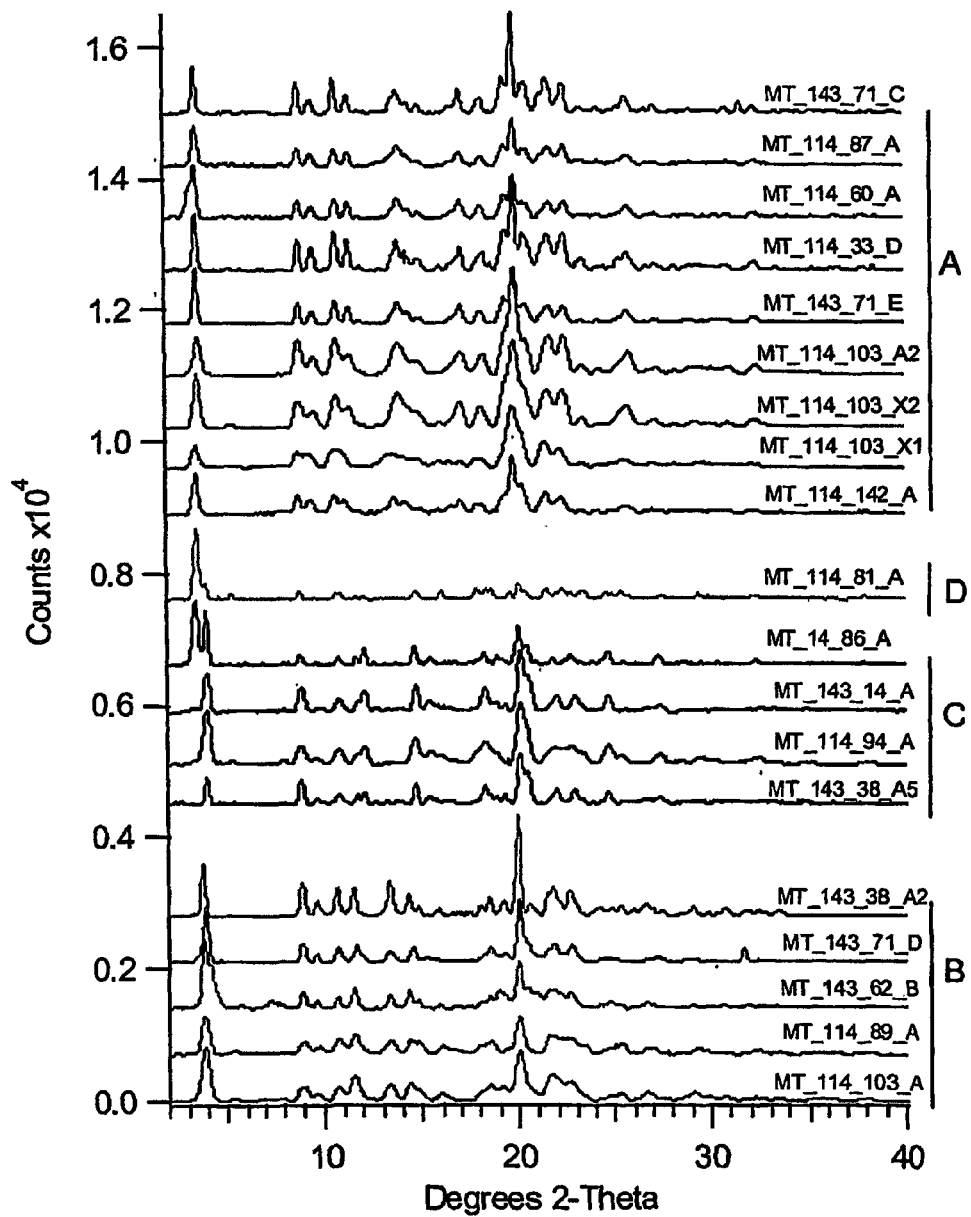
FIG. 61 shows PXRD diffractograms of multiple celecoxib sodium salt samples with various hydration states prepared by Example 25.

Multiple celecoxib sodium salt samples, all form M1, varying in hydration (believed to range from about 0.5-4 equivalents of $H_2O$ per equivalent of celecoxib) were assayed by PXRD. The PXRD patterns were then grouped based on shared peaks. Several groups were identified with four shown in FIG. 61. Group D is consistent with a mixture of amorphous and crystalline celecoxib sodium. Table 4 lists PXRD peaks characteristic in common to groups A, B, and C and peaks that are specific to each group.

TABLE 4

Celecoxib Sodium Salt Hydrate PXRD Data

| Peaks common to all Variants of form M1 | Peaks for form M1_A | Peaks for form M1_B | Peaks for form M1_C |
|---|---|---|---|
| 3.7 ± 0.3° | 9.5 ± 0.2° | 9.5 ± 0.2° | 12.1 ± 0.2° |
| 8.9 ± 0.2° | 11.3 ± 0.2° | 11.4 ± 0.2° | 14.7 ± 0.2° |
| 10.7 ± 0.2° | 17.2 ± 0.2° | 13.3 ± 0.2° | |
| 20 ± 0.2° | | 14.4 ± 0.2° | |
| 21.8 ± 0.3° | | | |

Example 26

Hydrate of Celecoxib Potassium Salt

A celecoxib potassium salt hydrate was prepared. To a solution of celecoxib (233.4 mg; 0.6120 mmol) in a methanolic potassium hydroxide solution (1.008 M; 0.606 0.611 mL) was added wet methanol (methanol 1.0 mL; water 0.100 mL). The solution was then reduced nearly to dryness (0.5 mL) via evaporation with flowing nitrogen gas. To the residual solution was added diethyl ether (6.0 mL) and the mixture was stirred. Within one minute, crystals started forming and the solid was completely crystallized within 10 minutes. The solid was then filtered and allowed to air dry. The solid was characterized via TGA and PXRD.

Figure 63:
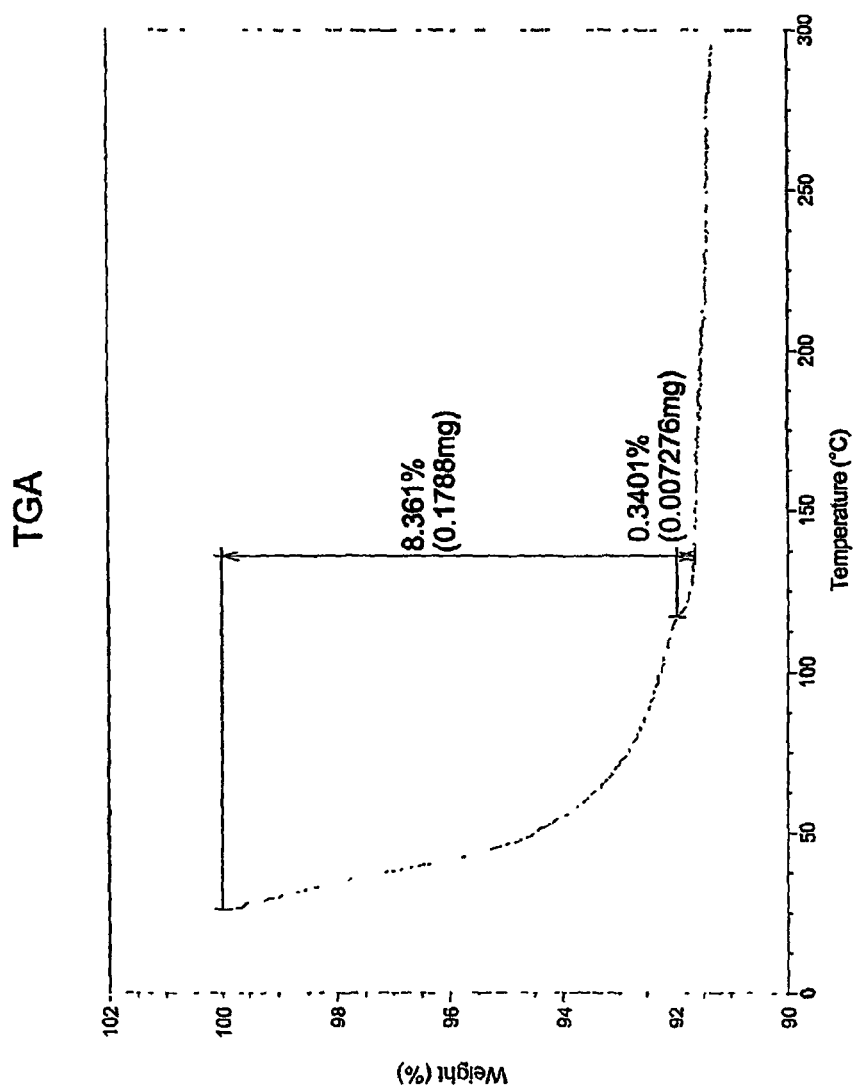
FIG. 63 shows a TGA thermogram of celecoxib potassium salt hydrate.
Figure 64:
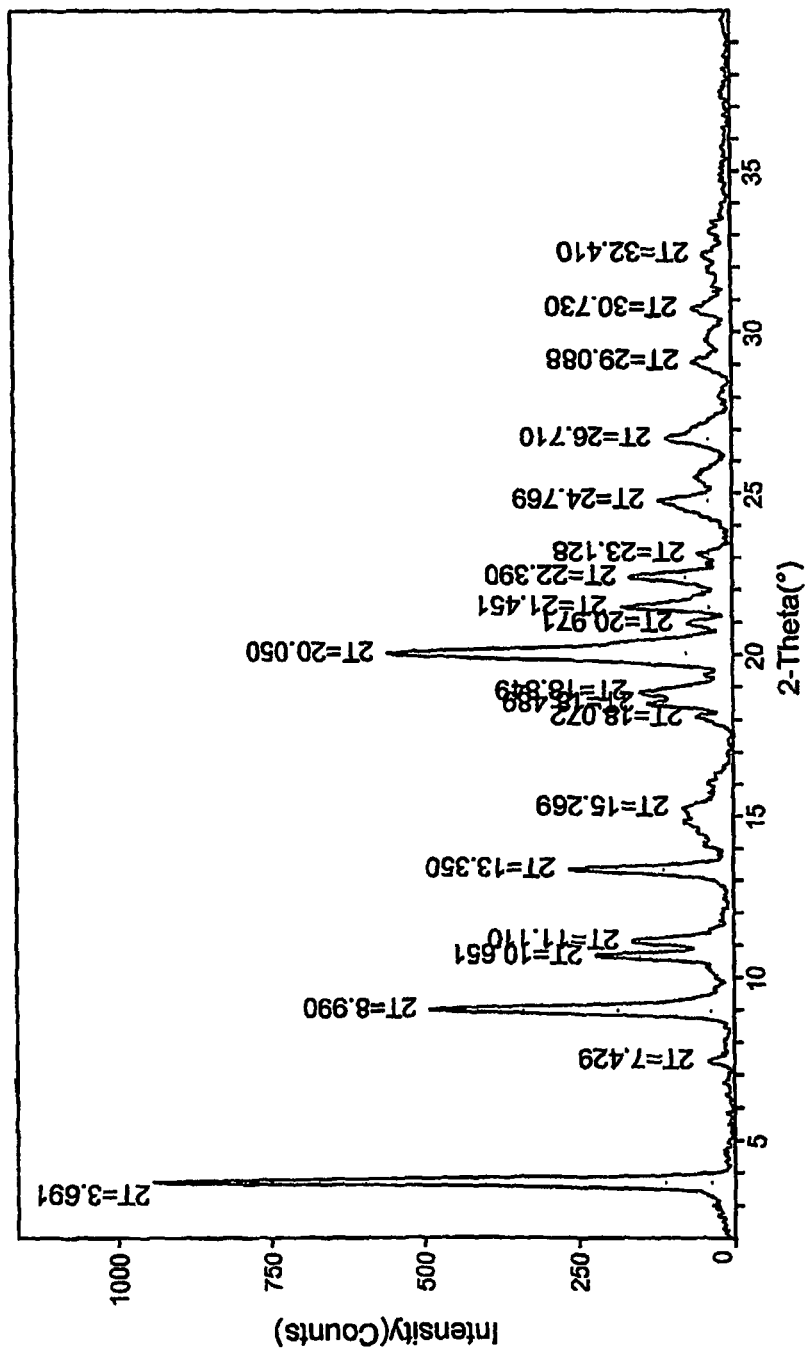
FIG. 64 shows a PXRD diffractogram of celecoxib potassium salt hydrate.

The results of TGA and PXRD are shown in FIGS. 63 and 64. FIG. 63 shows the results of TGA where an 8.36% weight loss was observed between room temperature and 140 degrees C. The PXRD pattern has characteristic peaks at 2-theta angles shown in FIG. 64. Any 1, 2, 3, 4, 5, 6, 7, 8, 9, 10, or more peaks can be used to characterize the celecoxib potassium hydrate, including for example, peaks at 3.69, 8.99, 10.65, 11.11, 13.35, 20.05, 21.45, 22.39, 24.77, and 26.71 degrees 2-theta.

Example 27

Preparation of Celecoxib Sodium Salt Using Sodium Chloride

To a solution of celecoxib (1.787 g; 4.686 mmol) in 1 M sodium hydroxide (5.0 mL; 5.0 mmol) was added a solution of 1 M sodium chloride (5 mL). The mixture was stirred and cooled to give slow crystallization of celecoxib sodium salt. The solid was collected via filtration and was washed with additional 1 M sodium chloride (10 mL). The solid was allowed to dry under flowing nitrogen gas.

Figure 65:
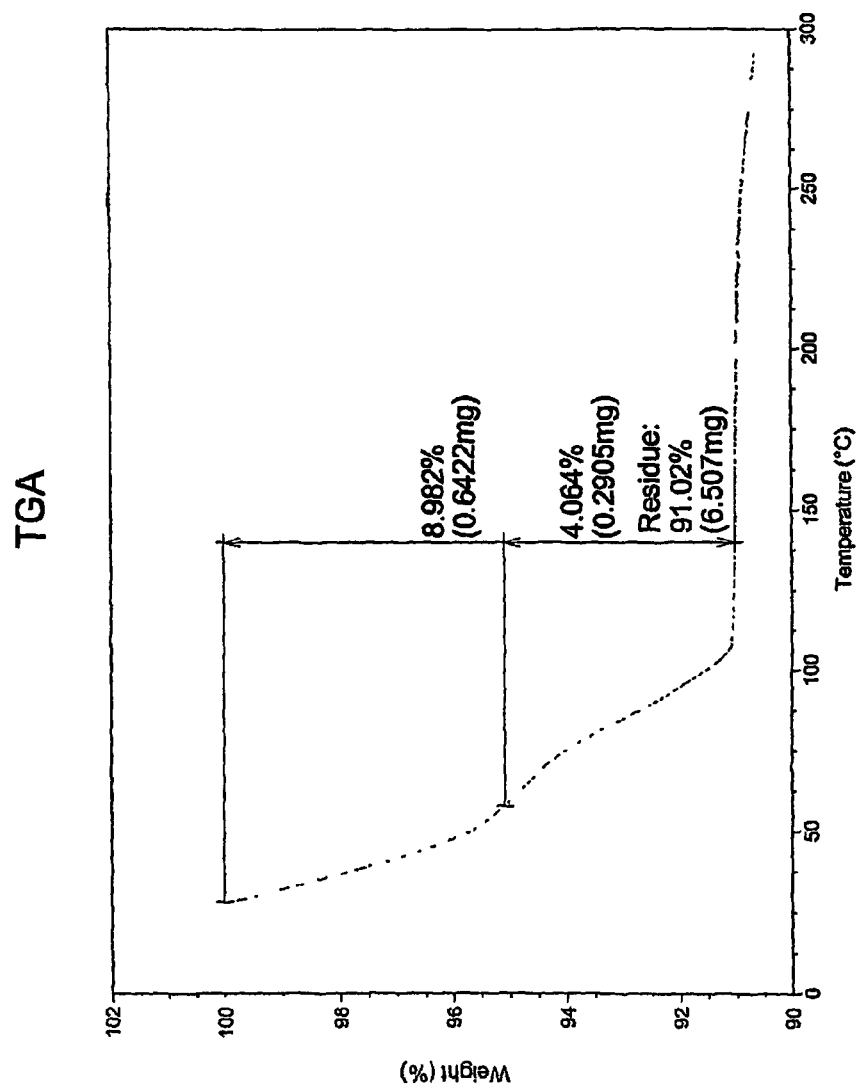
FIG. 65 shows a TGA thermogram of celecoxib sodium salt prepared with sodium chloride.
Figure 66:
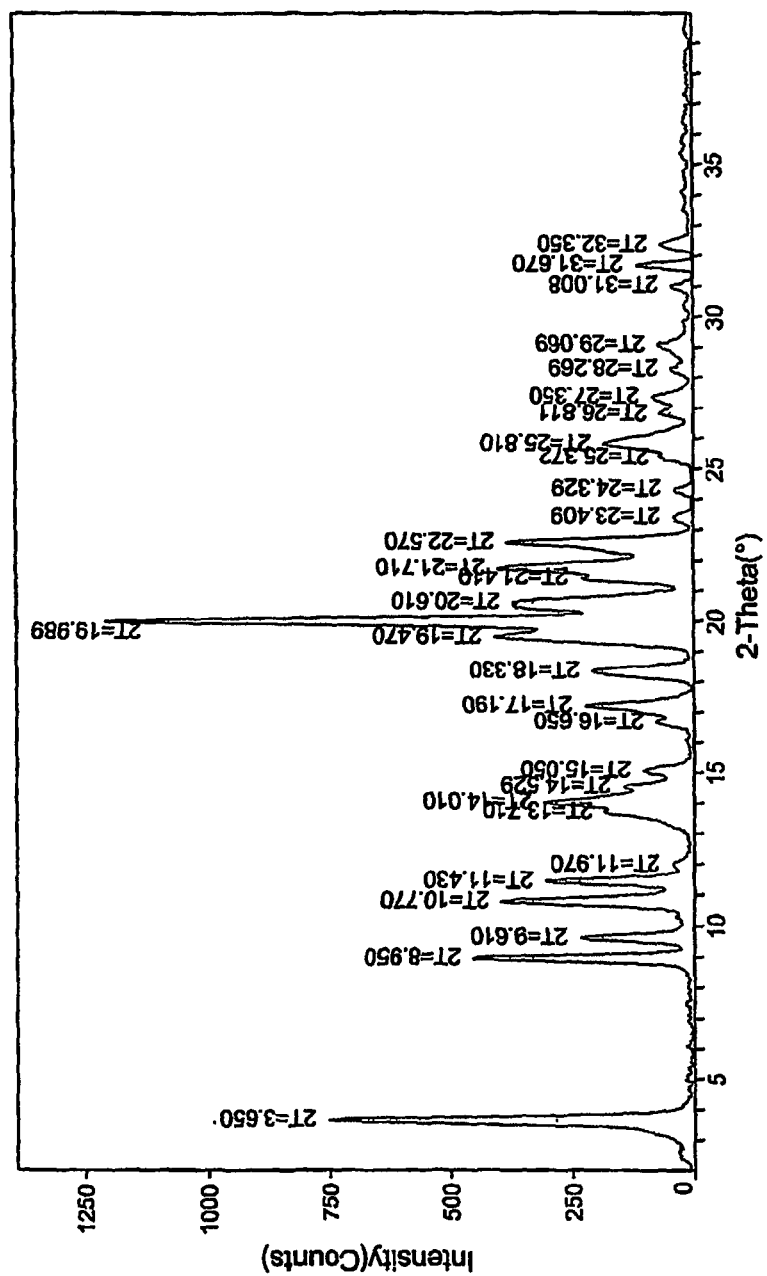
FIG. 66 shows a PXRD diffractogram of celecoxib sodium salt prepared with sodium chloride.

The results of TGA and PXRD are shown in FIGS. 65 and 66. FIG. 65 shows the results of TGA where an 8.98 percent weight loss was observed between room temperature and 140 degrees C. including a 4.06 percent weight loss between about 50 degrees C. and 140 degrees C. The PXRD pattern has characteristic peaks at 2-theta angles shown in FIG. 66. Any 1, 2, 3, 4, 5, 6, 7, 8, 9, 10, 11, 12, or more peaks can be used to characterize the celecoxib sodium salt, including for example, peaks at 3.65, 8.95, 9.61, 10.77, 11.43, 14.01, 17.19, 18.33, 19.47, 19.99, 20.61, 21.71, 22.57, and 25.81 degrees 2-theta.

Example 28

In Vitro Dissolution Study of Incubated Celecoxib Sodium Hydrate Salt Formulations In-vitro dissolution was performed on celecoxib formulations pre and post incubation at 40 degrees C. for 18 weeks. The composition of the test formulations was: (i) celecoxib sodium hydrate salt, hydroxypropylcellulose (HPC), and poloxamer 407; (ii) celecoxib sodium hydrate salt, hydroxypropylcellulose (HPC), poloxamer 407, and PEG 400; and (iii) celecoxib sodium propylene glycol solvate, hydroxypropylcellulose (HPC), and poloxamer 407. Dissolution was performed using 5 times diluted simulated gastric fluid (0.3 mM Triton X-100) at 37 degrees C. in 20 mL scintillation vials with a magnetic stirrer.

Figure 67:
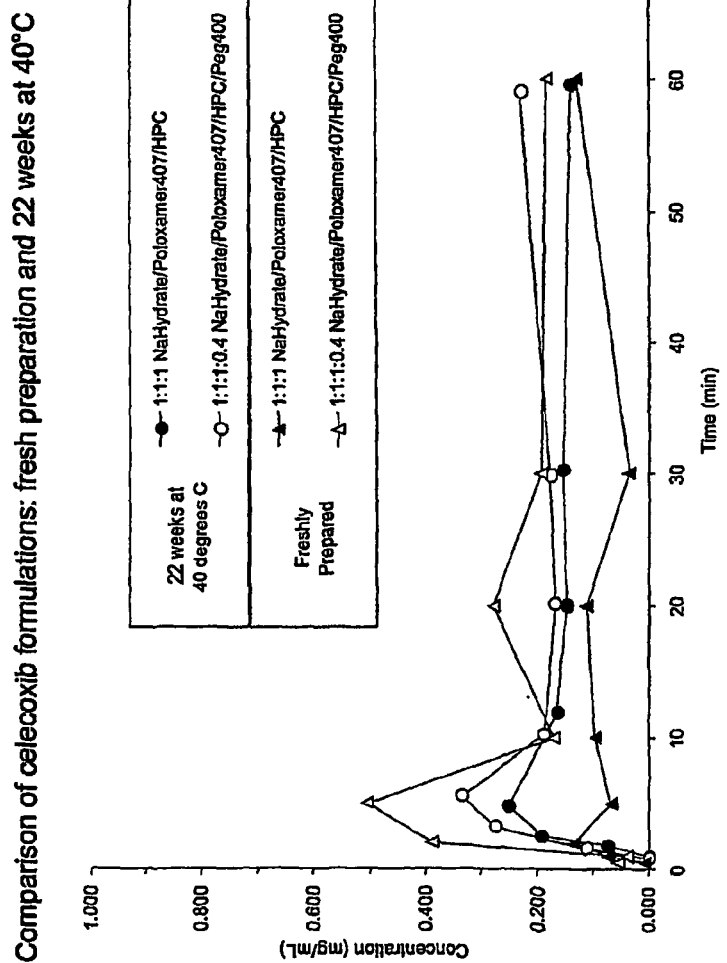
FIG. 67 shows a dissolution profile of celecoxib sodium salt hydrate.

As illustrated in FIG. 67, the dissolution profiles for formulations (ii) and (iii) post 40 degrees C. incubation displayed small losses in peak dissolution magnitudes versus the fresh formulations. This loss, however, should not impact the in-vivo bioavailability and dose-response properties of celecoxib, as was observed in the dog pharmacokinetics section, where it was shown that in-vitro dissolution profiles of varying peak magnitude correlate with dog pharmacokinetic profiles (i.e., the in-vivo-in-vitro correlation). In contrast to the dissolution behavior of formulations (ii) and (iii), formulation (i) exhibited improved dissolution which may result from slight melting of Pluronic F127 at 40° C. Melted Pluronic F127 may provide a benefit to dissolution similar to that provided by Pluronic L44 and PEG400.

Example 29

Controlled Release Formulation of Celecoxib Sodium Propylene Glycol Solvate A membrane coated system was selected to achieve controlled release of celecoxib. The membrane, an erodible polymer with low water permeability, controlled the release of celecoxib through an erosion process. The membrane is used to facilitate erosion of the coating in water without permitting the water to enter the interior of the pellet. The rate of celecoxib release was controlled by applying the polymer at increasing membrane thicknesses to sub-populations of pellets within the final formulation dose. Pellets with a thin polymer coat release celecoxib more quickly than pellets that have a thicker polymer coat. Modulation of the coating thickness across many pellets results in a distribution of drug release profiles. Factors that affect the rate of polymer erosion include polymer type, plasticizer content, temperature, solvent, curing, and coat thickness. The formulation used in this example was comprised of celecoxib sodium propylene glycol solvate, Pluronic F127, and hydroxypropylcelluse (100,000 MW) at equal weight equivalents of celecoxib free acid. The formulation was supplemented with magnesium stearate at a concentration of 0.05 weight percent to aid in the compression and ejection of pellets. This formulation comprised 30.4 weight percent celecoxib free acid.

Pellets were compressed at 10.3 MPa into 2 mm diameter pellets of cylindrical shape. The cylindrical pellets had an average height of 1 mm and average weight of 3.8 mg. Polymer coatings (e.g., cellulose acetate phthalate (CAP), polyvinyl acetate crotonic acid copolymer) were applied using a spray coater. The values of coating thicknesses ranged from 15 to 70 micrometers The application of the polymer coat was designed to delay the release of celecoxib and prevent its rapid conversion to the free acid form prior to absorption. To elucidate how the coating affects delayed release and dissolution during a transit through the stomach, an assay was developed that employed both SGF and SIF. This assay was a two step process where, dissolution was performed in SGF in the first step, and the SGF medium was replaced with SIF medium to complete the dissolution assay in the second step. Two assumptions were made: (1) the typical transit time in the stomach for small food particles is 30 minutes; and (2) solubilized celecoxib is quickly absorbed thus justifying complete exchange of SGF having solubilized celecoxib with SIF.

Figure 68:
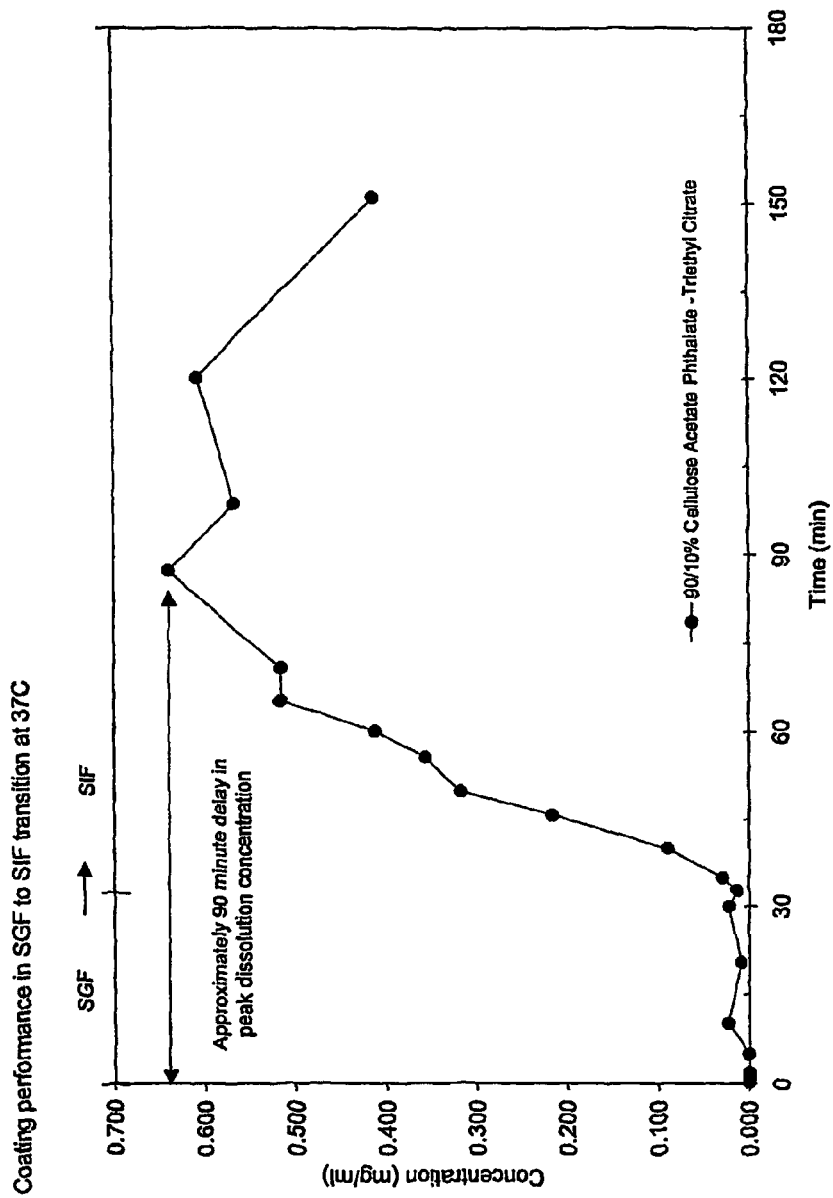
FIG. 68 shows in vitro dissolution data of a controlled release formulation of celecoxib.

In vitro dissolution was tested in both simulated gastric and intestinal fluids in the fasted state. As a specific example, dissolution was performed in simulated gastric fluid on celecoxib sodium propylene glycol pellets coated with cellulose acetate phthalate containing 10 percent by weight triethyl citrate plasticizer (approximately 64 μm coating thickness). After about 30 minutes, the dissolution media was transferred to simulated intestinal fluid. The dissolution profile showed no celecoxib release in the first 30 minutes which is consistent with the behavior of enteric coatings in low pH solutions. Once in the simulated intestinal fluid, the coating began to erode and celecoxib sodium was released. A maximum concentration of 0.64 mg/ml was obtained after about 90 minutes in the assay (See FIG. 68). This example demonstrates that controlled release can be achieved by applying varying coating thicknesses with discrete populations of pellets in a drug capsule. The controlled release of celecoxib can be achieved through a combination of coated formulation pellets and/or a combination of formulation powder with coated formulation pellets.

Example 30

Dynamic Moisture Sorption Analysis of Celecoxib Salts, Hydrates, Solvates, and Co-Crystals Moisture sorption analysis was performed using the DVS-1 apparatus (Surface Measurement Systems, Monarch Beach, Calif.) with a Calm D-200 microbalance (Thermo Calm, Madison, Wis.). Each sample was placed in a clean glass crucible and equilibrated in the apparatus at a specified relative humidity (RH) level. Initial equilibration was performed in the DVS apparatus, unless otherwise specified. After initial equilibration, RH was varied and change in mass was recorded over time as an indication of moisture sorption. RH was controlled by varying flow rates of dry and water saturated nitrogen streams at 25 degrees C.; the total combined flow rate of both streams was kept constant at 200 standard cubic meters per minute. A full humidity cycle typically refers to a ramp from 0 to 95 percent RH and back down 0 percent RH, unless otherwise specified. Mass equilibration at each humidity level was obtained when the change in mass per time value (i.e., dm/dt) was less than 2 micrograms/min. After the assay, change in mass, due to water sorption, was mathematically converted to water molar equivalents per dry compound molar equivalent. Form analysis was performed at the end of the assay on select samples using powder x-ray diffraction pattern (PXRD; D/Max Rapid, Rigaku, Danvers, Mass.). Samples were packed into 3 mm diameter borosilicate capillary tubes for the analysis.

Celecoxib Sodium Hydrate

Figure 71:
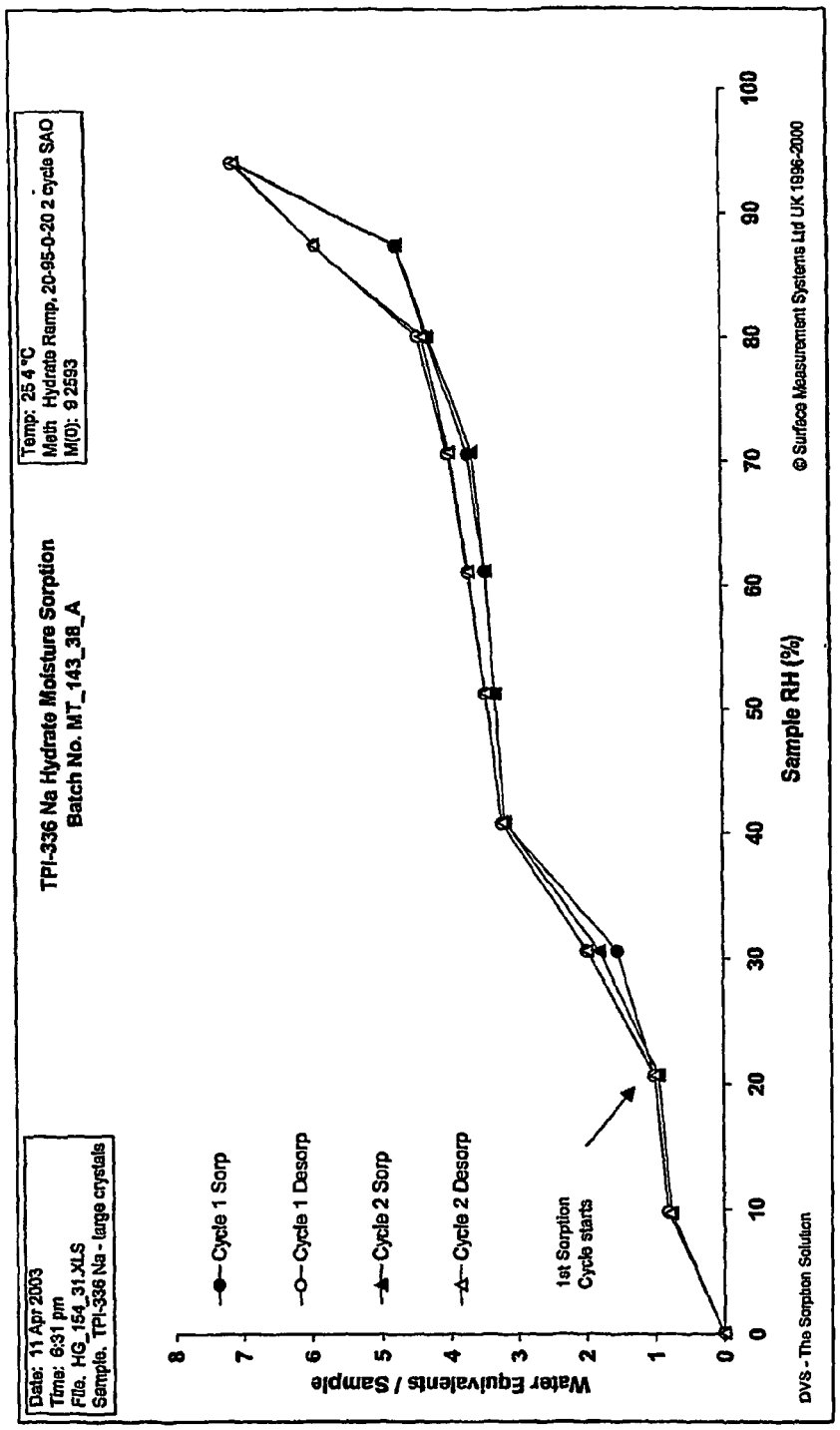
FIG. 71 shows dynamic vapor sorption data of celecoxib sodium hydrate.

Celecoxib sodium hydrate (dry mass: 9.2593 mg, dry molecular weight: 404.36, temperature: 25.4 degrees C.) was initially equilibrated at 20 percent RH at 25 degrees C. RH was ramped up from 20 percent to 95 percent RH, and then ramped down to 0 percent RH. Two complete humidity cycles were performed as illustrated in FIG. 71. The moisture sorption isotherms for both cycles overlapped indicating a lack of irreversible form changes. In the transition from 0 to 10 percent RH the compound adsorbed 1 water molar equivalent per dry compound. Water sorption increased steadily from 20 to 40 percent RH until approximately 3 water equivalents were obtained at 40 percent RH. The trihydrate was kinetically stable in the 40 to 70 percent RH range. At RH values greater than 70%, water sorption continued to rise until deliquescence occurred at 95 percent RH. Key observations in this assay were the formation of forms consistent with a tri-hydrate designation in the 40 to 70 percent RH range and a monohydrate designation in the 10 to 20 percent RH range.

Celecoxib Potassium

Figure 72A:
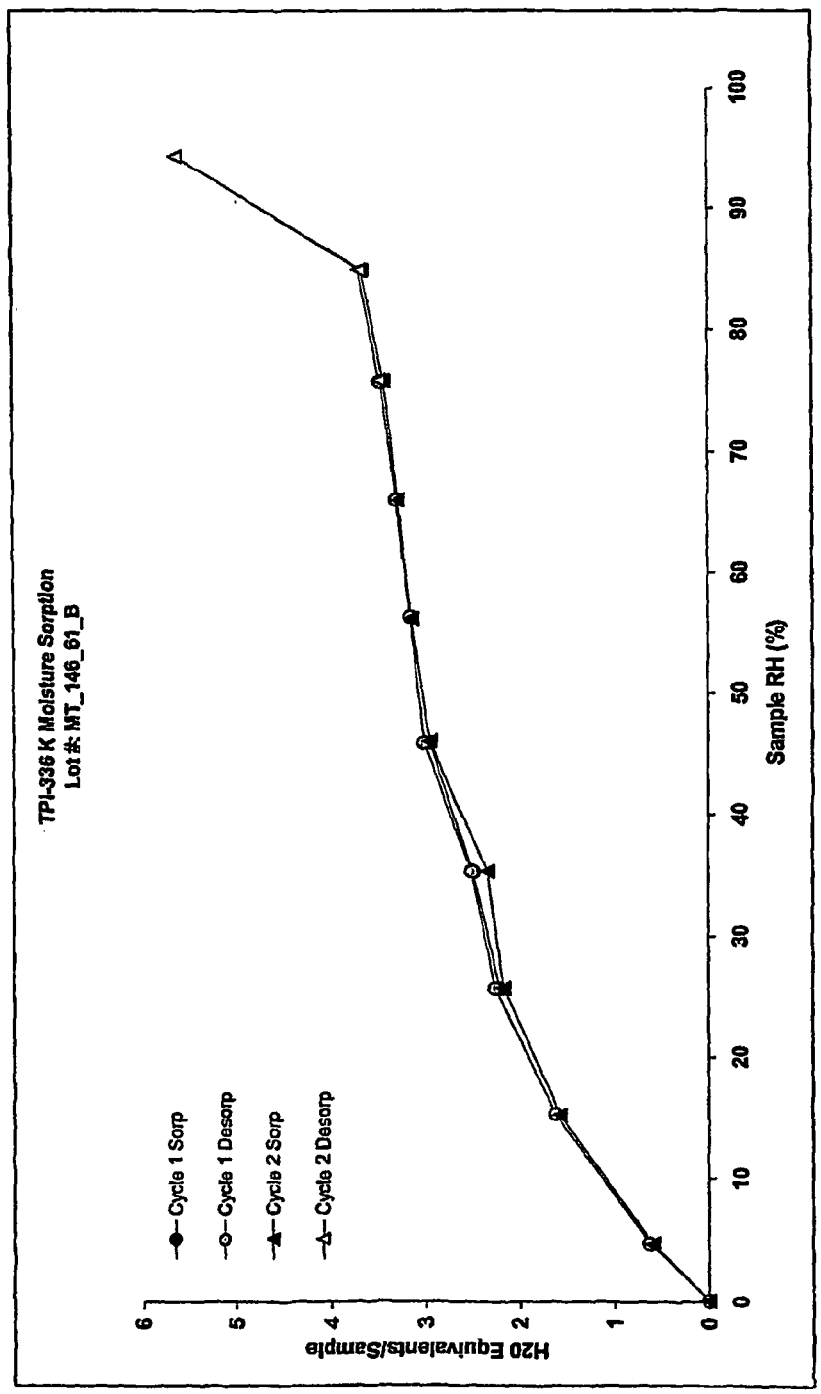
FIGS. 72A-B show dynamic vapor sorption data of celecoxib potassium salt and PXRD data.
Figure 72B:
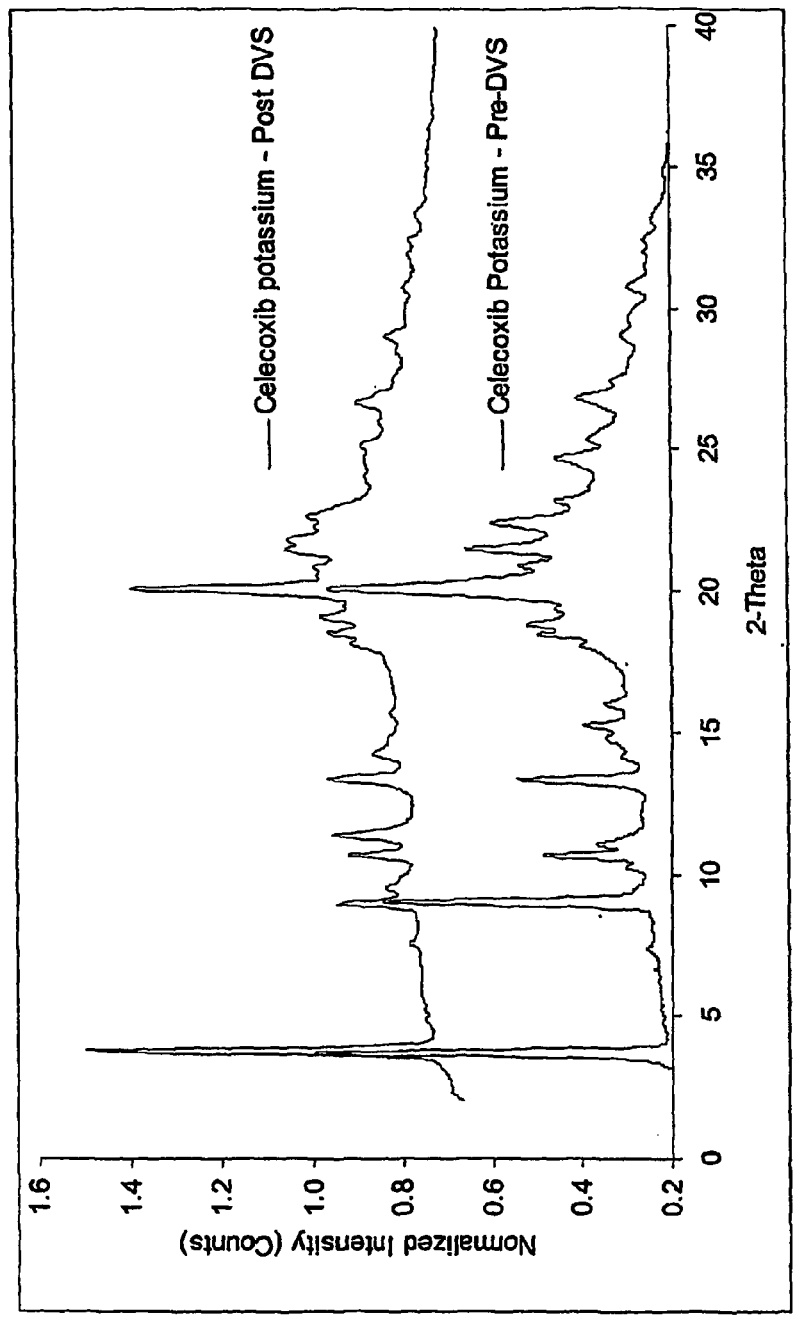

Celecoxib potassium (dry mass: 15.8563 mg, dry molecular weight: 419.48, temperature: 25.5 degrees C.) was initially equilibrated at 0 percent RH at 25 degrees C. RH was then ramped from 0 to 95 percent RH in a two cycle experiment, as illustrated in FIG. 72A. Water sorption was strongly dependent on RH with immediate adsorption occurring at very low RH levels, and deliquescence occurring at 95 percent RH. The analysis was characterized by very low hysteresis and large amounts of water uptake. A PXRD pattern taken at the end of the assay, FIG. 72B, showed the compound to be in the crystalline state. Small changes in form are apparent, as compared to the pre-incubation PXRD, indicating some crystal rearrangement (i.e., polymorphism) associated with moisture sorption. The pre-incubation PXRD is representative of celecoxib potassium that had been equilibrated at room temperature and ambient humidity.

Celecoxib Sodium Propylene Glycol Solvate

Figure 73:
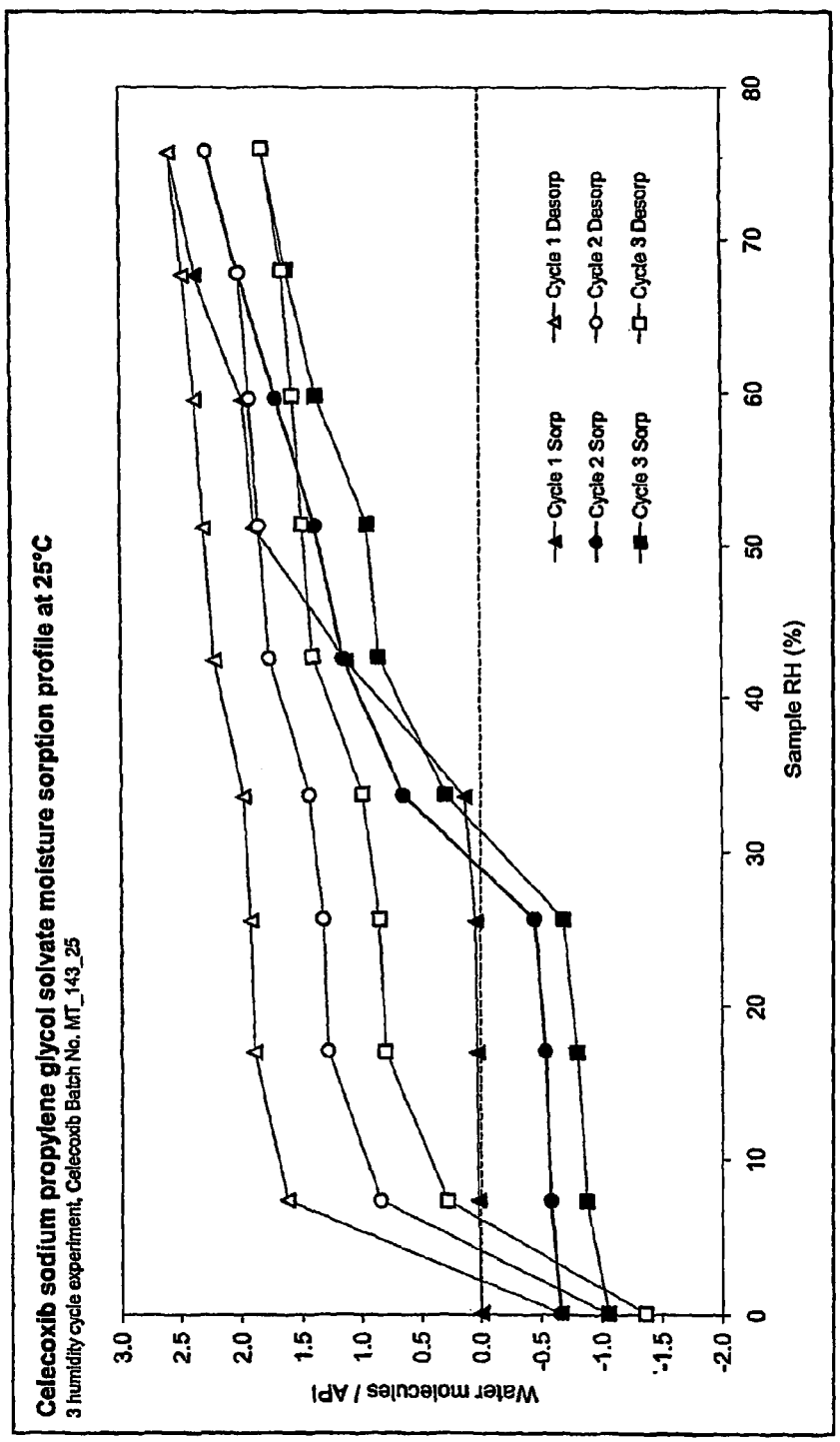
FIG. 73 shows dynamic vapor sorption data of celecoxib sodium propylene glycol solvate.

Celecoxib sodium propylene glycol solvate (dry mass: 19.4851 mg, dry molecular weight: 480.45, temperature: 25.8 degrees C.) was initially equilibrated at 0 percent RH at 25 degrees C. RH was ramped from 0 to 75 percent RH in a three cycle experiment as illustrated in FIG. 73. No change in mass was observed from 0 to 34 percent RH, indicating the presence of a stable anhydrous form over this range. At 40 percent RH, the compound gained one water molar equivalent and monotonically keeps increasing in water content up to 75 percent RH.

The desorption cycle was characterized by significant hysteresis which is consistent with hydration processes. During water desorption water was shed very slowly until a dihydrate was formed below 40 percent RH. The dihydrate was stable from 33 to 17 percent RH. Upon further drying to 0 percent RH, the sample continued to lose water before equilibrating at a weight lower than the original dry weight (i.e., 0 percent RH in Cycle 1 Sorp). The additional loss of mass suggests propylene glycol was released during the RH transitions. Assuming that the compound was dry (i.e., without water) at 0 percent RH, the calculated propylene glycol loss was 0.16 equivalents. Two additional humidity cycles were run to verify these observations. The additional cycles showed similar trends to the first cycle, but on a lower y-axis scale due to the propylene glycol mass loss. Furthermore, additional mass loss was observed at the end of each cycle. The total calculated propylene glycol loss at the end of the second and third cycles was 0.25 and 0.32 mass equivalents of propylene glycol respectively.

Figure 74:
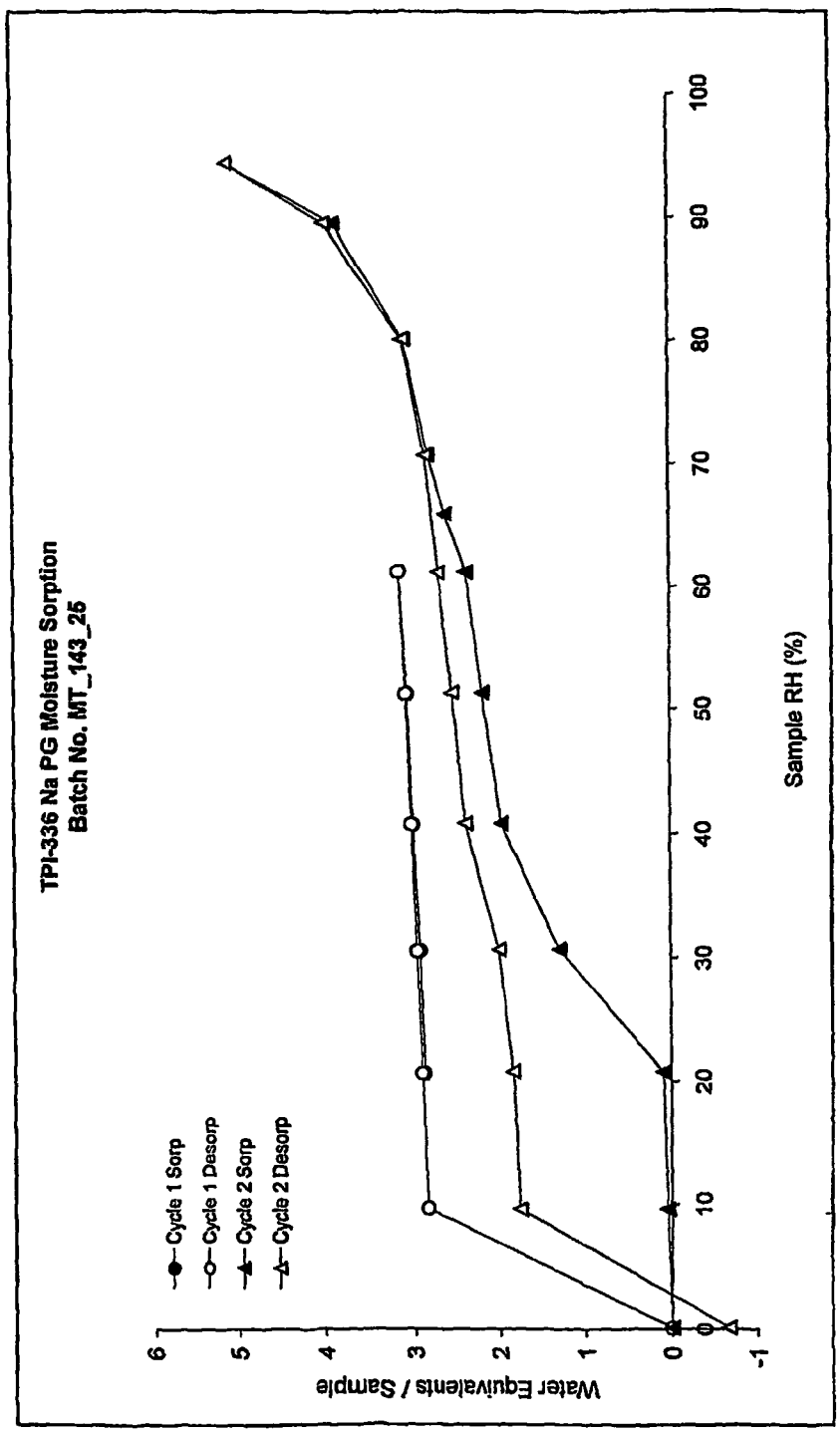
FIG. 74 shows dynamic vapor sorption data of celecoxib sodium propylene glycol solvate.

A second dynamic moisture sorption analysis was completed with celecoxib sodium propylene glycol solvate. In this trial, the sample was incubated at 55 percent RH at room temperature for 72 hours in a salt bath solution. In the moisture sorption analysis, the sample was removed from the 55 percent RH chamber and equilibrated at 20 percent RH at 25 degrees C. in the dynamic moisture sorption instrument. RH was then ramped from 20 to 60 percent RH and down to 0 percent RH in the first cycle. As shown in FIG. 74, a stable trihydrate was observed from 10 to 60 percent RH. At 0 percent RH, the water molecules were shed to yield an anhydrous form.

In the second humidity cycle, water began to adsorb at RH values greater than 20 percent. At 40 percent RH, 2 water equivalents had been absorbed which is consistent with a dihydrate form designation. This dihydrate was stable from 40 to 60 percent RH. At greater RH, water content exponentially increased and deliquescence was observed at 95 percent RH. The desorption cycle was characterized by significant hysteresis below 70 percent RH. Between 30 and 10 percent RH the dihydrate form was reestablished. Upon further drying to 0 percent RH the sample equilibrated at a weight lower the than original dry weight of the compound. Assuming that the sample was completely dry, the calculated propylene glycol loss was estimated to be 0.16 molar equivalents.

Figure 75:
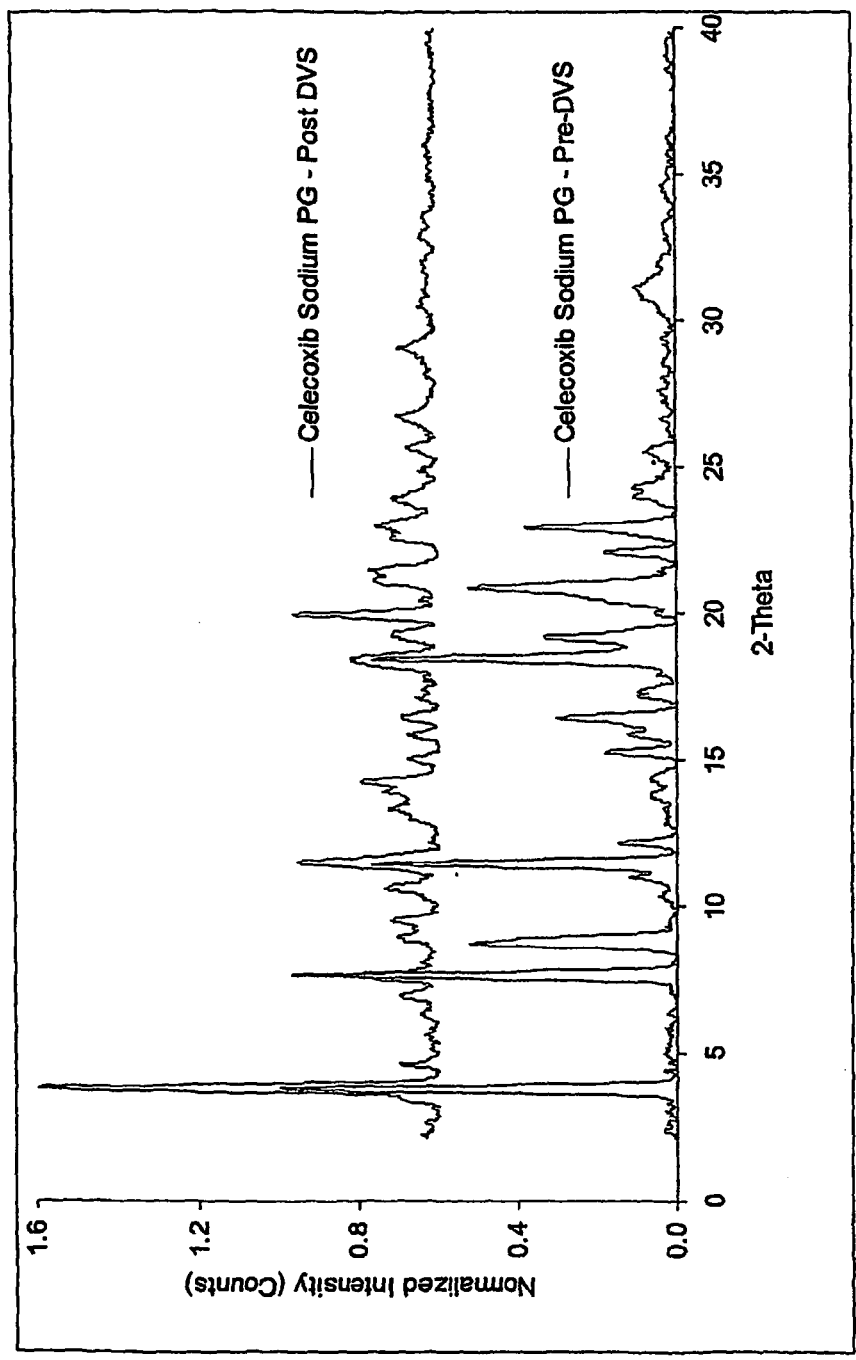
FIG. 75 shows a comparison of PXRD diffractograms of celecoxib sodium propylene glycol solvate.

A third humidity assay was begun, but was stopped shortly thereafter at 30 percent RH prior to equilibration. As shown in FIG. 75, a PXRD pattern taken at this time showed form conversion, with respect to the starting material, suggesting that water sorption involves rearrangement of the crystal structure.

The primary difference observed in this study, with respect to the first celecoxib sodium propylene glycol solvate analysis, was the presence of a stable trihydrate form in 10 to 60 percent RH region following equilibration at 55 percent RH for 72 hours. Because the observations made in the second humidity cycle were remarkably consistent with those made in the prior assay, assay reproducibility was confirmed. These findings suggests that the dihydrate form was kinetically stable for extended time periods of time (i.e., hours) before converting to a thermodynamically stable trihydrate form.

Celecoxib Potassium Propylene Glycol Solvate

Figure 76:
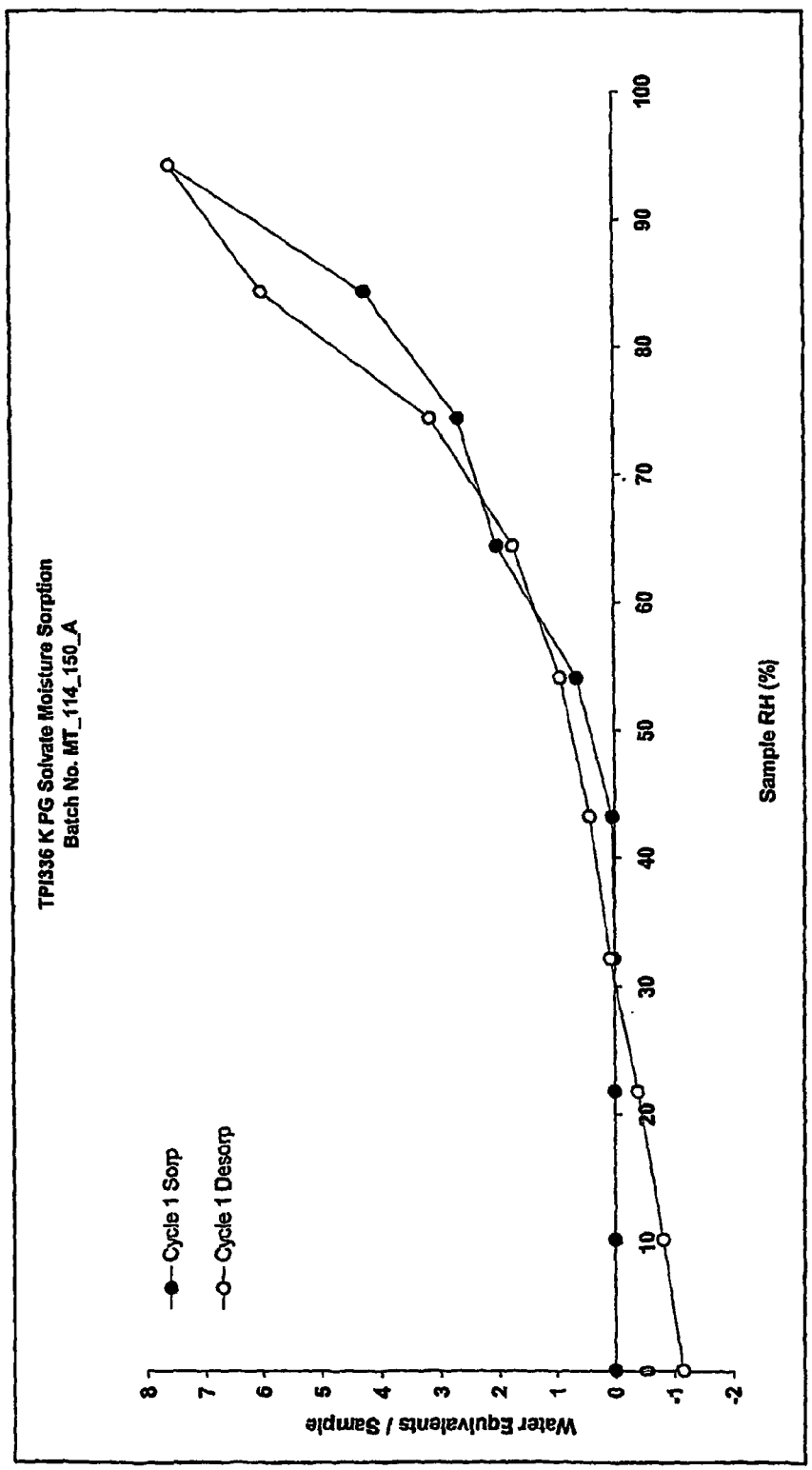
FIG. 76 shows dynamic vapor sorption data of celecoxib potassium propylene glycol solvate.

Celecoxib potassium propylene glycol solvate (dry mass: 17.2584 mg, dry molecular weight: 496.57, temperature 25.1 degrees C.) was initially equilibrated in 0 percent RH at 25 degrees C. RH was ramped from 0 to 95 percent RH in a one cycle experiment as illustrated in FIG. 76. No change in mass was observed from 0 to 43 percent RH, indicating the presence of a stable anhydrous form over this range. Above 43 percent RH, water sorption increased exponentially with increasing percent RH until. Deliquescence was observed at 95 percent RH.

Figure 77:
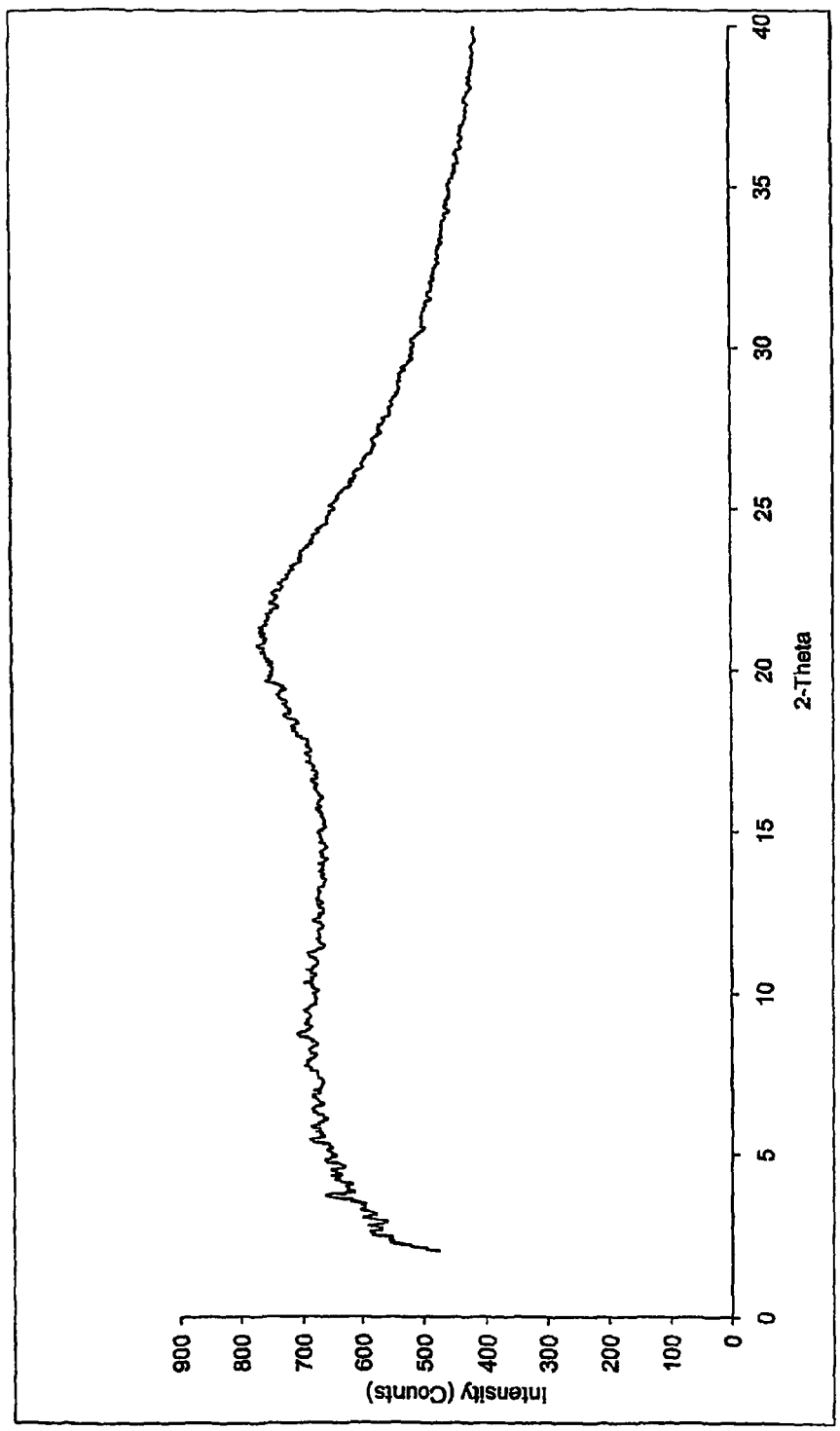
FIG. 77 shows a PXRD diffractogram of celecoxib potassium propylene glycol solvate.

The desorption cycle was characterized by negative hysteresis consistent with that observed for the sodium propylene glycol solvate form. At 30 percent RH the sample equilibrated at a mass below that of the initial dry mass of the sample. This mass loss, attributed to removal of propylene glycol, was calculated to be 0.27 equivalents at 0 percent RH. A PXRD pattern (see FIG. 77) taken at the end of the assay showed the sample had converted to an amorphous form.

Celecoxib Lithium Propylene Glycol Solvate

Figure 78:
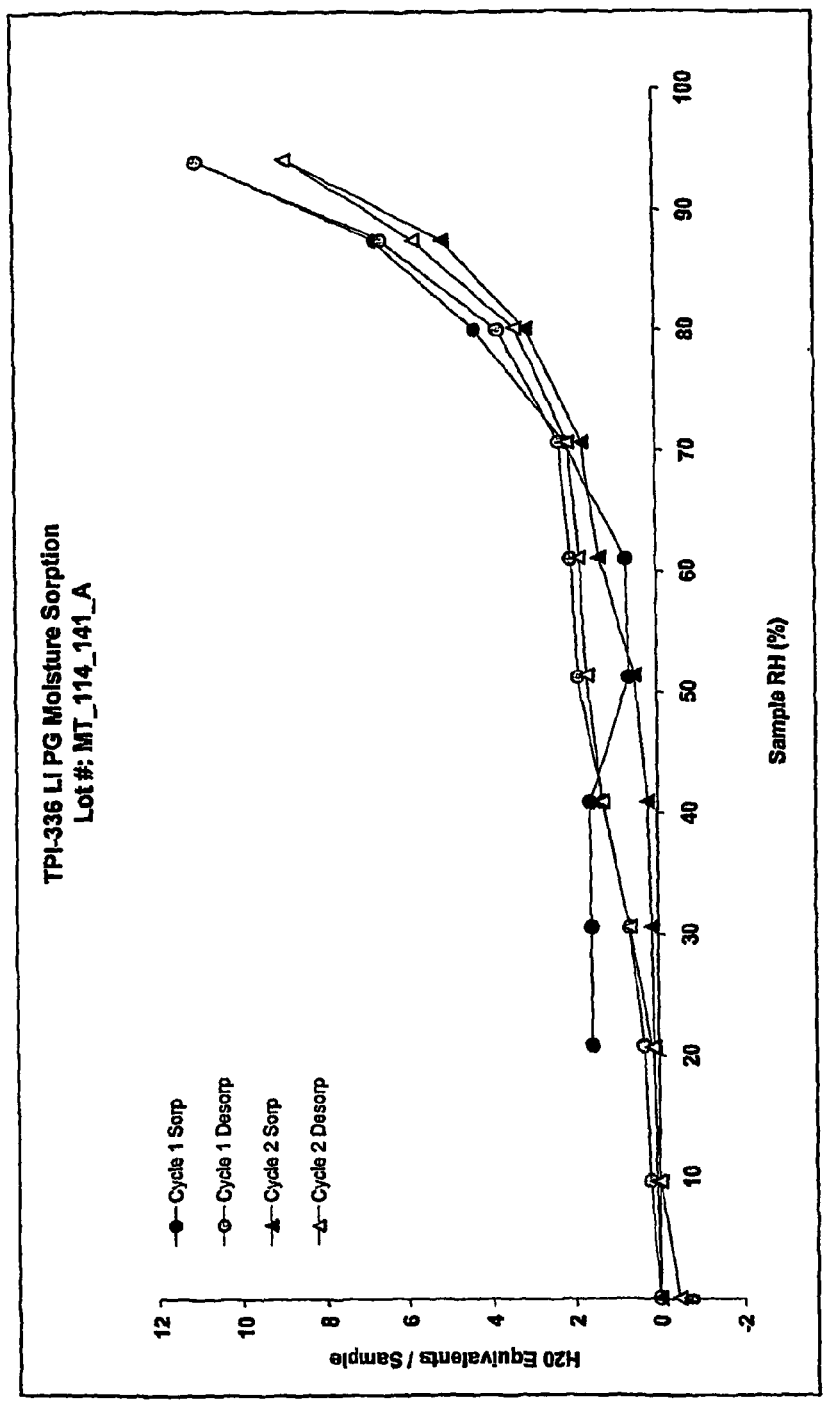
FIG. 78 shows dynamic vapor sorption data of celecoxib lithium propylene glycol solvate.

Celecoxib lithium propylene glycol solvate (dry mass: 5.5916 mg, dry molecular weight: 387.32, temperature: 25.5 degrees C.) was initially equilibrated at 20 percent RH at 25 degrees C. RH was ramped up from 20 to 95 percent RH and back down to 0 percent RH. Two complete humidity cycles were performed as illustrated in FIG. 78. In the initial 20 to 50 percent RH transition the data shows 1 molar water equivalent was desorbed, assuming PG was not lost at this stage. Above 60 percent RH water sorption increased exponentially with increasing percent RH before deliquescence occurred at 95 percent RH.

Figure 79:
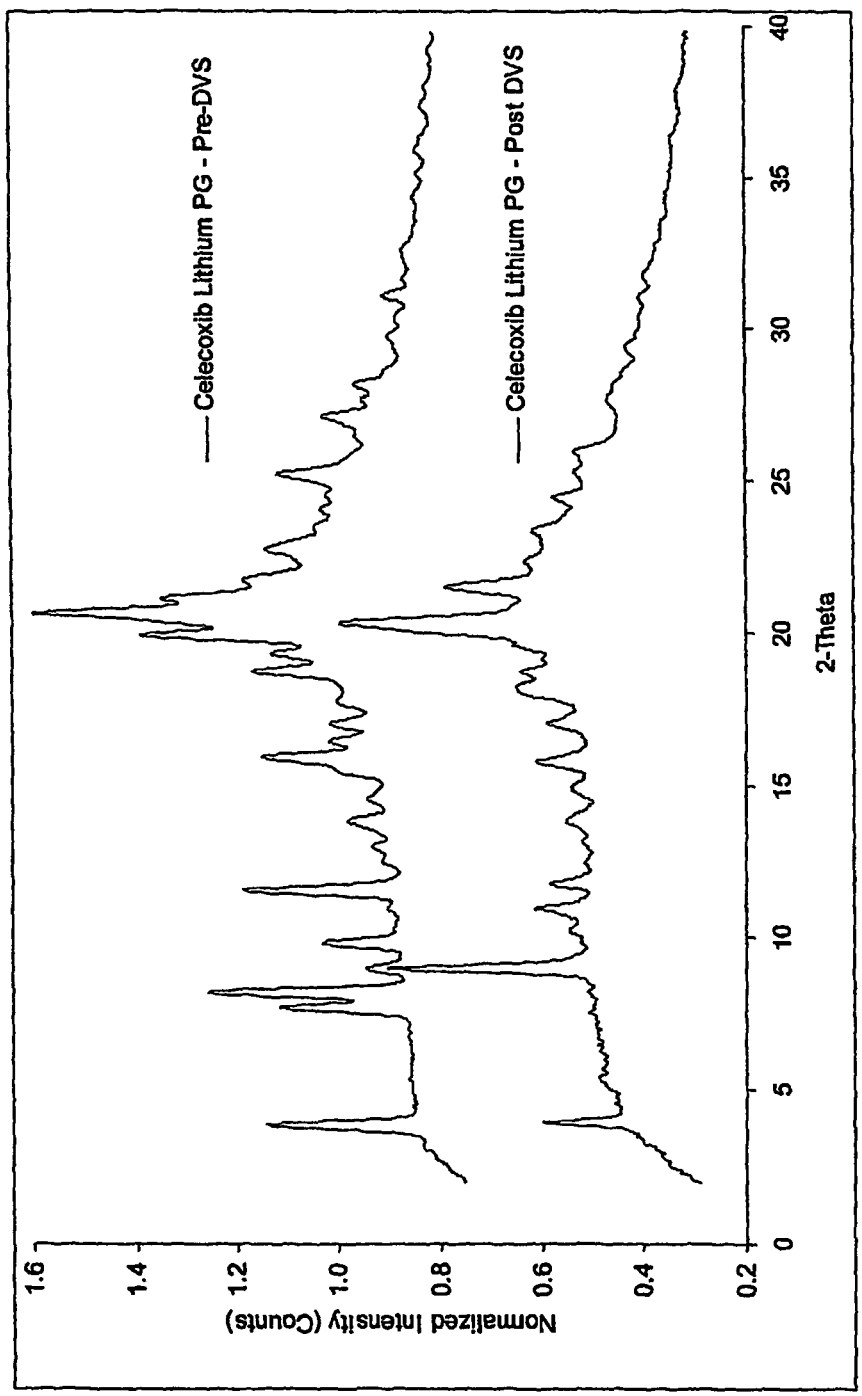
FIG. 79 shows a comparison of PXRD diffractograms of celecoxib lithium propylene glycol solvate.

In the desorption cycles, a lower dry weight was, consistently obtained after equilibration in 0% RH. The decreasing dry weight obtained at 0 percent RH was consistent with the properties of other propylene glycol forms and suggests loss of propylene glycol during the RH ramp cycles. The calculated propylene glycol loss was 0.11 molar equivalents. A PXRD pattern, FIG. 79, taken at the end of the assay showed a change in crystalline form during the assay.

Celecoxib:Nicotinamide Co-Crystal

Figure 80:
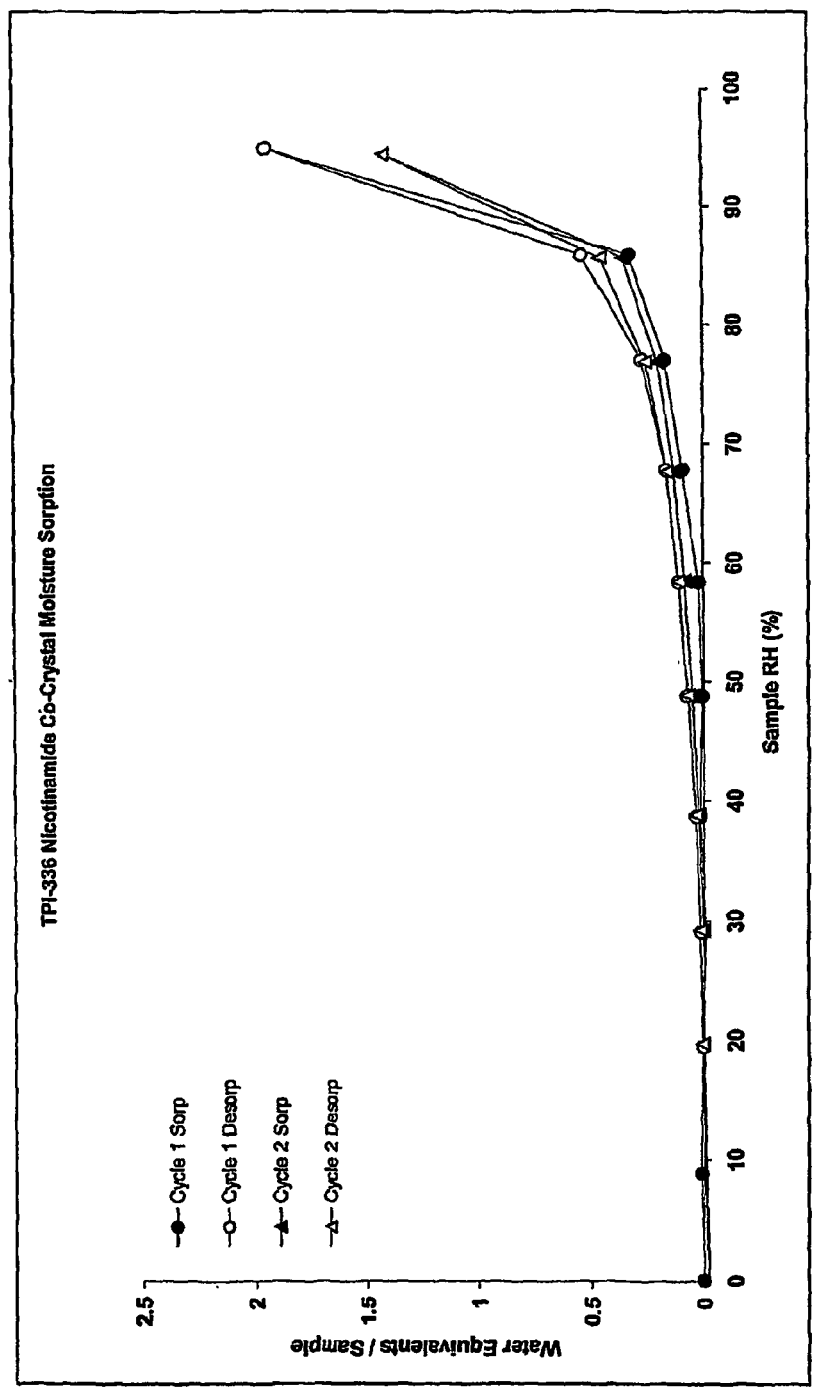
FIG. 80 shows dynamic vapor sorption data of a celecoxib: nicotinamide co-crystal.

Celecoxib:Nicotinamide co-crystal (dry mass: 3.129 mg, dry molecular weight: 1044.8, temperature: 25.3 degrees C.) was initially equilibrated at 0 percent RH at 25 degrees C. RH was ramped from 0 to 95 percent RH in a two cycle experiment, as illustrated in FIG. 80. The co-crystal was not hygroscopic below 70 percent RH. The small amount of water content observed in the figure is attributed to surface adsorption. Above 70 percent RH, water content increased gradually and reached a peak concentration of 2 water molecules per mole of co-crystal at 95 percent RH. The desorption cycle was characterized by minimal hysteresis.

Example 31

Amorphous Celecoxib Potassium Salt: Preparation Method MO-116-55B

To celecoxib (105.3 mg; 0.2761 mmol) was added aqueous 3M KOH (0.090 ml; 0.27 mmol) to give a suspension. The suspension was gently warmed and to it was added methanol (0.3 mL) which yielded a colorless solution. The solution was cooled to room temperature and the volatiles were subsequently evaporated with flowing nitrogen gas. The resulting amorphous solid was characterized via DSC, Raman spectroscopy, and PXRD.

Figure 81:
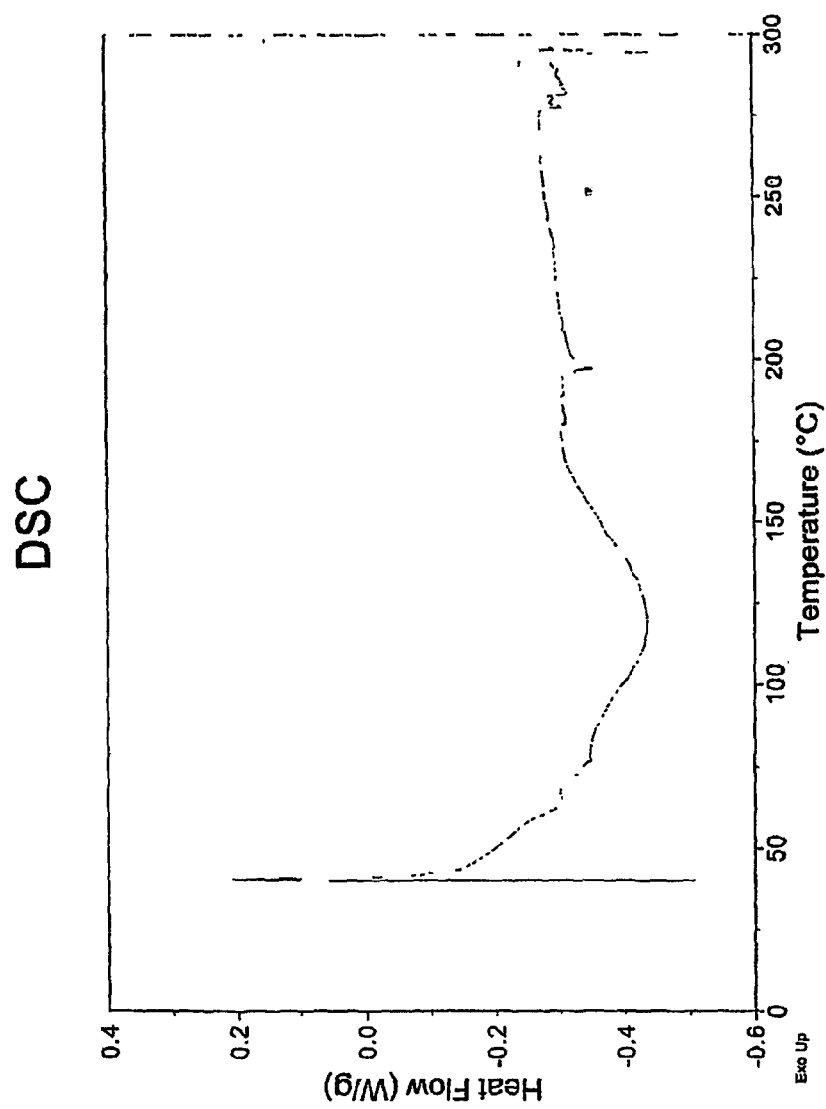
FIG. 81 shows a DSC thermogram of amorphous celecoxib potassium salt.
Figure 82:
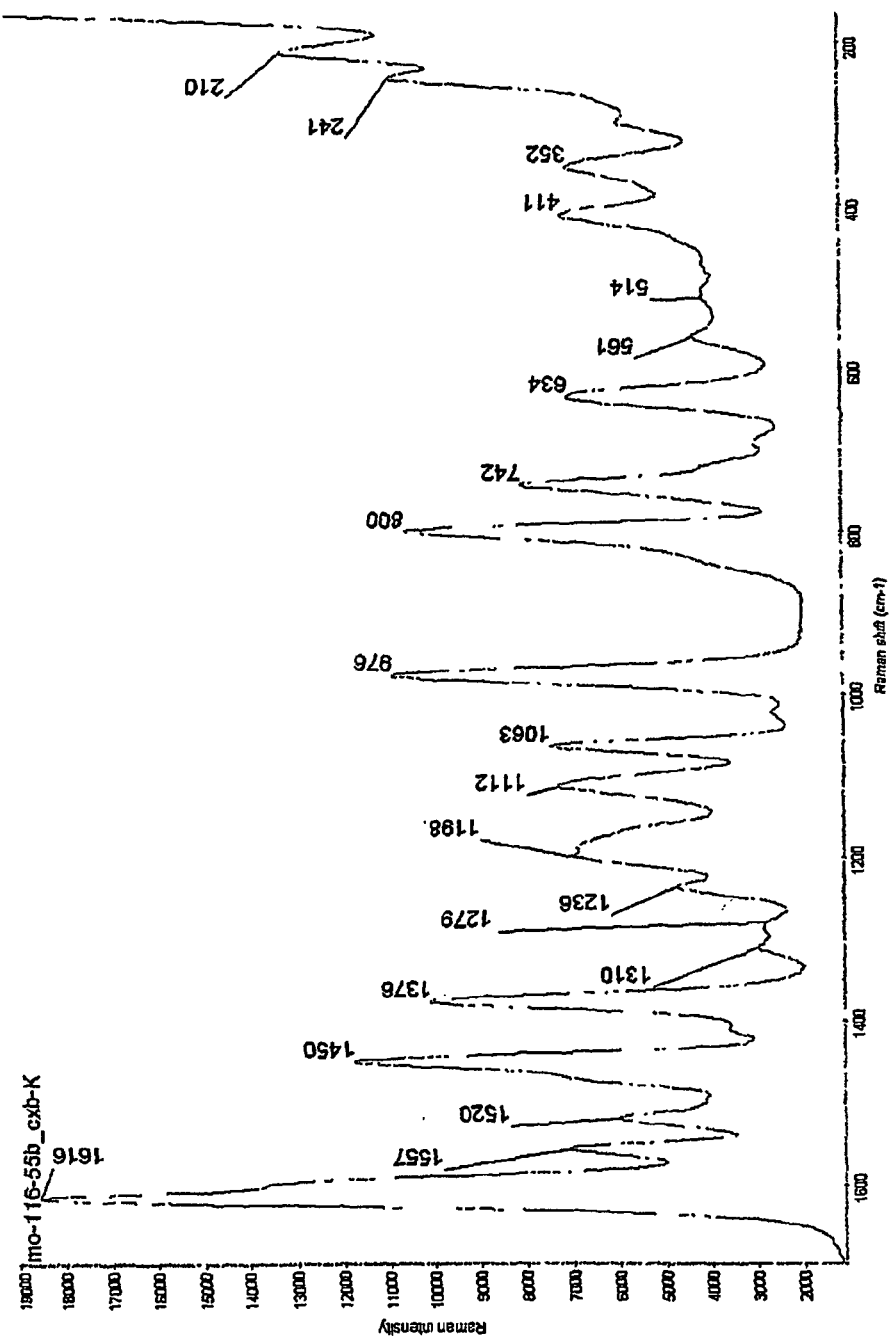
FIG. 82 shows a Raman spectrum of amorphous celecoxib potassium salt.
Figure 83:
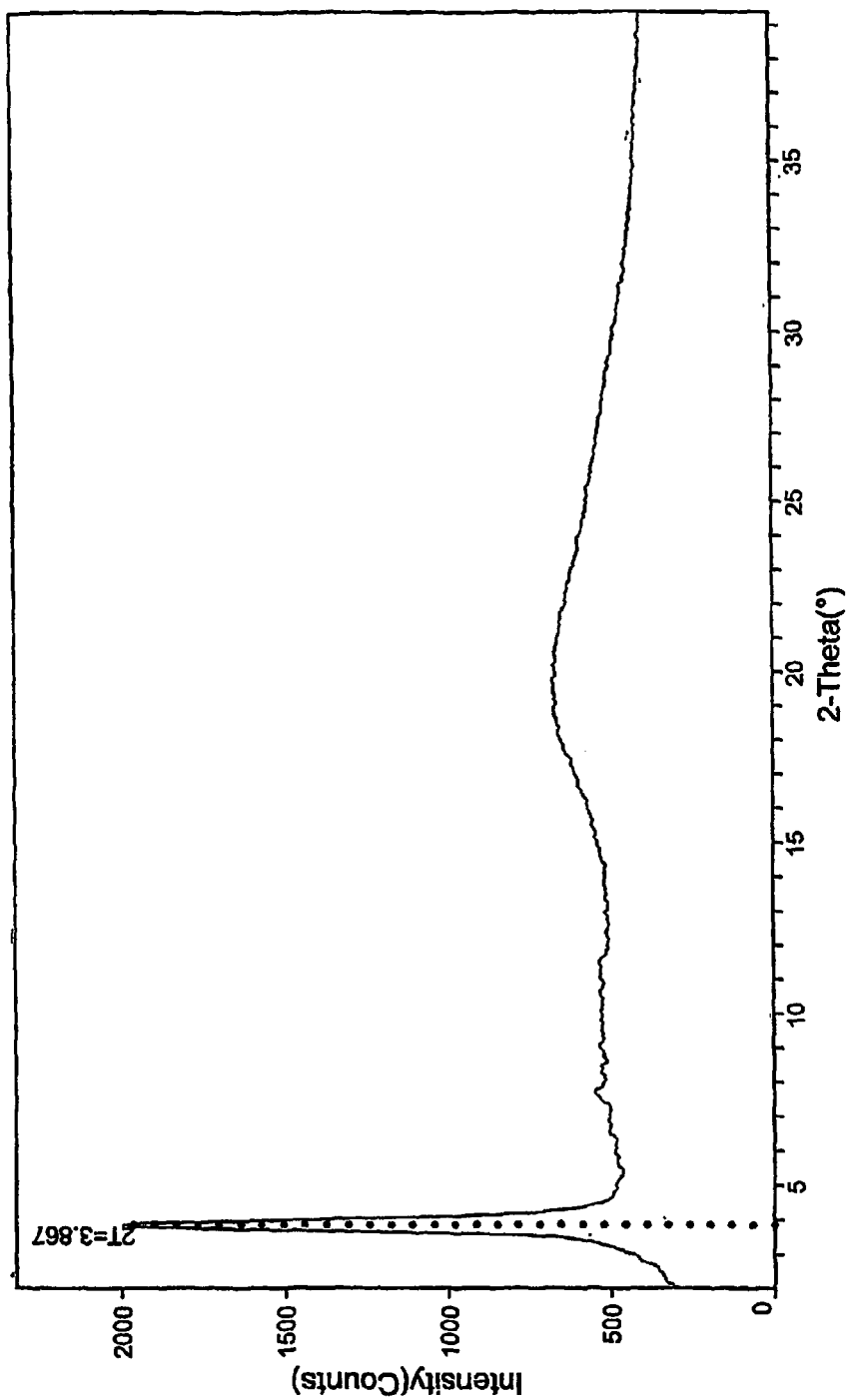
FIG. 83 shows a PXRD diffractogram of amorphous celecoxib potassium salt.

The DSC is depicted in FIG. 81. The Raman spectrum is depicted in FIG. 82 and shows characteristic Raman shift peaks (cm$^{-1}$) at positions including, but not limited to any one or a combination of any two, any three, any four, any five, any six, any seven, any eight, any nine, any ten, or all eleven of the peaks 1616, 1450, 1376, 1236, 1198, 1112, 1063, 976, 800, 742, or 634 cm$^{-1}$, or any one or combinations of 2, 3, 4, 5, 6, 7, 8, 9, 10, 11, 12, 13, 14 or more peaks of FIG. 82. The PXRD pattern is depicted in FIG. 83 for which one peak is observed at 3.87 degrees 2-theta.

Example 32

Crystallization of Celecoxib and Valdecoxib with Various Ethers

Celecoxib:18-crown-6 Co-crystal

To solid 18-crown-6 (118.1 mg; 0.447 mmol) was added a solution of celecoxib (157.8 mg; 0.4138 mmol) in diethyl ether (10.0 mL). The opaque solid dissolved immediately and a white solid subsequently began to crystallize very rapidly. The solid was collected via filtration and was washed with additional diethyl ether (5 mL).

The solid was allowed to air dry and was characterized via TGA, DSC, and PXRD. Unit cell determination by single crystal X-Ray diffraction is consistent with a 2:1 adduct (celecoxib:18-crown-6). The co-crystal has a higher melting point (189 degrees C.) than celecoxib (156-159 degrees C.).

Figure 84:
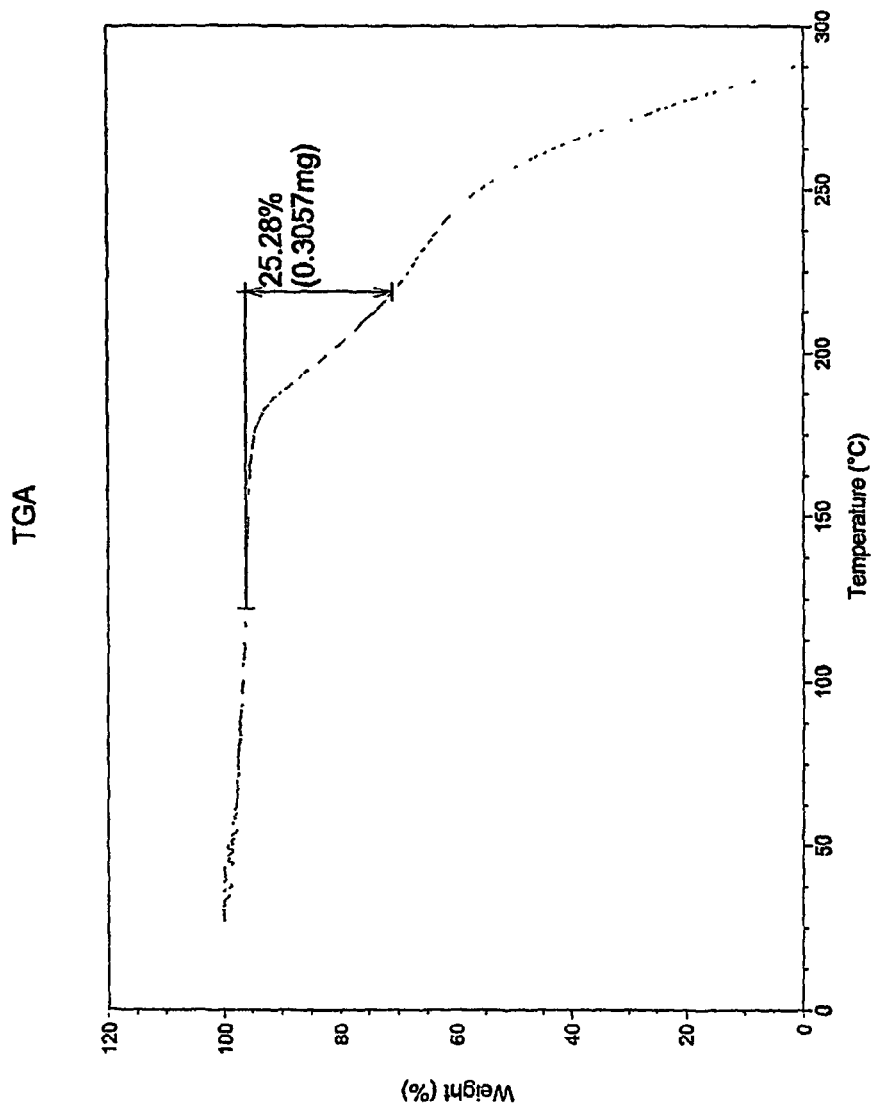
FIG. 84 shows a TGA thermogram of a celecoxib:18-crown-6 co-crystal.
Figure 85:
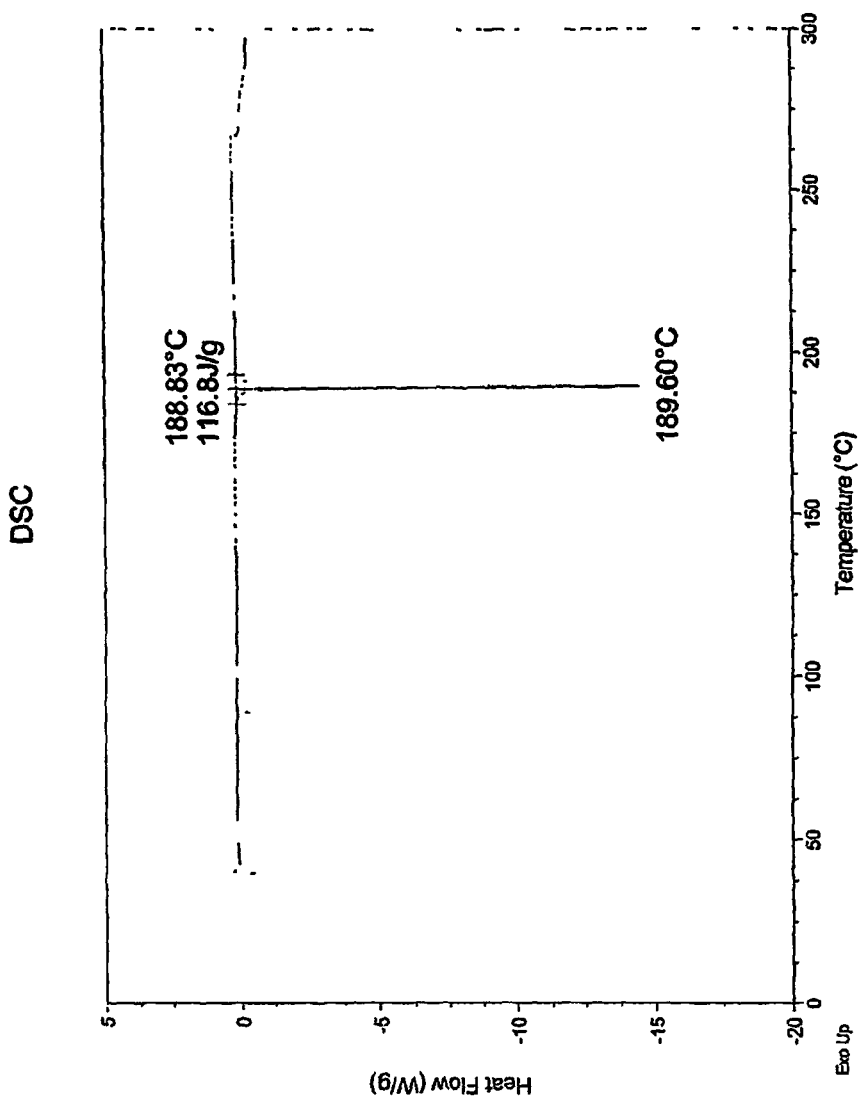
FIG. 85 shows a DSC thermogram of a celecoxib:18-crown-6 co-crystal.
Figure 86:
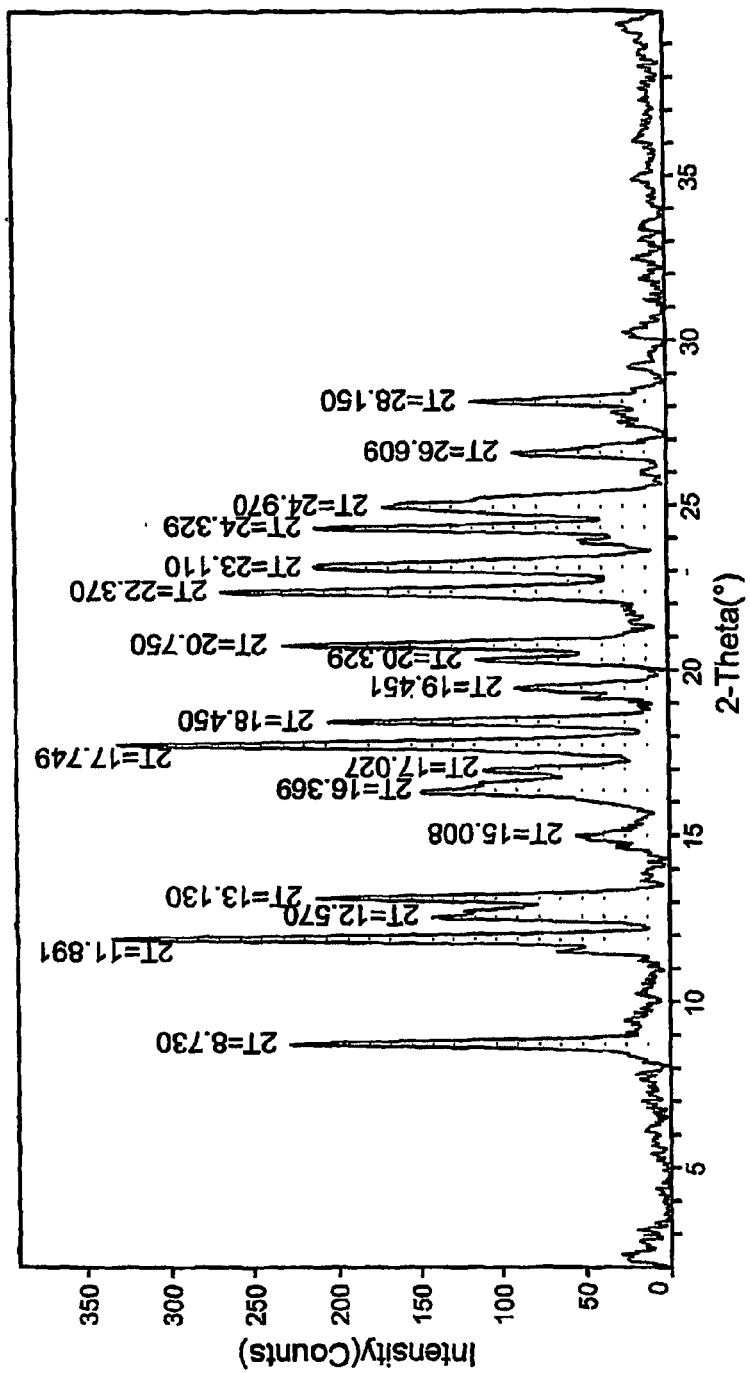
FIG. 86 shows a PXRD diffractogram of a celecoxib:18-crown-6 co-crystal.

FIG. 84 shows the TGA thermogram of the celecoxib:18-crown-6 co-crystal. Results of the TGA analysis show an approximate 25 percent weight loss between about 125 degrees C. and 220 degrees C. FIG. 85 shows the DSC thermogram of the celecoxib:18-crown-6 co-crystal. Results of the DSC analysis shows an endotherm at 189.6 degrees C. FIG. 86 shows the PXRD diffractogram of the celecoxib:18-crown-6 co-crystal. Peaks can be seen at 2-theta angles including, but not limited to, 8.73, 11.89, 13.13, 16.37, 17.75, 18.45, 20.75, 22.37, and 23.11 degrees. The crystal can be characterized by any one or combination of any two, any three, any four, any five, any six, any seven, any eight, or all nine of the above angles or any one or any combination of 2-theta angles of FIG. 86.

Celecoxib 15-crown-5 Solvate

To a solution of celecoxib (165.2 mg; 0.4332 mmol) in diethyl ether (5.0 mL) was added a solution of 15-crown-5 (0.095 mL; 0.48 mmol) in diethyl ether (1.0 mL). The volatiles were allowed to evaporate slowly yielding an oil. The oil was then recrystallized from ethanol (5 mL). The recrystallization also yielded an oil that crystallized after 1 week without agitation. The solid was found to be a 15-crown-5 solvate of celecoxib.

Figure 87:
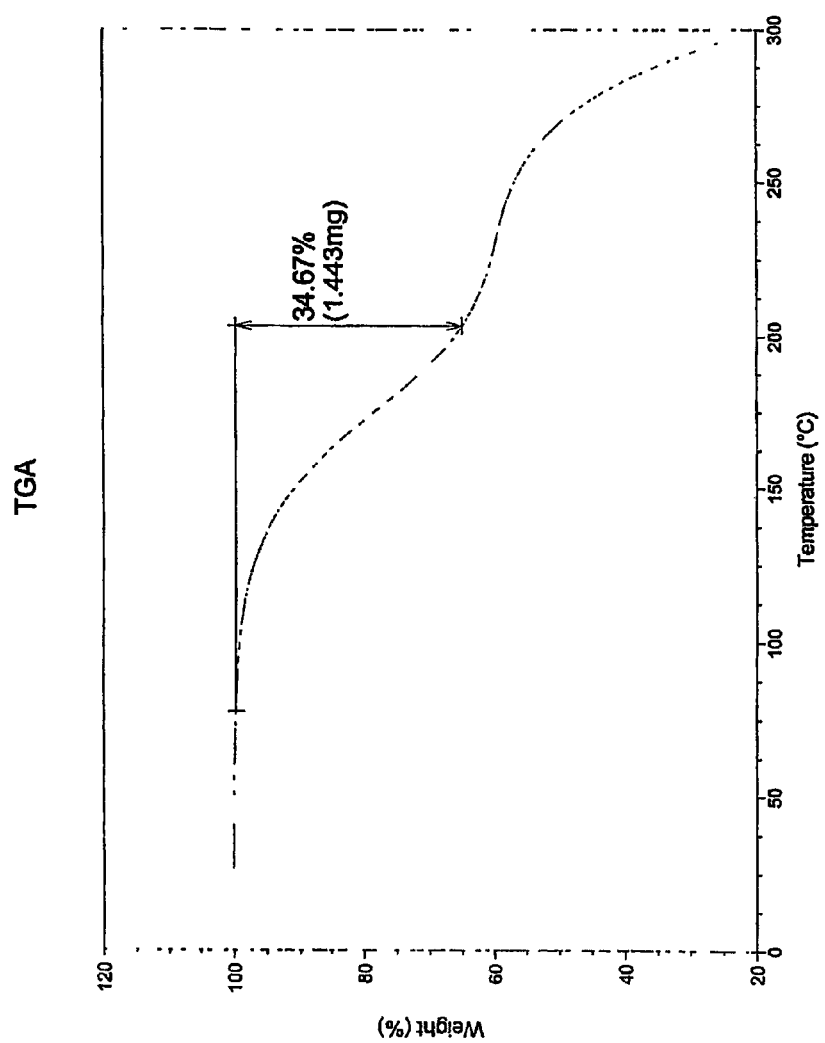
FIG. 87 shows a TGA thermogram of celecoxib 15-crown-5 solvate.
Figure 88:
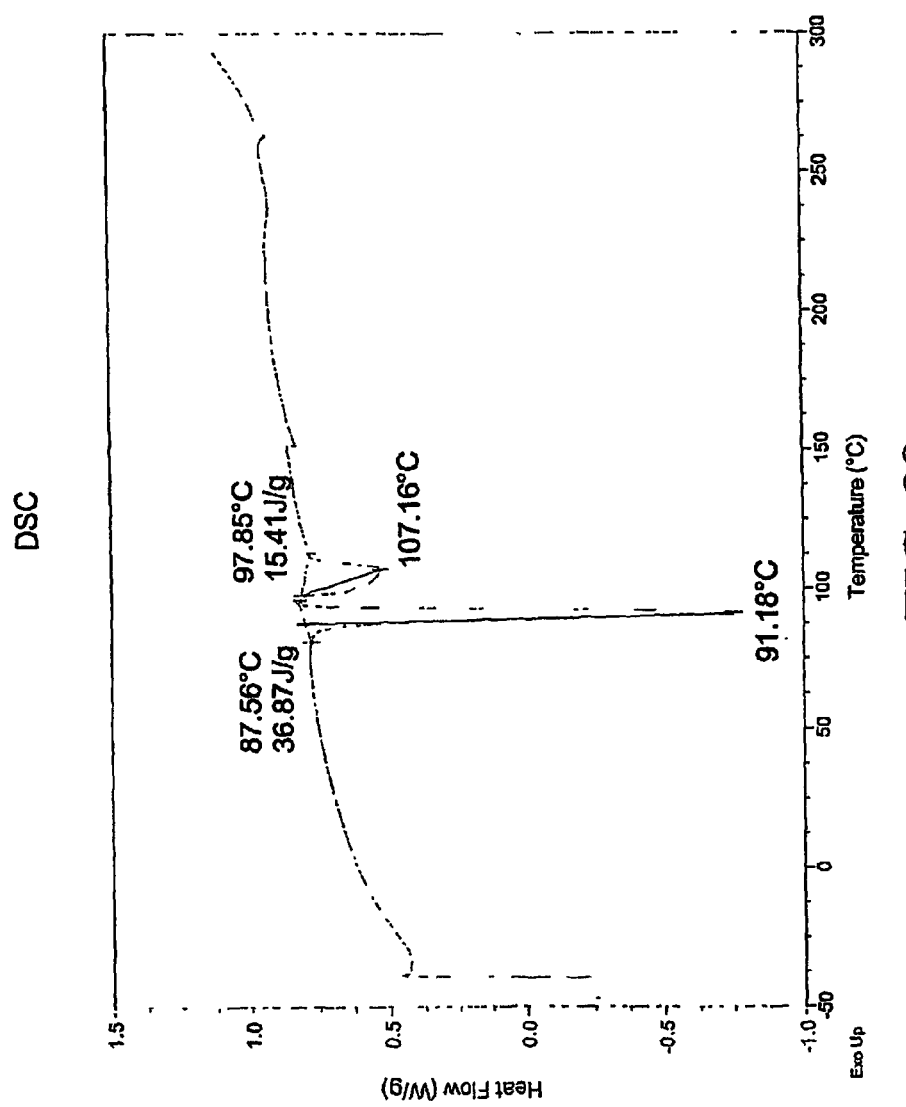
FIG. 88 shows a DSC thermogram of celecoxib 15-crown-5 solvate.
Figure 89:
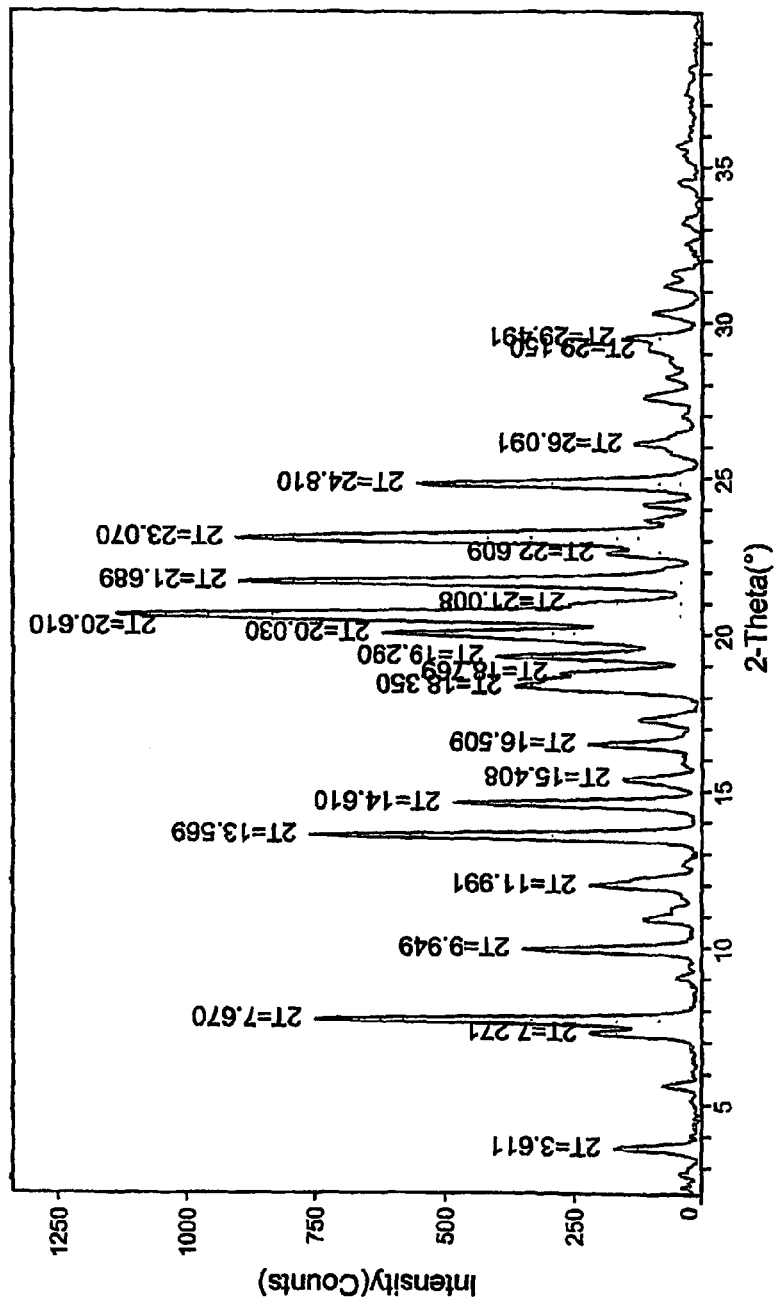
FIG. 89 shows a PXRD diffractogram of celecoxib 15-crown-5 solvate.

The solid was characterized via TGA, DSC, and PXRD. The TGA data shows a loss of 34.67 weight percent which is consistent with 1 molar equivalent of 15-crown-5 per mole of celecoxib (See FIG. 87). DSC shows a melting point at 91.2 degrees C. which is significantly lower than that of the 18-crown-6 analogue (189 degrees C.) and free celecoxib (156-159 degrees C.). The DSC thermogram is shown in FIG. 88. FIG. 89 shows the PXRD diffractogram of the celecoxib 15-crown-5 solvate. Peaks can be seen at 2-theta angles including, but not limited to, 7.67, 13.57, 14.61, 20.61, 21.69, 23.07, and 24.81 degrees. The crystal can be characterized by any one or a combination of any two, any three, any four, any five, any six, or all seven of the above angles or any one or any combination of 2-theta angles of FIG. 89.

Celecoxib Diglyme Solvate

To a solution of celecoxib (129.3 mg; 0.3390 mmol) in diethyl ether (5.0 mL) was added a solution of diglyme (0.100 mL; 0.698 mmol) in diethyl ether (3.0 mL). The volatiles were allowed to evaporate slowly yielding a white solid. The solid continued to crystallize as the solvent was reduced (2 mL) and subsequently cooled. The white powder was collected via filtration and air-dried. The solid was found to be a diglyme solvate of celecoxib.

Figure 90:
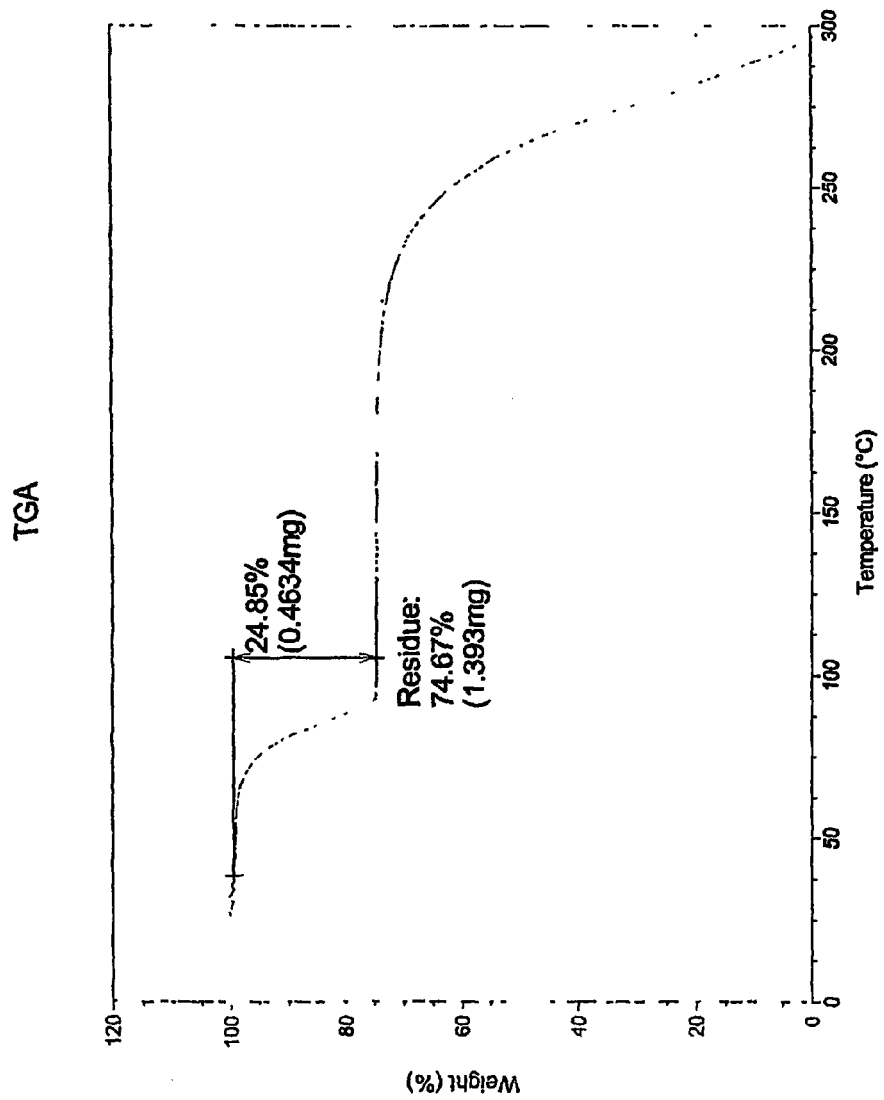
FIG. 90 shows a TGA thermogram of celecoxib diglyme solvate.
Figure 91:
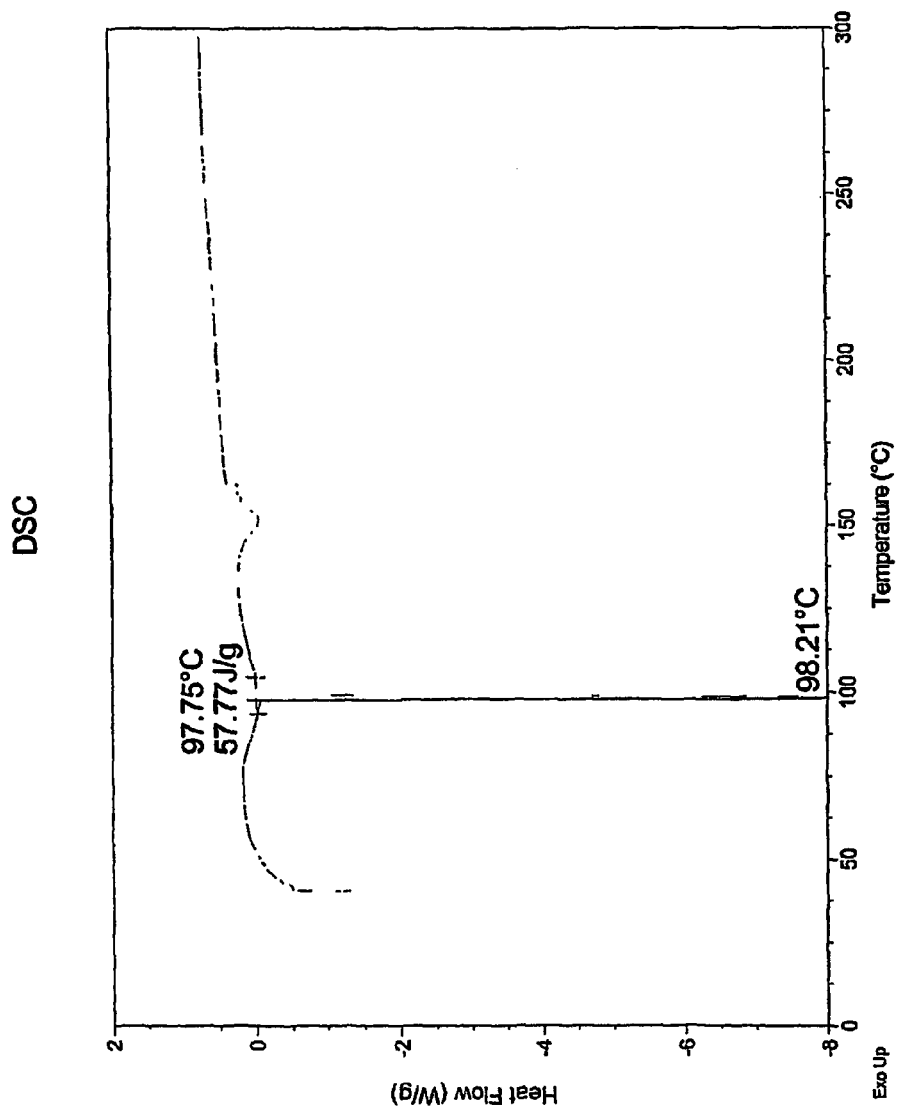
FIG. 91 shows a DSC thermogram of celecoxib diglyme solvate.
Figure 92:
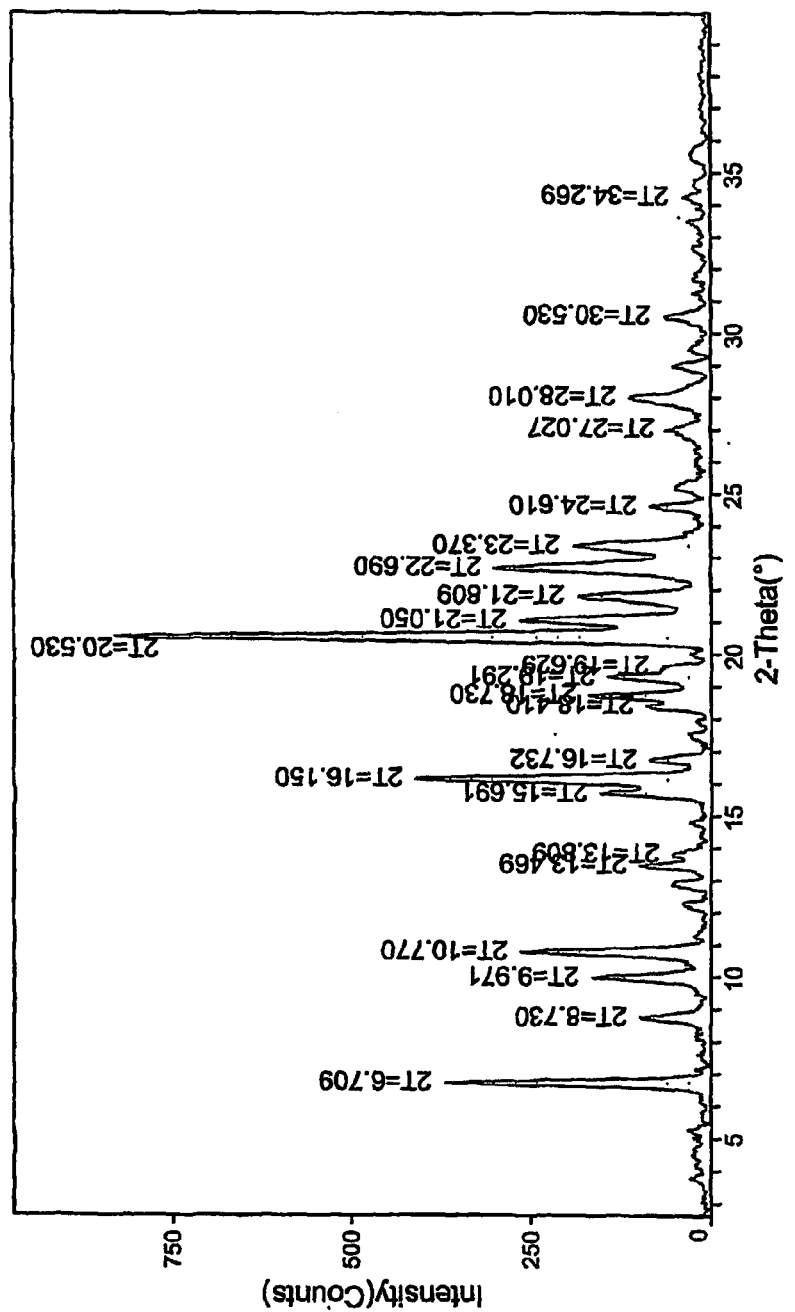
FIG. 92 shows a PXRD diffractogram of celecoxib diglyme solvate.

The solid was characterized via TGA, DSC, and PXRD. The TGA data shows a loss of 24.85 weight percent which is consistent with 1 molar equivalent of diglyme per mole of celecoxib (See FIG. 90). The melting point of the solvate is shown to be 98.2 degrees C. by DSC, which is significantly lower than celecoxib (156-159 degrees C.)). The DSC thermogram is shown in FIG. 91. FIG. 92 shows the PXRD diffractogram of the celecoxib diglyme solvate. Peaks can be seen at 2-theta angles including, but not limited to, 6.71, 10.77, 16.15, 20.53, 21.05, 21.81, and 22.69 degrees. The crystal can be characterized by any one or a combination of any two, any three, any four, any five, any six, or all seven of the above angles or any one or any combination of 2-theta angles of FIG. 92.

Valdecoxib:18-crown-6 Co-Crystal

Figure 93:
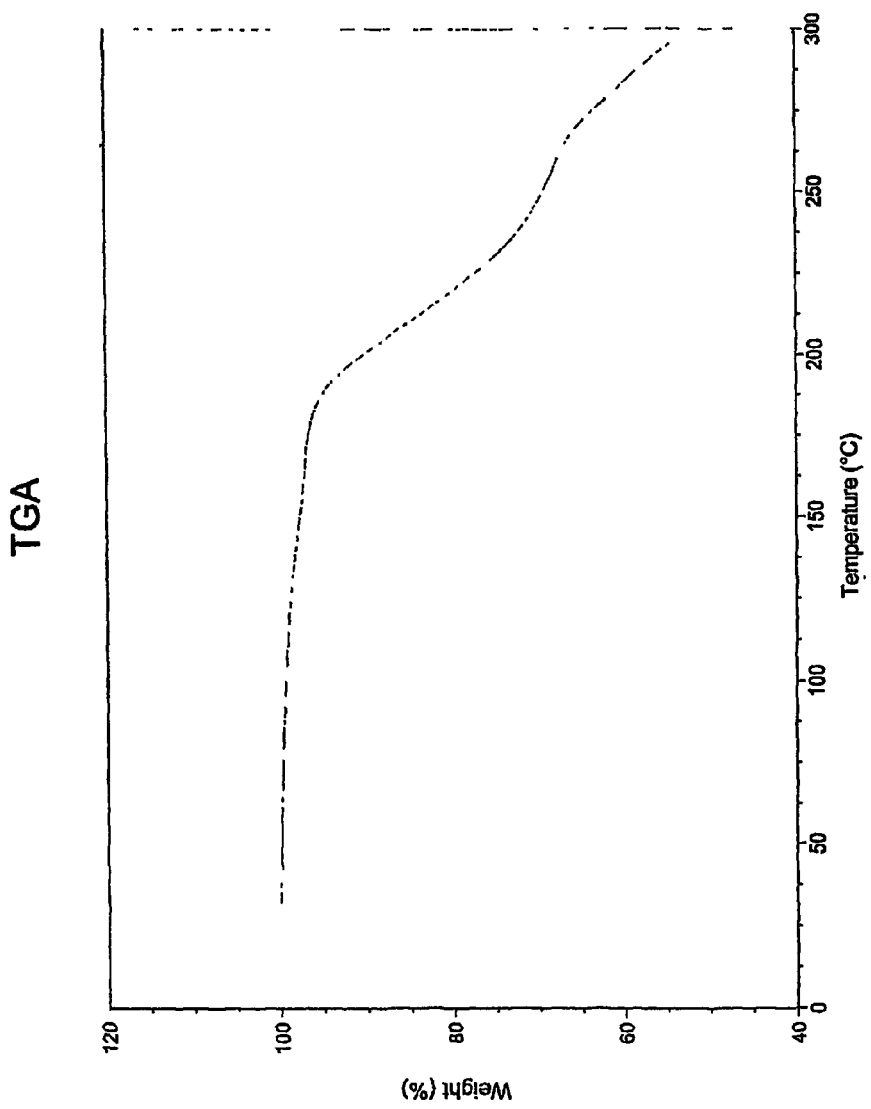
FIG. 93 shows a TGA thermogram of a valdecoxib:18-crown-6 co-crystal.
Figure 94:
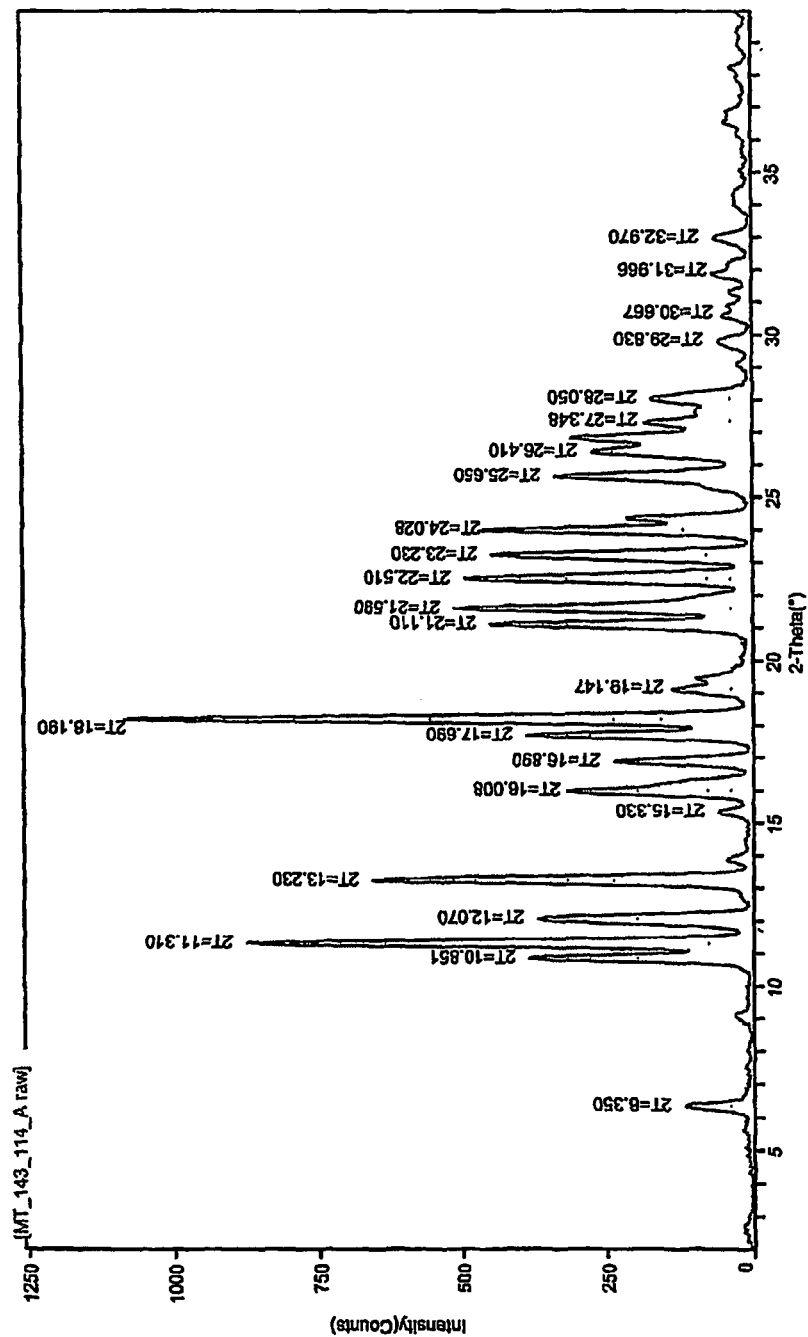
FIG. 94 shows a PXRD diffractogram of a valdecoxib:18-crown-6 co-crystal.
Figure 95:
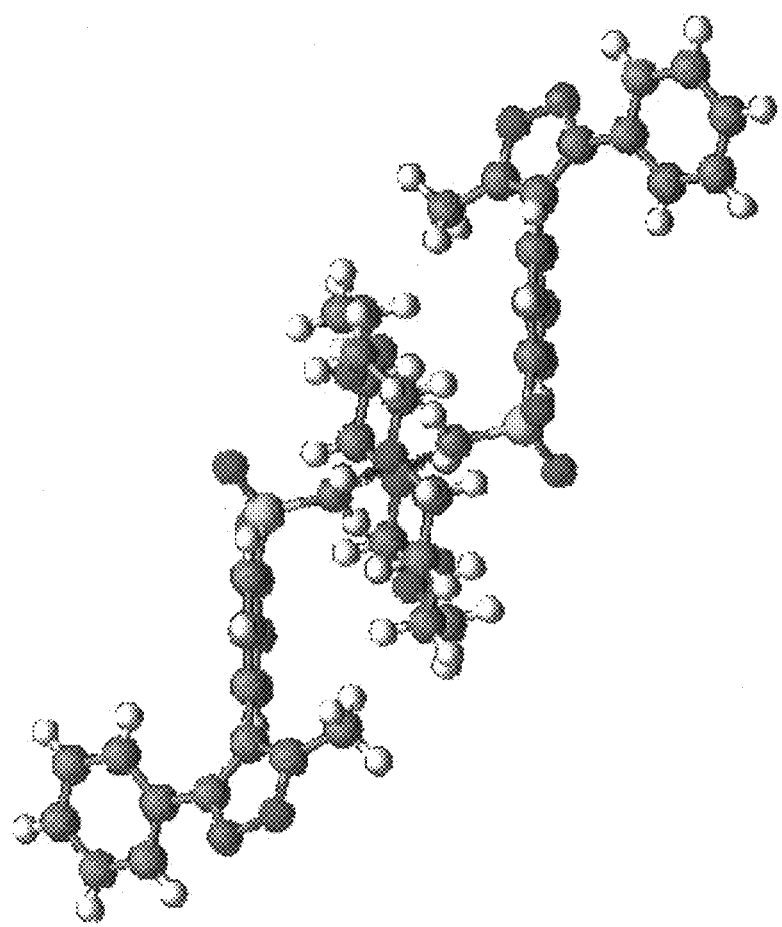
FIG. 95 shows a single-crystal packing diagram for valdecoxib:18-crown-6 co-crystal.

To a solution of valdecoxib (33.3 mg; 0.107 mmol) in tetrahydrofuran (2.0 mL) is added a solution of 18-Crown-6 (30.2 mg; 0.114 mmol) in tetrahydrofuran (2.0 mL). The solution was stirred and was allowed to slowly evaporate. After evaporation to dryness, the residual solid was a white crystalline material. A single crystal was removed for single crystal X-ray diffraction and was found to be a 2:1 adduct with two independent supramolecular complexes in the asymmetric unit. TGA analysis of the valdecoxib:18-crown-6 co-crystal is shown in FIG. 93. FIG. 94 shows the PXRD diffractogram of the valdecoxib:18-crown-6 co-crystal. Peaks can be seen at 2-theta angles including, but not limited to, 11.31, 13.23, 16.01, 17.69, 18.19, 21.11, 21.59, 22.51, 23.23, and 24.03 degrees. The crystal can be characterized by any one or a combination of any two, any three, any four, any five, any six, any seven, any eight, any nine, or all ten of the above angles or any one or any combination of 2-theta angles of FIG. 94. FIG. 95 shows the single crystal structure of the valdecoxib:18-crown-6 co-crystal.

Single-crystal x-ray data for the valdecoxib:18-crown-6 co-crystal 2:1 are as follows:

| | |
|---|---|
| Empirical formula | C44 H52 N4 O12 S2 |
| Formula weight | 893.02 |
| Temperature | 100(2) K |
| Wavelength | 0.71073 angstroms |
| Unit cell dimensions | a = 10.1721(11) angstroms    alpha = 83.127(2) deg. |
| | b = 13.7178(15) angstroms    beta = 73.362(2) deg. |
| | c = 16.7202(18) angstroms    gamma = 89.017(2) deg. |
| Volume | 2219.0(4) $Å^3$ |
| Z, Calculated density | 2, 1.337 $Mg/m^3$ |
| Absorption coefficient | 0.187 $mm^{-1}$ |
| F(000) | 944 |
| Reflections collected/unique | 13432/9849 [R(int) = 0.0330] |
| Refinement method | Full-matrix least-squares on $F^2$ |
| Data/restraints/parameters | 9849/0/559 |
| Goodness-of-fit on $F^2$ | 0.995 |
| Final R indices [I>2sigma(I)] | R1 = 0.0594, wR2 = 0.1345 |
| R indices (all data) | R1 = 0.1097, wR2 = 0.1573 |

The above co-crystals and solvates exemplify the importance of the ether-sulfonamide interaction. This ether-sulfonamide interaction is highly favorable and plays an important role in the formulations of the present invention.

Example 33

Celecoxib NMP Solvate

To solid celecoxib (127 mg; 0.333 mmol) was added N-methyl-2-pyrrolidone (0.75 mL) to give a white suspension. The mixture was heated to 75 degrees C. and held at this temperature for 3 minutes at which point the solid dissolved to give a colorless solution. The solution was cooled to room temperature and then cooled to 5 degrees C. for three days. After three days, colorless hexagonal crystals had formed. The mother liquor was decanted and the solid was suspended in pentane (2 mL) and filtered. The solid was air dried and collected. The solid was found to be a 1:1 N-Methyl-2-pyrrolidone (NMP) solvate of celecoxib.

Figure 96:
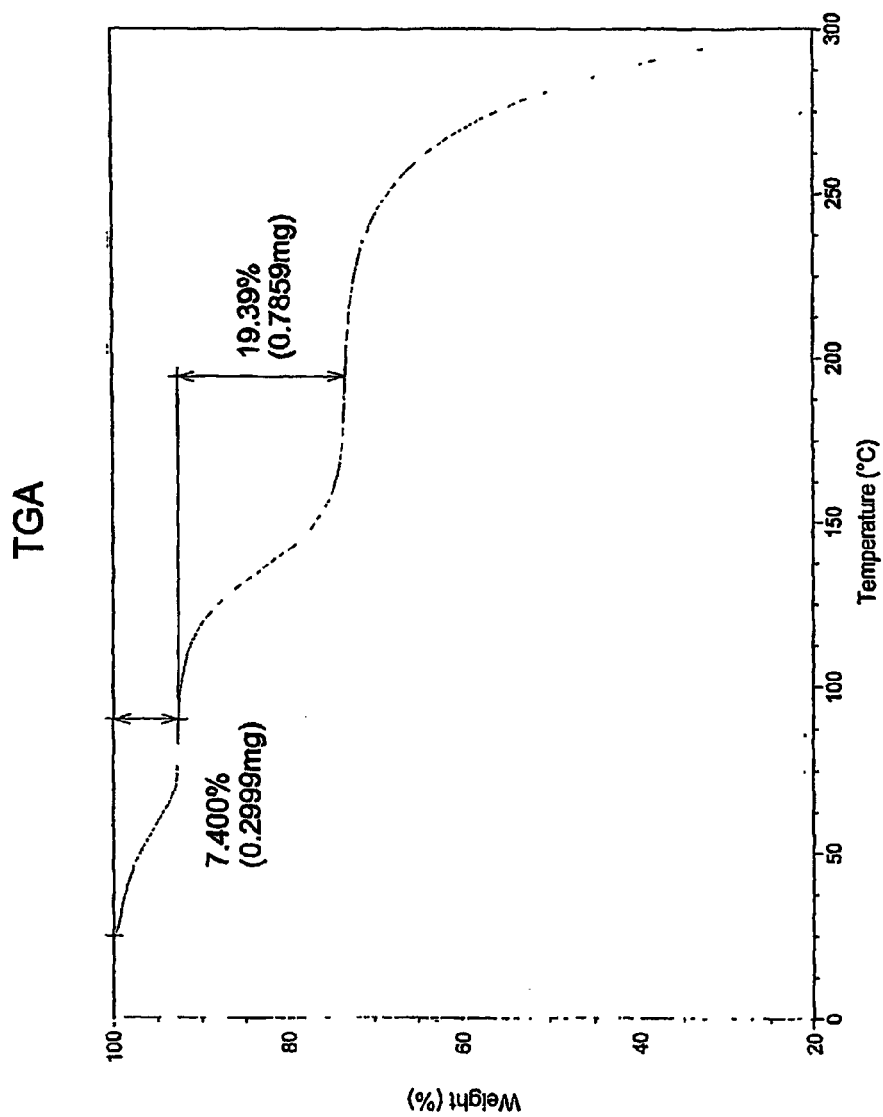
FIG. 96 shows a TGA thermogram of celecoxib NMP solvate.
Figure 97:
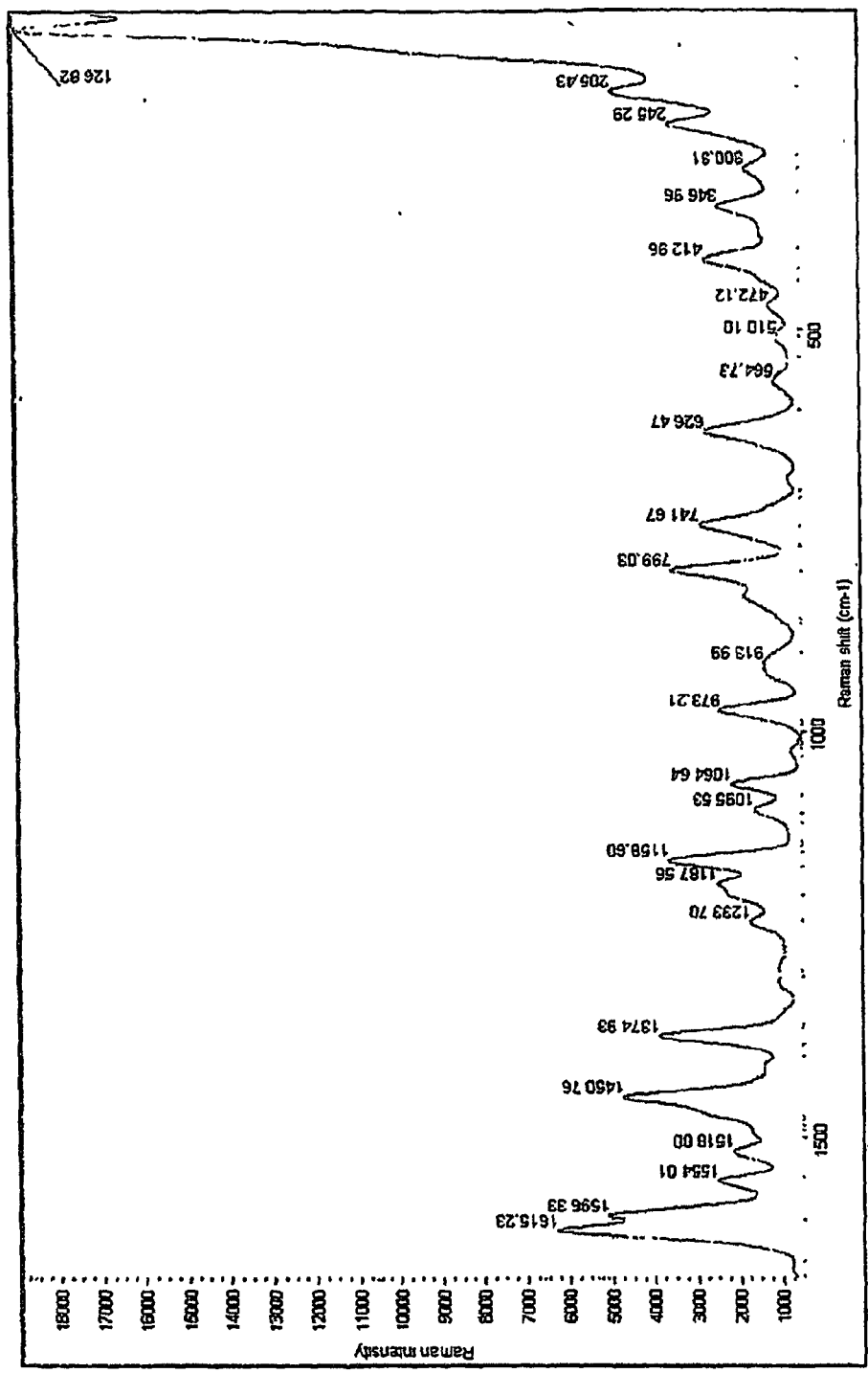
FIG. 97 shows a Raman spectrum of celecoxib NMP solvate.
Figure 98:
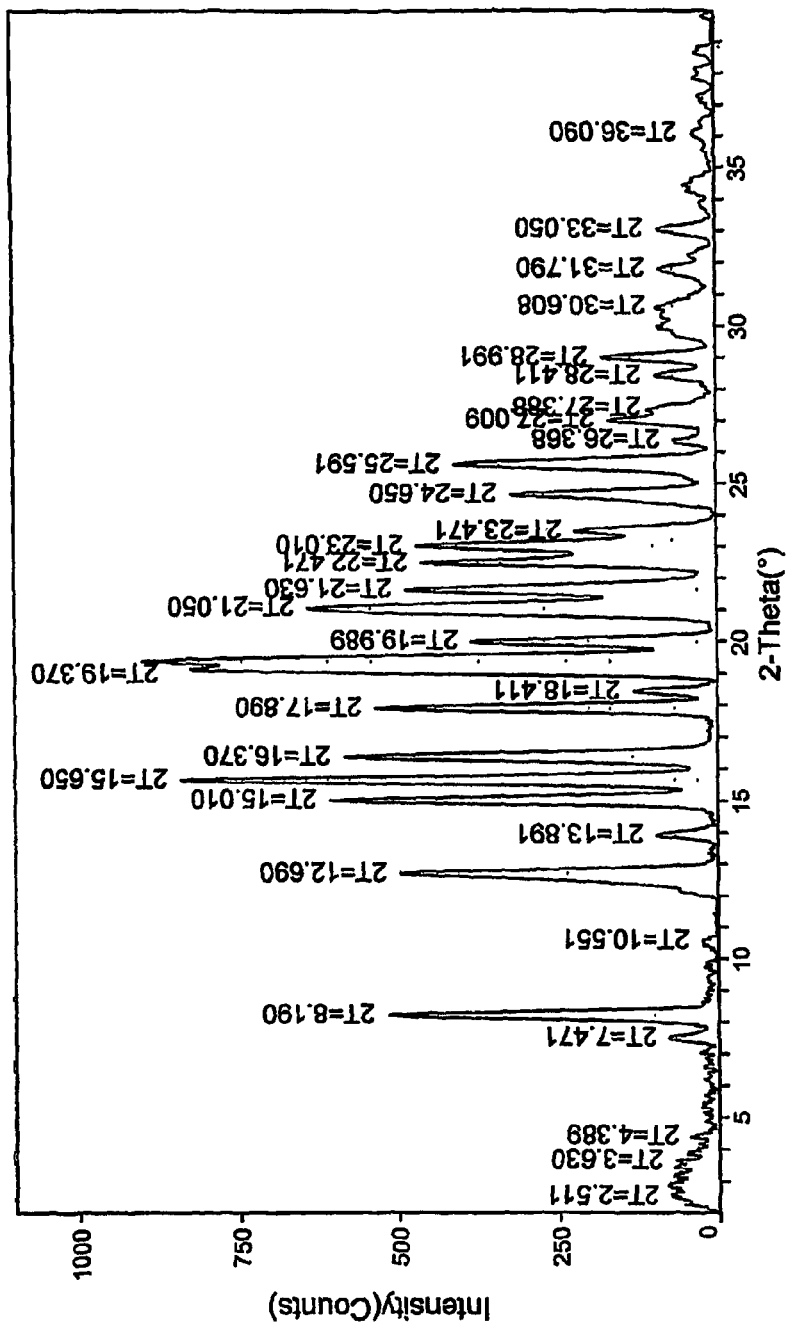
FIG. 98 shows a PXRD diffractogram of celecoxib NMP solvate.

The solid was characterized by TGA, Raman spectroscopy, and PXRD. TGA data show an initial loss of 7.40% weight loss between room temperature and 60 degrees C. which is attributed to residual solvent (See FIG. 96). Between about 95 degrees C. and about 165 degrees C., the solvate loses 19.39 percent weight. This loss represents 1:1 molar equivalent of NMP to celecoxib. The residual solvent can be removed to give the pure solvate. Raman scattering peaks were found at, for example, 1615, 1451, 1375, 1159, 973, 799, 741, and 626 $cm^{-1}$. Any one, any two, any three, any four, any five, any six, any seven, or all eight of the above or any one or a combination of peaks in FIG. 97 can be used to characterize the crystal. FIG. 98 shows the PXRD diffractogram of the celecoxib:NMP solvate. Peaks can be seen at 2-theta angles including, but not limited to, 8.19, 12.69, 15.01, 15.65, 16.37, 17.89, 19.37, 21.05 and 23.01 degrees. The crystal can be characterized by any one or a combination of any two, any three, any four, any five, any six, any seven, any eight, or all nine of the above angles or any one or any combination of 2-theta angles of FIG. 98.

Single-crystal x-ray data for the celecoxib:NMP co-crystal at 100 K is as follows:

| | | |
|---|---|---|
| Empirical formula | C22 H23 F3 N4 O3 S | |
| Formula weight | 480.50 | |
| Temperature | 100(2) K | |
| Wavelength | 0.71073 angstroms | |
| Crystal system | Monoclinic | |
| Space group | P2(1)/n | |
| Unit cell dimensions | a = 21.1232(14) angstroms | alpha = 90°. |
| | b = 9.2669(6) angstroms | beta = 102.5320(10)°. |
| | c = 23.8250(16) angstroms | gamma = 90°. |
| Volume | 4552.5(5) $Å^3$ | |
| Z | 8 | |
| Density (calculated) | 1.402 $Mg/m^3$ | |
| Absorption coefficient | 0.199 $mm^{-1}$ | |
| F(000) | 2000 | |
| Crystal size | 0.20 × 0.15 × 0.10 $mm^3$ | |
| Theta range for data collection | 1.17 to 28.33°. | |
| Index ranges | −26 <= h <= 28, −11 <= k <= 12, −31 <= l <= 25 | |
| Reflections collected | 27520 | |
| Independent reflections | 10573 [R(int) = 0.0366] | |
| Completeness to theta = 28.33° | 93.0% | |
| Absorption correction | None | |
| Refinement method | Full-matrix least-squares on $F^2$ | |
| Data/restraints/parameters | 10573/0/729 | |
| Goodness-of-fit on $F^2$ | 1.026 | |

-continued

| | |
|---|---|
| Final R indices [I > 2sigma(I)] | R1 = 0.0580, wR2 = 0.1386 |
| R indices (all data) | R1 = 0.0873, wR2 = 0.1547 |
| Largest diff. peak and hole | 0.694 and −0.655 e.Å$^{-3}$ |

Figure 99:
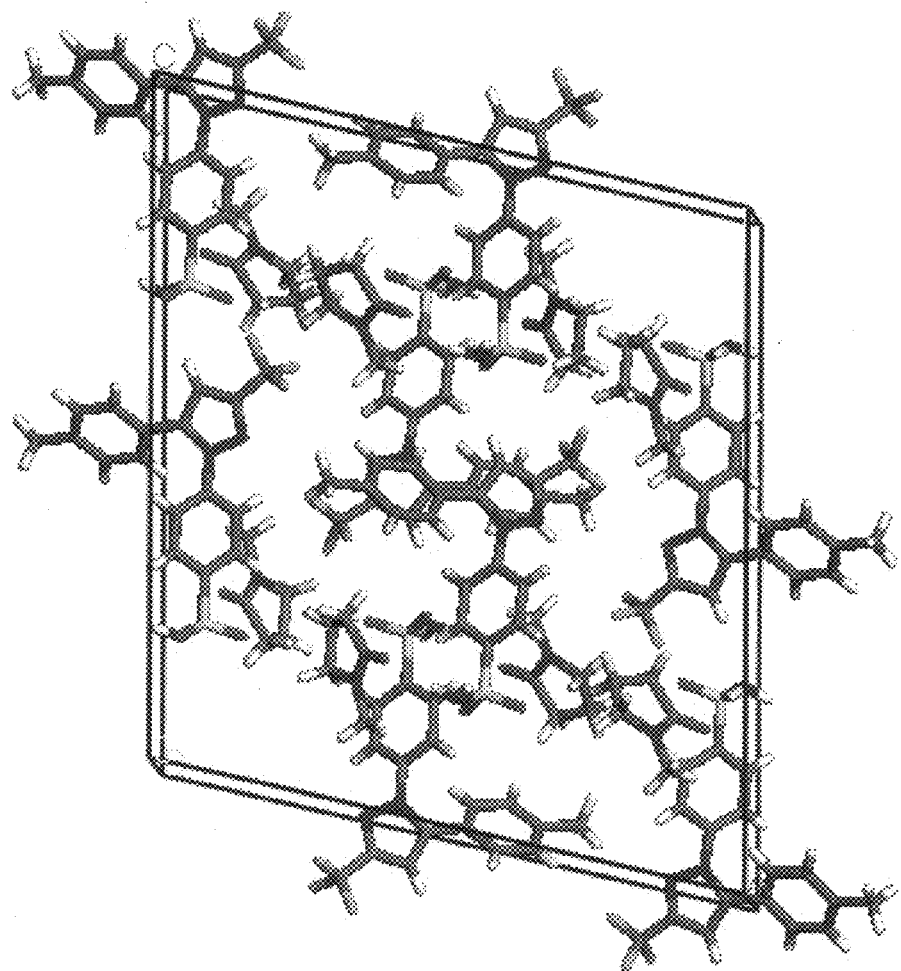
FIG. 99 shows a packing diagram for celecoxib NMP solvate at 100 K.

FIG. 99 shows a packing diagram for the celecoxib:NMP solvate at 100 K. Single-crystal x-ray data for the celecoxib:NMP co-crystal at 571 K is as follows:

| | | |
|---|---|---|
| Empirical formula | C22 H23 F3 N4 O3 S | |
| Formula weight | 480.50 | |
| Temperature | 571(2) K | |
| Wavelength | 0.71073 angstroms | |
| Crystal system | Monoclinic | |
| Space group | P2(1)/c | |
| Unit cell dimensions | a = 12.0017(10) angstroms | alpha = 90°. |
| | b = 9.0910(7) angstroms | beta = 101.338(2)°. |
| | c = 21.9595(18) angstroms | gamma = 90°. |
| Volume | 2349.2(3) Å$^3$ | |
| Z | 4 | |
| Density (calculated) | 1.359 Mg/m$^3$ | |
| Absorption coefficient | 0.192 mm$^{-1}$ | |
| F(000) | 1000 | |
| Crystal size | 0.20 × 0.15 × 0.15 mm$^3$ | |
| Theta range for data collection | 1.73 to 28.33°. | |
| Index ranges | −14 <= h <= 15, −12 <= k <= 11, −29 <= l <= 24 | |
| Reflections collected | 14668 | |
| Independent reflections | 5509 [R(int) = 0.0226] | |
| Completeness to theta = 28.33° | 94.2% | |
| Absorption correction | None | |
| Refinement method | Full-matrix least-squares on F$^2$ | |
| Data/restraints/parameters | 5509/0/328 | |
| Goodness-of-fit on F$^2$ | 1.041 | |
| Final R indices [I > 2sigma(I)] | R1 = 0.0597, wR2 = 0.1698 | |
| R indices (all data) | R1 = 0.0950, wR2 = 0.1958 | |
| Largest diff. peak and hole | 0.455 and −0.217 e.Å$^{-3}$ | |

Figure 100:
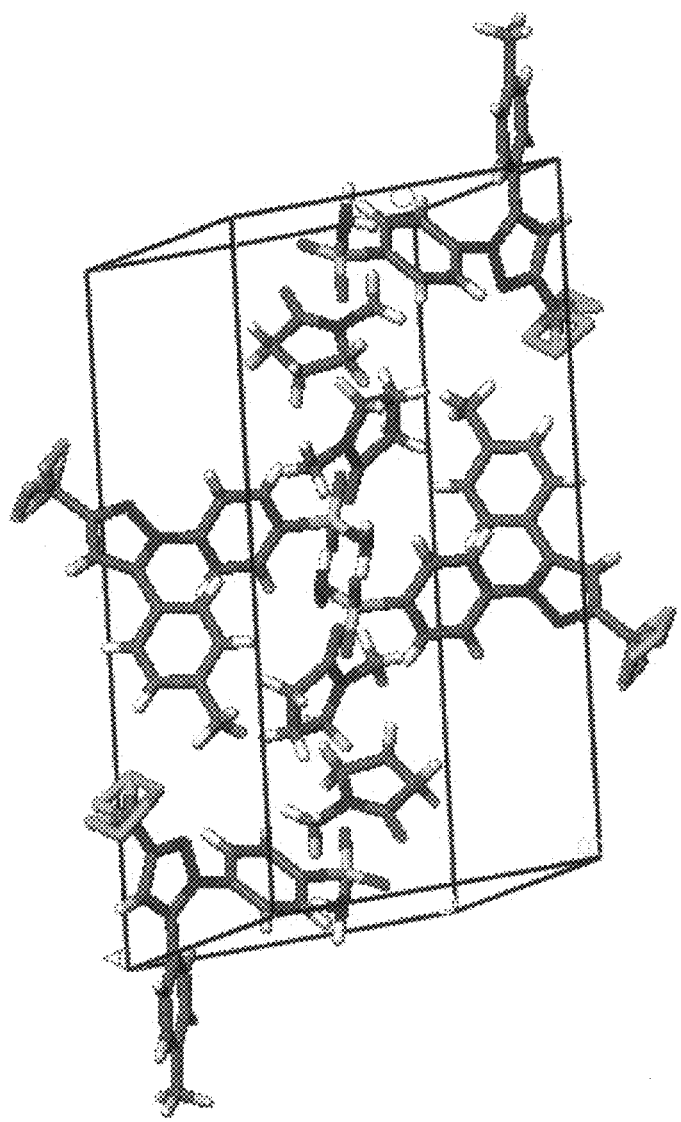
FIG. 100 shows a packing diagram for celecoxib NMP solvate at 571 K.

FIG. 100 shows a packing diagram for the celecoxib:NMP solvate at 571 K.

Example 34

Dissolution of Celecoxib Sodium Formulations with Potential Precipitation Inhibitors The dissolution profile in SGF of solid mixtures of celecoxib sodium with excipients was studied at room temperature. Those mixtures that provided concentrations greater than 0.10 mg/mL at any time point studied are included in FIG. 10.

Poloxamer 237, vitamin E TPGS (TPGS), and Gelucire 50/13 were all effective at providing elevated concentrations for some period of time. PVP and poloxamer 188 were less effective, but maintained measurable concentrations for at least some period. The TPGS solutions appeared mostly clear, and were clear after filtration. The Poloxamer 237 samples appeared milky, even after filtration.

Figure 7:
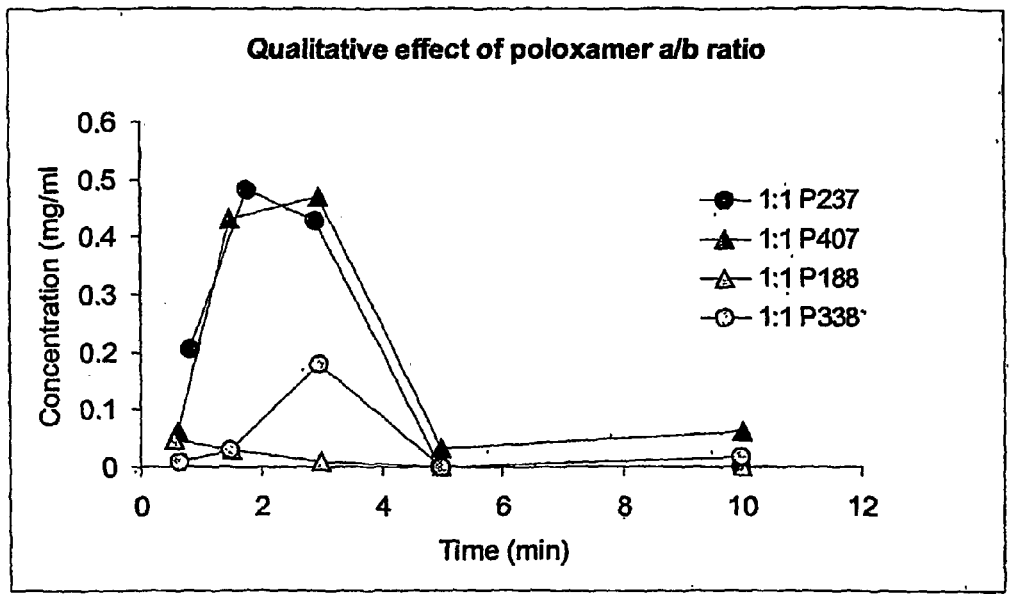
FIG. 7 shows the effect of varying ratios of ethylene glycol to propylene glycol subunits in poloxamers on the concentration of celecoxib sodium salt in solution.
Figure 7:

Since the mixtures with poloxamer 237 and 188 led to widely different solubility profiles, other poloxamers were studied as well, and the relationship between poloxamer structure and dissolution profile was evaluated (see FIG. 7). The weight ratio of drug to poloxamer is 1:1 for all profiles shown on the plot. Poloxamers 237 and 407 have a clear enhancement effect relative to poloxamers 188 and 338.

Poloxamers are block copolymers of polyethyleneglycol (PEG) and polypropyleneglycol (PPG). FIG. 7 also shows the block composition for each poloxamer studied. The solubility is enhanced by poloxamers containing a high composition of the PPG block.

Figure 8:
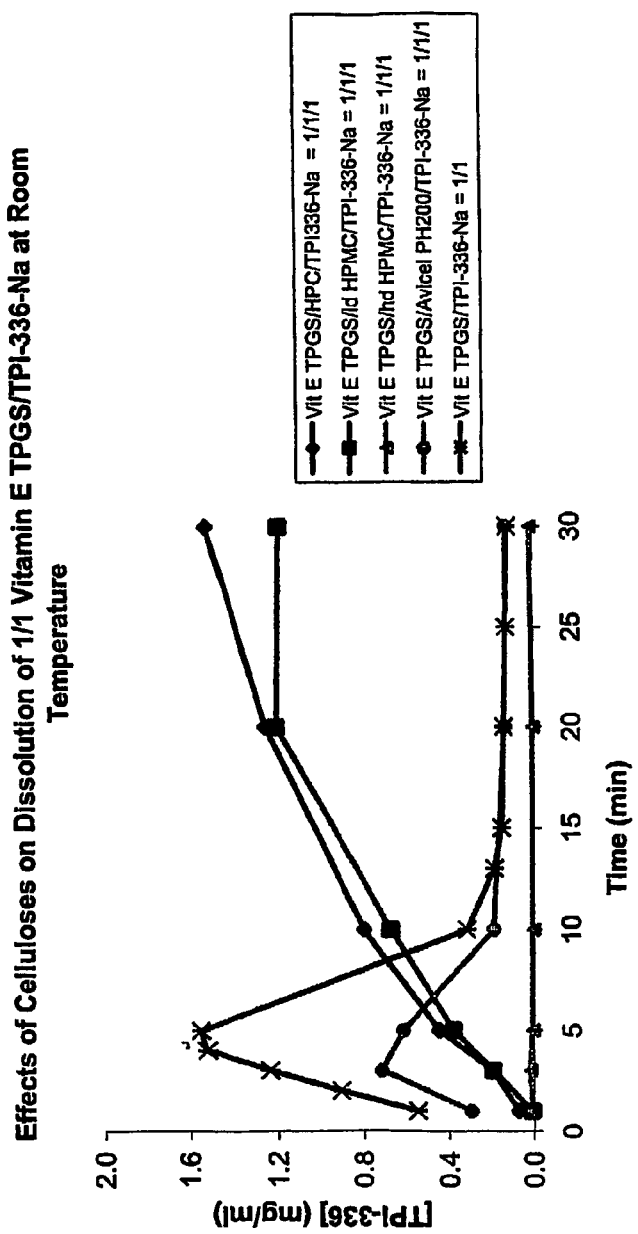
FIG. 8 shows the effect of different celluloses on the dissolution of various compositions comprising equal weights of cellulose (hydroxypropylcellulose (HPC, 100,000 kDa), low-viscosity hydroxypropylmethylcellulose (low-density HPMC, viscosity 80-120 cps), high-viscosity hydroxypropylmethylcellulose (high-density HPMC, viscosity 15,000 cps), or microcrystalline cellulose (Avicel PH200)), in d-alpha-tocopherol polyethylene glycol-1000 succinate (vitamin E TPGS) and celecoxib sodium.
Figure 9:
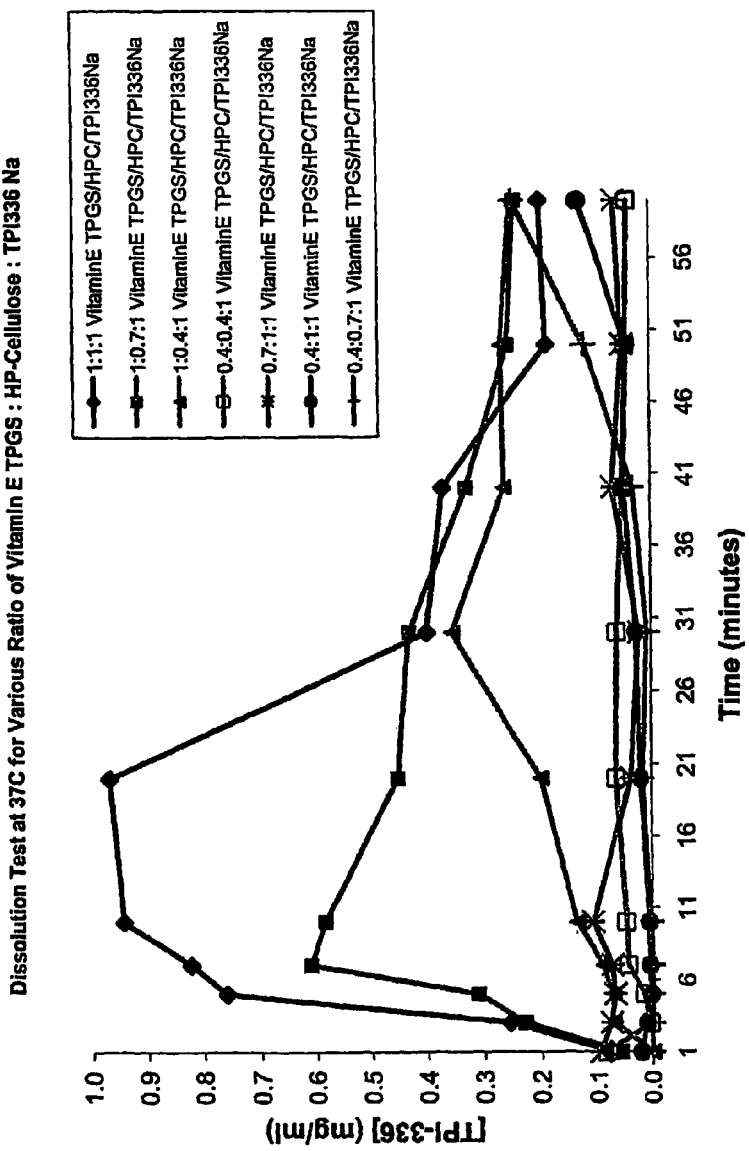
FIG. 9 shows the dissolution at 37 degrees C. for compositions comprising various weight ratios of d-alpha-tocopherol polyethylene glycol-1000 succinate (vitamin E TGPS), hydroxypropylcellulose, and celecoxib sodium salt.
Figure 10:
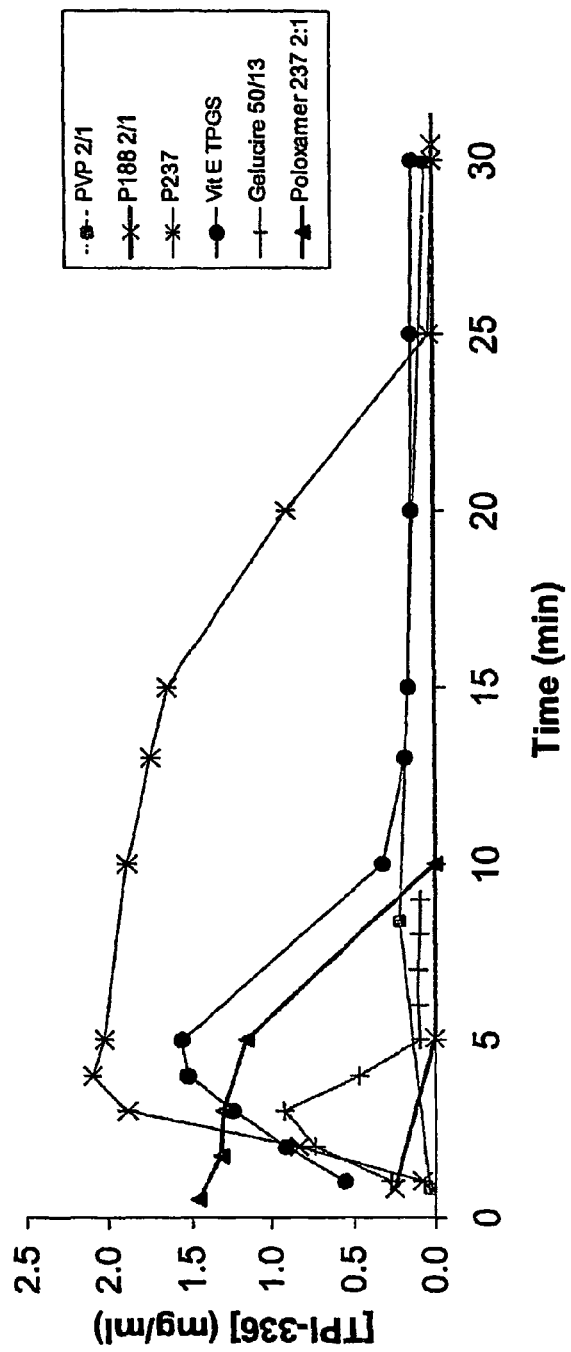
FIG. 10 shows the dissolution profile of celecoxib sodium salt in simulated gastric fluid (SGF) from solid mixtures with excipients at room temperature. The legend indicates the excipient and the weight ratio of excipient to celecoxib sodium (if unmarked, 1:1). Excipients include polyvinylpyrrolidone (PVP), poloxamer 188 (P188), poloxamer 237 (P237), d-alpha-tocopherol polyethylene glycol-1000 succinate (vitamin E TPGS), and Gelucire™ 50/13.
Figure 11:
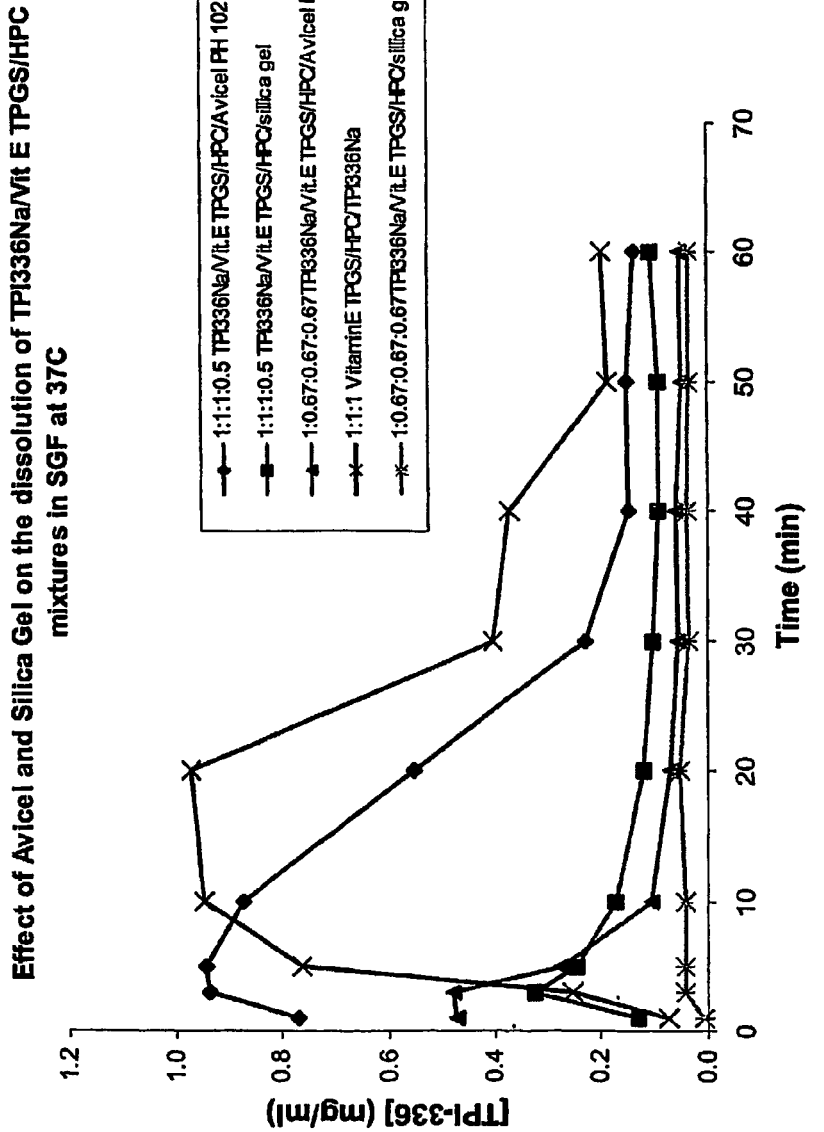
FIG. 11 shows the effect of Avicel microcrystalline cellulose and silica gel on the dissolution of mixtures of celecoxib sodium salt, d-alpha-tocopherol polyethylene glycol-1000 succinate (vit E TGPS), and hydroxypropylcellulose (HPC) mixtures in simulated gastric fluid (SGF) at 37 degrees C. The legend indicates the weight ratios of the components.
Figure 12:
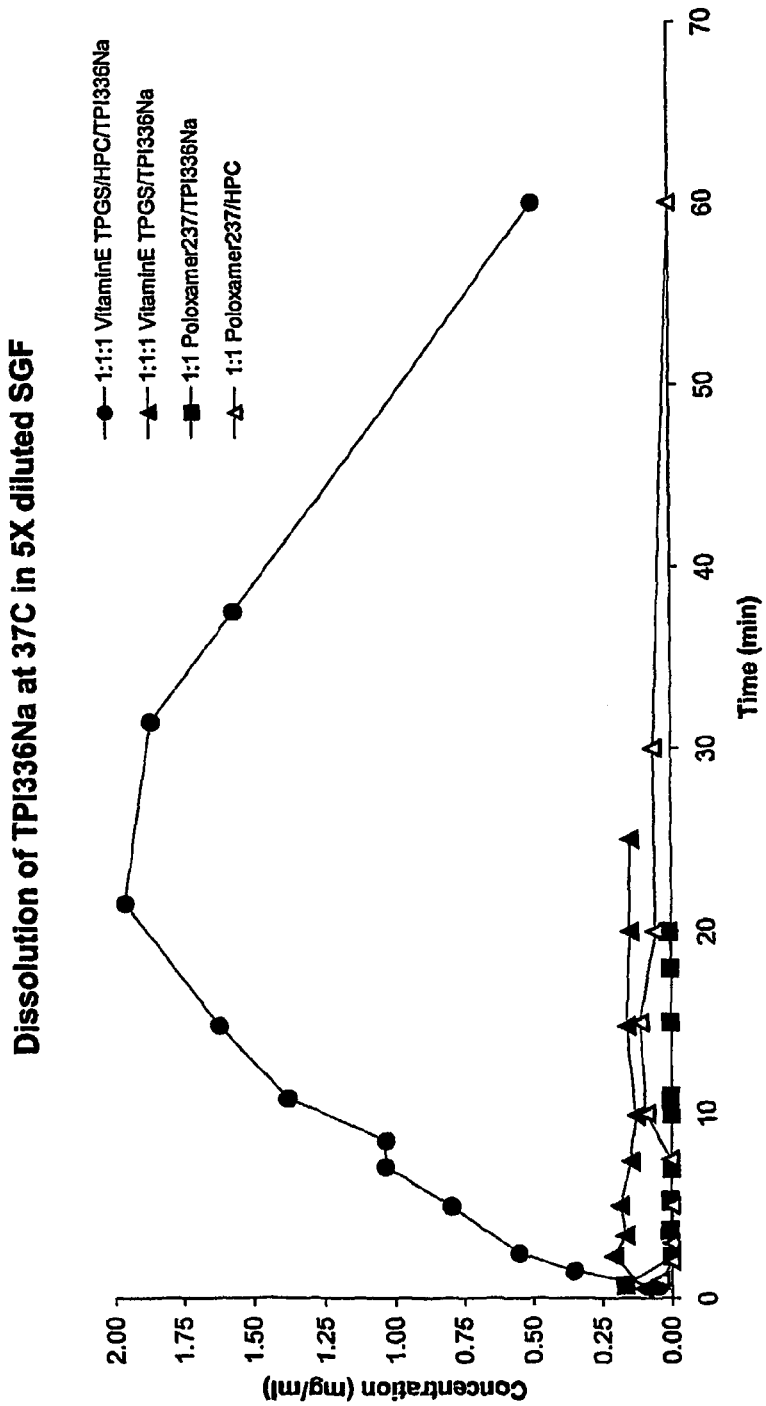
FIG. 12 shows the dissolution of celecoxib sodium salt in 5-times diluted simulated gastric fluid, with excipients including d-alpha-tocopherol polyethylene glycol-1000 succinate (vitamin E TPGS), hydroxypropylcellulose (HPC), and poloxamer 237. The legend indicates the weight ratios of the components.

FIG. 8 shows the effects of celluloses on dissolution of 1:1 TPGS:celecoxib sodium at room temperature. The effect of excipient loading and ratio on the dissolution profile was tested and found to have a profound impact on the dissolution profile (see FIG. 9). FIG. 10 shows a dissolution profile of celecoxib sodium in SGF from solid mixtures with excipients at room temperature. FIG. 11 shows the effect of Avicel and silica gel on the dissolution of celecoxib sodium, TPGS, HPC formulations in SGF at 37 degrees C. FIG. 12 shows the dissolution of celecoxib sodium salt in several formulations at 37 degrees C. in 5 times diluted SGF.

It is noted that as used in the Figures, the terms "TPI-336" and "TPI-336" refer to celecoxib or a salt of celecoxib depending upon the context.

The invention claimed is:

1. A pharmaceutical composition comprising: (a) a salt form of celecoxib; (b) d-alpha-tocopherol polyethylene glycol-1000 succinate (vitamin E TPGS); and (c); an enhancer selected from the group consisting of hydroxypropylcellulose and hydroxypropylmethylcellulose; wherein the composition retards crystallization or precipitation of the celecoxib for at least 5 minutes in gastric fluid conditions, wherein the pharmaceutical composition is formulated in a form suitable for oral administration.

2. The pharmaceutical composition according to claim 1, wherein crystallization or precipitation is retarded for at least 20 minutes.

3. The pharmaceutical composition according to claim 1, wherein crystallization or precipitation is retarded for at least 40 minutes.

4. The pharmaceutical composition according to claim 1, wherein crystallization or precipitation is retarded for at least 60 minutes.

5. The pharmaceutical composition according to claim 1, wherein the salt form of the celexoxib is an alkali metal or alkaline earth metal salt.

6. The pharmaceutical composition according to claim 1, wherein the salt form of the API is a sodium, potassium, lithium, or calcium salt.

7. The pharmaceutical composition according to claim 1, wherein the bioavailability of the composition orally administered is at least 70%.

8. The pharmaceutical composition according to claim 1, wherein the bioavailability of the composition orally administered is as least 80%.

9. The pharmaceutical composition according to claim 1, wherein the bioavailability of the composition orally administered is as least 90%.

10. The pharmaceutical composition according to claim 1, wherein the $C_{max}$ is at least 2 fold greater than a neutral form in vivo or in an in vitro dissolution assay.

11. The pharmaceutical composition according to claim 1, wherein the $C_{max}$ is at least 4 fold greater than a neutral form in vivo or in an in vitro dissolution assay.

12. The pharmaceutical composition according to claim 1, wherein the $C_{max}$ is at least 10 fold greater than a neutral form in vivo or in an in vitro dissolution assay.

13. The pharmaceutical composition according to claim 1, wherein the bioavailability of the composition is at least 50% greater than a neutral form.

14. The pharmaceutical composition according to claim 1, wherein the bioavailability of the composition is at least 2 fold that of a neutral form.

15. The pharmaceutical composition according to claim 1, wherein the bioavailability of the composition is at least 5 fold that of a neutral form.

* * * * *